US011898183B2

(12) United States Patent
Murali et al.

(10) Patent No.: US 11,898,183 B2
(45) Date of Patent: Feb. 13, 2024

(54) PROGRAMMED MICROORGANISMS TO ATTENUATE A DISEASE

(71) Applicants: Panchapagesa Muthuswamy Murali, Tamil Nadu (IN); Arumbuliyur Sathish Kumar, Tamil Nadu (IN); Shriram Raghavan, Tamil Nadu (IN)

(72) Inventors: Panchapagesa Muthuswamy Murali, Tamil Nadu (IN); Arumbuliyur Sathish Kumar, Tamil Nadu (IN); Shriram Raghavan, Tamil Nadu (IN)

( * ) Notice: Subject to any disclaimer, the term of this patent is extended or adjusted under 35 U.S.C. 154(b) by 302 days.

(21) Appl. No.: 17/344,265

(22) Filed: Jun. 10, 2021

(65) Prior Publication Data

US 2022/0033867 A1 Feb. 3, 2022

Related U.S. Application Data

(60) Provisional application No. 63/058,662, filed on Jul. 30, 2020.

(51) Int. Cl.

| | |
|---|---|
| ***C12P 17/04*** | (2006.01) |
| ***A61K 31/7048*** | (2006.01) |
| ***A61K 35/74*** | (2015.01) |
| ***C12N 9/02*** | (2006.01) |
| ***C12N 9/04*** | (2006.01) |
| ***C12N 9/10*** | (2006.01) |
| ***C12N 9/88*** | (2006.01) |
| ***C12N 9/00*** | (2006.01) |

(52) U.S. Cl.

CPC .......... *C12P 17/04* (2013.01); *A61K 31/7048* (2013.01); *A61K 35/74* (2013.01); *C12N 9/0004* (2013.01); *C12N 9/0006* (2013.01); *C12N 9/0042* (2013.01); *C12N 9/0069* (2013.01); *C12N 9/0071* (2013.01); *C12N 9/0073* (2013.01); *C12N 9/1007* (2013.01); *C12N 9/1029* (2013.01); *C12N 9/88* (2013.01); *C12N 9/93* (2013.01); *C12Y 101/01331* (2015.07); *C12Y 106/02004* (2013.01); *C12Y 114/13036* (2013.01); *C12Y 201/01104* (2013.01); *C12Y 203/01099* (2013.01); *C12Y 403/01024* (2013.01); *C12Y 602/01012* (2013.01); *C07K 2319/00* (2013.01)

(58) Field of Classification Search

None

See application file for complete search history.

(56) References Cited

U.S. PATENT DOCUMENTS

2005/0026866 A1 2/2005 Pawelek

OTHER PUBLICATIONS

Agrawal et al.; "Bacteriolytic therapy can generate a potent immune response against experimental tumors"; PNAS; vol. 101 No. 42; Oct. 2004; p. 15172-15177.

Saier Jr. et al.; "The Major Facilitator Superfamily"; J. Mol. Microbiol. Biotechnol.; vol. 1(2); 1999; p. 257-279.

Saier Jr. et al.; "The Transporter Classification Database: recent advances"; Nucleic Acids Research; vol. 37; Jan. 2009; p. D274-D278.

Altenhoefer et al.; "The probiotic *Escherichia coli* strain Nissle 1917 interferes with invasion of human intestinal epithelial cells by diferent enteroinvasive bacterial pathogens"; FEMS Immunology and Medical Microbiology; vol. 40; 2004; p. 223-229.

Bay et al.; "Diversity and evolution of the small multidrug resistance protein family"; BMC Evolutionary Biology; vol. 9; 2009; 27 pages.

Dang et al.; "Combination bacteriolytic therapy for the treatment of experimental tumors"; PNAS; vol. 98 No. 26; Dec. 2001; p. 15155-15160.

Fisher et al.; "Evaluation of the Worth of Corynebacterium parvum in Conjunction With Chemotherapy as Adjuvant Treatment for Primary Breast Cancer"; Cancer; vol. 66 No. 2; 1990; p. 220-227.

Jia et al.; "Oral Delivery of Tumor-Targeting *Salmonella* to Treat Cancer in Mice"; Bacterial Therapy of Cancer; Chapter3; 2005; p. 25-33.

Lee et al.; "A Propionate-Inducible Expression System for Enteric Bacteria"; Applied and Environmental Microbiology; vol. 71 No. 11; Nov. 2005; p. 6856-6862.

Lee et al.; "Endostatin gene therapy delivered by *Salmonella choleraesuis* in murine tumor models"; The Journal of Gene Medicine; vol. 6; 2004; p. 1382-1393.

Lee et al.; "Systemic Administration of Attenuated *Salmonella choleraesuis* in Combination with Cisplatin for Cancer Therapy"; Molecular Therapy; vol. 11 No. 5; May 2005; p. 707-716.

Lee et al.; "Systemic administration of attenuated *Salmonella choleraesuis* carrying thrombospondin-1 gene leads to tumor-specific transgene expression, delayed tumor growth and prolonged survival in the murine melanoma model"; Cancer Gene Therapy; vol. 12; 2005; p. 175-184.

Lodinova-Zadnikova et al.; "Effect of Preventive Administration of a Nonpathogenic *Escherichia coli*Strain on the Colonization of the Intestine with Microbial Pathogens in Newborn Infants"; Biology of the Neonate; vol. 71; 1997; p. 224-232.

(Continued)

*Primary Examiner* — Manjunath N Rao
*Assistant Examiner* — Jae W Lee
(74) *Attorney, Agent, or Firm* — BakerHostetler

(57) ABSTRACT

The present disclosure discloses a recombinant microbe producing podophyllotoxin, or its derivatives, comprising genes encoding phenyl alanine ammonia-lyase (PAL), cinnamate-4-hydroxylate (C4H), 4-coumaroyl CoA-ligase (4CL), hydroxycinnamoyl-CoA quinate hydroxycinnamoyl-transferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), cytochrome P450 oxidoreductase CYP719, O-methyltransferase (OMT), cytochrome P450 oxidoreductase CYP71, and 2-oxoglutarate/Fe(II)-dependent dioxygenase (2-ODD). Also disclosed herein is a method for producing podophyllotoxin or its derivatives. Moreover, a method of treating cancer is also disclosed.

17 Claims, 3 Drawing Sheets

Specification includes a Sequence Listing.

(56) References Cited

OTHER PUBLICATIONS

Loeffler et al.; "Attenuated *Salmonella* engineered to produce human cytokine LIGHT inhibit tumor growth"; PNAS; vol. 104 No. 31; Jul. 2007; p. 12879-12883.

Malmgren et al.; "Localization of the Vegetative Form of Clostridium tetani in Mouse Tumors Following Intravenous Spore Administration"; Cancer Research; vol. 15; 1955; p. 473-478.

Parker et al.; "Effect of H'istolyticus Infection and Toxin on Transplantable Mouse Tumors"; Experimental Biology and Medicine; vol. 66; 1947; p. 461-467.

Reister et al.; "Complete genome sequence of the Gram-negative probiotic *Escherichia coli* strain Nissle 1917"; Journal of Biotechnology; vol. 187; 2014; p. 106-107.

Rembacken et al.; "Non-pathogenic *Escherichia coli* versus mesalazine for the treatment of ulcerative colitis: a randomised trial"; The Lancet; vol. 354; Aug. 1999; p. 635-639.

Schultz et al.; "Clinical Use of *E. coli* Nissle 1917 in Inflammatory Bowel Disease"; Clinical Review—Inflamm Bowel Disease; vol. 14 No. 7; Jul. 2008; p. 1012-1018.

Sonnenborn et al.; "The non-pathogenic *Escherichia coli* strain Nissle 1917—features of a versatile probiotic"; Microbial Ecology in Health and Disease; vol. 21; 2009; p. 122-158.

Ukena et al.; "Probiotic *Escherichia coli* Nissle 1917 Inhibits Leaky Gut by Enhancing Mucosal Integrity"; PLos ONE; Issue 12—e1308; Dec. 2007; 9 pages.

Yi et al.; "Antitumor effect of cytosine deaminase/5-fluorocytosine suicide gene therapy system mediated by Bifidobacterium infantis on melanoma1"; Acta Pharmacologica Sinica; vol. 26; May 2005; p. 629-634.

Zhao et al.; "Tumor-targeting bacterial therapy with amino acid auxotrophs of GFP-expressing *Salmonella typhimurium*"; PNAS; vol. 102 No. 3; Jan. 2005; p. 755-760.

Zhao et al.; "Targeted Therapy with a *Salmonella typhimurium* Leucine-Arginine Auxotroph Cures Orthotopic Human Breast Tumors in Nude Mice"; Cancer Research; vol. 66; Aug. 2006; p. 7647-7652.

Top image: HPLC analysis of *E.coli* Nissle producing etoposide expressed under AraC regulatory unit (induced with arabionose), Etoposide formation Etoposide retention time (RT) : 3.6 minutes (x-axis)
Lower image: HPLC analysis of *E.coli* Nissle producing etoposide expressed under AraC regulatory unit (NO arabionose). No Etoposide formation

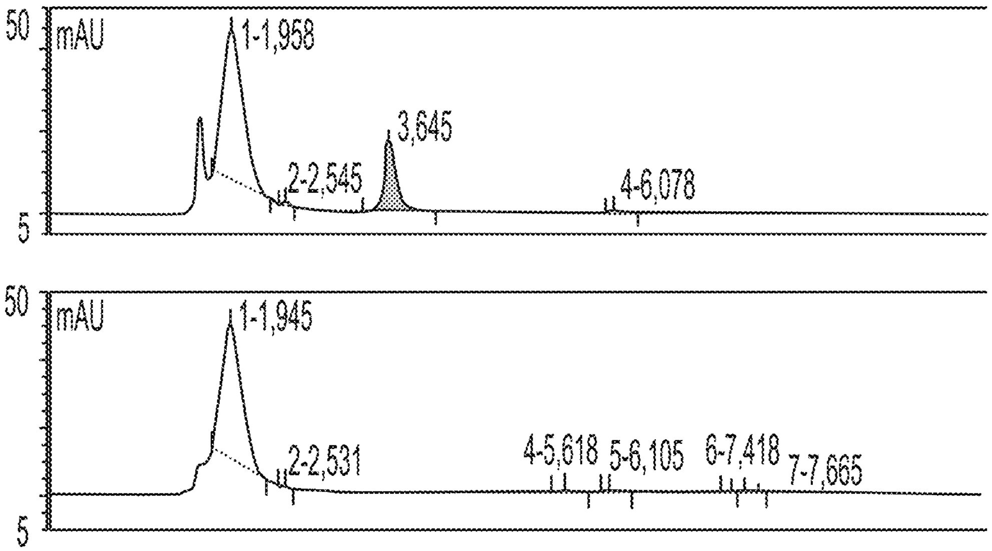

FIG. 1

Upper image: HPLC analysis of *E.coli* Nissle producing etoposide expressed under NorR regulatory unit (nitric oxide). No Etoposide formation
Lower image: HPLC analysis of *E.coli* Nissle producing etoposide expressed under NorR regulatory unit (No nitric oxide), Etoposide formation Etoposide retention time (RT) : 3.6 minutes (x-axis)

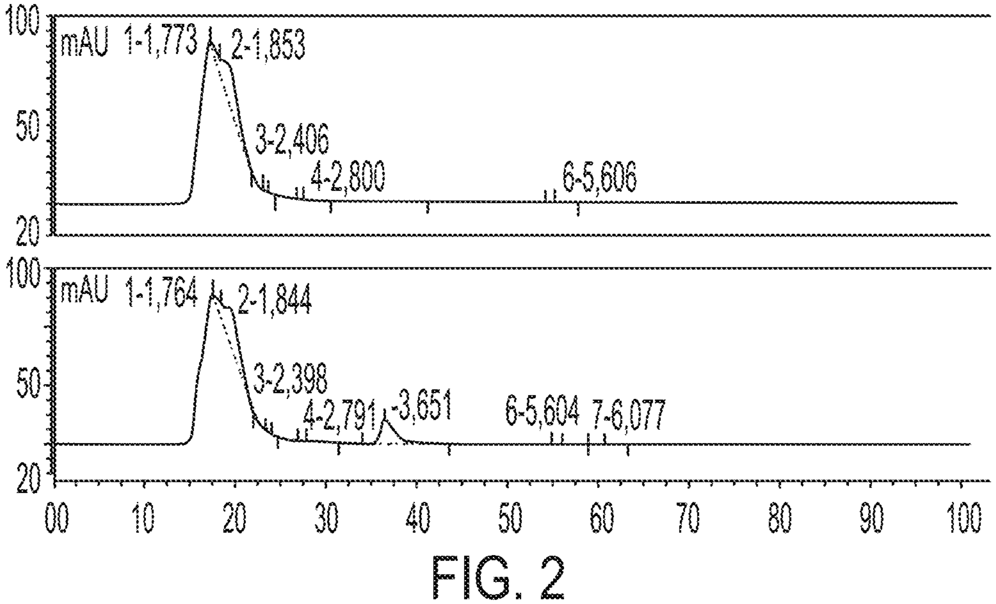

FIG. 2

Upper image: HPLC analysis of *E.coli* Nissle producing etoposide expressed under FNR regulatory unit (aerobic conditions). No Etoposide formation
Lower image: HPLC analysis of *E.coli* Nissle producing etoposide expressed under FNR regulatory unit (Hypoxic conditions), Etoposide formation - retention time (RT): 3.6 minutes (x-axis)

A

B

SEQUENCE LISTING

```
<160> NUMBER OF SEQ ID NOS: 64

<210> SEQ ID NO 1
<211> LENGTH: 2148
<212> TYPE: DNA
<213> ORGANISM: Rhodosporidium toruloides

<400> SEQUENCE: 1

atggcgccgt ctctggactc tatctctcac tctttcgcga acggtgttgc gtctgcgaaa     60

caggcggtta acggtgcgtc taccaacctg gcggttgcgg gttctcacct gccgaccacc    120

caggttaccc aggttgacat cgttgaaaaa atgctggcgg cgccgaccga ctctaccctg    180

gaactggacg gttactctct gaacctgggt gacgttgttt ctgcggcgcg taaaggtcgt    240

ccggttcgtg ttaaagactc tgacgaaatc cgttctaaaa tcgacaaatc tgttgaattc    300

ctgcgttctc agctgtctat gtctgtttac ggtgttacca ccggtttcgg tggttctgcg    360

gacacccgta ccgaagacgc gatctctctg cagaaagcgc tgctggaaca ccagctgtgc    420

ggtgttctgc cgtcttcttt cgactctttc cgtctgggtc gtggtctgga aaactctctg    480

ccgctggaag ttgttcgtgg tgcgatgacc atccgtgtta actctctgac ccgtggtcac    540

tctgcggttc gtctggttgt tctggaagcg ctgaccaact tcctgaacca cggtatcacc    600

ccgatcgttc cgctgcgtgg taccatctct gcgtctggtg acctgtctcc gctgtcttac    660

atcgcggcgg cgatctctgg tcacccggac tctaaagttc acgttgttca cgaaggtaaa    720

gaaaaaatcc tgtacgcgcg tgaagcgatg gcgctgttca acctggaacc ggttgttctg    780

ggtccgaaag aaggtctggg tctggttaac ggtaccgcgg tttctgcgtc tatggcgacc    840

ctggcgctgc acgacgcgca catgctgtct ctgctgtctc agtctctgac cgcgatgacc    900

gttgaagcga tggttggtca cgcgggttct ttccacccgt tcctgcacga cgttacccgt    960

ccgcacccga cccagatcga agttgcgggt aacatccgta aactgctgga aggttctcgt   1020

ttcgcggttc accacgaaga agaagttaaa gttaaagacg acgaaggtat cctgcgtcag   1080

gaccgttacc cgctgcgtac ctctccgcag tggctgggtc cgctggtttc tgacctgatc   1140

cacgcgcacg cggttctgac catcgaagcg ggtcagtcta ccaccgacaa cccgctgatc   1200

gacgttgaaa acaaaacctc tcaccacggt ggtaacttcc aggcggcggc ggttgcgaac   1260

accatggaaa aaacccgtct gggtctggcg cagatcggta aactgaactt cacccagctg   1320

accgaaatgc tgaacgcggg tatgaaccgt ggtctgccgt cttgcctggc ggcggaagac   1380

ccgtctctgt cttaccactg caaaggtctg gacatcgcgg cggcggcgta cacctctgaa   1440

ctgggtcacc tggcgaaccc ggttaccacc cacgttcagc cggcggaaat ggcgaaccag   1500

gcggttaact ctctggcgct gatctctgcg cgtcgtacca ccgaatctaa cgacgttctg   1560
```

-continued

```
tctctgctgc tggcgaccca cctgtactgc gttctgcagg cgatcgacct gcgtgcgatc   1620

gaattcgaat tcaaaaaaca gttcggtccg gcgatcgttt ctctgatcga ccagcacttc   1680

ggttctgcga tgaccggttc taacctgcgt gacgaactgg ttgaaaaagt taacaaaacc   1740

ctggcgaaac gtctggaaca gaccaactct tacgacctgg ttccgcgttg gcacgacgcg   1800

ttctctttcg cggcgggtac cgttgttgaa gttctgtctt ctacctctct gtctctggcg   1860

gcggttaacg cgtggaaagt tgcggcggcg gaatctgcga tctctctgac ccgtcaggtt   1920

cgtgaaacct tctggtctgc ggcgtctacc tcttctccgg cgctgtctta cctgtctccg   1980

cgtacccaga tcctgtacgc gttcgttcgt gaagaactgg gtgttaaagc gcgtcgtggt   2040

gacgttttcc tgggtaaaca ggaagttacc atcggttcta acgtttctaa aatctacgaa   2100

gcgatcaaat ctggtcgtat caacaacgtt ctgctgaaaa tgctggcg                2148
```

<210> SEQ ID NO 2
<211> LENGTH: 716
<212> TYPE: PRT
<213> ORGANISM: Rhodosporidium toruloides

<400> SEQUENCE: 2

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270
```

-continued

```
Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685
```

-continued

```
Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715


<210> SEQ ID NO 3
<211> LENGTH: 2130
<212> TYPE: DNA
<213> ORGANISM: Populus kitakamiensis

<400> SEQUENCE: 3

atggaattct gccaggactc tcgtaacggt aacggttctc cgggtttcaa caccaacgac      60

ccgctgaact ggggtatggc ggcggaatct ctgaaaggtt ctcacctgga cgaagttaaa     120

cgtatgatcg aagaataccg taacccggtt gttaaactgg gtggtgaaac cctgaccatc     180

ggtcaggtta ccgcgatcgc gtctcgtgac gttggtgtta tggttgaact gtctgaagaa     240

gcgcgtgcgg gtgttaaagc gtcttctgac tgggttatgg actctatgtc taaaggtacc     300

gactcttacg gtgttaccac cggtttcggt gcgacctctc accgtcgtac caaacagggt     360

ggtgaactgc agaaagaact gatccgtttc ctgaacgcgg gtatcttcgg taacggtacc     420

gaatcttctc acaccctgcc gcgttctgcg acccgtgcgg cgatgctggt tcgtaccaac     480

accctgctgc agggttactc tggtatccgt ttcgaaatgc tggaagcgat caccaaaatg     540

atcaaccaca acatcacccc gtgcctgccg ctgcgtggta ccatcaccgc gtctggtgac     600

ctggttccgc tgtcttacat cgcgggtctg ctgaccggtc gtccgaactc taaagcggtt     660

ggtccgaacg gtgaaccgct gaccccggcg gaagcgttca cccaggcggg tatcgacggt     720

ggtttcttcg aactgcagcc gaaagaaggt ctggcgctgg ttaacggtac cgcggttggt     780

tctggtctgg cgtctatggt tctgttcgaa gcgaacgttc tggcgatcct gtctgaagtt     840

ctgtctgcga tcttcgcgga agttatgcag ggtaaaccgg aattcaccga ccacctgacc     900

cacaaactga aacaccaccc gggtcagatc gttgcggcgg cgatcatgga acacatcctg     960

gacggttctg cgtacgttaa agaagcgcag aaactgcacg aaatcgaccc gctgcagaaa    1020

ccgaaacagg accgtcacgc gctgcgtacc tctccgcagt ggctgggtcc gctgatcgaa    1080

gttatccgta cctctaccaa aatgatcgaa cgtgaaatca actctgttaa cgacaacccg    1140

ctgatcgacg tttctcgtaa caaagcgctg cacggtggta acttccaggg taccccgatc    1200

ggtgtttcta tggacaacac ccgtctggcg atcgcgtcta tcggtaaact gatgttcgcg    1260

cagttctctg aactggttaa cgacctgtac aacaacggtc tgccgtctaa cctgaccggt    1320

ggtcgtaacc cgtctctgga ctacggtttc aaaggtgcgg aaatcgcgat ggcgtcttac    1380

tgctctgaac tgcagttcct ggaccagtct tgcaccaacc acgttcagtc tgcggaacag    1440

cacaaccagg acgttaactc tctgggtctg atctcttctc gtaaaaccgc ggaagcgatc    1500

gacatcctga aactgatgtc taccaccttc ctggttggtc tgtgccactc tgttgacctg    1560

cgtcacatcg aagaaaacct gaaaaacacc gttaaaatct ctgtttctca gctgccgcgt    1620

gttctgacca tgggtttcaa cggtgaactg cacccgtctc gtttctgcga aaaagacctg    1680

ctgaaagttg ttgaccgtga acacgttttc tcttacatcg acgacccgtg ctctgcgacc    1740

tacccgctga tgcagaaact gcgtcaggtt ctggttgaac acgcgctggt taacggtgaa    1800

aaagttcgta actctaccac ctctatcttc cagaaaatcg gttctttcga agaagaactg    1860

aaaaccctgc tgccgaaaga agttgaatct gcgcgtctgg aagttgaaaa cggtaacccg    1920

gcgatcccga accgtatcaa agaatgccgt tcttacccgc tgtacaaatt cgttcgtgaa    1980
```

```
gaactgggta cctctctgct gaccggtgaa aaagttaaat ctccgggtga agaattcgac   2040

aaagttttca ccgcgatctg cgcgggtaaa ctgatcgacc cgctgctgga atgcctgaaa   2100

gaatgggacg gtgcgccgct gccgatctgc                                     2130


<210> SEQ ID NO 4
<211> LENGTH: 710
<212> TYPE: PRT
<213> ORGANISM: Populus kitakamiensis

<400> SEQUENCE: 4

Met Glu Phe Cys Gln Asp Ser Arg Asn Gly Asn Gly Ser Pro Gly Phe
1               5                   10                  15

Asn Thr Asn Asp Pro Leu Asn Trp Gly Met Ala Ala Glu Ser Leu Lys
            20                  25                  30

Gly Ser His Leu Asp Glu Val Lys Arg Met Ile Glu Glu Tyr Arg Asn
        35                  40                  45

Pro Val Val Lys Leu Gly Gly Glu Thr Leu Thr Ile Gly Gln Val Thr
    50                  55                  60

Ala Ile Ala Ser Arg Asp Val Gly Val Met Val Glu Leu Ser Glu Glu
65                  70                  75                  80

Ala Arg Ala Gly Val Lys Ala Ser Ser Asp Trp Val Met Asp Ser Met
                85                  90                  95

Ser Lys Gly Thr Asp Ser Tyr Gly Val Thr Thr Gly Phe Gly Ala Thr
            100                 105                 110

Ser His Arg Arg Thr Lys Gln Gly Gly Glu Leu Gln Lys Glu Leu Ile
        115                 120                 125

Arg Phe Leu Asn Ala Gly Ile Phe Gly Asn Gly Thr Glu Ser Ser His
    130                 135                 140

Thr Leu Pro Arg Ser Ala Thr Arg Ala Ala Met Leu Val Arg Thr Asn
145                 150                 155                 160

Thr Leu Leu Gln Gly Tyr Ser Gly Ile Arg Phe Glu Met Leu Glu Ala
                165                 170                 175

Ile Thr Lys Met Ile Asn His Asn Ile Thr Pro Cys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Gly Pro Asn Gly
    210                 215                 220

Glu Pro Leu Thr Pro Ala Glu Ala Phe Thr Gln Ala Gly Ile Asp Gly
225                 230                 235                 240

Gly Phe Phe Glu Leu Gln Pro Lys Glu Gly Leu Ala Leu Val Asn Gly
                245                 250                 255

Thr Ala Val Gly Ser Gly Leu Ala Ser Met Val Leu Phe Glu Ala Asn
            260                 265                 270

Val Leu Ala Ile Leu Ser Glu Val Leu Ser Ala Ile Phe Ala Glu Val
        275                 280                 285

Met Gln Gly Lys Pro Glu Phe Thr Asp His Leu Thr His Lys Leu Lys
    290                 295                 300

His His Pro Gly Gln Ile Val Ala Ala Ala Ile Met Glu His Ile Leu
305                 310                 315                 320

Asp Gly Ser Ala Tyr Val Lys Glu Ala Gln Lys Leu His Glu Ile Asp
                325                 330                 335

Pro Leu Gln Lys Pro Lys Gln Asp Arg His Ala Leu Arg Thr Ser Pro
```

```
            340                 345                 350

Gln Trp Leu Gly Pro Leu Ile Glu Val Ile Arg Thr Ser Thr Lys Met
        355                 360                 365

Ile Glu Arg Glu Ile Asn Ser Val Asn Asp Asn Pro Leu Ile Asp Val
    370                 375                 380

Ser Arg Asn Lys Ala Leu His Gly Gly Asn Phe Gln Gly Thr Pro Ile
385                 390                 395                 400

Gly Val Ser Met Asp Asn Thr Arg Leu Ala Ile Ala Ser Ile Gly Lys
                405                 410                 415

Leu Met Phe Ala Gln Phe Ser Glu Leu Val Asn Asp Leu Tyr Asn Asn
            420                 425                 430

Gly Leu Pro Ser Asn Leu Thr Gly Gly Arg Asn Pro Ser Leu Asp Tyr
        435                 440                 445

Gly Phe Lys Gly Ala Glu Ile Ala Met Ala Ser Tyr Cys Ser Glu Leu
    450                 455                 460

Gln Phe Leu Asp Gln Ser Cys Thr Asn His Val Gln Ser Ala Glu Gln
465                 470                 475                 480

His Asn Gln Asp Val Asn Ser Leu Gly Leu Ile Ser Ser Arg Lys Thr
                485                 490                 495

Ala Glu Ala Ile Asp Ile Leu Lys Leu Met Ser Thr Thr Phe Leu Val
            500                 505                 510

Gly Leu Cys His Ser Val Asp Leu Arg His Ile Glu Glu Asn Leu Lys
        515                 520                 525

Asn Thr Val Lys Ile Ser Val Ser Gln Leu Pro Arg Val Leu Thr Met
    530                 535                 540

Gly Phe Asn Gly Glu Leu His Pro Ser Arg Phe Cys Glu Lys Asp Leu
545                 550                 555                 560

Leu Lys Val Val Asp Arg Glu His Val Phe Ser Tyr Ile Asp Asp Pro
                565                 570                 575

Cys Ser Ala Thr Tyr Pro Leu Met Gln Lys Leu Arg Gln Val Leu Val
            580                 585                 590

Glu His Ala Leu Val Asn Gly Glu Lys Val Arg Asn Ser Thr Thr Ser
        595                 600                 605

Ile Phe Gln Lys Ile Gly Ser Phe Glu Glu Glu Leu Lys Thr Leu Leu
    610                 615                 620

Pro Lys Glu Val Glu Ser Ala Arg Leu Glu Val Glu Asn Gly Asn Pro
625                 630                 635                 640

Ala Ile Pro Asn Arg Ile Lys Glu Cys Arg Ser Tyr Pro Leu Tyr Lys
                645                 650                 655

Phe Val Arg Glu Glu Leu Gly Thr Ser Leu Leu Thr Gly Glu Lys Val
            660                 665                 670

Lys Ser Pro Gly Glu Glu Phe Asp Lys Val Phe Thr Ala Ile Cys Ala
        675                 680                 685

Gly Lys Leu Ile Asp Pro Leu Leu Glu Cys Leu Lys Glu Trp Asp Gly
    690                 695                 700

Ala Pro Leu Pro Ile Cys
705                 710
```

<210> SEQ ID NO 5
<211> LENGTH: 2181
<212> TYPE: DNA
<213> ORGANISM: Strobilurus tenacellus

<400> SEQUENCE: 5

-continued

```
atgccgatca cccacgaaca gccgaacggt ttccactcta aacagctgaa cggttctggt     60

atcgcgaaag cgaaagcgat gccgtacccg tctgacctgc tgtctcactt cgttaaacag    120

cacctggaac tggaatctta caaaaacggt caggaaatcg aaatcgacgg ttactctctg    180

tctatctctg cggtttctgc ggcggcgcgt tacaacgcgc cggttatcct gcgtgactct    240

tctaccatcc gtgaccgtct ggaaaaagcg cgttctgtta tcgttgaaaa aatcgaaggt    300

tctaaatctg tttacggtgt ttctaccggt ttcggtggtt ctgcggacac ccgtacctct    360

aacaccctgg cgctgggtaa cgcgctgctg cagcaccagc actctggtgt tctgccgtct    420

accaccaaca ccctgtctgt tctgccgctg ctggacccga tcgcgtctac ctctatgccg    480

gaatcttggg ttcgtggtgc gatcctgatc cgtatcaact ctctgatccg tggtcactct    540

ggtgttcgtt gggaactgat cgcgaaaatg gttgaactgc tgcaggcgaa catcaccccg    600

ctggttccgc tgcgtggttc tatctctgcg tctggtgacc tgtctccgct gtcttacgtt    660

gcgggtaccc tgatgggtaa cccgtctatc cgtgttttcg acggtccggc ggcgttcggt    720

gcgcgtcaga tcgtttcttc tgttaaagcg ctggaagaac acaacatcac cccgatctct    780

ctgctggcga aagaacacct gggtatcctg aacggtaccg cgttctctgc gtctgttgcg    840

tctctggttc tgtctgacgt tacccacctg gcgatgctgg cgcaggtttg caccgcgatg    900

ggtaccgaag ttctgctggg tgaacgtatg aactacgcgc cgttcatcca cgcggttgcg    960

cgtccgcacc cgggtcagac cgaagcggcg cgtaccatct gggacctgct gtctggttct   1020

aaactggcgc acggtcacga agaagaagtt accatcgacc aggaccaggg tgaactgcgt   1080

caggaccgtt acccgctgcg taccgcgccg cagttcctgg gtccgcagat cgaagacatc   1140

ctgtctgcgc tgaacaccgt taccctggaa tgcaactcta ccaccgacaa cccgctgatc   1200

gacggtgaaa ccggtgacat ccaccacggt ggtaacttcc aggcgatgtc tgtttctaac   1260

gcgatggaaa aaacccgtct gtctctgcac cacatcggta aactgctgtt cgcgcagtgc   1320

gcggaactgg ttcacccgga catgaaccgt ggtctgccgc cgtctctggc ggcgaccgac   1380

ccgtctatca actaccacgg taaaggtatc gacatcggta tcgcggcgta cgtttctgaa   1440

ctgggttacc tggcgaaccc ggtttctacc cacatccagt ctgcggaact gcacaaccag   1500

gcggttaact ctctggcgct gatctctgcg cgtgcgacca tcaactctct ggaagttctg   1560

tctctgctga cctcttctta cctgtacatg ctgtgccagg cgtacgacct gcgtgcgctg   1620

caggcggact tccgtcaggg tctggcggaa atcgttcagg aagaactgcg tgcgcacttc   1680

tctgcgcaca tcgaatctct ggacgaatct ccgctgttcg acaaagttat ctcttctatg   1740

tacaaagaac tgaaccacac caccaccatg gacgcggttc cgcgtatggt taaagttgcg   1800

ggtgcgtcta cctctctgct ggttgacttc ttcatggcga accagacctc tgacgcgatg   1860

tctgttgcgg cgctgaccgc gctgccgaaa ttccgtgaaa ccgttgcgct gcgtgcggcg   1920

gcgaaactgg ttgcgctgcg tgaagaatac ctgctgggtg cgcgtggtcc ggcgccggcg   1980

tctgcgtggc tgggtcgtac ccgtccgatc tacgaattca tccgtgttac cctgggtatc   2040

cgtatgcacg gtaccgaaaa cctgggtgtt ttccagcagg gtctgggtgt tcaggacgtt   2100

accatcggtc agaacgtttc tctgatccac gaagcgatcc gtgacggtaa aatgcgtggt   2160

gttgttgttg gtctgttcgc g                                              2181
```

<210> SEQ ID NO 6
<211> LENGTH: 727
<212> TYPE: PRT
<213> ORGANISM: Strobilurus tenacellus

<400> SEQUENCE: 6

Met Pro Ile Thr His Glu Gln Pro Asn Gly Phe His Ser Lys Gln Leu
1               5                   10                  15

Asn Gly Ser Gly Ile Ala Lys Ala Lys Ala Met Pro Tyr Pro Ser Asp
            20                  25                  30

Leu Leu Ser His Phe Val Lys Gln His Leu Glu Leu Glu Ser Tyr Lys
        35                  40                  45

Asn Gly Gln Glu Ile Glu Ile Asp Gly Tyr Ser Leu Ser Ile Ser Ala
    50                  55                  60

Val Ser Ala Ala Ala Arg Tyr Asn Ala Pro Val Ile Leu Arg Asp Ser
65                  70                  75                  80

Ser Thr Ile Arg Asp Arg Leu Glu Lys Ala Arg Ser Val Ile Val Glu
                85                  90                  95

Lys Ile Glu Gly Ser Lys Ser Val Tyr Gly Val Ser Thr Gly Phe Gly
            100                 105                 110

Gly Ser Ala Asp Thr Arg Thr Ser Asn Thr Leu Ala Leu Gly Asn Ala
        115                 120                 125

Leu Leu Gln His Gln His Ser Gly Val Leu Pro Ser Thr Thr Asn Thr
    130                 135                 140

Leu Ser Val Leu Pro Leu Leu Asp Pro Ile Ala Ser Thr Ser Met Pro
145                 150                 155                 160

Glu Ser Trp Val Arg Gly Ala Ile Leu Ile Arg Ile Asn Ser Leu Ile
                165                 170                 175

Arg Gly His Ser Gly Val Arg Trp Glu Leu Ile Ala Lys Met Val Glu
            180                 185                 190

Leu Leu Gln Ala Asn Ile Thr Pro Leu Val Pro Leu Arg Gly Ser Ile
        195                 200                 205

Ser Ala Ser Gly Asp Leu Ser Pro Leu Ser Tyr Val Ala Gly Thr Leu
    210                 215                 220

Met Gly Asn Pro Ser Ile Arg Val Phe Asp Gly Pro Ala Ala Phe Gly
225                 230                 235                 240

Ala Arg Gln Ile Val Ser Ser Val Lys Ala Leu Glu Glu His Asn Ile
                245                 250                 255

Thr Pro Ile Ser Leu Leu Ala Lys Glu His Leu Gly Ile Leu Asn Gly
            260                 265                 270

Thr Ala Phe Ser Ala Ser Val Ala Ser Leu Val Leu Ser Asp Val Thr
        275                 280                 285

His Leu Ala Met Leu Ala Gln Val Cys Thr Ala Met Gly Thr Glu Val
    290                 295                 300

Leu Leu Gly Glu Arg Met Asn Tyr Ala Pro Phe Ile His Ala Val Ala
305                 310                 315                 320

Arg Pro His Pro Gly Gln Thr Glu Ala Ala Arg Thr Ile Trp Asp Leu
                325                 330                 335

Leu Ser Gly Ser Lys Leu Ala His Gly His Glu Glu Glu Val Thr Ile
            340                 345                 350

Asp Gln Asp Gln Gly Glu Leu Arg Gln Asp Arg Tyr Pro Leu Arg Thr
        355                 360                 365

Ala Pro Gln Phe Leu Gly Pro Gln Ile Glu Asp Ile Leu Ser Ala Leu
    370                 375                 380

Asn Thr Val Thr Leu Glu Cys Asn Ser Thr Thr Asp Asn Pro Leu Ile
385                 390                 395                 400

Asp Gly Glu Thr Gly Asp Ile His His Gly Gly Asn Phe Gln Ala Met

```
                405                 410                 415

Ser Val Ser Asn Ala Met Glu Lys Thr Arg Leu Ser Leu His His Ile
            420                 425                 430

Gly Lys Leu Leu Phe Ala Gln Cys Ala Glu Leu Val His Pro Asp Met
        435                 440                 445

Asn Arg Gly Leu Pro Pro Ser Leu Ala Ala Thr Asp Pro Ser Ile Asn
    450                 455                 460

Tyr His Gly Lys Gly Ile Asp Ile Gly Ile Ala Ala Tyr Val Ser Glu
465                 470                 475                 480

Leu Gly Tyr Leu Ala Asn Pro Val Ser Thr His Ile Gln Ser Ala Glu
                485                 490                 495

Leu His Asn Gln Ala Val Asn Ser Leu Ala Leu Ile Ser Ala Arg Ala
            500                 505                 510

Thr Ile Asn Ser Leu Glu Val Leu Ser Leu Leu Thr Ser Ser Tyr Leu
        515                 520                 525

Tyr Met Leu Cys Gln Ala Tyr Asp Leu Arg Ala Leu Gln Ala Asp Phe
    530                 535                 540

Arg Gln Gly Leu Ala Glu Ile Val Gln Glu Glu Leu Arg Ala His Phe
545                 550                 555                 560

Ser Ala His Ile Glu Ser Leu Asp Glu Ser Pro Leu Phe Asp Lys Val
                565                 570                 575

Ile Ser Ser Met Tyr Lys Glu Leu Asn His Thr Thr Thr Met Asp Ala
            580                 585                 590

Val Pro Arg Met Val Lys Val Ala Gly Ala Ser Thr Ser Leu Leu Val
        595                 600                 605

Asp Phe Phe Met Ala Asn Gln Thr Ser Asp Ala Met Ser Val Ala Ala
    610                 615                 620

Leu Thr Ala Leu Pro Lys Phe Arg Glu Thr Val Ala Leu Arg Ala Ala
625                 630                 635                 640

Ala Lys Leu Val Ala Leu Arg Glu Glu Tyr Leu Leu Gly Ala Arg Gly
                645                 650                 655

Pro Ala Pro Ala Ser Ala Trp Leu Gly Arg Thr Arg Pro Ile Tyr Glu
            660                 665                 670

Phe Ile Arg Val Thr Leu Gly Ile Arg Met His Gly Thr Glu Asn Leu
        675                 680                 685

Gly Val Phe Gln Gln Gly Leu Gly Val Gln Asp Val Thr Ile Gly Gln
    690                 695                 700

Asn Val Ser Leu Ile His Glu Ala Ile Arg Asp Gly Lys Met Arg Gly
705                 710                 715                 720

Val Val Val Gly Leu Phe Ala
                725
```

<210> SEQ ID NO 7
<211> LENGTH: 2133
<212> TYPE: DNA
<213> ORGANISM: Artificial Sequence
<220> FEATURE:
<223> OTHER INFORMATION: Depicts the nucleic acid sequuence encoding Phenylalanine ammonia-lyase (PAL) of Penicillium antarcticum

<400> SEQUENCE: 7

```
atgtctccgg cgtcttacac cgcgaccccg gtttcttctc tggttacccc gtctcacccg      60

accccgcaca aagacgaaac cctgaaatct tgggcgaaaa tcggttctct ggttcaccgt     120

ggtgttgtta acgttgacgg tgaaaccctg gacatcgcgt ctgttgttgc ggttgcgcgt     180
```

-continued

```
ttcgaaggtt gcggtgcgaa agtttctaaa gacaccaaag ttaccgaacg tgttgaagcg    240
ggtatcgaaa ccttcaacga ctacctgtac aaaggttact gcatctacgg tgttaacacc    300
ggtttcggtg gttctgcgga cacccgtacc tctgacgtta tccgtctgca gcagtctctg    360
ctgcagctga cccagtctgg tatcctgtct ggttctgact tctctccgcg tatgggtgac    420
tacaacctgt cttctcacgc gatgccggtt acctgggttc gtgcgaccat gctggttcgt    480
tgcaaccacc tgctgcgtgg tcactctggt gttcgtctgg aaatcatcga caccgttctg    540
cgtctgctgc gtgcgggtct gaccccgatc atcccgctgc gtggttctat ctctgcgtct    600
ggtgacctga tgccgctgtc ttacctggtt ggtatcctgg aaggtaaccc ggacatcaaa    660
gtttactggg accgtaaacc ggaagcggcg atcgtttctg cgaccaaagc gctggaaatc    720
atcggtatcc cgccgttcat cctgaaaccg aaagaaggtc tgtctctgat caacggttct    780
gcggcgtctg cggcggttgc gtctctggcg gcgcacgaag cgtctcagct ggttctgctg    840
gcgcagggtc tgaccgcgct gacctgcgaa gcgatgatgg gtaacgcgga aaactaccac    900
gaattcccgg cgaaaatccg tccgcacccg ggtcagatcg aagttgcggc gaacatccgt    960
aaaggtatca tcaactctaa actgatcgaa acctctggta ccaaagaccg tctgcgtcag   1020
ggtctgatcc aggaccgtta cgcgctgcgt ggtgcgtctc agtggctggg tccggttgtt   1080
gaagacctgc gtctggcgat ccagcagctg accaccgaac tgaactctac ccaggacaac   1140
ccggttatcg actctgaatc tggtgaagtt tacttctgct ctaacttcca ggcggcgtct   1200
gtttctatgg cgatggaaaa aacccgtggt ggtctgcaga tgatcggtaa actgctgttc   1260
tcttactctt ctgaactgat caacccggac atgaacaaag gtctgccggc gaacctggcg   1320
gcggacgacc cgtctctgtc tttcaccatg aaaggtgttg acatcaacat ggcggcgtac   1380
atgtctgaac tgggtttcct ggcgaactct gttacctctc acgttcagtc tgcggaaatg   1440
aacaaccagc cgatcaactc tctggcgctg atctctgcgc gttacaccct gcaggcggtt   1500
gaactggttt ctatgatgtc tgcggcgctg ctgtacgtta cctgccaggc ggttgacctg   1560
cgtatcctgc acgaaacctt cctggaaaac ctgtactctg ttctgtacct ggcgttcgac   1620
tctgttcaga tgcgtcagga caaatcttct gcgatccgta ccgaactgct gcaggcgctg   1680
cgtaactctt ggggtcactc tgcgcgtgac gacctgtctg ttcgtatcca ggcgctgtct   1740
accgcgatgg cgccggttct gctggcgaac gcgaaagaac tgtctaccga agacccgttc   1800
gcggttatcg aacacctgca gaaagaaatc cgtcaggaag cgaaaaccct gttcctgggt   1860
ctgcgtgtta aatctttctg cggtgacctg aacgcggaat cttctctggg tccggcggcg   1920
aaagcgctgt accgtttcgt tcgtcgtgaa ctggacgttc cgttccactg cggtatcggt   1980
gaacacccga ccggtgacac cgaagcggcg gcggacatcc cgccgcgtcc gcgtaaaacc   2040
gttggttctt ggatctctat catctacgac gcgatccgtg acggtcgtat ccgtcagccg   2100
ctgggtgacg actggcgttg ctgcaacggt ttc                                2133
```

<210> SEQ ID NO 8
<211> LENGTH: 711
<212> TYPE: PRT
<213> ORGANISM: Artificial Sequence
<220> FEATURE:
<223> OTHER INFORMATION: Depicts the amino acid sequence of Phenylalanine ammonia-lyase (PAL) of Penicillium antarcticum

<400> SEQUENCE: 8

```
Met Ser Pro Ala Ser Tyr Thr Ala Thr Pro Val Ser Ser Leu Val Thr
1               5                   10                  15
```

```
Pro Ser His Pro Thr Pro His Lys Asp Glu Thr Leu Lys Ser Trp Ala
            20                  25                  30

Lys Ile Gly Ser Leu Val His Arg Gly Val Val Asn Val Asp Gly Glu
        35                  40                  45

Thr Leu Asp Ile Ala Ser Val Val Ala Val Ala Arg Phe Glu Gly Cys
    50                  55                  60

Gly Ala Lys Val Ser Lys Asp Thr Lys Val Thr Glu Arg Val Glu Ala
65                  70                  75                  80

Gly Ile Glu Thr Phe Asn Asp Tyr Leu Tyr Lys Gly Tyr Cys Ile Tyr
                85                  90                  95

Gly Val Asn Thr Gly Phe Gly Gly Ser Ala Asp Thr Arg Thr Ser Asp
            100                 105                 110

Val Ile Arg Leu Gln Gln Ser Leu Leu Gln Leu Thr Gln Ser Gly Ile
        115                 120                 125

Leu Ser Gly Ser Asp Phe Ser Pro Arg Met Gly Asp Tyr Asn Leu Ser
    130                 135                 140

Ser His Ala Met Pro Val Thr Trp Val Arg Ala Thr Met Leu Val Arg
145                 150                 155                 160

Cys Asn His Leu Leu Arg Gly His Ser Gly Val Arg Leu Glu Ile Ile
                165                 170                 175

Asp Thr Val Leu Arg Leu Leu Arg Ala Gly Leu Thr Pro Ile Ile Pro
            180                 185                 190

Leu Arg Gly Ser Ile Ser Ala Ser Gly Asp Leu Met Pro Leu Ser Tyr
        195                 200                 205

Leu Val Gly Ile Leu Glu Gly Asn Pro Asp Ile Lys Val Tyr Trp Asp
    210                 215                 220

Arg Lys Pro Glu Ala Ala Ile Val Ser Ala Thr Lys Ala Leu Glu Ile
225                 230                 235                 240

Ile Gly Ile Pro Pro Phe Ile Leu Lys Pro Lys Glu Gly Leu Ser Leu
                245                 250                 255

Ile Asn Gly Ser Ala Ala Ser Ala Ala Val Ala Ser Leu Ala Ala His
            260                 265                 270

Glu Ala Ser Gln Leu Val Leu Leu Ala Gln Gly Leu Thr Ala Leu Thr
        275                 280                 285

Cys Glu Ala Met Met Gly Asn Ala Glu Asn Tyr His Glu Phe Pro Ala
    290                 295                 300

Lys Ile Arg Pro His Pro Gly Gln Ile Glu Val Ala Ala Asn Ile Arg
305                 310                 315                 320

Lys Gly Ile Ile Asn Ser Lys Leu Ile Glu Thr Ser Gly Thr Lys Asp
                325                 330                 335

Arg Leu Arg Gln Gly Leu Ile Gln Asp Arg Tyr Ala Leu Arg Gly Ala
            340                 345                 350

Ser Gln Trp Leu Gly Pro Val Val Glu Asp Leu Arg Leu Ala Ile Gln
        355                 360                 365

Gln Leu Thr Thr Glu Leu Asn Ser Thr Gln Asp Asn Pro Val Ile Asp
    370                 375                 380

Ser Glu Ser Gly Glu Val Tyr Phe Cys Ser Asn Phe Gln Ala Ala Ser
385                 390                 395                 400

Val Ser Met Ala Met Glu Lys Thr Arg Gly Gly Leu Gln Met Ile Gly
                405                 410                 415

Lys Leu Leu Phe Ser Tyr Ser Ser Glu Leu Ile Asn Pro Asp Met Asn
            420                 425                 430
```

-continued

```
Lys Gly Leu Pro Ala Asn Leu Ala Ala Asp Asp Pro Ser Leu Ser Phe
        435                 440                 445

Thr Met Lys Gly Val Asp Ile Asn Met Ala Ala Tyr Met Ser Glu Leu
    450                 455                 460

Gly Phe Leu Ala Asn Ser Val Thr Ser His Val Gln Ser Ala Glu Met
465                 470                 475                 480

Asn Asn Gln Pro Ile Asn Ser Leu Ala Leu Ile Ser Ala Arg Tyr Thr
                485                 490                 495

Leu Gln Ala Val Glu Leu Val Ser Met Met Ser Ala Ala Leu Leu Tyr
            500                 505                 510

Val Thr Cys Gln Ala Val Asp Leu Arg Ile Leu His Glu Thr Phe Leu
        515                 520                 525

Glu Asn Leu Tyr Ser Val Leu Tyr Leu Ala Phe Asp Ser Val Gln Met
    530                 535                 540

Arg Gln Asp Lys Ser Ser Ala Ile Arg Thr Glu Leu Leu Gln Ala Leu
545                 550                 555                 560

Arg Asn Ser Trp Gly His Ser Ala Arg Asp Asp Leu Ser Val Arg Ile
                565                 570                 575

Gln Ala Leu Ser Thr Ala Met Ala Pro Val Leu Leu Ala Asn Ala Lys
            580                 585                 590

Glu Leu Ser Thr Glu Asp Pro Phe Ala Val Ile Glu His Leu Gln Lys
        595                 600                 605

Glu Ile Arg Gln Glu Ala Lys Thr Leu Phe Leu Gly Leu Arg Val Lys
    610                 615                 620

Ser Phe Cys Gly Asp Leu Asn Ala Glu Ser Ser Leu Gly Pro Ala Ala
625                 630                 635                 640

Lys Ala Leu Tyr Arg Phe Val Arg Arg Glu Leu Asp Val Pro Phe His
                645                 650                 655

Cys Gly Ile Gly Glu His Pro Thr Gly Asp Thr Glu Ala Ala Ala Asp
            660                 665                 670

Ile Pro Pro Arg Pro Arg Lys Thr Val Gly Ser Trp Ile Ser Ile Ile
        675                 680                 685

Tyr Asp Ala Ile Arg Asp Gly Arg Ile Arg Gln Pro Leu Gly Asp Asp
    690                 695                 700

Trp Arg Cys Cys Asn Gly Phe
705                 710
```

<210> SEQ ID NO 9
<211> LENGTH: 2208
<212> TYPE: DNA
<213> ORGANISM: Ganoderma sinense

<400> SEQUENCE: 9

```
atgccgggtt acaccctgac caaaacccag tctacctcta ccttcgaacc gtctccggtt      60

accctgaaaa aagcggcggt ttcttctccg ctgcacgcgg aaccggaact gccgaaacag     120

tcttctgcgc cgaccctgct gcacaaattc gttgaagcgc accgtgcgct gaacaactac     180

aaacagggtc agccgatcgt tgttgacggt cagaccctgt ctatcccggc ggttgcggcg     240

gttgcgcgtt acaacgcgga cgttgttctg gacgactctt ctgacatcca gacccgtgtt     300

ctgaaatctc gtcaggttat cgttgacaaa gtttcttctc agaaatctgt ttacggtgtt     360

tctaccggtt tcggtggttc tgcggacacc cgtacctctg acccgctgac cctgggtctg     420

gcgctgttcc agcaccagca ctgcggtgtt ctgccgtctg acaccgactc tgttccggtt     480

gcgctgccgc tgctggaccc gctgacctct acctctatgc cggaatcttg ggttcgtggt     540
```

gcgatcctga tccgtatgaa ctctctgatc cgtggtcact ctggtgttcg ttgggaactg 600
atcgaacgta tgtctgcgct gctgcgtgaa aacatcgttc cgctggttcc gctgcgtggt 660
tctatctctg cgtctggtga cctgtctccg ctgtcttaca tcgcgggtct gctgatcggt 720
aacccgtcta tccgtgtttt cgacggtccg tctaccttcc gtggtcgtcg tatcgtttct 780
tctcgtgaag cgctgtctgc gcaccacatc gaaccgatct ctctgggttc taaagaacac 840
ctgggtatcc tgaacggtac cgcgttctct gcgtctgttg gtgcgctggc ggttcacgaa 900
gcggttcacc tgtctctgct gggtcaggtt tgcaccgcga tgtgcaccga agcgatgctg 960
ggtgcgaaag gttctttcgc gccgttcatc cactctgttg cgcgtccgca cccgggtcag 1020
gttgaagttg cggaaaccgt taccgacctg ctggaaggtt ctcacttcgc ggttaccgcg 1080
gaagaagaaa aacacatctc tgcggacatc ggtgaactgc gtcaggaccg ttacccgctg 1140
cgtacctctg cgcagttcct gggtccgcag gttgaagacg ttctgtctgc gttcgcggcg 1200
atcaccatcg aatgcaactc taccaccgac aacccgctga tcgacggtga aaccggtgaa 1260
gttcaccacg gtggtaactt ccaggcgatg tctgttacca acgcgatgga aaaaacccgt 1320
ctggcgatgc accacatcgg taaactgctg ttcgcgcagt gcaccgaact gctgaacccg 1380
tctatgaacc gtggtctgcc gccgaacctg gcggcgaccg acccgtctca caactacttc 1440
gcgaaaggtg ttgacatcca cgcggcggcg tacgttggtg aactgggtta cctggcgaac 1500
ccggtttcta cccacgttca gtctgcggaa atgcacaacc aggcggttaa ctctctggcg 1560
ctgatctctg cgcgtgcgac cctgaactct ctggaagttc tgtctatcct gacctcttct 1620
ttcctgtacg ttctgtgcca ggcgctggac ctgcgtgcga tgcagcacga attcgaactg 1680
gaagttgacg gtatcctgcg tcagcagctg gcgctgtctt tcggtcgtca cctgtctgcg 1740
gcggacctgg acgcgctgtt ctctgttctg tctcgtcacg ttcgtcgttc tctggaaacc 1800
acctctacca tggacgcggc gctgcgtatg cgtaccgttg cggcggcgac caccaccccg 1860
ttcgttgact tctgcgcgaa acgtaacacc tctctggacc tggacgaaat cgttgcgttc 1920
cgtgcgggtc tgtctgaagg tatggttggt tctctggttc gtctgcgtga agaatacctg 1980
cgtggttcta aaggtccggc gccggcggcg aaatacctgg gtcgttctcg tgcggtttac 2040
gaattcgttc gtgttaccct gggtatccgt atgcacggtt ctgaaaacct gcacgacttc 2100
aaagaaggtc cgggtgttga agacccgacc atcggtcagg acatcgcgct gatccacgaa 2160
gcgatccgtg acggtaaaat gcaggacgtt gttgttggta tcttcgcg 2208

<210> SEQ ID NO 10
<211> LENGTH: 750
<212> TYPE: PRT
<213> ORGANISM: Ganoderma sinense

<400> SEQUENCE: 10

Met Pro Ala Pro Ser Asp Thr Arg Thr Thr Pro Arg Arg Ser Tyr Ser
1 5 10 15

Ile Ser Gly Gly His Met Met Arg Asp Thr Thr Val Leu Lys Pro Glu
20 25 30

Lys Ser Thr Ala Pro Pro Ser Pro Thr Thr Tyr Leu Ala Thr Pro Val
35 40 45

Leu Pro Ser Ser Gln Gly Arg Pro Thr Ala Leu Val Glu Lys Phe Ile
50 55 60

Gln Asn Phe Lys Asp Ile Glu Ser His Lys Asn Gly Lys Ala Ile Val
65 70 75 80

```
Val Asp Gly Gln Asn Leu Ser Ile Ala Ala Val Thr Ala Ala Ala Arg
                85                  90                  95

Tyr Asn Ala Pro Val Val Leu Asp Glu Ser Phe Ala Val Ala Val Lys
            100                 105                 110

Leu Glu Lys Ser Arg Lys Val Val Thr Asp Lys Met Ser Asn Gly Thr
        115                 120                 125

Ser Val Tyr Gly Val Ser Thr Gly Phe Gly Gly Ser Ala Thr Thr Arg
    130                 135                 140

Thr Asp Glu Pro Ile Leu Leu Gly Asn Ala Leu Leu Gln His Gln His
145                 150                 155                 160

Ser Gly Val Leu Pro Ser Ser Thr Lys Lys Leu Glu Ala Leu Pro Leu
                165                 170                 175

Leu Asp Pro Ile Ala Ser Thr Ser Met Pro Glu Ser Trp Val Arg Gly
            180                 185                 190

Ala Ile Leu Ile Arg Met Asn Ser Leu Ile Arg Gly His Ser Gly Val
        195                 200                 205

Arg Arg Glu Leu Ile Glu Lys Met Gly Asp Leu Leu Arg Glu Asn Ile
    210                 215                 220

Thr Pro Leu Val Pro Leu Arg Gly Ser Ile Ser Ala Ser Gly Asp Leu
225                 230                 235                 240

Ser Pro Leu Ser Tyr Ile Ala Gly Thr Leu Ile Gly Asn Pro Ser Ile
                245                 250                 255

Arg Val Phe Asp Gly Pro Thr Ala Phe Gly Ala Arg Gln Ile Val Ser
            260                 265                 270

Ser Arg Lys Ala Leu Glu Ala His Gly Ile Ala Pro Leu Pro Leu Ala
        275                 280                 285

Ser Lys Glu His Leu Gly Ile Leu Asn Gly Thr Ala Phe Ser Ala Ser
    290                 295                 300

Val Ala Ser Leu Val Leu Asn Asp Ala Val His Met Gly Leu Leu Ala
305                 310                 315                 320

Gln Val Cys Thr Ala Met Gly Thr Glu Ala Leu Asn Gly Thr Arg Leu
                325                 330                 335

Ser Phe Asp Ser Phe Ile Asn Cys Thr Ala Arg Pro His Pro Gly Gln
            340                 345                 350

Ile Glu Thr Ala Arg Asn Met Trp Asn Leu Leu Glu Gly Ser Lys Phe
        355                 360                 365

Ala Val Thr Glu Glu Glu Glu Val Ser Ile Lys Glu Asp Gly Gly Val
    370                 375                 380

Leu Arg Gln Asp Arg Tyr Pro Leu Arg Thr Ala Pro Gln Phe Ile Gly
385                 390                 395                 400

Pro Gln Val Glu Asp Leu Leu His Ala Val Glu Thr Ile Thr Ile Glu
                405                 410                 415

Cys Asn Ser Thr Thr Asp Asn Pro Leu Val Asp Gly Glu Thr Gly Thr
            420                 425                 430

Val His His Gly Gly Asn Phe Gln Ala Met Ala Val Ser Asn Ala Met
        435                 440                 445

Glu Lys Thr Arg Leu Ala Leu His His Leu Gly Lys Ile Leu Phe Ala
    450                 455                 460

Gln Cys Ala Glu Leu Met Asp Pro Ala Met Asn Arg Gly Leu Pro Pro
465                 470                 475                 480

Ser Leu Ala Ala Thr Asp Pro Ser Leu Asp Tyr His Cys Lys Gly Ile
                485                 490                 495
```

```
Asp Ile Gly Thr Ala Ala Tyr Val Ala Glu Leu Gly Tyr Leu Ala Asn
            500                 505                 510

Pro Val Ser Thr His Ile Gln Ser Ala Glu Met His Asn Gln Ala Val
        515                 520                 525

Asn Ser Met Ala Leu Val Ser Gly Arg Ala Thr Ile Asn Ser Leu Glu
    530                 535                 540

Val Leu Ser Ile Leu Ile Ser Ser Tyr Leu Tyr Ala Leu Cys Gln Ala
545                 550                 555                 560

Leu Asp Leu Arg Ala Leu Gln Ser Glu Phe Met Asp Gly Leu Val Asn
                565                 570                 575

Val Val Ser Glu Glu Phe Asp Ala Ala Phe Gly Leu Ser Pro Ser Glu
            580                 585                 590

Ala Ala Pro Val Lys Ile Ala Leu Phe Lys Glu Leu Lys Lys Thr Phe
        595                 600                 605

Glu Glu Thr Ser Ile Leu Asp Ala Gly Glu Arg Met Val Lys Val Ala
    610                 615                 620

Ala Ser Ala Thr Val Ile Ile Val Asp His Phe Thr Gly Pro Ala Ala
625                 630                 635                 640

Lys Glu Glu Asn Val Ser Ser Leu Ser Ser Leu Pro Ser Phe Arg Ser
                645                 650                 655

Lys Val Ala Ser Arg Leu Thr Thr Leu Leu Asp Gln Leu Arg Arg Asp
            660                 665                 670

Tyr Leu Leu Gly Ala Arg Gly Pro Ala Pro Ala Ser Arg Phe Leu Asn
        675                 680                 685

Lys Thr Arg Pro Val Tyr Glu Phe Val Arg Leu Thr Leu Gly Ile Arg
    690                 695                 700

Met His Gly Ser Glu Asn Tyr His Arg Phe Ala Asn Gly Leu Gly Val
705                 710                 715                 720

Glu Asp Ile Thr Val Gly Gly Asn Val Ser Leu Ile His Glu Ala Ile
                725                 730                 735

Arg Asp Gly Lys Leu Gln Ser Val Val Ala Asn Leu Phe Ser
            740                 745                 750


<210> SEQ ID NO 11
<211> LENGTH: 2787
<212> TYPE: DNA
<213> ORGANISM: Artificial Sequence
<220> FEATURE:
<223> OTHER INFORMATION: Depicts the nucleic acid sequence of Cinnamte 4
      hydroxylase 4 coumarate coenzyme ligase fusion (C4H4CL) of
      Azospirillum sp.

<400> SEQUENCE: 11

atggacctgc tgctgctgga aaaaaccctg ctggcgctgt tcatcgcggc gaccatcgcg      60

atcaccatct ctaaactgcg tggtaaacgt ttcaaactgc cgccgggtcc gatcccggtt     120

ccggttttcg gtaactggct gcaggttggt gacgacctga accaccgtaa cctgaccgac     180

ctggcgaaac gtttcggtga catcttcctg ctgcgtatgg gtcagcgtaa cctggttgtt     240

gtttcttctc cggaactggc gaaagaagtt ctgcacaccc agggtgttga attcggttct     300

cgtacccgta acgttgtttt cgacatcttc accggtaaag gtcaggacat ggttttcacc     360

gtttacggta ccctggcgga aatgcgtcgt atcatgaccg ttccgttctt caccaacaaa     420

gttgttcagc agtaccgttt cggttgggaa ttcgaagcgc agtctgttgt tgacgacgtt     480

aaaaaaaacc cggaagcgtg ctcttctggt atcgttctgc gtcgtcgtct gcagctgatg     540

atgtacaaca tcatgtaccg tatcatgttc gaccgtcgtt tcgaatctga agaagacccg     600
```

-continued

```
ctgttcgtta aactgaaagc gctgaacggt gaacgttctc gtctggcgca gtctttcgaa    660
tacaactacg gtgacttcat cccgatcctg cgtccgttcc tgaaaggtta cctgaaactg    720
tgcaaagaag ttaaagaccg tcgtctgcag ctgttcaaag actacttcgt tgacgaacgt    780
aaaaaactgg gttctaccaa atctaccacc aacgaaggtc tgaaatgcgc gatcgaccac    840
atcctggacg cgcagcagaa aggtgaaatc aacgacgaca acgttctgta catcgttgaa    900
aacatcaacg ttgcggcgat cgaaaccacc ctgtggtcta tcgaatgggg tatcgcggaa    960
ctggttaacc accagaaaat ccagaacaaa gttcgtgaag aaatcgaccg tgttctgggt   1020
ccgggtcacc aggttaccga accggacctg cagaaactgc cgtacctgca ggcggttatc   1080
aaagaaaccc tgcgtctgcg tatggcgatc ccgctgctgg ttccgcacat gaacctgcac   1140
gacgcgaaac tgtctggttt cgacatcccg gcggaatcta aaatcctggt taacgcgtgg   1200
tggctggcga acaacccggc gcagtggaaa aaaccggaag aattccgtcc ggaacgtttc   1260
ctggaagaag aatctcacgt tgaagcgaac ggtaacgact tccgttacct gccgttcggt   1320
gttggtcgtc gttcttgccc gggtatcatc ctggcgctgc cgatcctggg tatcaccctg   1380
ggtcgtctgg ttcagaactt cgaactgctg ccgccgccgg gtcagtctaa aatcgacacc   1440
gcggaaaaag gtggtcagtt ctctctgcac atcctgaaac actctaccat cgtttgcaaa   1500
ccgcgttctt tcaacggtgg tggtggttct ggtggtggtg gttctggtgg tggtggttct   1560
atgaccatcc agcgttggtg gcgtaaccgt gaatctctga accgtgttct gtgcgacctg   1620
ctggcgggtg aattcgcgcg tctgcgtccg ggtggttctc cgccggcgca cccgcaccgt   1680
tggccggaaa ccctgccgct gggtccggac ggtgttggtg cggactctct ggacctgctg   1740
cagctggcgg cggcgctgaa cgaagcgctg cacctgcacc gttctggtat cgaagactac   1800
ctgctgatgc accgtaccgt tggtgactgg ctggacgttt gcgaagcggc gctgggtcgt   1860
ttcgacggtg cgctgtcttt ccgtacctct ggttctaccg gtgaaggtaa acgttgcgaa   1920
cacccgctgg cggcgctgga agaagaagcg gacgcgctgg cggcgctgct gtctggtggt   1980
gcggaagcgc cgcgtcgtgt tgtttctgtt gttccggcgc accacatcta cggtttcctg   2040
ttcaccgttc tgctgccgga ccgtctggcg gttccggttg ttgacggtcg tggtacctct   2100
ccgggtggtc tggcggcgcg tctgggtccg ggtgacctgg ttgttgcgca cccggactgg   2160
tggggtgcgc tgctgcgttc tggtgcggcg ctgccggacg gtgttaccgg tacctcttct   2220
accgcgccgt gcccgccgga caccgcgcgt ggtgttcgtg gtgttggtct ggcgcgtctg   2280
gttgaagttt tcggttcttc tgaaaccgcg ggtctgggtt ggcgtgaatc tccggacgcg   2340
ccgttccgtc cgttcccgtg gtggcgtttc ggtgacgacg gtcgtgttac ccgtcgtctg   2400
gcggacggta ccgttctgtc tgcgaccctg caggaccgtc tgtctcacga cgaagaaggt   2460
ttccgtccgt ctggtcgtct ggacaccgtt gttcaggttg gtggtgttaa cgtttctctg   2520
gcgggtgttc aggcgcacct ggcgggtcac ccggacgttg aagcggcggc ggttcgtctg   2580
atgcgtccgg aagaaggtac ccgtctgaaa gcgttcatcg ttccggcgcg taccgcgccg   2640
ccgcgtgaag aactgtaccg tcgtctgacc gactggatcg aagcgaccct gccggcgccg   2700
caccgtccgc gtgcgctggc gttcggtccg gcgctgccgg ttaacggtat gggtaaaccg   2760
tgcgactggc cgctggcgac ctgccgt                                       2787
```

<210> SEQ ID NO 12
<211> LENGTH: 929
<212> TYPE: PRT

-continued

```
<213> ORGANISM: Artificial Sequence
<220> FEATURE:
<223> OTHER INFORMATION: Depicts the amino acid sequence of the enzyme
      Cinnamte 4 hydroxylase 4 coumarate coenzyme ligase fusion (C4H4CL)

<400> SEQUENCE: 12

Met Asp Leu Leu Leu Leu Glu Lys Thr Leu Leu Ala Leu Phe Ile Ala
1               5                   10                  15

Ala Thr Ile Ala Ile Thr Ile Ser Lys Leu Arg Gly Lys Arg Phe Lys
            20                  25                  30

Leu Pro Pro Gly Pro Ile Pro Val Pro Val Phe Gly Asn Trp Leu Gln
        35                  40                  45

Val Gly Asp Asp Leu Asn His Arg Asn Leu Thr Asp Leu Ala Lys Arg
    50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Thr Leu Ala Glu Met
        115                 120                 125

Arg Arg Ile Met Thr Val Pro Phe Phe Thr Asn Lys Val Val Gln Gln
    130                 135                 140

Tyr Arg Phe Gly Trp Glu Phe Glu Ala Gln Ser Val Val Asp Asp Val
145                 150                 155                 160

Lys Lys Asn Pro Glu Ala Cys Ser Ser Gly Ile Val Leu Arg Arg Arg
                165                 170                 175

Leu Gln Leu Met Met Tyr Asn Ile Met Tyr Arg Ile Met Phe Asp Arg
            180                 185                 190

Arg Phe Glu Ser Glu Glu Asp Pro Leu Phe Val Lys Leu Lys Ala Leu
        195                 200                 205

Asn Gly Glu Arg Ser Arg Leu Ala Gln Ser Phe Glu Tyr Asn Tyr Gly
    210                 215                 220

Asp Phe Ile Pro Ile Leu Arg Pro Phe Leu Lys Gly Tyr Leu Lys Leu
225                 230                 235                 240

Cys Lys Glu Val Lys Asp Arg Arg Leu Gln Leu Phe Lys Asp Tyr Phe
                245                 250                 255

Val Asp Glu Arg Lys Lys Leu Gly Ser Thr Lys Ser Thr Thr Asn Glu
            260                 265                 270

Gly Leu Lys Cys Ala Ile Asp His Ile Leu Asp Ala Gln Gln Lys Gly
        275                 280                 285

Glu Ile Asn Asp Asp Asn Val Leu Tyr Ile Val Glu Asn Ile Asn Val
    290                 295                 300

Ala Ala Ile Glu Thr Thr Leu Trp Ser Ile Glu Trp Gly Ile Ala Glu
305                 310                 315                 320

Leu Val Asn His Gln Lys Ile Gln Asn Lys Val Arg Glu Glu Ile Asp
                325                 330                 335

Arg Val Leu Gly Pro Gly His Gln Val Thr Glu Pro Asp Leu Gln Lys
            340                 345                 350

Leu Pro Tyr Leu Gln Ala Val Ile Lys Glu Thr Leu Arg Leu Arg Met
        355                 360                 365

Ala Ile Pro Leu Leu Val Pro His Met Asn Leu His Asp Ala Lys Leu
    370                 375                 380
```

-continued

```
Ser Gly Phe Asp Ile Pro Ala Glu Ser Lys Ile Leu Val Asn Ala Trp
385                 390                 395                 400

Trp Leu Ala Asn Asn Pro Ala Gln Trp Lys Lys Pro Glu Glu Phe Arg
                405                 410                 415

Pro Glu Arg Phe Leu Glu Glu Glu Ser His Val Glu Ala Asn Gly Asn
            420                 425                 430

Asp Phe Arg Tyr Leu Pro Phe Gly Val Gly Arg Arg Ser Cys Pro Gly
        435                 440                 445

Ile Ile Leu Ala Leu Pro Ile Leu Gly Ile Thr Leu Gly Arg Leu Val
    450                 455                 460

Gln Asn Phe Glu Leu Leu Pro Pro Pro Gly Gln Ser Lys Ile Asp Thr
465                 470                 475                 480

Ala Glu Lys Gly Gly Gln Phe Ser Leu His Ile Leu Lys His Ser Thr
                485                 490                 495

Ile Val Cys Lys Pro Arg Ser Phe Asn Gly Gly Gly Gly Ser Gly Gly
            500                 505                 510

Gly Gly Ser Gly Gly Gly Gly Ser Met Thr Ile Gln Arg Trp Trp Arg
        515                 520                 525

Asn Arg Glu Ser Leu Asn Arg Val Leu Cys Asp Leu Leu Ala Gly Glu
    530                 535                 540

Phe Ala Arg Leu Arg Pro Gly Gly Ser Pro Pro Ala His Pro His Arg
545                 550                 555                 560

Trp Pro Glu Thr Leu Pro Leu Gly Pro Asp Gly Val Gly Ala Asp Ser
                565                 570                 575

Leu Asp Leu Leu Gln Leu Ala Ala Ala Leu Asn Glu Ala Leu His Leu
            580                 585                 590

His Arg Ser Gly Ile Glu Asp Tyr Leu Leu Met His Arg Thr Val Gly
        595                 600                 605

Asp Trp Leu Asp Val Cys Glu Ala Ala Leu Gly Arg Phe Asp Gly Ala
    610                 615                 620

Leu Ser Phe Arg Thr Ser Gly Ser Thr Gly Glu Gly Lys Arg Cys Glu
625                 630                 635                 640

His Pro Leu Ala Ala Leu Glu Glu Glu Ala Asp Ala Leu Ala Ala Leu
                645                 650                 655

Leu Ser Gly Gly Ala Glu Ala Pro Arg Arg Val Val Ser Val Val Pro
            660                 665                 670

Ala His His Ile Tyr Gly Phe Leu Phe Thr Val Leu Leu Pro Asp Arg
        675                 680                 685

Leu Ala Val Pro Val Val Asp Gly Arg Gly Thr Ser Pro Gly Gly Leu
    690                 695                 700

Ala Ala Arg Leu Gly Pro Gly Asp Leu Val Val Ala His Pro Asp Trp
705                 710                 715                 720

Trp Gly Ala Leu Leu Arg Ser Gly Ala Ala Leu Pro Asp Gly Val Thr
                725                 730                 735

Gly Thr Ser Ser Thr Ala Pro Cys Pro Pro Asp Thr Ala Arg Gly Val
            740                 745                 750

Arg Gly Val Gly Leu Ala Arg Leu Val Glu Val Phe Gly Ser Ser Glu
        755                 760                 765

Thr Ala Gly Leu Gly Trp Arg Glu Ser Pro Asp Ala Pro Phe Arg Pro
    770                 775                 780

Phe Pro Trp Trp Arg Phe Gly Asp Asp Gly Arg Val Thr Arg Arg Leu
785                 790                 795                 800

Ala Asp Gly Thr Val Leu Ser Ala Thr Leu Gln Asp Arg Leu Ser His
```

```
                805                 810                 815

Asp Glu Glu Gly Phe Arg Pro Ser Gly Arg Leu Asp Thr Val Val Gln
            820                 825                 830

Val Gly Gly Val Asn Val Ser Leu Ala Gly Val Gln Ala His Leu Ala
        835                 840                 845

Gly His Pro Asp Val Glu Ala Ala Ala Val Arg Leu Met Arg Pro Glu
    850                 855                 860

Glu Gly Thr Arg Leu Lys Ala Phe Ile Val Pro Ala Arg Thr Ala Pro
865                 870                 875                 880

Pro Arg Glu Glu Leu Tyr Arg Arg Leu Thr Asp Trp Ile Glu Ala Thr
                885                 890                 895

Leu Pro Ala Pro His Arg Pro Arg Ala Leu Ala Phe Gly Pro Ala Leu
            900                 905                 910

Pro Val Asn Gly Met Gly Lys Pro Cys Asp Trp Pro Leu Ala Thr Cys
        915                 920                 925

Arg
```

<210> SEQ ID NO 13
<211> LENGTH: 2868
<212> TYPE: DNA
<213> ORGANISM: Coffea canephora

<400> SEQUENCE: 13

```
atgaaaatcg aagttaaaga atctaccatg gttcgtccgg cgcaggaaac cccgggtcgt     60

aacctgtgga actctaacgt tgacctggtt gttccgaact tccacacccc gtctgtttac    120

ttctaccgtc cgaccggttc ttctaacttc ttcgacgcga aagttctgaa agacgcgctg    180

tctcgtgcgc tggttccgtt ctacccgatg gcgggtcgtc tgaaacgtga cgaagacggt    240

cgtatcgaaa tcgaatgcaa cggtgaaggt gttctgttcg ttgaagcgga atctgacggt    300

gttgttgacg acttcggtga cttcgcgccg accctggaac tgcgtcgtct gatcccggcg    360

gttgactact ctcagggtat ctcttcttac gcgctgctgg ttctgcaggt tacctacttc    420

aaatgcggtg gtgtttctct gggtgttggt atgcgtcacc acgcggcgga cggtttctct    480

ggtctgcact tcatcaactc ttggtctgac atggcgcgtg gtctggacgt taccctgccg    540

ccgttcatcg accgtaccct gctgcgtgcg cgtgacccgc cgcagccgca gttccagcac    600

atcgaatacc agccgccgcc ggcgctgaaa gtttctccgc agaccgcgaa atctgactct    660

gttccggaaa ccgcggtttc tatcttcaaa ctgacccgtg aacagatctc tgcgctgaaa    720

gcgaaatcta aagaagacgg taacaccatc tcttactctt cttacgaaat gctggcgggt    780

cacgtttggc gttgcgcgtg caaagcgcgt ggtctggaag ttgaccaggg taccaaactg    840

tacatcgcga ccgacggtcg tgcgcgtctg cgtccgtctc tgccgccggg ttacttcggt    900

aacgttatct tcaccgcgac cccgatcgcg atcgcgggtg acctggaatt caaaccggtt    960

tggtacgcgg cgtctaaaat ccacgacgcg ctggcgcgta tggacaacga ctacctgcgt   1020

tctgcgctgg actacctgga actgcagccg gacctgaaag cgctggttcg tggtgcgcac   1080

accttcaaat gcccgaacct gggtatcacc tcttgggttc gtctgccgat ccacgacgcg   1140

gacttcggtt ggggtcgtcc gatcttcatg ggtccgggtg gtatcgcgta cgaaggtctg   1200

tctttcatcc tgccgtctcc gaccaacgac ggttctatgt ctgttgcgat ctctctgcag   1260

ggtgaacaca tgaaactgtt ccagtctttc ctgtacgaca tcggtggtgg tggttctggt   1320

ggtggtggtt ctggtggtgg tggttctatg gcgctgctgc tgatcctgct gccggttgcg   1380
```

```
ttcatcttcc tggcgtactc tctgtacgaa cgtctgcgtt tcaaactgcc gccgggtccg   1440

cgtccgaaac cggttgttgg taacatctac gacatcaaac cggttcgttt caaatgctac   1500

gcggaatggt ctaaactgta cggtccgatc ttctctgttt acttcggttc tcagctgaac   1560

accgttgtta acaccgcgga actggcgaaa gaagttctga aagacaacga ccagcagctg   1620

gcggaccgtt accgttctcg tccgtctgcg cgtatgtctc gtaacggtca ggacctgatc   1680

tgggcggact acggtccgca ctacgttaaa gttcgtaaac tgtgcaacct ggaactgttc   1740

accccgaaac gtctggaagg tctgcgtccg ctgcgtgaag acgaagttac cgcgatggtt   1800

gactctatct tcaaagactg caccaaaccg gaaaacaaag gtaaatctct gctgatgcgt   1860

aactacctgg gttctgttgc gttcaacaac atcacccgtc tgaccttcgg taaacgtttc   1920

atgaactctg aaggtgttgt tgacgaacag ggtcaggaat tcaaaggtat cgtttctaac   1980

ggtatccgta tcggtgcgaa actgtctgtt gcggaccaca tcccgtggct gcgttggatg   2040

ttcgttggtg aaaacgaaga cctggacaaa cacaacgcgc gtcgtgacaa actgacccgt   2100

atgatcatgg aagaacacac cctggcgcgt cagaaatctg gtaacaccaa acagcacttc   2160

gttgacgcgc tgctgaccct gcagaaacag tacgaactgt ctgacgacac cgttatcggt   2220

ctgctgtggg acatgatcac cgcgggtatg gacaccacca ccatctctgt tgaatgggcg   2280

atggcggaac tggttaaaaa cccgcgtgtt cagcagaaag cgcaggaaga actggaccgt   2340

gttatcggtt ctgaccgtat catgaccgaa gcggacttcg cgaaactgcc gtacctgcag   2400

tgcgttgcga aagaagcgct gcgtctgcac ccgccgaccc cgctgatgct gccgcaccgt   2460

gcgaacgcga acgttaaaat cggtggttac gacatcccga aaggttctat cgttcacgtt   2520

aacgtttggg cgatcgcgcg tgacccggcg gcgtggaaaa acccgctgga attccgtccg   2580

gaacgtttcc tggaagaaga cgttgacatc aaaggtcacg actaccgtct gctgccgttc   2640

ggtgcgggtc gtcgtatctg cccgggtgcg cagctggcgc tgaacctggt tacctctatg   2700

ctgggtcacc tgctgcacca cttcacctgg tctccgccgc cgggtgttcg tccggaagaa   2760

atcgacctgg aagaatctcc gggtaccgtt acctacatgc gtaccccgct gcaggcggtt   2820

gcgaccccgc gtctgccggc gcacctgtac aaccgtgttc cggttgaa              2868
```

```
<210> SEQ ID NO 14
<211> LENGTH: 956
<212> TYPE: PRT
<213> ORGANISM: Coffea canephora

<400> SEQUENCE: 14

Met Lys Ile Glu Val Lys Glu Ser Thr Met Val Arg Pro Ala Gln Glu
1               5                   10                  15

Thr Pro Gly Arg Asn Leu Trp Asn Ser Asn Val Asp Leu Val Val Pro
            20                  25                  30

Asn Phe His Thr Pro Ser Val Tyr Phe Tyr Arg Pro Thr Gly Ser Ser
        35                  40                  45

Asn Phe Phe Asp Ala Lys Val Leu Lys Asp Ala Leu Ser Arg Ala Leu
    50                  55                  60

Val Pro Phe Tyr Pro Met Ala Gly Arg Leu Lys Arg Asp Glu Asp Gly
65                  70                  75                  80

Arg Ile Glu Ile Glu Cys Asn Gly Glu Gly Val Leu Phe Val Glu Ala
                85                  90                  95

Glu Ser Asp Gly Val Val Asp Asp Phe Gly Asp Phe Ala Pro Thr Leu
            100                 105                 110
```

-continued

```
Glu Leu Arg Arg Leu Ile Pro Ala Val Asp Tyr Ser Gln Gly Ile Ser
        115                 120                 125

Ser Tyr Ala Leu Leu Val Leu Gln Val Thr Tyr Phe Lys Cys Gly Gly
    130                 135                 140

Val Ser Leu Gly Val Gly Met Arg His His Ala Ala Asp Gly Phe Ser
145                 150                 155                 160

Gly Leu His Phe Ile Asn Ser Trp Ser Asp Met Ala Arg Gly Leu Asp
                165                 170                 175

Val Thr Leu Pro Pro Phe Ile Asp Arg Thr Leu Leu Arg Ala Arg Asp
            180                 185                 190

Pro Pro Gln Pro Gln Phe Gln His Ile Glu Tyr Gln Pro Pro Pro Ala
        195                 200                 205

Leu Lys Val Ser Pro Gln Thr Ala Lys Ser Asp Ser Val Pro Glu Thr
    210                 215                 220

Ala Val Ser Ile Phe Lys Leu Thr Arg Glu Gln Ile Ser Ala Leu Lys
225                 230                 235                 240

Ala Lys Ser Lys Glu Asp Gly Asn Thr Ile Ser Tyr Ser Ser Tyr Glu
                245                 250                 255

Met Leu Ala Gly His Val Trp Arg Cys Ala Cys Lys Ala Arg Gly Leu
            260                 265                 270

Glu Val Asp Gln Gly Thr Lys Leu Tyr Ile Ala Thr Asp Gly Arg Ala
        275                 280                 285

Arg Leu Arg Pro Ser Leu Pro Pro Gly Tyr Phe Gly Asn Val Ile Phe
    290                 295                 300

Thr Ala Thr Pro Ile Ala Ile Ala Gly Asp Leu Glu Phe Lys Pro Val
305                 310                 315                 320

Trp Tyr Ala Ala Ser Lys Ile His Asp Ala Leu Ala Arg Met Asp Asn
                325                 330                 335

Asp Tyr Leu Arg Ser Ala Leu Asp Tyr Leu Glu Leu Gln Pro Asp Leu
            340                 345                 350

Lys Ala Leu Val Arg Gly Ala His Thr Phe Lys Cys Pro Asn Leu Gly
        355                 360                 365

Ile Thr Ser Trp Val Arg Leu Pro Ile His Asp Ala Asp Phe Gly Trp
    370                 375                 380

Gly Arg Pro Ile Phe Met Gly Pro Gly Gly Ile Ala Tyr Glu Gly Leu
385                 390                 395                 400

Ser Phe Ile Leu Pro Ser Pro Thr Asn Asp Gly Ser Met Ser Val Ala
                405                 410                 415

Ile Ser Leu Gln Gly Glu His Met Lys Leu Phe Gln Ser Phe Leu Tyr
            420                 425                 430

Asp Ile Gly Gly Gly Gly Ser Gly Gly Gly Gly Ser Gly Gly Gly Gly
        435                 440                 445

Ser Met Ala Leu Leu Leu Ile Leu Leu Pro Val Ala Phe Ile Phe Leu
    450                 455                 460

Ala Tyr Ser Leu Tyr Glu Arg Leu Arg Phe Lys Leu Pro Pro Gly Pro
465                 470                 475                 480

Arg Pro Lys Pro Val Val Gly Asn Ile Tyr Asp Ile Lys Pro Val Arg
                485                 490                 495

Phe Lys Cys Tyr Ala Glu Trp Ser Lys Leu Tyr Gly Pro Ile Phe Ser
            500                 505                 510

Val Tyr Phe Gly Ser Gln Leu Asn Thr Val Val Asn Thr Ala Glu Leu
        515                 520                 525

Ala Lys Glu Val Leu Lys Asp Asn Asp Gln Gln Leu Ala Asp Arg Tyr
```

-continued

```
    530                 535                 540

Arg Ser Arg Pro Ser Ala Arg Met Ser Arg Asn Gly Gln Asp Leu Ile
545                 550                 555                 560

Trp Ala Asp Tyr Gly Pro His Tyr Val Lys Val Arg Lys Leu Cys Asn
                565                 570                 575

Leu Glu Leu Phe Thr Pro Lys Arg Leu Glu Gly Leu Arg Pro Leu Arg
            580                 585                 590

Glu Asp Glu Val Thr Ala Met Val Asp Ser Ile Phe Lys Asp Cys Thr
        595                 600                 605

Lys Pro Glu Asn Lys Gly Lys Ser Leu Leu Met Arg Asn Tyr Leu Gly
    610                 615                 620

Ser Val Ala Phe Asn Asn Ile Thr Arg Leu Thr Phe Gly Lys Arg Phe
625                 630                 635                 640

Met Asn Ser Glu Gly Val Val Asp Glu Gln Gly Gln Glu Phe Lys Gly
                645                 650                 655

Ile Val Ser Asn Gly Ile Arg Ile Gly Ala Lys Leu Ser Val Ala Asp
            660                 665                 670

His Ile Pro Trp Leu Arg Trp Met Phe Val Gly Glu Asn Glu Asp Leu
        675                 680                 685

Asp Lys His Asn Ala Arg Arg Asp Lys Leu Thr Arg Met Ile Met Glu
    690                 695                 700

Glu His Thr Leu Ala Arg Gln Lys Ser Gly Asn Thr Lys Gln His Phe
705                 710                 715                 720

Val Asp Ala Leu Leu Thr Leu Gln Lys Gln Tyr Glu Leu Ser Asp Asp
                725                 730                 735

Thr Val Ile Gly Leu Leu Trp Asp Met Ile Thr Ala Gly Met Asp Thr
            740                 745                 750

Thr Thr Ile Ser Val Glu Trp Ala Met Ala Glu Leu Val Lys Asn Pro
        755                 760                 765

Arg Val Gln Gln Lys Ala Gln Glu Glu Leu Asp Arg Val Ile Gly Ser
    770                 775                 780

Asp Arg Ile Met Thr Glu Ala Asp Phe Ala Lys Leu Pro Tyr Leu Gln
785                 790                 795                 800

Cys Val Ala Lys Glu Ala Leu Arg Leu His Pro Pro Thr Pro Leu Met
                805                 810                 815

Leu Pro His Arg Ala Asn Ala Asn Val Lys Ile Gly Gly Tyr Asp Ile
            820                 825                 830

Pro Lys Gly Ser Ile Val His Val Asn Val Trp Ala Ile Ala Arg Asp
        835                 840                 845

Pro Ala Ala Trp Lys Asn Pro Leu Glu Phe Arg Pro Glu Arg Phe Leu
    850                 855                 860

Glu Glu Asp Val Asp Ile Lys Gly His Asp Tyr Arg Leu Leu Pro Phe
865                 870                 875                 880

Gly Ala Gly Arg Arg Ile Cys Pro Gly Ala Gln Leu Ala Leu Asn Leu
                885                 890                 895

Val Thr Ser Met Leu Gly His Leu Leu His His Phe Thr Trp Ser Pro
            900                 905                 910

Pro Pro Gly Val Arg Pro Glu Glu Ile Asp Leu Glu Glu Ser Pro Gly
        915                 920                 925

Thr Val Thr Tyr Met Arg Thr Pro Leu Gln Ala Val Ala Thr Pro Arg
    930                 935                 940

Leu Pro Ala His Leu Tyr Asn Arg Val Pro Val Glu
945                 950                 955
```

<210> SEQ ID NO 15
<211> LENGTH: 783
<212> TYPE: DNA
<213> ORGANISM: Artificial Sequence
<220> FEATURE:
<223> OTHER INFORMATION: Depicts the nucleic acid sequence encoding Caffeoyl CoA O-methyltransferase (CCoAOMT)

<400> SEQUENCE: 15
atgtctacca ccaccaccac ccagaccaaa accgaaaccc agtctcagac cggtgcgcag 60
aacggtgcgg aacagcagac ccgtcactct gaagttggtc acaaatctct gctgcagtct 120
gacgcgctgt accagtacat cctggaaacc tctgtttacc cgcgtgaacc ggaatgcatg 180
aaagaactgc gtgacatcac cgcgaaacac ccgtggaacc tgatgaccac ctctgcggac 240
gaaggtcagt tcctgaacct gctgctgaaa ctgatcggtg cgaaaaaaac catggaaatc 300
ggtgtttaca ccggttactc tctgctggcg accgcgctgg cgatcccgga agacggtacc 360
atcctggcga tggacatcaa ccgtgaaaac tacgaactgg gtctgccggt tatcgaaaaa 420
gcgggtgttg cgcacaaaat cgacttccgt gaaggtccgg cgctgccggt tctggaccag 480
ctgatcgaag acccggcgaa cctgggttct ttcgacttca tcttcgttga cgcggacaaa 540
gacaactacc tgaactacca caaacgtctg atcgaactgg ttaaagttgg tggtgttatc 600
ggttacgaca acaccctgtg gaacggttct gttgttctgc cggcggacgc gccgatgcgt 660
aaatacatcc gttactaccg tgacttcgtt ctggaactga acaaagcgct ggcggcggac 720
ccgcgtatcg aaatctctca gctgccggtt ggtgacggta tcaccctgtg ccgtcgtgtt 780
aaa 783

<210> SEQ ID NO 16
<211> LENGTH: 261
<212> TYPE: PRT
<213> ORGANISM: Artificial Sequence
<220> FEATURE:
<223> OTHER INFORMATION: Depicts the amino acid sequence of enzyme Caffeoyl CoA O-methyltransferase (CCoAOMT)

<400> SEQUENCE: 16

Met Ser Thr Thr Thr Thr Thr Gln Thr Lys Thr Glu Thr Gln Ser Gln
1               5                   10                  15

Thr Gly Ala Gln Asn Gly Ala Glu Gln Gln Thr Arg His Ser Glu Val
            20                  25                  30

Gly His Lys Ser Leu Leu Gln Ser Asp Ala Leu Tyr Gln Tyr Ile Leu
        35                  40                  45

Glu Thr Ser Val Tyr Pro Arg Glu Pro Glu Cys Met Lys Glu Leu Arg
    50                  55                  60

Asp Ile Thr Ala Lys His Pro Trp Asn Leu Met Thr Thr Ser Ala Asp
65                  70                  75                  80

Glu Gly Gln Phe Leu Asn Leu Leu Leu Lys Leu Ile Gly Ala Lys Lys
                85                  90                  95

Thr Met Glu Ile Gly Val Tyr Thr Gly Tyr Ser Leu Leu Ala Thr Ala
            100                 105                 110

Leu Ala Ile Pro Glu Asp Gly Thr Ile Leu Ala Met Asp Ile Asn Arg
        115                 120                 125

Glu Asn Tyr Glu Leu Gly Leu Pro Val Ile Glu Lys Ala Gly Val Ala
    130                 135                 140

His Lys Ile Asp Phe Arg Glu Gly Pro Ala Leu Pro Val Leu Asp Gln

```
145                 150                 155                 160

Leu Ile Glu Asp Pro Ala Asn Leu Gly Ser Phe Asp Phe Ile Phe Val
                165                 170                 175

Asp Ala Asp Lys Asp Asn Tyr Leu Asn Tyr His Lys Arg Leu Ile Glu
            180                 185                 190

Leu Val Lys Val Gly Gly Val Ile Gly Tyr Asp Asn Thr Leu Trp Asn
        195                 200                 205

Gly Ser Val Val Leu Pro Ala Asp Ala Pro Met Arg Lys Tyr Ile Arg
    210                 215                 220

Tyr Tyr Arg Asp Phe Val Leu Glu Leu Asn Lys Ala Leu Ala Ala Asp
225                 230                 235                 240

Pro Arg Ile Glu Ile Ser Gln Leu Pro Val Gly Asp Gly Ile Thr Leu
                245                 250                 255

Cys Arg Arg Val Lys
            260


<210> SEQ ID NO 17
<211> LENGTH: 747
<212> TYPE: DNA
<213> ORGANISM: Artificial Sequence
<220> FEATURE:
<223> OTHER INFORMATION: Depicts the nucleic acid sequence of Caffeoyl
      CoA O-methyltransferase (CCoAOMT) of Chamaecyparis formosensis

<400> SEQUENCE: 17

atggcgaccg ttgaagcgac caaagactct acccagcagg tttctcgtca ccaggaagtt     60

ggtcacaaat ctctgctgca gtctgacgcg ctgtaccagt acatcctgga aacctctgtt    120

tacccgcgtg aaccggaacc gatgcgtgaa ctgcgtgaaa tcaccgcgaa acacccgtgg    180

aacctgatga ccacctctgc ggacgaaggt cagttcctgc acctgctgct gaaactgatc    240

aacgcgaaaa acaccatgga aatcggtgtt tacaccggtt actctctgct gtctaccgcg    300

ctggcgctgc cggacgacgg taaaatcctg gcgatggaca tcaaccgtga aaactacgaa    360

ctgggtctgc cggttatcca gaaagcgggt gttgcgcaca aatcgactt ccgtgaaggt     420

ccggcgctgc cggttctgga ccagatgctg gaaaacaaag aaatgcacgg ttctttcgac    480

ttcatcttcg ttgacgcgga caaagacaac tacctgaact accacaaacg tctgatcgac    540

ctggttaaaa tcggtggtgt tatcggttac gacaacaccc tgtggaacgg ttctgttgtt    600

gcgccgccgg acgcgccgat gcgtaaatac gttcgttact accgtgactt cgttatcgaa    660

ctgaacaaag cgctggcggc ggacccgcgt atcgaaatct ctcagatccc ggttggtgac    720

ggtatcaccc tgtgccgtcg tatcatc                                         747


<210> SEQ ID NO 18
<211> LENGTH: 249
<212> TYPE: PRT
<213> ORGANISM: Artificial Sequence
<220> FEATURE:
<223> OTHER INFORMATION: Depicts the amino acid sequence of Caffeoyl CoA
      O-methyltransferase (CCoAOMT) of Chamaecyparis formosensis

<400> SEQUENCE: 18

Met Ala Thr Val Glu Ala Thr Lys Asp Ser Thr Gln Gln Val Ser Arg
1               5                   10                  15

His Gln Glu Val Gly His Lys Ser Leu Leu Gln Ser Asp Ala Leu Tyr
            20                  25                  30

Gln Tyr Ile Leu Glu Thr Ser Val Tyr Pro Arg Glu Pro Glu Pro Met
        35                  40                  45
```

```
Arg Glu Leu Arg Glu Ile Thr Ala Lys His Pro Trp Asn Leu Met Thr
    50                  55                  60

Thr Ser Ala Asp Glu Gly Gln Phe Leu His Leu Leu Leu Lys Leu Ile
65                  70                  75                  80

Asn Ala Lys Asn Thr Met Glu Ile Gly Val Tyr Thr Gly Tyr Ser Leu
                85                  90                  95

Leu Ser Thr Ala Leu Ala Leu Pro Asp Asp Gly Lys Ile Leu Ala Met
            100                 105                 110

Asp Ile Asn Arg Glu Asn Tyr Glu Leu Gly Leu Pro Val Ile Gln Lys
        115                 120                 125

Ala Gly Val Ala His Lys Ile Asp Phe Arg Glu Gly Pro Ala Leu Pro
    130                 135                 140

Val Leu Asp Gln Met Leu Glu Asn Lys Glu Met His Gly Ser Phe Asp
145                 150                 155                 160

Phe Ile Phe Val Asp Ala Asp Lys Asp Asn Tyr Leu Asn Tyr His Lys
                165                 170                 175

Arg Leu Ile Asp Leu Val Lys Ile Gly Gly Val Ile Gly Tyr Asp Asn
            180                 185                 190

Thr Leu Trp Asn Gly Ser Val Val Ala Pro Pro Asp Ala Pro Met Arg
        195                 200                 205

Lys Tyr Val Arg Tyr Tyr Arg Asp Phe Val Ile Glu Leu Asn Lys Ala
    210                 215                 220

Leu Ala Ala Asp Pro Arg Ile Glu Ile Ser Gln Ile Pro Val Gly Asp
225                 230                 235                 240

Gly Ile Thr Leu Cys Arg Arg Ile Ile
                245
```

<210> SEQ ID NO 19
<211> LENGTH: 936
<212> TYPE: DNA
<213> ORGANISM: Linum usitatissimum

<400> SEQUENCE: 19

```
atgggtcgtt gccgtgttct ggttgttggt ggtaccggtt acatcggtaa acgtatcgtt     60

aaagcgtcta tcgaacacgg tcacgacacc tacgttctga aacgtccgga aaccggtctg    120

gacatcgaaa aattccagct gctgctgtct ttcaaaaaac agggtgcgca cctggttgaa    180

gcgtctttct ctgaccacga atctctggtt cgtgcggtta aactggttga cgttgttatc    240

tgcaccgttt ctggtgcgca ctctcgttct ctgctgctgc agctgaaact ggttgaagcg    300

atcaaagaag cgggtaacgt taaacgtttc atcccgtctg aattcggtat ggacccggcg    360

cgtatgggtg acgcgctgga accgggtcgt gaaaccttcg acctgaaaat ggttgttcgt    420

aaagcgatcg aagacgcgaa catcccgcac acctacatct ctgcgaactg cttcggtggt    480

tacttcgttg gtaacctgtc tcagctgggt ccgctgaccc cgccgtctga caaagttacc    540

atctacggtg acggtaacgt taaagttgtt tacatggacg aagacgacgt tgcgacctac    600

accatcatga ccatcgaaga cgaccgtacc ctgaacaaaa ccatgtactt ccgtccgccg    660

gaaaacgtta tcacccaccg tcagctggtt gaaacctggg aaaaactgtc tggtaaccag    720

ctgcagaaaa ccgaactgtc ttctcaggac ttcctggcgc tgatggaagg taaagacgtt    780

gcggaacaga tcgttatcgg tcacctgtac cacatctact acgaaggttg cctgaccaac    840

ttcgacatcg acgcggacca ggaccaggtt gaagcgtctt ctctgtaccc ggaagttgaa    900

tacacccgta tgaaagacta cctgatgatc tacctg                              936
```

<210> SEQ ID NO 20
<211> LENGTH: 312
<212> TYPE: PRT
<213> ORGANISM: Linum usitatissimum

<400> SEQUENCE: 20

```
Met Gly Arg Cys Arg Val Leu Val Val Gly Gly Thr Gly Tyr Ile Gly
1               5                   10                  15

Lys Arg Ile Val Lys Ala Ser Ile Glu His Gly His Asp Thr Tyr Val
            20                  25                  30

Leu Lys Arg Pro Glu Thr Gly Leu Asp Ile Glu Lys Phe Gln Leu Leu
        35                  40                  45

Leu Ser Phe Lys Lys Gln Gly Ala His Leu Val Glu Ala Ser Phe Ser
    50                  55                  60

Asp His Glu Ser Leu Val Arg Ala Val Lys Leu Val Asp Val Val Ile
65                  70                  75                  80

Cys Thr Val Ser Gly Ala His Ser Arg Ser Leu Leu Leu Gln Leu Lys
                85                  90                  95

Leu Val Glu Ala Ile Lys Glu Ala Gly Asn Val Lys Arg Phe Ile Pro
            100                 105                 110

Ser Glu Phe Gly Met Asp Pro Ala Arg Met Gly Asp Ala Leu Glu Pro
        115                 120                 125

Gly Arg Glu Thr Phe Asp Leu Lys Met Val Val Arg Lys Ala Ile Glu
    130                 135                 140

Asp Ala Asn Ile Pro His Thr Tyr Ile Ser Ala Asn Cys Phe Gly Gly
145                 150                 155                 160

Tyr Phe Val Gly Asn Leu Ser Gln Leu Gly Pro Leu Thr Pro Pro Ser
                165                 170                 175

Asp Lys Val Thr Ile Tyr Gly Asp Gly Asn Val Lys Val Val Tyr Met
            180                 185                 190

Asp Glu Asp Asp Val Ala Thr Tyr Thr Ile Met Thr Ile Glu Asp Asp
        195                 200                 205

Arg Thr Leu Asn Lys Thr Met Tyr Phe Arg Pro Pro Glu Asn Val Ile
    210                 215                 220

Thr His Arg Gln Leu Val Glu Thr Trp Glu Lys Leu Ser Gly Asn Gln
225                 230                 235                 240

Leu Gln Lys Thr Glu Leu Ser Ser Gln Asp Phe Leu Ala Leu Met Glu
                245                 250                 255

Gly Lys Asp Val Ala Glu Gln Ile Val Ile Gly His Leu Tyr His Ile
            260                 265                 270

Tyr Tyr Glu Gly Cys Leu Thr Asn Phe Asp Ile Asp Ala Asp Gln Asp
        275                 280                 285

Gln Val Glu Ala Ser Ser Leu Tyr Pro Glu Val Glu Tyr Thr Arg Met
    290                 295                 300

Lys Asp Tyr Leu Met Ile Tyr Leu
305                 310
```

<210> SEQ ID NO 21
<211> LENGTH: 837
<212> TYPE: DNA
<213> ORGANISM: Juglans regia

<400> SEQUENCE: 21

```
atgaacggta cctcttctct gctggcgccg atcgcgaaac gtctggcggg taaagttgcg      60
```

```
ctgatcaccg gtggtgcgtc tggtatcggt gaatctaccg cgcgtctgtt cgcggaacag    120

ggtgcgaaag ttatcatcgc ggacgttcag gacgaactgg gtttctctgt ttctcaggac    180

aaatctatca acggtgcgat ctcttacatc cactgcgacg ttacctctga atctgacgtt    240

cagaacgcgg ttaacaccgc ggtttctaaa cacggtaaac tggacatcat gttcaacacc    300

gcgggttgca ccggtcagaa caaagcgtct atcctggacc acgaacagaa agactacaaa    360

accgttttcg acgttaacgt tctgggttct ttcctgggtg cgaaacacgc ggcgaaagtt    420

atgatcccgg ttaaacgtgg taccatcctg ttcaccgcgt cttgcgttac cgaatctcac    480

ggtctggcgt ctcactctta caccgcgtct aaacacgcgg ttgttggtct gaccaaaaac    540

ctgtgcgttg aactgggtca gtacggtatc cgtgttaact gcatctctcc gtacggtgcg    600

gcgaccccgc tgttcctgaa aggtatgggt atcgacaaaa aagaaaaagc ggaagaaatc    660

ctgtcttctg cggcgaacct gaaaggtccg gttctggaag cgggtgacct ggcggaagcg    720

gcgctgttcc tggcgtctga agaatctaaa tacgtttctg ttctgaacct ggttgttgac    780

ggtggttact ctgcgaccaa cgttgcgttc accgaaacca tccagaaatt cttcacc       837
```

```
<210> SEQ ID NO 22
<211> LENGTH: 279
<212> TYPE: PRT
<213> ORGANISM: Juglans regia

<400> SEQUENCE: 22

Met Asn Gly Thr Ser Ser Leu Leu Ala Pro Ile Ala Lys Arg Leu Ala
1               5                   10                  15

Gly Lys Val Ala Leu Ile Thr Gly Gly Ala Ser Gly Ile Gly Glu Ser
            20                  25                  30

Thr Ala Arg Leu Phe Ala Glu Gln Gly Ala Lys Val Ile Ile Ala Asp
        35                  40                  45

Val Gln Asp Glu Leu Gly Phe Ser Val Ser Gln Asp Lys Ser Ile Asn
    50                  55                  60

Gly Ala Ile Ser Tyr Ile His Cys Asp Val Thr Ser Glu Ser Asp Val
65                  70                  75                  80

Gln Asn Ala Val Asn Thr Ala Val Ser Lys His Gly Lys Leu Asp Ile
                85                  90                  95

Met Phe Asn Thr Ala Gly Cys Thr Gly Gln Asn Lys Ala Ser Ile Leu
            100                 105                 110

Asp His Glu Gln Lys Asp Tyr Lys Thr Val Phe Asp Val Asn Val Leu
        115                 120                 125

Gly Ser Phe Leu Gly Ala Lys His Ala Ala Lys Val Met Ile Pro Val
    130                 135                 140

Lys Arg Gly Thr Ile Leu Phe Thr Ala Ser Cys Val Thr Glu Ser His
145                 150                 155                 160

Gly Leu Ala Ser His Ser Tyr Thr Ala Ser Lys His Ala Val Val Gly
                165                 170                 175

Leu Thr Lys Asn Leu Cys Val Glu Leu Gly Gln Tyr Gly Ile Arg Val
            180                 185                 190

Asn Cys Ile Ser Pro Tyr Gly Ala Ala Thr Pro Leu Phe Leu Lys Gly
        195                 200                 205

Met Gly Ile Asp Lys Lys Glu Lys Ala Glu Glu Ile Leu Ser Ser Ala
    210                 215                 220

Ala Asn Leu Lys Gly Pro Val Leu Glu Ala Gly Asp Leu Ala Glu Ala
225                 230                 235                 240
```

-continued

```
Ala Leu Phe Leu Ala Ser Glu Glu Ser Lys Tyr Val Ser Val Leu Asn
                245                 250                 255

Leu Val Val Asp Gly Gly Tyr Ser Ala Thr Asn Val Ala Phe Thr Glu
            260                 265                 270

Thr Ile Gln Lys Phe Phe Thr
        275
```

<210> SEQ ID NO 23
<211> LENGTH: 1455
<212> TYPE: DNA
<213> ORGANISM: Papaver somniferum

<400> SEQUENCE: 23

```
atgatcatgt ctaacctgtg gatcctgacc ctgatctcta ccatcctggc ggttttcgcg     60

gcggttctga tcatcttccg tcgtcgtatc tctgcgtcta ccaccgaatg gccggttggt    120

ccgaaaaccc tgccgatcat cggtaacctg cacatcctgg gtggtaccgc gctgcacgtt    180

gttctgcaca aactggcgga agtttacggt tctgttatga ccatctggat cggttcttgg    240

aaaccggtta tcatcgtttc tgacttcgac cgtgcgtggg aagttctggt taacaaatct    300

tctgactact ctgcgcgtga aatgccggaa atcaccaaaa tcggtaccgc gaactggcgt    360

accatctctt cttctgactc tggtccgttc tgggcgaccc tgcgtaaagg tctgcagtct    420

gttgcgctgt ctccgcagca cctggcgtct cagaccgcgc accaggaacg tgacatcatc    480

aaactgatca aaaacctgaa agacgaagcg gcgtctggta tggttaaacc gctggaccac    540

ctgaaaaaag cgaccgttcg tctgatctct cgtctgatct acggtcagga cttcgacgac    600

gacaaatacg ttgaagacat gcacgacgtt atcgaattcc tgatccgtat ctctggttac    660

gcgcagctgg cggaagtttt ctactacgcg aaatacctgc cgggtcacaa acgtgcggtt    720

accggtgcgg aagaagcgaa acgtcgtgtt atcgcgctgg ttcgtccgtt cctgcagtct    780

aacccggcga ccaacaccta cctgcacttc ctgaaatctc agctgtaccc ggaagaagtt    840

atcatcttcg cgatcttcga agcgtacctg ctgggtgttg actctacctc ttctaccacc    900

gcgtgggcgc tggcgttcct gatccgtgaa ccgtctgttc aggaaaaact gtaccaggaa    960

ctgaaaaact tcaccgcgaa caacaaccgt accatgctga aagttgaaga cgttaacaaa   1020

ctgccgtacc tgcaggcggt tgttaaagaa accatgcgta tgaaaccgat cgcgccgctg   1080

gcgatcccgc acaaagcgtg caaagacacc tctctgatgg gtaaaaaagt tgacaaaggt   1140

accaaagtta tggttaacat ccacgcgctg caccacaccg aaaaagtttg gaaagaaccg   1200

tacaaattca tcccggaacg tttcctgcag aaacacgaca aagcgatgga acagtctctg   1260

ctgccgttct ctgcgggtat gcgtatctgc gcgggtatgg aactgggtaa actgcagttc   1320

tctttctctc tggcgaacct ggttaacgcg ttcaaatggt cttgcgtttc tgacggtgtt   1380

ctgccggaca tgtctgacct gctgggtttc gttctgttca tgaaaacccc gctggaagcg   1440

cgtatcgttc cgcgt                                                    1455
```

<210> SEQ ID NO 24
<211> LENGTH: 486
<212> TYPE: PRT
<213> ORGANISM: Papaver somniferum

<400> SEQUENCE: 24

```
Met Ile Met Ser Asn Leu Trp Ile Leu Thr Leu Ile Ser Thr Ile Leu
1               5                   10                  15

Ala Val Phe Ala Ala Val Leu Ile Ile Phe Arg Arg Arg Ile Ser Ala
```

-continued

```
            20                  25                  30

Ser Thr Thr Glu Trp Pro Val Gly Pro Lys Thr Leu Pro Ile Ile Gly
        35                  40                  45

Asn Leu His Ile Leu Gly Gly Thr Ala Leu His Val Val Leu His Lys
    50                  55                  60

Leu Ala Glu Val Tyr Gly Ser Val Met Thr Ile Trp Ile Gly Ser Trp
65                  70                  75                  80

Lys Pro Val Ile Ile Val Ser Asp Phe Asp Arg Ala Trp Glu Val Leu
                85                  90                  95

Val Asn Lys Ser Ser Asp Tyr Ser Ala Arg Glu Met Pro Glu Ile Thr
            100                 105                 110

Lys Ile Gly Thr Ala Asn Trp Arg Thr Ile Ser Ser Ser Asp Ser Gly
        115                 120                 125

Pro Phe Trp Ala Thr Leu Arg Lys Gly Leu Gln Ser Val Ala Leu Ser
    130                 135                 140

Pro Gln His Leu Ala Ser Gln Thr Ala His Gln Glu Arg Asp Ile Ile
145                 150                 155                 160

Lys Leu Ile Lys Asn Leu Lys Asp Glu Ala Ala Ser Gly Met Val Lys
                165                 170                 175

Pro Leu Asp His Leu Lys Lys Ala Thr Val Arg Leu Ile Ser Arg Leu
            180                 185                 190

Ile Tyr Gly Gln Asp Phe Asp Asp Asp Lys Tyr Val Glu Asp Met His
        195                 200                 205

Asp Val Ile Glu Phe Leu Ile Arg Ile Ser Gly Tyr Ala Gln Leu Ala
    210                 215                 220

Glu Val Phe Tyr Tyr Ala Lys Tyr Leu Pro Gly His Lys Arg Ala Val
225                 230                 235                 240

Thr Gly Ala Glu Glu Ala Lys Arg Arg Val Ile Ala Leu Val Arg Pro
                245                 250                 255

Phe Leu Gln Ser Asn Pro Ala Thr Asn Thr Tyr Leu His Phe Leu Lys
            260                 265                 270

Ser Gln Leu Tyr Pro Glu Glu Val Ile Ile Phe Ala Ile Phe Glu Ala
        275                 280                 285

Tyr Leu Leu Gly Val Asp Ser Thr Ser Ser Thr Thr Ala Trp Ala Leu
    290                 295                 300

Ala Phe Leu Ile Arg Glu Pro Ser Val Gln Glu Lys Leu Tyr Gln Glu
305                 310                 315                 320

Leu Lys Asn Phe Thr Ala Asn Asn Asn Arg Thr Met Leu Lys Val Glu
                325                 330                 335

Asp Val Asn Lys Leu Pro Tyr Leu Gln Ala Val Val Lys Glu Thr Met
            340                 345                 350

Arg Met Lys Pro Ile Ala Pro Leu Ala Ile Pro His Lys Ala Cys Lys
        355                 360                 365

Asp Thr Ser Leu Met Gly Lys Lys Val Asp Lys Gly Thr Lys Val Met
    370                 375                 380

Val Asn Ile His Ala Leu His His Thr Glu Lys Val Trp Lys Glu Pro
385                 390                 395                 400

Tyr Lys Phe Ile Pro Glu Arg Phe Leu Gln Lys His Asp Lys Ala Met
                405                 410                 415

Glu Gln Ser Leu Leu Pro Phe Ser Ala Gly Met Arg Ile Cys Ala Gly
            420                 425                 430

Met Glu Leu Gly Lys Leu Gln Phe Ser Phe Ser Leu Ala Asn Leu Val
        435                 440                 445
```

-continued

```
Asn Ala Phe Lys Trp Ser Cys Val Ser Asp Gly Val Leu Pro Asp Met
    450                 455                 460

Ser Asp Leu Leu Gly Phe Val Leu Phe Met Lys Thr Pro Leu Glu Ala
465                 470                 475                 480

Arg Ile Val Pro Arg Leu
                485


<210> SEQ ID NO 25
<211> LENGTH: 1482
<212> TYPE: DNA
<213> ORGANISM: Artificial Sequence
<220> FEATURE:
<223> OTHER INFORMATION: Depicts the nucleic acid sequence encoding
      CYP719 of Cinnamomum micranthum

<400> SEQUENCE: 25

atggaagcga tctggaccgc ggttgcgatc ggtatcgcgg cggcggttct gatggcgttc      60

cgtggtcgtc agcgtcagcg tctgtctcgt aaaccgaccc agtggccgcc gggtccgacc     120

cgtctgccgc tgatcggtaa catgcaccag atcctgctga aggtggtga cccgttccac      180

gttgcgatca acaaactggc gcaggtttac ggtccgctga tgaccgtttg gttcggtacc     240

cgtcagccga ccatcatcgt ttctgaccac aacctggttt gggaagttct ggtttctaaa     300

tctgcggact acgcggcgcg tgaaatcccg atcaccctga aaccgtctct ggcggacttc     360

cgtaccatcg tttcttctaa cgcgggtccg ctgtggcact ctctgcgtcg tggtctgcag     420

aacggtgcga tcggtccgca ctctctgtct ctgcaggcgc cgttccagga atctgacatg     480

gcgcagatga tcaacaacat gatcaaagaa gcgaacctga acggtggtgt tgttaaaccg     540

ttcccgcaca tccgtcgtgc gatcatcaaa ctgctggcgc gtatctgctt cggttgcgac     600

ttctctgacg aagaattcga cgcgaccatg gacttcatgg ttgaagaagc gctgcgttac     660

tctgacgact ctcgtatcct ggacaccttc ccgccggcgc gtttcctgcc gtctgttaaa     720

cgtgcggtta tgcagatgga aaaagttaaa ctgcgtctga tggaatgcat cggtcgtccg     780

ctggactctc cgctgccgcc gacctgctac gcgcacttcc tgctgtctca gtctttcccg     840

cgtgaagttg cgatcttctc tatcttcgaa ctgttcctgc tgggtgttga ctctaccggt     900

tctaccacca tgtggggtct gggtctgctg atgcagaacc aggaagcgca gcagaaactg     960

taccaggaaa tccgtgaaca cgcgtcttgc aacgaaaaag gtgttgttaa agttgaagaa    1020

ctgggtaaac tggaatacct gcaggcggtt gcgaaagaaa ccatgcgtat gaaaccgatc    1080

gcgccgctgg cggttccgca ccaggcggcg cgtgacacca ccctggacgg tctgcacgtt    1140

gcggaaggta ccaccgttct ggcgaacctg tacgcgctgc actacgaccc gaaagtttgg    1200

gacgaaccgg aacgtttcaa accggaacgt ttcctggaat cttctaaaga attcctgggt    1260

aaacgtggtc agtactcttt cctgccgttc ggtgcgggta tgcgtgcgtg cgcgggtatg    1320

gaagttggta aactgcagct gccgttcgcg atctgcaacc tggttaacgc gttcaactgg    1380

tctaacgttg ttgaaaaaga agcgccgaaa ctgatcgaag gtttctcttt catcctgtct    1440

atgaaaaccc cgctggaagc gcgtatcgtt ccgcgtggta tc                       1482


<210> SEQ ID NO 26
<211> LENGTH: 494
<212> TYPE: PRT
<213> ORGANISM: Artificial Sequence
<220> FEATURE:
<223> OTHER INFORMATION: Depicts the amino acid sequence of CYP719 of
      Cinnamomum micranthum
```

<400> SEQUENCE: 26

Met Glu Ala Ile Trp Thr Ala Val Ala Ile Gly Ile Ala Ala Ala Val
1               5                   10                  15

Leu Met Ala Phe Arg Gly Arg Gln Arg Gln Arg Leu Ser Arg Lys Pro
            20                  25                  30

Thr Gln Trp Pro Pro Gly Pro Thr Arg Leu Pro Leu Ile Gly Asn Met
        35                  40                  45

His Gln Ile Leu Leu Lys Gly Gly Asp Pro Phe His Val Ala Ile Asn
    50                  55                  60

Lys Leu Ala Gln Val Tyr Gly Pro Leu Met Thr Val Trp Phe Gly Thr
65                  70                  75                  80

Arg Gln Pro Thr Ile Ile Val Ser Asp His Asn Leu Val Trp Glu Val
                85                  90                  95

Leu Val Ser Lys Ser Ala Asp Tyr Ala Ala Arg Glu Ile Pro Ile Thr
            100                 105                 110

Leu Lys Pro Ser Leu Ala Asp Phe Arg Thr Ile Val Ser Ser Asn Ala
        115                 120                 125

Gly Pro Leu Trp His Ser Leu Arg Arg Gly Leu Gln Asn Gly Ala Ile
    130                 135                 140

Gly Pro His Ser Leu Ser Leu Gln Ala Pro Phe Gln Glu Ser Asp Met
145                 150                 155                 160

Ala Gln Met Ile Asn Asn Met Ile Lys Glu Ala Asn Leu Asn Gly Gly
                165                 170                 175

Val Val Lys Pro Phe Pro His Ile Arg Arg Ala Ile Ile Lys Leu Leu
            180                 185                 190

Ala Arg Ile Cys Phe Gly Cys Asp Phe Ser Asp Glu Glu Phe Asp Ala
        195                 200                 205

Thr Met Asp Phe Met Val Glu Glu Ala Leu Arg Tyr Ser Asp Asp Ser
    210                 215                 220

Arg Ile Leu Asp Thr Phe Pro Pro Ala Arg Phe Leu Pro Ser Val Lys
225                 230                 235                 240

Arg Ala Val Met Gln Met Glu Lys Val Lys Leu Arg Leu Met Glu Cys
                245                 250                 255

Ile Gly Arg Pro Leu Asp Ser Pro Leu Pro Pro Thr Cys Tyr Ala His
            260                 265                 270

Phe Leu Leu Ser Gln Ser Phe Pro Arg Glu Val Ala Ile Phe Ser Ile
        275                 280                 285

Phe Glu Leu Phe Leu Leu Gly Val Asp Ser Thr Gly Ser Thr Thr Met
    290                 295                 300

Trp Gly Leu Gly Leu Leu Met Gln Asn Gln Glu Ala Gln Gln Lys Leu
305                 310                 315                 320

Tyr Gln Glu Ile Arg Glu His Ala Ser Cys Asn Glu Lys Gly Val Val
                325                 330                 335

Lys Val Glu Glu Leu Gly Lys Leu Glu Tyr Leu Gln Ala Val Ala Lys
            340                 345                 350

Glu Thr Met Arg Met Lys Pro Ile Ala Pro Leu Ala Val Pro His Gln
        355                 360                 365

Ala Ala Arg Asp Thr Thr Leu Asp Gly Leu His Val Ala Glu Gly Thr
    370                 375                 380

Thr Val Leu Ala Asn Leu Tyr Ala Leu His Tyr Asp Pro Lys Val Trp
385                 390                 395                 400

Asp Glu Pro Glu Arg Phe Lys Pro Glu Arg Phe Leu Glu Ser Ser Lys

```
                405                 410                 415

Glu Phe Leu Gly Lys Arg Gly Gln Tyr Ser Phe Leu Pro Phe Gly Ala
            420                 425                 430

Gly Met Arg Ala Cys Ala Gly Met Glu Val Gly Lys Leu Gln Leu Pro
        435                 440                 445

Phe Ala Ile Cys Asn Leu Val Asn Ala Phe Asn Trp Ser Asn Val Val
    450                 455                 460

Glu Lys Glu Ala Pro Lys Leu Ile Glu Gly Phe Ser Phe Ile Leu Ser
465                 470                 475                 480

Met Lys Thr Pro Leu Glu Ala Arg Ile Val Pro Arg Gly Ile
                485                 490


<210> SEQ ID NO 27
<211> LENGTH: 1017
<212> TYPE: DNA
<213> ORGANISM: Papaver somniferum

<400> SEQUENCE: 27

atggaagttg tttctaaaat cgaccaggaa aaccaggcga aaatctggaa acagatcttc      60

ggtttcgcgg aatctctggt tctgaaatgc gcggttcagc tggaaatcgc ggaaaccctg     120

cacaacaacg ttaaaccgat gtctctgtct gaactggcgt ctaaactgcc ggcgcagccg     180

gttaacgaag accgtctgta ccgtatcctg cacttcctgg ttcacatgaa actgttcaac     240

aaagacgcga ccacccagaa atactctctg gcgccgccgg cgaaatacct gctgaaaggt     300

tgggaaaaat ctatggttcc gtctatcctg tctgttaccg acaaagactt caccgcgccg     360

tggaaccacc tgggtgacgg tctgaccggt aactgcaacg cgttcgaaaa agcgctgggt     420

aaaggtatcc gtgtttacat gcgtgaaaac ccggaaaaag accagctgtt caacgaaggt     480

atggcgtgcg acacccgtct gttcgcgtct gcgctggtta acgaatgcaa atctatcttc     540

tctgacggta tcaacaccct ggcgggtgtt ggtcgtggta ccggtaccgc ggttaaagcg     600

atctctaaag cgttcccgga catcaaatgc accatccacg acctgccgga agttacctct     660

aaaaactcta aaatcccgcg tgacgttttc aaatctgttc cgtctgcgga cgcgatcttc     720

atgaaatcta tcctgcacga atggaacgac gaagaatgca tccagatcct gaaacgttgc     780

aaagaagcga tcccgaaagg tggtaaagtt atcatcgcgg acgttgttat cgacatggac     840

tctacccacc cgtactctaa atctcgtctg gcgatggacc tggcgatgat gctgcacacc     900

ggtggtaaag aacgtaccga agaagactgg aaaaaactga tcgacgcggc gggtttcgcg     960

tcttgcaaaa tcaccaaact gtctgcgctg cagtctgtta tcgaagcgta cccgcac       1017


<210> SEQ ID NO 28
<211> LENGTH: 339
<212> TYPE: PRT
<213> ORGANISM: Papaver somniferum

<400> SEQUENCE: 28

Met Glu Val Val Ser Lys Ile Asp Gln Glu Asn Gln Ala Lys Ile Trp
1               5                   10                  15

Lys Gln Ile Phe Gly Phe Ala Glu Ser Leu Val Leu Lys Cys Ala Val
            20                  25                  30

Gln Leu Glu Ile Ala Glu Thr Leu His Asn Asn Val Lys Pro Met Ser
        35                  40                  45

Leu Ser Glu Leu Ala Ser Lys Leu Pro Ala Gln Pro Val Asn Glu Asp
    50                  55                  60
```

```
Arg Leu Tyr Arg Ile Leu His Phe Leu Val His Met Lys Leu Phe Asn
65                  70                  75                  80

Lys Asp Ala Thr Thr Gln Lys Tyr Ser Leu Ala Pro Pro Ala Lys Tyr
                85                  90                  95

Leu Leu Lys Gly Trp Glu Lys Ser Met Val Pro Ser Ile Leu Ser Val
            100                 105                 110

Thr Asp Lys Asp Phe Thr Ala Pro Trp Asn His Leu Gly Asp Gly Leu
        115                 120                 125

Thr Gly Asn Cys Asn Ala Phe Glu Lys Ala Leu Gly Lys Gly Ile Arg
    130                 135                 140

Val Tyr Met Arg Glu Asn Pro Glu Lys Asp Gln Leu Phe Asn Glu Gly
145                 150                 155                 160

Met Ala Cys Asp Thr Arg Leu Phe Ala Ser Ala Leu Val Asn Glu Cys
                165                 170                 175

Lys Ser Ile Phe Ser Asp Gly Ile Asn Thr Leu Ala Gly Val Gly Arg
            180                 185                 190

Gly Thr Gly Thr Ala Val Lys Ala Ile Ser Lys Ala Phe Pro Asp Ile
        195                 200                 205

Lys Cys Thr Ile His Asp Leu Pro Glu Val Thr Ser Lys Asn Ser Lys
    210                 215                 220

Ile Pro Arg Asp Val Phe Lys Ser Val Pro Ser Ala Asp Ala Ile Phe
225                 230                 235                 240

Met Lys Ser Ile Leu His Glu Trp Asn Asp Glu Glu Cys Ile Gln Ile
                245                 250                 255

Leu Lys Arg Cys Lys Glu Ala Ile Pro Lys Gly Gly Lys Val Ile Ile
            260                 265                 270

Ala Asp Val Val Ile Asp Met Asp Ser Thr His Pro Tyr Ser Lys Ser
        275                 280                 285

Arg Leu Ala Met Asp Leu Ala Met Met Leu His Thr Gly Gly Lys Glu
    290                 295                 300

Arg Thr Glu Glu Asp Trp Lys Lys Leu Ile Asp Ala Ala Gly Phe Ala
305                 310                 315                 320

Ser Cys Lys Ile Thr Lys Leu Ser Ala Leu Gln Ser Val Ile Glu Ala
                325                 330                 335

Tyr Pro His


<210> SEQ ID NO 29
<211> LENGTH: 1116
<212> TYPE: DNA
<213> ORGANISM: Artificial Sequence
<220> FEATURE:
<223> OTHER INFORMATION: Depicts the nucleic acid sequence encoding
      O-methyltransferase 3 (OMT) of Sinopodophyllum hexandrum

<400> SEQUENCE: 29

atggaaatgg cgccgaccat ggacctggaa atccgtaacg gtaacggtta cggtgactct      60

ggtgaagaac tgctggcggc gcaggcgcac atctacaacc acatcttcaa cttcatctct     120

tctatggcgc tgaaatgcgc ggttgaactg aacatcccgg aaatcctgca caaccaccag     180

ccgaaagcgg ttaccctgtc tgaactggtt caggcgctgc agatcccgca ggcgaaatct     240

gcgtgcctgt accgtctgct gcgtatcctg gttcactctg gtttcttcgc gatcaccaaa     300

atccagtctg aaggtgacga agaaggttac ctgccgaccc tgtcttctaa actgctgctg     360

aaaaaccacc cgatgtctat gtctccgtgc ctgctgggtc tggttaaccc gaccatggtt     420

gcgccgatgc acttcttctc tgactggttc aaacgttctg acgacatgac cccgttcgaa     480
```

```
gcgacccacg gtgcgtctct gtggaaatac ttcggtgaaa ccccgcacat ggcggaaatc    540

ttcaacgaag cgatgggttg cgaaacccgt ctggcgatgt ctgttgttct gaaagaatgc    600

aaaggtaaac tggaaggtat ctcttctctg gttgacgttg gtggtggtac cggtaacgtt    660

ggtcgtgcga tcgcggaagc gttcccgaac gttaaatgca ccgttctgga cctgccgcag    720

gttgttggta acctgaaagg ttctaacaac ctggaattcg tttctggtga catgttccag    780

ttcatcccgc cggcggacgt tgttttcctg aaatggatcc tgcacgactg gaacgacgaa    840

gaatgcatca aaatcctgaa acgttgcaaa gaagcgatcc cgtctaaaga agaaggtggt    900

aaactgatca tcatcgacat ggttgttaac gaccacaaca aaggttctta cgaatctacc    960

gaaacccagc tgttctacga cctgaccctg atggcgctgc tgaccggtac cgaacgtacc   1020

gaaaccgaat ggaaaaaact gttcgttgcg gcgggtttca cctcttacat catctctccg   1080

gttctgggtc tgaaatctat catcgaagtt ttcccg                             1116
```

```
<210> SEQ ID NO 30
<211> LENGTH: 372
<212> TYPE: PRT
<213> ORGANISM: Artificial Sequence
<220> FEATURE:
<223> OTHER INFORMATION: Depcits amino acid sequence of
      O-methyltransferase 3 (OMT) of Sinopodophyllum hexandrum

<400> SEQUENCE: 30

Met Glu Met Ala Pro Thr Met Asp Leu Glu Ile Arg Asn Gly Asn Gly
1               5                   10                  15

Tyr Gly Asp Ser Gly Glu Glu Leu Leu Ala Ala Gln Ala His Ile Tyr
            20                  25                  30

Asn His Ile Phe Asn Phe Ile Ser Ser Met Ala Leu Lys Cys Ala Val
        35                  40                  45

Glu Leu Asn Ile Pro Glu Ile Leu His Asn His Gln Pro Lys Ala Val
    50                  55                  60

Thr Leu Ser Glu Leu Val Gln Ala Leu Gln Ile Pro Gln Ala Lys Ser
65                  70                  75                  80

Ala Cys Leu Tyr Arg Leu Leu Arg Ile Leu Val His Ser Gly Phe Phe
                85                  90                  95

Ala Ile Thr Lys Ile Gln Ser Glu Gly Asp Glu Glu Gly Tyr Leu Pro
            100                 105                 110

Thr Leu Ser Ser Lys Leu Leu Leu Lys Asn His Pro Met Ser Met Ser
        115                 120                 125

Pro Cys Leu Leu Gly Leu Val Asn Pro Thr Met Val Ala Pro Met His
    130                 135                 140

Phe Phe Ser Asp Trp Phe Lys Arg Ser Asp Asp Met Thr Pro Phe Glu
145                 150                 155                 160

Ala Thr His Gly Ala Ser Leu Trp Lys Tyr Phe Gly Glu Thr Pro His
                165                 170                 175

Met Ala Glu Ile Phe Asn Glu Ala Met Gly Cys Glu Thr Arg Leu Ala
            180                 185                 190

Met Ser Val Val Leu Lys Glu Cys Lys Gly Lys Leu Glu Gly Ile Ser
        195                 200                 205

Ser Leu Val Asp Val Gly Gly Gly Thr Gly Asn Val Gly Arg Ala Ile
    210                 215                 220

Ala Glu Ala Phe Pro Asn Val Lys Cys Thr Val Leu Asp Leu Pro Gln
225                 230                 235                 240
```

```
Val Val Gly Asn Leu Lys Gly Ser Asn Asn Leu Glu Phe Val Ser Gly
                245                 250                 255

Asp Met Phe Gln Phe Ile Pro Pro Ala Asp Val Val Phe Leu Lys Trp
            260                 265                 270

Ile Leu His Asp Trp Asn Asp Glu Glu Cys Ile Lys Ile Leu Lys Arg
        275                 280                 285

Cys Lys Glu Ala Ile Pro Ser Lys Glu Glu Gly Gly Lys Leu Ile Ile
    290                 295                 300

Ile Asp Met Val Val Asn Asp His Asn Lys Gly Ser Tyr Glu Ser Thr
305                 310                 315                 320

Glu Thr Gln Leu Phe Tyr Asp Leu Thr Leu Met Ala Leu Leu Thr Gly
                325                 330                 335

Thr Glu Arg Thr Glu Thr Glu Trp Lys Lys Leu Phe Val Ala Ala Gly
            340                 345                 350

Phe Thr Ser Tyr Ile Ile Ser Pro Val Leu Gly Leu Lys Ser Ile Ile
        355                 360                 365

Glu Val Phe Pro
    370
```

<210> SEQ ID NO 31
<211> LENGTH: 1503
<212> TYPE: DNA
<213> ORGANISM: Artificial Sequence
<220> FEATURE:
<223> OTHER INFORMATION: Depicts the nucleic acis sequence encoding
      CYP71 of Cinnamomum micranthum

<400> SEQUENCE: 31

```
atggcgctgc tgctgtctct gctgttcttc gcgtctgcgc tgatcttcct gctgaaactg     60

aacggtcagc gtgcgaacaa aaccgacgtt ccgccgtctc cgccgaaact gccgctgatc    120

ggtaacctgc accagctggg taccctgccg caccgttctc tgcgttctct ggcgggtaaa    180

tacggtccgc tgatgctgct gtacctgggt cgtatcccga ccctgatcgt ttcttctgaa    240

gaaatggcgg aacagatcat gaaaacccac gacctgatct tcgcgtctcg tccgtctatc    300

accgcggcga aagaactgct gtacggttgc accgacctgg cgttcgcgtc ttacggtgaa    360

tactggcgtc aggttcgtaa aatgtgcgtt ctggaactgc tgtctatcaa acgtgttaac    420

tctttccgtt ctatcatgga agaagaagtt ggtctgatga tcgaacgtat ctctcagtct    480

tcttctaccg gtgcggcggt taacctggcg gaactgttcc tgtctctgac cggtggtacc    540

atcgcgcgtg cggcgctggg taaaaaatac gaaggtgaag cggaagaagg tcgtaacaaa    600

tacgcggacc tggttaaaga actgcacgcg ctgctgggtg cgttctctgt tggtgactac    660

ttcccgtctc tggcgtgggt tgacgttgtt accggtctgc acggtaaact gaaacgtaac    720

tctcgtgaac tggaccgttt cctggaccag gttatcgaac accacctgat gcgtccgctg    780

gacggttgcg acgttggtga acacaccgac ctggttgacg ttatgctgca ggttcagaaa    840

gactctaacc gtgacatcca cctgacccgt gacaacatca aagcgatcat cctggacatg    900

ttctctgcgg gtaccgacac caccgcgctg accctggaat gggttatggc ggaactggcg    960

aaacacccga acgttatgaa aaaagcgcag ggtgaagttc gtcgtgttgt tgacgttaaa   1020

gcgaacatct ctgaagaaca cctgtgccag ctgaactaca tgaaatctat catcaaagaa   1080

accctgcgtc tgcacccgcc ggcgccgctg ctggttccgc gtgaatctac caccaacgtt   1140

aaaatccaga acttccacat cccgccgaaa acccgtgttt tcatcaacgc gtacgcgatc   1200

ggtcgtgacc cgacctcttg ggaaaacccg gaagaattcc tgccggaacg tttcgcgaac   1260
```

```
aactctgttg acttcaaagg tcaggacttc cagttcatcc cgttcggtgc gggtcgtcgt   1320

ggttgcccgg gtctgtcttt cgcgatcacc tctctggaac tggcgctggc gaacctgctg   1380

tactggttcg actgggaact gccgcagggt gttaccgaag aagacctgga catgtctgaa   1440

gcgctgggta tcaccgttca caaaaaactg ccgctgtacc tggttccgaa aaaccacttc   1500

tct                                                                 1503
```

<210> SEQ ID NO 32
<211> LENGTH: 501
<212> TYPE: PRT
<213> ORGANISM: Artificial Sequence
<220> FEATURE:
<223> OTHER INFORMATION: Depicts the amino sequence of CYP71 of Cinnamomum micranthum

<400> SEQUENCE: 32

```
Met Ala Leu Leu Leu Ser Leu Leu Phe Phe Ala Ser Ala Leu Ile Phe
1               5                   10                  15

Leu Leu Lys Leu Asn Gly Gln Arg Ala Asn Lys Thr Asp Val Pro Pro
            20                  25                  30

Ser Pro Pro Lys Leu Pro Leu Ile Gly Asn Leu His Gln Leu Gly Thr
        35                  40                  45

Leu Pro His Arg Ser Leu Arg Ser Leu Ala Gly Lys Tyr Gly Pro Leu
    50                  55                  60

Met Leu Leu Tyr Leu Gly Arg Ile Pro Thr Leu Ile Val Ser Ser Glu
65                  70                  75                  80

Glu Met Ala Glu Gln Ile Met Lys Thr His Asp Leu Ile Phe Ala Ser
                85                  90                  95

Arg Pro Ser Ile Thr Ala Ala Lys Glu Leu Leu Tyr Gly Cys Thr Asp
            100                 105                 110

Leu Ala Phe Ala Ser Tyr Gly Glu Tyr Trp Arg Gln Val Arg Lys Met
        115                 120                 125

Cys Val Leu Glu Leu Leu Ser Ile Lys Arg Val Asn Ser Phe Arg Ser
    130                 135                 140

Ile Met Glu Glu Glu Val Gly Leu Met Ile Glu Arg Ile Ser Gln Ser
145                 150                 155                 160

Ser Ser Thr Gly Ala Ala Val Asn Leu Ala Glu Leu Phe Leu Ser Leu
                165                 170                 175

Thr Gly Gly Thr Ile Ala Arg Ala Ala Leu Gly Lys Lys Tyr Glu Gly
            180                 185                 190

Glu Ala Glu Glu Gly Arg Asn Lys Tyr Ala Asp Leu Val Lys Glu Leu
        195                 200                 205

His Ala Leu Leu Gly Ala Phe Ser Val Gly Asp Tyr Phe Pro Ser Leu
    210                 215                 220

Ala Trp Val Asp Val Val Thr Gly Leu His Gly Lys Leu Lys Arg Asn
225                 230                 235                 240

Ser Arg Glu Leu Asp Arg Phe Leu Asp Gln Val Ile Glu His His Leu
                245                 250                 255

Met Arg Pro Leu Asp Gly Cys Asp Val Gly Glu His Thr Asp Leu Val
            260                 265                 270

Asp Val Met Leu Gln Val Gln Lys Asp Ser Asn Arg Asp Ile His Leu
        275                 280                 285

Thr Arg Asp Asn Ile Lys Ala Ile Ile Leu Asp Met Phe Ser Ala Gly
    290                 295                 300
```

-continued

```
Thr Asp Thr Thr Ala Leu Thr Leu Glu Trp Val Met Ala Glu Leu Ala
305                 310                 315                 320

Lys His Pro Asn Val Met Lys Lys Ala Gln Gly Glu Val Arg Arg Val
                325                 330                 335

Val Asp Val Lys Ala Asn Ile Ser Glu Glu His Leu Cys Gln Leu Asn
            340                 345                 350

Tyr Met Lys Ser Ile Ile Lys Glu Thr Leu Arg Leu His Pro Pro Ala
        355                 360                 365

Pro Leu Leu Val Pro Arg Glu Ser Thr Thr Asn Val Lys Ile Gln Asn
    370                 375                 380

Phe His Ile Pro Pro Lys Thr Arg Val Phe Ile Asn Ala Tyr Ala Ile
385                 390                 395                 400

Gly Arg Asp Pro Thr Ser Trp Glu Asn Pro Glu Glu Phe Leu Pro Glu
                405                 410                 415

Arg Phe Ala Asn Asn Ser Val Asp Phe Lys Gly Gln Asp Phe Gln Phe
            420                 425                 430

Ile Pro Phe Gly Ala Gly Arg Arg Gly Cys Pro Gly Leu Ser Phe Ala
        435                 440                 445

Ile Thr Ser Leu Glu Leu Ala Leu Ala Asn Leu Leu Tyr Trp Phe Asp
    450                 455                 460

Trp Glu Leu Pro Gln Gly Val Thr Glu Glu Asp Leu Asp Met Ser Glu
465                 470                 475                 480

Ala Leu Gly Ile Thr Val His Lys Lys Leu Pro Leu Tyr Leu Val Pro
                485                 490                 495

Lys Asn His Phe Ser
            500


<210> SEQ ID NO 33
<211> LENGTH: 711
<212> TYPE: DNA
<213> ORGANISM: Microcystis viridis

<400> SEQUENCE: 33

atgaccaccg acttcatcga aatctacgaa cgtgcgctgc gtcgtgaact gtgcgaagaa      60

atccgtcacc gtttcgaagc gtctaaccgt aaatctgacg gtcgtatcgg tcacggtgtt     120

gacaaatcta aaaaaaactc taccgacatc accatcaccg gtctgtctga atggtctgac     180

ctgcactctc agatcctgga ctctaccctg cgtcacctga tgctgtacat ccgtaaatac     240

ccgtacctga tcacctctgc gttcgcgctg tctctgcagg aaccggcgac cggtctggtt     300

cgtccgctga ccgcgtctga cgttggtgcg gcgtctgacc tggaactggg tgaatacctg     360

ttccgtgttt tccgtccggg tgcgatcaac gttcagaaat actctaaatc tctgggtggt     420

tactactact ggcactctga aatctacccg cgtgacccgg cggcggaaac cctgcaccgt     480

gttctgctgt tcatgttcta cctgaacgac gttgaacgtg gtggtgaaac cgaattcctg     540

taccaggaac gtaaactgaa accgacctct ggtaccatgg ttatcgcgcc ggcgggtttc     600

acccacaccc accgtggtaa cgttccggaa tctcacgaca aatacatcct gacctcttgg     660

atcctgttca accgtgcgga acagctgtac ccgcgtaaac cgaacccggc g              711


<210> SEQ ID NO 34
<211> LENGTH: 237
<212> TYPE: PRT
<213> ORGANISM: Microcystis viridis

<400> SEQUENCE: 34
```

```
Met Thr Thr Asp Phe Ile Glu Ile Tyr Glu Arg Ala Leu Arg Arg Glu
1               5                   10                  15

Leu Cys Glu Glu Ile Arg His Arg Phe Glu Ala Ser Asn Arg Lys Ser
            20                  25                  30

Asp Gly Arg Ile Gly His Gly Val Asp Lys Ser Lys Lys Asn Ser Thr
        35                  40                  45

Asp Ile Thr Ile Thr Gly Leu Ser Glu Trp Ser Asp Leu His Ser Gln
    50                  55                  60

Ile Leu Asp Ser Thr Leu Arg His Leu Met Leu Tyr Ile Arg Lys Tyr
65                  70                  75                  80

Pro Tyr Leu Ile Thr Ser Ala Phe Ala Leu Ser Leu Gln Glu Pro Ala
                85                  90                  95

Thr Gly Leu Val Arg Pro Leu Thr Ala Ser Asp Val Gly Ala Ala Ser
            100                 105                 110

Asp Leu Glu Leu Gly Glu Tyr Leu Phe Arg Val Phe Arg Pro Gly Ala
        115                 120                 125

Ile Asn Val Gln Lys Tyr Ser Lys Ser Leu Gly Gly Tyr Tyr Tyr Trp
    130                 135                 140

His Ser Glu Ile Tyr Pro Arg Asp Pro Ala Ala Glu Thr Leu His Arg
145                 150                 155                 160

Val Leu Leu Phe Met Phe Tyr Leu Asn Asp Val Glu Arg Gly Gly Glu
                165                 170                 175

Thr Glu Phe Leu Tyr Gln Glu Arg Lys Leu Lys Pro Thr Ser Gly Thr
            180                 185                 190

Met Val Ile Ala Pro Ala Gly Phe Thr His Thr His Arg Gly Asn Val
        195                 200                 205

Pro Glu Ser His Asp Lys Tyr Ile Leu Thr Ser Trp Ile Leu Phe Asn
    210                 215                 220

Arg Ala Glu Gln Leu Tyr Pro Arg Lys Pro Asn Pro Ala
225                 230                 235
```

<210> SEQ ID NO 35
<211> LENGTH: 756
<212> TYPE: DNA
<213> ORGANISM: Nitrospira moscoviensis

<400> SEQUENCE: 35

```
atggtttcta acatggcgat gggtatcacc gaagcggttg accgtgcggt tgcggcgctg      60

gacgttgacc gtctgcaccg tgaatactgg gaacagaacg aattcctggt tatccgtcag     120

ttcctgccgc gtgcgttcgt tgaagaagtt ctggttccgc aggcgcaggg tgttaaaacc     180

gaactgaacc gtaactacat cccgggtcac aaaaaaggtg gttctgtttc ttactacacc     240

gttcgtcgtc gtgcgccgct gttcctggac ctgtaccgtt ctgactcttt ccgtgcgttc     300

ctggaccgtc tggttgacgc gaaactgctg ctgtgcccgg aaaacgaccc gcactcttgc     360

gcgctgtact actacaccga accgggtgac cacatcggtt tccactacga cacctcttac     420

tacaaaggtg cgcgttacac catcctgatg ggtctggttg accgttctac ccagtgcaaa     480

ctggtttgcg aactgttcaa agaccacccg accaaagcgc cgcagcgtct ggaactgatc     540

accgaaccgg gtgacatggt tatcttcaac ggtgacaaac tgtggcacgc ggttaccccg     600

ctgggtgaag gtgaagaacg tatcgcgctg accatggaat acgttaccaa cccggaaatg     660

ggtgcgttca aacgtctgta ctctaacctg aaagactctt tcgcgtactt cggtctgaaa     720

accgttttca aacaggcgct ggcgaaaaaa tcttct                               756
```

<210> SEQ ID NO 36
<211> LENGTH: 252
<212> TYPE: PRT
<213> ORGANISM: Nitrospira moscoviensis

<400> SEQUENCE: 36

Met Val Ser Asn Met Ala Met Gly Ile Thr Glu Ala Val Asp Arg Ala
1 5 10 15

Val Ala Ala Leu Asp Val Asp Arg Leu His Arg Glu Tyr Trp Glu Gln
20 25 30

Asn Glu Phe Leu Val Ile Arg Gln Phe Leu Pro Arg Ala Phe Val Glu
35 40 45

Glu Val Leu Val Pro Gln Ala Gln Gly Val Lys Thr Glu Leu Asn Arg
50 55 60

Asn Tyr Ile Pro Gly His Lys Lys Gly Gly Ser Val Ser Tyr Tyr Thr
65 70 75 80

Val Arg Arg Arg Ala Pro Leu Phe Leu Asp Leu Tyr Arg Ser Asp Ser
85 90 95

Phe Arg Ala Phe Leu Asp Arg Leu Val Asp Ala Lys Leu Leu Leu Cys
100 105 110

Pro Glu Asn Asp Pro His Ser Cys Ala Leu Tyr Tyr Tyr Thr Glu Pro
115 120 125

Gly Asp His Ile Gly Phe His Tyr Asp Thr Ser Tyr Tyr Lys Gly Ala
130 135 140

Arg Tyr Thr Ile Leu Met Gly Leu Val Asp Arg Ser Thr Gln Cys Lys
145 150 155 160

Leu Val Cys Glu Leu Phe Lys Asp His Pro Thr Lys Ala Pro Gln Arg
165 170 175

Leu Glu Leu Ile Thr Glu Pro Gly Asp Met Val Ile Phe Asn Gly Asp
180 185 190

Lys Leu Trp His Ala Val Thr Pro Leu Gly Glu Gly Glu Glu Arg Ile
195 200 205

Ala Leu Thr Met Glu Tyr Val Thr Asn Pro Glu Met Gly Ala Phe Lys
210 215 220

Arg Leu Tyr Ser Asn Leu Lys Asp Ser Phe Ala Tyr Phe Gly Leu Lys
225 230 235 240

Thr Val Phe Lys Gln Ala Leu Ala Lys Lys Ser Ser
245 250

<210> SEQ ID NO 37
<211> LENGTH: 771
<212> TYPE: DNA
<213> ORGANISM: Artificial Sequence
<220> FEATURE:
<223> OTHER INFORMATION: Depicts the nucleic acid sequence of 2-oxoglutarate/Fe(II)-dependent dioxygenase (2-ODD) of Nitrospira japonica

<400> SEQUENCE: 37
atgatgggtg gtgcgatgac cacccagacc ctggacacca tcgcggaagc ggttgaccag 60
gcggttgcgc gtctggactt cgaccgtctg caccgtgaat actgggaaca gaacgaattc 120
ctggttatcc cgcagttcct ggaccgtgcg atggttgaag aatggctggt tccgcaggcg 180
cagggtgtta aaggtgacct gaaccgtaac tacatcccgg gtcacaaaaa aggtggttct 240
gtttcttact acaccgttat ggaaaaagcg ccgcgtttcc tggacctgta ccgttctcag 300
gttttcatcg aattcctgtc tcgtctgtct cacgcgaaac tgcgtctgtg cccggacaac 360
gacccgcact cttgcgcgct gtactactac accgaaccgg gtgaccacat cggtttccac 420
tacgacacct cttactacaa aggttctcgt tacaccatcc tgatgggtct ggttgaccag 480
tctacccact gcaaactggt ttgcgaactg ttcaaagacg acccggttcg tccgtctaaa 540
cgtctggaac tgatcaccca gccgggtgac atggttatct tcaacggtga caaactgtgg 600
cacgcggtta ccccgctggg tccgaacgaa gaacgtatcg cgctgaccat ggaatacgtt 660
accaacccgg acatgggtac cttcaaacgt ctgtactcta acctgaaaga ctctttcgcg 720
tacttcggtc tgcgtgcggt tttcaaacgt gcgctgtctc tgccgcgtcg t 771

<210> SEQ ID NO 38
<211> LENGTH: 257
<212> TYPE: PRT
<213> ORGANISM: Artificial Sequence
<220> FEATURE:
<223> OTHER INFORMATION: Depicts the amino acid sequence of Nitrospira japonica: 2-oxoglutarate/Fe(II)-dependent dioxygenase (2-ODD) of Nitrospira japonica

<400> SEQUENCE: 38

Met Met Gly Gly Ala Met Thr Thr Gln Thr Leu Asp Thr Ile Ala Glu
1 5 10 15

Ala Val Asp Gln Ala Val Ala Arg Leu Asp Phe Asp Arg Leu His Arg
20 25 30

Glu Tyr Trp Glu Gln Asn Glu Phe Leu Val Ile Pro Gln Phe Leu Asp
35 40 45

Arg Ala Met Val Glu Glu Trp Leu Val Pro Gln Ala Gln Gly Val Lys
50 55 60

Gly Asp Leu Asn Arg Asn Tyr Ile Pro Gly His Lys Lys Gly Gly Ser
65 70 75 80

Val Ser Tyr Tyr Thr Val Met Glu Lys Ala Pro Arg Phe Leu Asp Leu
85 90 95

Tyr Arg Ser Gln Val Phe Ile Glu Phe Leu Ser Arg Leu Ser His Ala
100 105 110

Lys Leu Arg Leu Cys Pro Asp Asn Asp Pro His Ser Cys Ala Leu Tyr
115 120 125

Tyr Tyr Thr Glu Pro Gly Asp His Ile Gly Phe His Tyr Asp Thr Ser
130 135 140

Tyr Tyr Lys Gly Ser Arg Tyr Thr Ile Leu Met Gly Leu Val Asp Gln
145 150 155 160

Ser Thr His Cys Lys Leu Val Cys Glu Leu Phe Lys Asp Asp Pro Val
165 170 175

Arg Pro Ser Lys Arg Leu Glu Leu Ile Thr Gln Pro Gly Asp Met Val
180 185 190

Ile Phe Asn Gly Asp Lys Leu Trp His Ala Val Thr Pro Leu Gly Pro
195 200 205

Asn Glu Glu Arg Ile Ala Leu Thr Met Glu Tyr Val Thr Asn Pro Asp
210 215 220

Met Gly Thr Phe Lys Arg Leu Tyr Ser Asn Leu Lys Asp Ser Phe Ala
225 230 235 240

Tyr Phe Gly Leu Arg Ala Val Phe Lys Arg Ala Leu Ser Leu Pro Arg
245 250 255

Arg

<210> SEQ ID NO 39

<211> LENGTH: 1575
<212> TYPE: DNA
<213> ORGANISM: Panax ginseng

<400> SEQUENCE: 39

```
atggaaacct tcctggcgca gctgtactct accaccacca tcgcggcgct gttcgttctg     60
ctggttctgt actacttctc tccgtggacc cgtatcaaca aaaaaaacgt tgcgccggaa    120
gcgggtggtg gttggccgat catcggtcac ctgcacctgc tgggtggttc taaactgccg    180
cacctggttt tcggttctat ggcggacaaa tacggtccga tcttcaccgt tcgtctgggt    240
gttcagcgtt ctctggttgt ttcttcttgg gaaatggtta aagacatctt caccaccaac    300
gacgttatcg tttctggtcg tccgaaattc ctggcggcga aacacctgtc ttacaactac    360
gcgatgttcg gtttctctcc gtacggttct ttctggctgg aactgcgtaa aatcacctct    420
ctgcagctgc tgtctaaccg tcgtctggaa ctgctgaaac acgttcgtgt ttctgaaatg    480
gaaatctcta tgcgtcagct gtacaaactg tggtctgaaa aaaaaaacgg ttctggtcgt    540
gttctgatgg acatgaaaaa atggttcggt gaactgaacc tgaacgttac cttccgtatg    600
gttgcgggta aacgttactt cggtggtggt gcggcgtcta acgacgaaga agcgcgtcgt    660
tgccgtcgtg ttgttcgtga attcttccgt ctgctgggtg ttgttgttgt tgcggactct    720
ctgccgttcc tgcgttggct ggacctgggt ggttacgaac gtgcgatgaa agaaaccgcg    780
cgtgaaatgg actctatcgt ttctgtttgg ctggaagaac accgtatcaa atctgactct    840
tctggtgacg acgcgaacat ggaacaggac ttcatggacg ttatgctgtc tgcggttaaa    900
aacgttgacc tgtgcggttt cgacgcgcac accgttatca aagcgacctg catggttatc    960
atctcttctg gtaccgacac caccaccgtt gaactgacct gggcgctgtg cctgctgctg   1020
aacaaccgtc acgttctgaa aaaagcgcag gaagaactgg acaacgttgt tggtaaacag   1080
cgtcgtgtta aagaatctga cctgaacaac ctgatctacc tgcaggcgat cgttaaagaa   1140
accctgcgtc tgtacccggc gggtcagctg ggtggtcagc gtgaattctc tgacgactgc   1200
accgttggtg gttaccacgt tccgaaacgt acccgtctgg ttgttaacct gtggaaactg   1260
caccgtgacc cgcgtatctg gtctgacccg accgaattcc gtccggaacg tttcctggaa   1320
cgtcacaaag aaatcgacgt taaaggtcag cacttcgaac tgatcccgtt cggtgcgggt   1380
cgtcgtgttt gcccgggtat caccttcggt ctgcagatgt tccacctggt tctggcgtct   1440
ctgctgcacg gtttcgacat ctctaccccg tctgacgcgc cggttgacat ggcggaaggt   1500
gcgggtctga ccaacgcgaa aatcaccccg ctggaaatcc tgatcgcgcc gcgtctgtct   1560
ccgtctctgt acgaa                                                    1575
```

<210> SEQ ID NO 40
<211> LENGTH: 525
<212> TYPE: PRT
<213> ORGANISM: Panax ginseng

<400> SEQUENCE: 40

```
Met Glu Thr Phe Leu Ala Gln Leu Tyr Ser Thr Thr Thr Ile Ala Ala
1               5                   10                  15

Leu Phe Val Leu Leu Val Leu Tyr Tyr Phe Ser Pro Trp Thr Arg Ile
            20                  25                  30

Asn Lys Lys Asn Val Ala Pro Glu Ala Gly Gly Gly Trp Pro Ile Ile
        35                  40                  45

Gly His Leu His Leu Leu Gly Gly Ser Lys Leu Pro His Leu Val Phe
    50                  55                  60
```

-continued

```
Gly Ser Met Ala Asp Lys Tyr Gly Pro Ile Phe Thr Val Arg Leu Gly
65                  70                  75                  80

Val Gln Arg Ser Leu Val Val Ser Ser Trp Glu Met Val Lys Asp Ile
                85                  90                  95

Phe Thr Thr Asn Asp Val Ile Val Ser Gly Arg Pro Lys Phe Leu Ala
            100                 105                 110

Ala Lys His Leu Ser Tyr Asn Tyr Ala Met Phe Gly Phe Ser Pro Tyr
        115                 120                 125

Gly Ser Phe Trp Leu Glu Leu Arg Lys Ile Thr Ser Leu Gln Leu Leu
    130                 135                 140

Ser Asn Arg Arg Leu Glu Leu Leu Lys His Val Arg Val Ser Glu Met
145                 150                 155                 160

Glu Ile Ser Met Arg Gln Leu Tyr Lys Leu Trp Ser Glu Lys Lys Asn
                165                 170                 175

Gly Ser Gly Arg Val Leu Met Asp Met Lys Lys Trp Phe Gly Glu Leu
            180                 185                 190

Asn Leu Asn Val Thr Phe Arg Met Val Ala Gly Lys Arg Tyr Phe Gly
        195                 200                 205

Gly Gly Ala Ala Ser Asn Asp Glu Glu Ala Arg Arg Cys Arg Arg Val
    210                 215                 220

Val Arg Glu Phe Phe Arg Leu Leu Gly Val Val Val Val Ala Asp Ser
225                 230                 235                 240

Leu Pro Phe Leu Arg Trp Leu Asp Leu Gly Gly Tyr Glu Arg Ala Met
                245                 250                 255

Lys Glu Thr Ala Arg Glu Met Asp Ser Ile Val Ser Val Trp Leu Glu
            260                 265                 270

Glu His Arg Ile Lys Ser Asp Ser Ser Gly Asp Asp Ala Asn Met Glu
        275                 280                 285

Gln Asp Phe Met Asp Val Met Leu Ser Ala Val Lys Asn Val Asp Leu
    290                 295                 300

Cys Gly Phe Asp Ala His Thr Val Ile Lys Ala Thr Cys Met Val Ile
305                 310                 315                 320

Ile Ser Ser Gly Thr Asp Thr Thr Thr Val Glu Leu Thr Trp Ala Leu
                325                 330                 335

Cys Leu Leu Leu Asn Asn Arg His Val Leu Lys Lys Ala Gln Glu Glu
            340                 345                 350

Leu Asp Asn Val Val Gly Lys Gln Arg Arg Val Lys Glu Ser Asp Leu
        355                 360                 365

Asn Asn Leu Ile Tyr Leu Gln Ala Ile Val Lys Glu Thr Leu Arg Leu
    370                 375                 380

Tyr Pro Ala Gly Gln Leu Gly Gly Gln Arg Glu Phe Ser Asp Asp Cys
385                 390                 395                 400

Thr Val Gly Gly Tyr His Val Pro Lys Arg Thr Arg Leu Val Val Asn
                405                 410                 415

Leu Trp Lys Leu His Arg Asp Pro Arg Ile Trp Ser Asp Pro Thr Glu
            420                 425                 430

Phe Arg Pro Glu Arg Phe Leu Glu Arg His Lys Glu Ile Asp Val Lys
        435                 440                 445

Gly Gln His Phe Glu Leu Ile Pro Phe Gly Ala Gly Arg Arg Val Cys
    450                 455                 460

Pro Gly Ile Thr Phe Gly Leu Gln Met Phe His Leu Val Leu Ala Ser
465                 470                 475                 480
```

```
Leu Leu His Gly Phe Asp Ile Ser Thr Pro Ser Asp Ala Pro Val Asp
                485                 490                 495

Met Ala Glu Gly Ala Gly Leu Thr Asn Ala Lys Ile Thr Pro Leu Glu
            500                 505                 510

Ile Leu Ile Ala Pro Arg Leu Ser Pro Ser Leu Tyr Glu
        515                 520                 525


<210> SEQ ID NO 41
<211> LENGTH: 1431
<212> TYPE: DNA
<213> ORGANISM: Malus domestica

<400> SEQUENCE: 41

atgaaaaaag ttgaactggt tttcatcccg tctccgggtg cgggtcacca cctgccgacc      60

ctgcagttcg ttaaacgtct gatcgaccgt aacgaccgta tctctatcac catcctggcg     120

atccagtctt acttcccgac caccctgtct tcttacacca aatctatcgc ggcgtctgaa     180

ccgcgtatcc gtttcatcga cgttccgcag ccgcaggacc gtccgccgca ggaaatgtac     240

aaatctcgtg cgcagatctt ctctctgtac atcgaatctc acgttccgtc tgttaaaaaa     300

atcatcacca acctggtttc ttcttctgcg aactcttctg actctatccg tgttgcggcg     360

ctggttgttg acctgttctg cgtttctatg atcgacgttg cgaaagaact gaacatcccg     420

tcttacctgt tcctgacctc taacgcgggt tacctggcgt tcatgctgca cctgccgatc     480

ctgcacgaaa aaaaccagat cgcggttgaa gaatctgacc cggactggtc tatcccgggt     540

atcgttcacc cggttccgcc gcgtgttctg ccggcggcgc tgaccgacgg tcgtctgtct     600

gcgtacatca aactggcgtc tcgtttccgt gaaacccgtg gtatcatcgt taacaccttc     660

gttgaactgg aaacccacgc gatcaccctg ttctctaacg acgaccgtgt tccgccggtt     720

tacccggttg gtccggttat cgacctggac gacggtcagg aacactctaa cctggaccag     780

gcgcagcgtg acaaaatcat caaatggctg gacgaccagc cgcagaaatc tgttgttttc     840

ctgtgcttcg gttctatggg ttctttcggt gcggaacagg ttaaagaaat cgcggttggt     900

ctggaacagt ctggtcagcg tttcctgtgg tctctgcgta tgccgtctcc gaaaggtatc     960

gttccgtctg actgctctaa cctggaagaa gttctgccgg acggtttcct ggaacgtacc    1020

aacggtaaaa aaggtctgat ctgcggttgg gcgccgcagg ttgaaatcct ggcgcactct    1080

gcgaccggtg gtttcctgtc tcactgcggt tggaactcta tcctggaatc tctgtggcac    1140

ggtgttccga tcgcgacctg gccgatgtac gcggaacagc agctgaacgc gttccgtatg    1200

gttcgtgaac tgggtatggc gctggaaatg cgtctggact acaaagcggg ttctgcggac    1260

gttgttggtg cggacgaaat cgaaaaagcg gttgttggtg ttatggaaaa agactctgaa    1320

gttcgtaaaa aagttgaaga aatgggtaaa atggcgcgta aagcggttaa agacggtggt    1380

tcttctttcg cgtctgttgg tcgtttcatc gaagacgtta tcggtcagaa c             1431


<210> SEQ ID NO 42
<211> LENGTH: 477
<212> TYPE: PRT
<213> ORGANISM: Malus domestica

<400> SEQUENCE: 42

Met Lys Lys Val Glu Leu Val Phe Ile Pro Ser Pro Gly Ala Gly His
1               5                   10                  15

His Leu Pro Thr Leu Gln Phe Val Lys Arg Leu Ile Asp Arg Asn Asp
            20                  25                  30
```

-continued

```
Arg Ile Ser Ile Thr Ile Leu Ala Ile Gln Ser Tyr Phe Pro Thr Thr
        35                  40                  45

Leu Ser Ser Tyr Thr Lys Ser Ile Ala Ala Ser Glu Pro Arg Ile Arg
    50                  55                  60

Phe Ile Asp Val Pro Gln Pro Gln Asp Arg Pro Pro Gln Glu Met Tyr
65                  70                  75                  80

Lys Ser Arg Ala Gln Ile Phe Ser Leu Tyr Ile Glu Ser His Val Pro
                85                  90                  95

Ser Val Lys Lys Ile Ile Thr Asn Leu Val Ser Ser Ser Ala Asn Ser
            100                 105                 110

Ser Asp Ser Ile Arg Val Ala Ala Leu Val Val Asp Leu Phe Cys Val
        115                 120                 125

Ser Met Ile Asp Val Ala Lys Glu Leu Asn Ile Pro Ser Tyr Leu Phe
    130                 135                 140

Leu Thr Ser Asn Ala Gly Tyr Leu Ala Phe Met Leu His Leu Pro Ile
145                 150                 155                 160

Leu His Glu Lys Asn Gln Ile Ala Val Glu Glu Ser Asp Pro Asp Trp
                165                 170                 175

Ser Ile Pro Gly Ile Val His Pro Val Pro Pro Arg Val Leu Pro Ala
            180                 185                 190

Ala Leu Thr Asp Gly Arg Leu Ser Ala Tyr Ile Lys Leu Ala Ser Arg
        195                 200                 205

Phe Arg Glu Thr Arg Gly Ile Ile Val Asn Thr Phe Val Glu Leu Glu
    210                 215                 220

Thr His Ala Ile Thr Leu Phe Ser Asn Asp Asp Arg Val Pro Pro Val
225                 230                 235                 240

Tyr Pro Val Gly Pro Val Ile Asp Leu Asp Asp Gly Gln Glu His Ser
                245                 250                 255

Asn Leu Asp Gln Ala Gln Arg Asp Lys Ile Ile Lys Trp Leu Asp Asp
            260                 265                 270

Gln Pro Gln Lys Ser Val Val Phe Leu Cys Phe Gly Ser Met Gly Ser
        275                 280                 285

Phe Gly Ala Glu Gln Val Lys Glu Ile Ala Val Gly Leu Glu Gln Ser
    290                 295                 300

Gly Gln Arg Phe Leu Trp Ser Leu Arg Met Pro Ser Pro Lys Gly Ile
305                 310                 315                 320

Val Pro Ser Asp Cys Ser Asn Leu Glu Glu Val Leu Pro Asp Gly Phe
                325                 330                 335

Leu Glu Arg Thr Asn Gly Lys Lys Gly Leu Ile Cys Gly Trp Ala Pro
            340                 345                 350

Gln Val Glu Ile Leu Ala His Ser Ala Thr Gly Gly Phe Leu Ser His
        355                 360                 365

Cys Gly Trp Asn Ser Ile Leu Glu Ser Leu Trp His Gly Val Pro Ile
    370                 375                 380

Ala Thr Trp Pro Met Tyr Ala Glu Gln Gln Leu Asn Ala Phe Arg Met
385                 390                 395                 400

Val Arg Glu Leu Gly Met Ala Leu Glu Met Arg Leu Asp Tyr Lys Ala
                405                 410                 415

Gly Ser Ala Asp Val Val Gly Ala Asp Glu Ile Glu Lys Ala Val Val
            420                 425                 430

Gly Val Met Glu Lys Asp Ser Glu Val Arg Lys Lys Val Glu Glu Met
        435                 440                 445

Gly Lys Met Ala Arg Lys Ala Val Lys Asp Gly Gly Ser Ser Phe Ala
```

450 455 460

Ser Val Gly Arg Phe Ile Glu Asp Val Ile Gly Gln Asn
465 470 475

<210> SEQ ID NO 43
<211> LENGTH: 1395
<212> TYPE: DNA
<213> ORGANISM: Artificial Sequence
<220> FEATURE:
<223> OTHER INFORMATION: Depicts the nucleic acid sequence encoding
Glycosyltransferase (UGT) of Lycium barbarum

<400> SEQUENCE: 43
atgggtcacc tggtttctac cgttgaaatg gcgaaacagc tggttgaccg tgaagaccag 60
ctgtctatca ccgttctgat catgaccctg ccgaccgaaa ccaaaatccc gtcttacacc 120
aaatctctgt cttctaacta cacctctcgt atccgtctgc tggaactgac ccagccggaa 180
acctctgtta acatgggttc tgcgacccac ccgatgaaat tcatgtctga attcatcacc 240
tcttacaaag gtcgtgttaa agacgcggtt gcggacatgt tctcttctct gtcttctgtt 300
aaactggcgg gtttcgttat cgacatgttc tgcaccgcga tgatcgacgt tgcgaacgac 360
ttcggtgttc cgtcttacct gttctacacc tctggtgcgg cgatgctggg tctgcagttc 420
cacttccagt ctctgatctc tcagaacgtt ctgtcttacc tggactctga atctgaagtt 480
ctgatcccga cctacatcaa cccggttccg gttaaattcc tgccgggtct gatcctggac 540
aacgacgaat actctatcat gttcctggac ctggcgggtc gtttcaaaga aaccaaaggt 600
atcatggtta acaccttcgt tgaagttgaa tctcacgcgc tgaaagcgct gtctgacgac 660
gaaaaaatcc cgccgatcta cccggttggt ccgatcctga acctgggtgg tggtaacgac 720
ggtcacggtg aagaatacga ctctatcatg aaatggctgg acggtcagcc gaactcttct 780
gttgttttcc tgtgcttcgg ttctatgggt tctttcgaag aagaccaggt taaagaagtt 840
gcgaacgcgc tggaatcttc tggttaccag ttcctgtggt ctctgcgtca gccgccgccg 900
aaagacaaac tgcagttccc gtctgaattc gaaaacctgg aagaagttct gccggaaggt 960
ttcctgcagc gtaccaaagg tcgtggtaaa atgatcggtt gggcgccgca ggttgcgatc 1020
ctgtctcacc cgtctgttgg tggtttcgtt tctcactgcg gttggaactc taccctggaa 1080
tctgttcgtt ctggtgttcc gatggcgacc tggccgatgt acgcggaaca gcagtctaac 1140
gcgttccagc tggttaaaga cctggaaatg gcggttgaaa tcaaaatgga ctaccgtaaa 1200
gacttcatga ccatcaacca gccggttctg gttaaagcgg aagaaatcgg taacggtatc 1260
cgtcagctga tggacctggt taacaaaatc cgtgcgaaag ttcgtaaaat gaaagaaaaa 1320
tctgaagcgg cgatcatgga aggtggttct tcttacgttg cgctgggtaa cttcgttgaa 1380
accgttatga aatct 1395

<210> SEQ ID NO 44
<211> LENGTH: 465
<212> TYPE: PRT
<213> ORGANISM: Artificial Sequence
<220> FEATURE:
<223> OTHER INFORMATION: Depcits the amino acid sequence of
Glycosyltransferase (UGT of Lycium barbarum

<400> SEQUENCE: 44

Met Gly His Leu Val Ser Thr Val Glu Met Ala Lys Gln Leu Val Asp
1 5 10 15

Arg Glu Asp Gln Leu Ser Ile Thr Val Leu Ile Met Thr Leu Pro Thr

```
            20                  25                  30

Glu Thr Lys Ile Pro Ser Tyr Thr Lys Ser Leu Ser Ser Asn Tyr Thr
        35                  40                  45

Ser Arg Ile Arg Leu Leu Glu Leu Thr Gln Pro Glu Thr Ser Val Asn
    50                  55                  60

Met Gly Ser Ala Thr His Pro Met Lys Phe Met Ser Glu Phe Ile Thr
65                  70                  75                  80

Ser Tyr Lys Gly Arg Val Lys Asp Ala Val Ala Asp Met Phe Ser Ser
                85                  90                  95

Leu Ser Ser Val Lys Leu Ala Gly Phe Val Ile Asp Met Phe Cys Thr
            100                 105                 110

Ala Met Ile Asp Val Ala Asn Asp Phe Gly Val Pro Ser Tyr Leu Phe
        115                 120                 125

Tyr Thr Ser Gly Ala Ala Met Leu Gly Leu Gln Phe His Phe Gln Ser
    130                 135                 140

Leu Ile Ser Gln Asn Val Leu Ser Tyr Leu Asp Ser Glu Ser Glu Val
145                 150                 155                 160

Leu Ile Pro Thr Tyr Ile Asn Pro Val Pro Val Lys Phe Leu Pro Gly
                165                 170                 175

Leu Ile Leu Asp Asn Asp Glu Tyr Ser Ile Met Phe Leu Asp Leu Ala
            180                 185                 190

Gly Arg Phe Lys Glu Thr Lys Gly Ile Met Val Asn Thr Phe Val Glu
        195                 200                 205

Val Glu Ser His Ala Leu Lys Ala Leu Ser Asp Asp Glu Lys Ile Pro
    210                 215                 220

Pro Ile Tyr Pro Val Gly Pro Ile Leu Asn Leu Gly Gly Gly Asn Asp
225                 230                 235                 240

Gly His Gly Glu Glu Tyr Asp Ser Ile Met Lys Trp Leu Asp Gly Gln
                245                 250                 255

Pro Asn Ser Ser Val Val Phe Leu Cys Phe Gly Ser Met Gly Ser Phe
            260                 265                 270

Glu Glu Asp Gln Val Lys Glu Val Ala Asn Ala Leu Glu Ser Ser Gly
        275                 280                 285

Tyr Gln Phe Leu Trp Ser Leu Arg Gln Pro Pro Pro Lys Asp Lys Leu
    290                 295                 300

Gln Phe Pro Ser Glu Phe Glu Asn Leu Glu Glu Val Leu Pro Glu Gly
305                 310                 315                 320

Phe Leu Gln Arg Thr Lys Gly Arg Gly Lys Met Ile Gly Trp Ala Pro
                325                 330                 335

Gln Val Ala Ile Leu Ser His Pro Ser Val Gly Gly Phe Val Ser His
            340                 345                 350

Cys Gly Trp Asn Ser Thr Leu Glu Ser Val Arg Ser Gly Val Pro Met
        355                 360                 365

Ala Thr Trp Pro Met Tyr Ala Glu Gln Gln Ser Asn Ala Phe Gln Leu
    370                 375                 380

Val Lys Asp Leu Glu Met Ala Val Glu Ile Lys Met Asp Tyr Arg Lys
385                 390                 395                 400

Asp Phe Met Thr Ile Asn Gln Pro Val Leu Val Lys Ala Glu Glu Ile
                405                 410                 415

Gly Asn Gly Ile Arg Gln Leu Met Asp Leu Val Asn Lys Ile Arg Ala
            420                 425                 430

Lys Val Arg Lys Met Lys Glu Lys Ser Glu Ala Ala Ile Met Glu Gly
        435                 440                 445
```

```
Gly Ser Ser Tyr Val Ala Leu Gly Asn Phe Val Glu Thr Val Met Lys
    450                 455                 460

Ser
465


<210> SEQ ID NO 45
<211> LENGTH: 1398
<212> TYPE: DNA
<213> ORGANISM: Cicer arietinum

<400> SEQUENCE: 45

atgaaaaaaa tcgaagttgt tttcatcccg tctccgggtg ttggtcacct gatctctacc     60

ctggaattcg cgaacctgct gatcaaccgt aacaaccgtc tgaacatcac cgttctggtt    120

atcaacttcc cgaaaaccgt tgaaaaacag accaactact ctctgaccga atctgaaaac    180

ctgcacgtta tcaacctgcc gcagaccacc acccacgttc cgtctacctc tgacgttggt    240

aactctatct ctgcgctggt tgaaacccag aaatctaacg ttaaacaggc ggtttctaac    300

ctgaccggta ccctggcggc gttcgttgtt gacatgttct gcaccaccat gatcgacgtt    360

gcgaacgaac tgggtgttcc gtctctggtt ttcttcacct ctggtgttgc gttcctgggt    420

ctgatgctgc acctgcacac catctgggaa cagcaggaca ccgaactgct gctgcagcag    480

gacgaactgg acatcccgtc tttcgcgaac ccggttgcga ccaacaccct gccgaccctg    540

gttctgcgta aagaatggga atcttctttc atcaaatacg gtaacggtct gaaaaaagcg    600

tctggtatca tcgttaactc tttccacgaa ctggaaccgc acgcggttcg ttctttcctg    660

gaagacccga ccctgcgtga cctgccgatc tacccggttg gtccgatcct gaacccgaaa    720

tctaacgttg actctgacga cgttatcaaa tggctggacg accagccgcc gtcttctgtt    780

gttttcctgt gcttcggttc tatgggtacc ttcgacgaag aacaggttcg tgaaatcgcg    840

ctggcgatcg aacgttctgg tgttcgtttc ctgtggtctc tgcgtaaacc gcagccgcag    900

ggtaccatgg ttccgccgtc tgactacacc ctgtctcaga tgctggaagt tctgccggaa    960

ggtttcctgg accgtaccgc gaacatcggt cgtgttatcg gttgggcgcc gcaggttcag   1020

gttctggcgc accaggcgac cggtggtttc gtttctcact gcggttggaa ctctaccctg   1080

gaatctatct actacggtgt tccgatcgcg acctggccgc tgttcgcgga acagcagacc   1140

aacgcgttcg aactggttcg tgaactgaaa atcgcggttg aaatcgcgct ggactaccgt   1200

ctggaattcg acatcggtcg taactacctg ctggacgcgg acaaaatcga acgtggtatc   1260

cgtggtgttc tggacaaaga cggtgaagtt cgtaaaaaag ttaaagaaat gtctcagaaa   1320

tctcgtaacg ttctgctgga aggtggttct tcttacacct acctgggtca gctgatcgac   1380

tacatcacca accaggtt                                                 1398


<210> SEQ ID NO 46
<211> LENGTH: 466
<212> TYPE: PRT
<213> ORGANISM: Cicer arietinum

<400> SEQUENCE: 46

Met Lys Lys Ile Glu Val Val Phe Ile Pro Ser Pro Gly Val Gly His
1               5                   10                  15

Leu Ile Ser Thr Leu Glu Phe Ala Asn Leu Leu Ile Asn Arg Asn Asn
            20                  25                  30

Arg Leu Asn Ile Thr Val Leu Val Ile Asn Phe Pro Lys Thr Val Glu
        35                  40                  45
```

```
Lys Gln Thr Asn Tyr Ser Leu Thr Glu Ser Glu Asn Leu His Val Ile
    50                  55                  60

Asn Leu Pro Gln Thr Thr Thr His Val Pro Ser Thr Ser Asp Val Gly
65                  70                  75                  80

Asn Ser Ile Ser Ala Leu Val Glu Thr Gln Lys Ser Asn Val Lys Gln
                85                  90                  95

Ala Val Ser Asn Leu Thr Gly Thr Leu Ala Ala Phe Val Val Asp Met
            100                 105                 110

Phe Cys Thr Thr Met Ile Asp Val Ala Asn Glu Leu Gly Val Pro Ser
        115                 120                 125

Leu Val Phe Phe Thr Ser Gly Val Ala Phe Leu Gly Leu Met Leu His
    130                 135                 140

Leu His Thr Ile Trp Glu Gln Gln Asp Thr Glu Leu Leu Leu Gln Gln
145                 150                 155                 160

Asp Glu Leu Asp Ile Pro Ser Phe Ala Asn Pro Val Ala Thr Asn Thr
                165                 170                 175

Leu Pro Thr Leu Val Leu Arg Lys Glu Trp Glu Ser Ser Phe Ile Lys
            180                 185                 190

Tyr Gly Asn Gly Leu Lys Lys Ala Ser Gly Ile Ile Val Asn Ser Phe
        195                 200                 205

His Glu Leu Glu Pro His Ala Val Arg Ser Phe Leu Glu Asp Pro Thr
    210                 215                 220

Leu Arg Asp Leu Pro Ile Tyr Pro Val Gly Pro Ile Leu Asn Pro Lys
225                 230                 235                 240

Ser Asn Val Asp Ser Asp Asp Val Ile Lys Trp Leu Asp Asp Gln Pro
                245                 250                 255

Pro Ser Ser Val Val Phe Leu Cys Phe Gly Ser Met Gly Thr Phe Asp
            260                 265                 270

Glu Glu Gln Val Arg Glu Ile Ala Leu Ala Ile Glu Arg Ser Gly Val
        275                 280                 285

Arg Phe Leu Trp Ser Leu Arg Lys Pro Gln Pro Gln Gly Thr Met Val
    290                 295                 300

Pro Pro Ser Asp Tyr Thr Leu Ser Gln Met Leu Glu Val Leu Pro Glu
305                 310                 315                 320

Gly Phe Leu Asp Arg Thr Ala Asn Ile Gly Arg Val Ile Gly Trp Ala
                325                 330                 335

Pro Gln Val Gln Val Leu Ala His Gln Ala Thr Gly Gly Phe Val Ser
            340                 345                 350

His Cys Gly Trp Asn Ser Thr Leu Glu Ser Ile Tyr Tyr Gly Val Pro
        355                 360                 365

Ile Ala Thr Trp Pro Leu Phe Ala Glu Gln Gln Thr Asn Ala Phe Glu
    370                 375                 380

Leu Val Arg Glu Leu Lys Ile Ala Val Glu Ile Ala Leu Asp Tyr Arg
385                 390                 395                 400

Leu Glu Phe Asp Ile Gly Arg Asn Tyr Leu Leu Asp Ala Asp Lys Ile
                405                 410                 415

Glu Arg Gly Ile Arg Gly Val Leu Asp Lys Asp Gly Glu Val Arg Lys
            420                 425                 430

Lys Val Lys Glu Met Ser Gln Lys Ser Arg Asn Val Leu Leu Glu Gly
        435                 440                 445

Gly Ser Ser Tyr Thr Tyr Leu Gly Gln Leu Ile Asp Tyr Ile Thr Asn
    450                 455                 460
```

Gln Val
465

<210> SEQ ID NO 47
<211> LENGTH: 1452
<212> TYPE: DNA
<213> ORGANISM: Barbarea vulgaris

<400> SEQUENCE: 47
atgaaatctg aactggtttt catcccgtac ccgggtatcg gtcacctgcg tccgaccgtt 60
gaagttgcga aactgctggt tgaccgtgaa ccgcgtctgt ctatctctgt tttcatcctg 120
ccgttcatct ctggtgacga agttggtgcg tctgactaca tctctgcgct gtctgcggcg 180
tctaacgacc gtctgcgtta caaagttatc ttcaccggtg accaggaaac cgcggaaccg 240
accaaactga ccctgcacat cgaaaaccag gttccgaaag ttcgtaccgc ggttgcgaaa 300
ctgatcgacg aatactctaa actgctggac tctccgaaaa tcgttggttt cgttctggac 360
atgttctgca cctctatgat cgacgttgcg aacgaattcg aactgccgtc ttacatgttc 420
ttcacctctt ctgcgggtat cctggcggtt tctttccacg ttcaggttct gtacgacgaa 480
aaaaaatgca acttctctga aaccatgttc gaagactctg aagcggaact gatcctgccg 540
tctctgaccc gtccgtaccc ggttaaatct ctgccgtacg cgctgttccg taccgaaatg 600
ctgatcatgc acgttaacct ggcgcgtcgt ttccgtgaac tgaaaggtat cctggttaac 660
accgttgacg aactggaacc gcacgcgctg aaattcctgc tgtctggtat caccccgccg 720
gcgtacccgg ttggtccgct gctgcacctg gaatctaacc aggacgacga atctgaagac 780
gaaaaacgtt ctgaaatcat catgtggctg gacgaacagc cggcgtcttc tgttgttttc 840
ctgtgcttcg gttctatggg tggtttctct gaagaacaga cccgtgaaat cgcgatcgcg 900
ctggaacgtt ctggtcaccg tttcctgtgg tctctgcgtc gtgaatctcc gaacatcgac 960
aaagaactgc cgggtgaatt caccaacctg gaagaagttc tgccggaagg tttcttcgac 1020
cgtaccaaag gtatcggtaa agttatcggt tgggcgccgc aggttgcggt tctggaaaac 1080
ccggcgatcg gtggtttcgt tacccacggt ggttggaact ctgttctgga atctctgtgg 1140
ttcggtgttc cgaccgcgat gtggccgctg tacgcggaac agaaattcaa cgcgttcgtt 1200
atggttgaag aactgggtct ggcggttgaa atcaaaaaat actggcgtgg tgacctgctg 1260
ctgggtcgtt ctgcgatgga aatcgttacc gcggacgaaa tcgaacgtgg tatcacctgc 1320
ctgatgcagc aggactctga cgttcgtaaa cgtgttaaag aaatgaaagg taaatgccac 1380
gttgcgctga tggacggtgg ttcttctacc ctggcgctgg acaaattcgt tgaagacgtt 1440
accaaaaaca tc 1452

<210> SEQ ID NO 48
<211> LENGTH: 484
<212> TYPE: PRT
<213> ORGANISM: Barbarea vulgaris

<400> SEQUENCE: 48

Met Lys Ser Glu Leu Val Phe Ile Pro Tyr Pro Gly Ile Gly His Leu
1 5 10 15

Arg Pro Thr Val Glu Val Ala Lys Leu Leu Val Asp Arg Glu Pro Arg
20 25 30

Leu Ser Ile Ser Val Phe Ile Leu Pro Phe Ile Ser Gly Asp Glu Val
35 40 45

Gly Ala Ser Asp Tyr Ile Ser Ala Leu Ser Ala Ala Ser Asn Asp Arg

-continued

```
    50                  55                  60

Leu Arg Tyr Lys Val Ile Phe Thr Gly Asp Gln Glu Thr Ala Glu Pro
65                  70                  75                  80

Thr Lys Leu Thr Leu His Ile Glu Asn Gln Val Pro Lys Val Arg Thr
                85                  90                  95

Ala Val Ala Lys Leu Ile Asp Glu Tyr Ser Lys Leu Leu Asp Ser Pro
            100                 105                 110

Lys Ile Val Gly Phe Val Leu Asp Met Phe Cys Thr Ser Met Ile Asp
        115                 120                 125

Val Ala Asn Glu Phe Glu Leu Pro Ser Tyr Met Phe Phe Thr Ser Ser
    130                 135                 140

Ala Gly Ile Leu Ala Val Ser Phe His Val Gln Val Leu Tyr Asp Glu
145                 150                 155                 160

Lys Lys Cys Asn Phe Ser Glu Thr Met Phe Glu Asp Ser Glu Ala Glu
                165                 170                 175

Leu Ile Leu Pro Ser Leu Thr Arg Pro Tyr Pro Val Lys Ser Leu Pro
            180                 185                 190

Tyr Ala Leu Phe Arg Thr Glu Met Leu Ile Met His Val Asn Leu Ala
        195                 200                 205

Arg Arg Phe Arg Glu Leu Lys Gly Ile Leu Val Asn Thr Val Asp Glu
    210                 215                 220

Leu Glu Pro His Ala Leu Lys Phe Leu Leu Ser Gly Ile Thr Pro Pro
225                 230                 235                 240

Ala Tyr Pro Val Gly Pro Leu Leu His Leu Glu Ser Asn Gln Asp Asp
                245                 250                 255

Glu Ser Glu Asp Glu Lys Arg Ser Glu Ile Ile Met Trp Leu Asp Glu
            260                 265                 270

Gln Pro Ala Ser Ser Val Val Phe Leu Cys Phe Gly Ser Met Gly Gly
        275                 280                 285

Phe Ser Glu Glu Gln Thr Arg Glu Ile Ala Ile Ala Leu Glu Arg Ser
    290                 295                 300

Gly His Arg Phe Leu Trp Ser Leu Arg Arg Glu Ser Pro Asn Ile Asp
305                 310                 315                 320

Lys Glu Leu Pro Gly Glu Phe Thr Asn Leu Glu Glu Val Leu Pro Glu
                325                 330                 335

Gly Phe Phe Asp Arg Thr Lys Gly Ile Gly Lys Val Ile Gly Trp Ala
            340                 345                 350

Pro Gln Val Ala Val Leu Glu Asn Pro Ala Ile Gly Gly Phe Val Thr
        355                 360                 365

His Gly Gly Trp Asn Ser Val Leu Glu Ser Leu Trp Phe Gly Val Pro
    370                 375                 380

Thr Ala Met Trp Pro Leu Tyr Ala Glu Gln Lys Phe Asn Ala Phe Val
385                 390                 395                 400

Met Val Glu Glu Leu Gly Leu Ala Val Glu Ile Lys Lys Tyr Trp Arg
                405                 410                 415

Gly Asp Leu Leu Leu Gly Arg Ser Ala Met Glu Ile Val Thr Ala Asp
            420                 425                 430

Glu Ile Glu Arg Gly Ile Thr Cys Leu Met Gln Gln Asp Ser Asp Val
        435                 440                 445

Arg Lys Arg Val Lys Glu Met Lys Gly Lys Cys His Val Ala Leu Met
    450                 455                 460

Asp Gly Gly Ser Ser Thr Leu Ala Leu Asp Lys Phe Val Glu Asp Val
465                 470                 475                 480
```

Thr Lys Asn Ile

<210> SEQ ID NO 49
<211> LENGTH: 1632
<212> TYPE: DNA
<213> ORGANISM: Artificial Sequence
<220> FEATURE:
<223> OTHER INFORMATION: Depicts the nucleic acid sequence encoding
2-Deoxy-d-ribose-5-phosphate aldolase (DERA) of Desulfatibacillum
aliphaticivorans

<400> SEQUENCE: 49

```
atgaccggtc cgaaaatctg cgttgttggt gcgtgcaaca tcgacctgat ctcttacgtt     60

gaacgtctgc cggttctggg tgaaaccctg cacggtaaaa aattctctat gggtttcggt    120

ggtaaaggtg cgaaccaggc ggttatggcg gcgaaactgg gtggtgaagt tgcgatggtt    180

ggtaaactgg gtcgtgacgt tttcggtgaa aacaccctgg cgaacttcaa aaaactgggt    240

gttaacgttt ctcacgttca cttcaccgaa gaagcgttct ctggtgttgc gccgatcgcg    300

gttgacgaca acggtgcgaa ctctatcatc atcgttaccg gtgcgtctga cctgctgtct    360

gcggaagaaa tccgtgcggc ggaaaacgcg atcgcgaaat ctaaagttct ggtttgccag    420

ctggaaatcc cgatggaaca gaacctggaa gcgctgcgta tcgcgcgtaa aaacaacgtt    480

ccgaccatct tcaacccggc gccggcgcgt ccgggtctgc cggacgaact gtaccagctg    540

tctgacatct tctgcccgaa cgaatctgaa accgaaatcc tgaccggtat gccggttgaa    600

accatggaac aggcggaaca ggcggcgaaa gcgctgctgg aacgtggtcc gaaaaccgtt    660

atcctgaccc tgggtgaacg tggttgcctg ctggttgacg cgaacggtgc gcgtcacatc    720

ccgacccgta aagttgaagc gatcgacacc accggtgcgg gtgactgctt cgttggttct    780

ctggcgttct tcctggcggc gggtaaatct ctggaagacg cgatcaaccg tgcgaacaaa    840

atcgcggcgg tttctgtttg cggtcagggt acccagtctt ctttcccggg tgcgtctgaa    900

ctggacccgg aaatcctgtc tgacatccag ccggcggaat ctcaggcgcc ggcgatgtct    960

gcgaaagacc tggcgcagta catcgaccac accctgctga aaccggaagc gccgctgtct   1020

gcgttcgaca aaatctgcga agaagcgatc ctgcaccagt tccgttctgt ttgcgttaac   1080

tcttgcaaaa tctcttacat cgcgaaaaaa ctgaaaggta ccggtgttga cgcgtgcgcg   1140

gttatcggtt tcccgctggg tgcgatgtct accgcggcga aagcgttcga agcgaaacag   1200

gcggttatgg acggtgcggc ggaactggac atggttatca acgttggtgc gctgaaatct   1260

ggtgacttcg acgcggtttt cgacgacatc aaagcggttc gtgacgcggc gccgctgccg   1320

atcatcctga aagttatcat cgaaacctgc ctgctgaccg acgaagaaaa agcgcgtgcg   1380

tgccgtatcg cgaaagcggc ggacgcggac ttcgttaaaa cctctaccgg tttctctacc   1440

ggtggtgcga ccctggaaga catcgcgctg atgcgtgaca ccgttggtcc gtacatgggt   1500

gttaaagcgt ctggtggtat caaagacgcg aaaaccgcga tcgcgatgat cgaagcgggt   1560

gcgacccgta tcggtgcggg tgcgggtgtt gaaatcgttt ctggtctgca gtctgacgcg   1620

gacggttctt ac                                                        1632
```

<210> SEQ ID NO 50
<211> LENGTH: 544
<212> TYPE: PRT
<213> ORGANISM: Artificial Sequence
<220> FEATURE:
<223> OTHER INFORMATION: Depicts the amino acid sequence of 2-Deoxy-d-
ribose-5-phosphate aldolase (DERA) of Desulfatibacillum aliphaticivorans

<400> SEQUENCE: 50

Met Thr Gly Pro Lys Ile Cys Val Val Gly Ala Cys Asn Ile Asp Leu
1               5                   10                  15

Ile Ser Tyr Val Glu Arg Leu Pro Val Leu Gly Glu Thr Leu His Gly
            20                  25                  30

Lys Lys Phe Ser Met Gly Phe Gly Gly Lys Gly Ala Asn Gln Ala Val
        35                  40                  45

Met Ala Ala Lys Leu Gly Gly Glu Val Ala Met Val Gly Lys Leu Gly
    50                  55                  60

Arg Asp Val Phe Gly Glu Asn Thr Leu Ala Asn Phe Lys Lys Leu Gly
65                  70                  75                  80

Val Asn Val Ser His Val His Phe Thr Glu Glu Ala Phe Ser Gly Val
                85                  90                  95

Ala Pro Ile Ala Val Asp Asp Asn Gly Ala Asn Ser Ile Ile Ile Val
            100                 105                 110

Thr Gly Ala Ser Asp Leu Leu Ser Ala Glu Glu Ile Arg Ala Ala Glu
        115                 120                 125

Asn Ala Ile Ala Lys Ser Lys Val Leu Val Cys Gln Leu Glu Ile Pro
    130                 135                 140

Met Glu Gln Asn Leu Glu Ala Leu Arg Ile Ala Arg Lys Asn Asn Val
145                 150                 155                 160

Pro Thr Ile Phe Asn Pro Ala Pro Ala Arg Pro Gly Leu Pro Asp Glu
                165                 170                 175

Leu Tyr Gln Leu Ser Asp Ile Phe Cys Pro Asn Glu Ser Glu Thr Glu
            180                 185                 190

Ile Leu Thr Gly Met Pro Val Glu Thr Met Glu Gln Ala Glu Gln Ala
        195                 200                 205

Ala Lys Ala Leu Leu Glu Arg Gly Pro Lys Thr Val Ile Leu Thr Leu
    210                 215                 220

Gly Glu Arg Gly Cys Leu Leu Val Asp Ala Asn Gly Ala Arg His Ile
225                 230                 235                 240

Pro Thr Arg Lys Val Glu Ala Ile Asp Thr Thr Gly Ala Gly Asp Cys
                245                 250                 255

Phe Val Gly Ser Leu Ala Phe Phe Leu Ala Ala Gly Lys Ser Leu Glu
            260                 265                 270

Asp Ala Ile Asn Arg Ala Asn Lys Ile Ala Ala Val Ser Val Cys Gly
        275                 280                 285

Gln Gly Thr Gln Ser Ser Phe Pro Gly Ala Ser Glu Leu Asp Pro Glu
    290                 295                 300

Ile Leu Ser Asp Ile Gln Pro Ala Glu Ser Gln Ala Pro Ala Met Ser
305                 310                 315                 320

Ala Lys Asp Leu Ala Gln Tyr Ile Asp His Thr Leu Leu Lys Pro Glu
                325                 330                 335

Ala Pro Leu Ser Ala Phe Asp Lys Ile Cys Glu Glu Ala Ile Leu His
            340                 345                 350

Gln Phe Arg Ser Val Cys Val Asn Ser Cys Lys Ile Ser Tyr Ile Ala
        355                 360                 365

Lys Lys Leu Lys Gly Thr Gly Val Asp Ala Cys Ala Val Ile Gly Phe
    370                 375                 380

Pro Leu Gly Ala Met Ser Thr Ala Ala Lys Ala Phe Glu Ala Lys Gln
385                 390                 395                 400

-continued

```
Ala Val Met Asp Gly Ala Ala Glu Leu Asp Met Val Ile Asn Val Gly
                405                 410                 415

Ala Leu Lys Ser Gly Asp Phe Asp Ala Val Phe Asp Asp Ile Lys Ala
            420                 425                 430

Val Arg Asp Ala Ala Pro Leu Pro Ile Ile Leu Lys Val Ile Ile Glu
        435                 440                 445

Thr Cys Leu Leu Thr Asp Glu Glu Lys Ala Arg Ala Cys Arg Ile Ala
    450                 455                 460

Lys Ala Ala Asp Ala Asp Phe Val Lys Thr Ser Thr Gly Phe Ser Thr
465                 470                 475                 480

Gly Gly Ala Thr Leu Glu Asp Ile Ala Leu Met Arg Asp Thr Val Gly
                485                 490                 495

Pro Tyr Met Gly Val Lys Ala Ser Gly Gly Ile Lys Asp Ala Lys Thr
            500                 505                 510

Ala Ile Ala Met Ile Glu Ala Gly Ala Thr Arg Ile Gly Ala Gly Ala
        515                 520                 525

Gly Val Glu Ile Val Ser Gly Leu Gln Ser Asp Ala Asp Gly Ser Tyr
    530                 535                 540
```

<210> SEQ ID NO 51
<211> LENGTH: 3993
<212> TYPE: DNA
<213> ORGANISM: Artificial Sequence
<220> FEATURE:
<223> OTHER INFORMATION: Depicts the nucleic acid sequence of ABD transporter gene

<400> SEQUENCE: 51

```
atggttgaag tttctgaaaa accgaacacc caggacgacg gtgtttctaa acaggaaaac     60

cgtaacccgg cgtcttcttc ttcttctacc tctgacaaag aaaaagttgc gaaaaaaggt    120

aactctgacg cgaccaaatc ttctaccccg gaagacctgg acgcgcagct ggcgcacctg    180

ccggaacacg aacgtgaaat cctgaaacag cagctgttca tcccggacgt taaagcgacc    240

tacggtaccc tgttccgtta cgcgacccgt aacgacatga tcttcctggc gatcgtttct    300

ctggcgtcta tcgcggcggg tgcggcgctg ccgctgttca ccgttctgtt cggttctctg    360

gcgggtacct tccgtgacat cgcgctgcac cgtatcacct acgacgaatt caactctatc    420

ctgacccgta actctctgta cttcgtttac ctgggtatcg cgcagttcat cctgctgtac    480

gtttctaccg ttggtttcat ctacgttggt gaacacatca cccagaaaat ccgtgcgaaa    540

tacctgcacg cgatcctgcg tcagaacatc ggtttcttcg acaaactggg tgcgggtgaa    600

gttaccaccc gtatcaccgc ggacaccaac ctgatccagg acggtatctc tgaaaaagtt    660

ggtctgaccc tgaccgcgct gtctaccttc ttctctgcgt tcatcatcgg ttacgttcgt    720

tactggaaac tggcgctgat ctgctcttct accatcgttg cgatgatcct ggttatgggt    780

ggtatctctc gtttcgttgt taaatctggt cgtatgaccc tggtttctta cggtgaaggt    840

ggtaccgttg cggaagaagt tatctcttct atccgtaacg cgaccgcgtt cggtacccag    900

gaaaaactgg cgcgtcagta cgaagttcac ctgaaagaag cgcgtaaatg gggtcgtcgt    960

ctgcagatga tgctgggtat catgttcggt tctatgatgg cgatcatgta ctctaactac   1020

ggtctgggtt tctggatggg ttctcgtttc ctggttggtg gtgaaaccga cctgtctgcg   1080

atcgttaaca tcctgctggc gatcgttatc ggttctttct ctatcggtaa cgttgcgccg   1140

aacacccagg cgttcgcgtc tgcgatctct gcgggtgcga aaatcttctc taccatcgac   1200

cgtgtttctg cgatcgaccc gggttctgac gaaggtgaca ccatcgaaaa cgttgaaggt   1260
```

accatcgaat tccgtggtat caaacacatc tacccgtctc gtccggaagt tgttgttatg 1320
gaagacatca acctggttgt tccgaaaggt aaaaccaccg cgctggttgg tccgtctggt 1380
tctggtaaat ctaccgttgt tggtctgctg gaacgtttct acaacccggt ttctggttct 1440
gttctgctgg acggtcgtga catcaaaacc ctgaacctgc gttggctgcg tcagcagatc 1500
tctctggttt ctcaggaacc gaccctgttc ggtaccacca tcttcgaaaa catccgtctg 1560
ggtctgatcg gttctccgat ggaaaacgaa tctgaagaac agatcaaaga acgtatcgtt 1620
tctgcggcga aagaagcgaa cgcgcacgac ttcatcatgg gtctgccgga cggttacgcg 1680
accgacgttg gtcagcgtgg tttcctgctg tctggtggtc agaaacagcg tatcgcgatc 1740
gcgcgtgcga tcgtttctga cccgaaaatc ctgctgctgg acgaagcgac ctctgcgctg 1800
gacaccaaat ctgaaggtgt tgttcaggcg gcgctggacg cggcgtctcg tggtcgtacc 1860
accatcgtta tcgcgcaccg tctgtctacc atcaaatctg cggacaacat cgttgttatc 1920
gttggtggtc gtatcgcgga acagggtacc cacgacgaac tggttgacaa aaaaggtacc 1980
tacctgcagc tggttgaagc gcagaaaatc aacgaagaac gtggtgaaga atctgaagac 2040
gaagcggttc tggaaaaaga aaaagaaatc tctcgtcaga tctctgttcc ggcgaaatct 2100
gttaactctg gtaaataccc ggacgaagac gttgaagcga acctgggtcg tatcgacacc 2160
aaaaaatctc tgtcttctgt tatcctgtct cagaaacgtt ctcaggaaaa cgaaaccgaa 2220
tactctctgg gtaccctgat ccgtttcatc gcgggtttca acaaaccgga acgtctgatc 2280
atgctgtgcg gtttcttctt cgcggttctg tctggtgcgg gtcagccggt tcagtctgtt 2340
ttcttcgcga aaggtatcac caccctgtct ctgccgccgt ctctgtacgg taaactgcgt 2400
gaagacgcga acttctggtc tctgatgttc ctgatgctgg gtctggttca gctggttacc 2460
cagtctgcgc agggtgttat cttcgcgatc tgctctgaat ctctgatcta ccgtgcgcgt 2520
tctaaatctt tccgtgcgat gctgcgtcag gacatcgcgt tcttcgacct gccggaaaac 2580
tctaccggtg cgctgacctc tttcctgtct accgaaacca aacacctgtc tggtgtttct 2640
ggtgcgaccc tgggtaccat cctgatggtt tctaccaccc tgatcgttgc gctgaccgtt 2700
gcgctggcgt tcggttggaa actggcgctg gtttgcatct ctaccgttcc ggttctgctg 2760
ctgtgcggtt tctaccgttt ctggatcctg gcgcagttcc agacccgtgc gaaaaaagcg 2820
tacgaatctt ctgcgtctta cgcgtgcgaa gcgacctctt ctatccgtac cgttgcgtct 2880
ctgacccgtg aacagggtgt tatggaaatc tacgaaggtc agctgaacga ccaggcgaaa 2940
aaatctctgc gttctgttgc gaaatcttct ctgctgtacg cggcgtctca gtctttctct 3000
ttcttctgcc tggcgctggg tttctggtac ggtggtggtc tgctgggtaa aggtgaatac 3060
aacgcgttcc agttcttcct gtgcatctct tgcgttatct tcggttctca gtctgcgggt 3120
atcgttttct ctttctctcc ggacatgggt aaagcgaaat ctgcggcggc ggacttcaaa 3180
cgtctgttcg accgtgttcc gaccatcgac atcgaatctc cggacggtga aaaactggaa 3240
accgttgaag gtaccatcga attccgtgac gttcacttcc gttacccgac ccgtccggaa 3300
cagccggttc tgcgtggtct gaacctgacc gttaaaccgg gtcagtacat cgcgctggtt 3360
ggtccgtctg gttgcggtaa atctaccacc atcgcgctgg ttgaacgttt ctacgacacc 3420
ctgtctggtg gtgtttacat cgacggtaaa gacatctctc gtctgaacgt taactcttac 3480
cgttctcacc tggcgctggt ttctcaggaa ccgaccctgt accagggtac catccgtgac 3540
aacgttctgc tgggtgttga ccgtgacgaa ctgccggacg aacaggtttt cgcggcgtgc 3600

-continued

```
aaagcggcga acatctacga cttcatcatg tctctgccgg acggtttcgg taccgttgtt   3660

ggttctaaag gttctatgct gtctggtggt cagaaacagc gtatcgcgat cgcgcgtgcg   3720

ctgatccgtg acccgaaagt tctgctgctg gacgaagcga cctctgcgct ggactctgaa   3780

tctgaaaaag ttgttcaggc ggcgctggac gcggcggcga aaggtcgtac caccatcgcg   3840

gttgcgcacc gtctgtctac catccagaaa gcggacatca tctacgtttt cgaccagggt   3900

cgtatcgttg aatctggtac ccaccacgaa ctgctgcaga acaaaggtcg ttactacgaa   3960

ctggttcaca tgcagtctct ggaaaaaacc cag                                3993
```

<210> SEQ ID NO 52
<211> LENGTH: 1331
<212> TYPE: PRT
<213> ORGANISM: Artificial Sequence
<220> FEATURE:
<223> OTHER INFORMATION: Depicts the amino acid sequence of ABC transporter

<400> SEQUENCE: 52

```
Met Val Glu Val Ser Glu Lys Pro Asn Thr Gln Asp Asp Gly Val Ser
1               5                   10                  15

Lys Gln Glu Asn Arg Asn Pro Ala Ser Ser Ser Ser Ser Thr Ser Asp
            20                  25                  30

Lys Glu Lys Val Ala Lys Lys Gly Asn Ser Asp Ala Thr Lys Ser Ser
        35                  40                  45

Thr Pro Glu Asp Leu Asp Ala Gln Leu Ala His Leu Pro Glu His Glu
    50                  55                  60

Arg Glu Ile Leu Lys Gln Gln Leu Phe Ile Pro Asp Val Lys Ala Thr
65                  70                  75                  80

Tyr Gly Thr Leu Phe Arg Tyr Ala Thr Arg Asn Asp Met Ile Phe Leu
                85                  90                  95

Ala Ile Val Ser Leu Ala Ser Ile Ala Ala Gly Ala Ala Leu Pro Leu
            100                 105                 110

Phe Thr Val Leu Phe Gly Ser Leu Ala Gly Thr Phe Arg Asp Ile Ala
        115                 120                 125

Leu His Arg Ile Thr Tyr Asp Glu Phe Asn Ser Ile Leu Thr Arg Asn
    130                 135                 140

Ser Leu Tyr Phe Val Tyr Leu Gly Ile Ala Gln Phe Ile Leu Leu Tyr
145                 150                 155                 160

Val Ser Thr Val Gly Phe Ile Tyr Val Gly Glu His Ile Thr Gln Lys
                165                 170                 175

Ile Arg Ala Lys Tyr Leu His Ala Ile Leu Arg Gln Asn Ile Gly Phe
            180                 185                 190

Phe Asp Lys Leu Gly Ala Gly Glu Val Thr Thr Arg Ile Thr Ala Asp
        195                 200                 205

Thr Asn Leu Ile Gln Asp Gly Ile Ser Glu Lys Val Gly Leu Thr Leu
    210                 215                 220

Thr Ala Leu Ser Thr Phe Phe Ser Ala Phe Ile Ile Gly Tyr Val Arg
225                 230                 235                 240

Tyr Trp Lys Leu Ala Leu Ile Cys Ser Ser Thr Ile Val Ala Met Ile
                245                 250                 255

Leu Val Met Gly Gly Ile Ser Arg Phe Val Val Lys Ser Gly Arg Met
            260                 265                 270

Thr Leu Val Ser Tyr Gly Glu Gly Gly Thr Val Ala Glu Glu Val Ile
        275                 280                 285
```

-continued

```
Ser Ser Ile Arg Asn Ala Thr Ala Phe Gly Thr Gln Glu Lys Leu Ala
    290                 295                 300

Arg Gln Tyr Glu Val His Leu Lys Glu Ala Arg Lys Trp Gly Arg Arg
305                 310                 315                 320

Leu Gln Met Met Leu Gly Ile Met Phe Gly Ser Met Met Ala Ile Met
                325                 330                 335

Tyr Ser Asn Tyr Gly Leu Gly Phe Trp Met Gly Ser Arg Phe Leu Val
            340                 345                 350

Gly Gly Glu Thr Asp Leu Ser Ala Ile Val Asn Ile Leu Leu Ala Ile
        355                 360                 365

Val Ile Gly Ser Phe Ser Ile Gly Asn Val Ala Pro Asn Thr Gln Ala
    370                 375                 380

Phe Ala Ser Ala Ile Ser Ala Gly Ala Lys Ile Phe Ser Thr Ile Asp
385                 390                 395                 400

Arg Val Ser Ala Ile Asp Pro Gly Ser Asp Glu Gly Asp Thr Ile Glu
                405                 410                 415

Asn Val Glu Gly Thr Ile Glu Phe Arg Gly Ile Lys His Ile Tyr Pro
            420                 425                 430

Ser Arg Pro Glu Val Val Val Met Glu Asp Ile Asn Leu Val Val Pro
        435                 440                 445

Lys Gly Lys Thr Thr Ala Leu Val Gly Pro Ser Gly Ser Gly Lys Ser
    450                 455                 460

Thr Val Val Gly Leu Leu Glu Arg Phe Tyr Asn Pro Val Ser Gly Ser
465                 470                 475                 480

Val Leu Leu Asp Gly Arg Asp Ile Lys Thr Leu Asn Leu Arg Trp Leu
                485                 490                 495

Arg Gln Gln Ile Ser Leu Val Ser Gln Glu Pro Thr Leu Phe Gly Thr
            500                 505                 510

Thr Ile Phe Glu Asn Ile Arg Leu Gly Leu Ile Gly Ser Pro Met Glu
        515                 520                 525

Asn Glu Ser Glu Glu Gln Ile Lys Glu Arg Ile Val Ser Ala Ala Lys
    530                 535                 540

Glu Ala Asn Ala His Asp Phe Ile Met Gly Leu Pro Asp Gly Tyr Ala
545                 550                 555                 560

Thr Asp Val Gly Gln Arg Gly Phe Leu Leu Ser Gly Gly Gln Lys Gln
                565                 570                 575

Arg Ile Ala Ile Ala Arg Ala Ile Val Ser Asp Pro Lys Ile Leu Leu
            580                 585                 590

Leu Asp Glu Ala Thr Ser Ala Leu Asp Thr Lys Ser Glu Gly Val Val
        595                 600                 605

Gln Ala Ala Leu Asp Ala Ala Ser Arg Gly Arg Thr Thr Ile Val Ile
    610                 615                 620

Ala His Arg Leu Ser Thr Ile Lys Ser Ala Asp Asn Ile Val Val Ile
625                 630                 635                 640

Val Gly Gly Arg Ile Ala Glu Gln Gly Thr His Asp Glu Leu Val Asp
                645                 650                 655

Lys Lys Gly Thr Tyr Leu Gln Leu Val Glu Ala Gln Lys Ile Asn Glu
            660                 665                 670

Glu Arg Gly Glu Glu Ser Glu Asp Glu Ala Val Leu Glu Lys Glu Lys
        675                 680                 685

Glu Ile Ser Arg Gln Ile Ser Val Pro Ala Lys Ser Val Asn Ser Gly
    690                 695                 700

Lys Tyr Pro Asp Glu Asp Val Glu Ala Asn Leu Gly Arg Ile Asp Thr
```

-continued

```
705                 710                 715                 720

Lys Lys Ser Leu Ser Ser Val Ile Leu Ser Gln Lys Arg Ser Gln Glu
                725                 730                 735

Asn Glu Thr Glu Tyr Ser Leu Gly Thr Leu Ile Arg Phe Ile Ala Gly
            740                 745                 750

Phe Asn Lys Pro Glu Arg Leu Ile Met Leu Cys Gly Phe Phe Phe Ala
        755                 760                 765

Val Leu Ser Gly Ala Gly Gln Pro Val Gln Ser Val Phe Phe Ala Lys
    770                 775                 780

Gly Ile Thr Thr Leu Ser Leu Pro Pro Ser Leu Tyr Gly Lys Leu Arg
785                 790                 795                 800

Glu Asp Ala Asn Phe Trp Ser Leu Met Phe Leu Met Leu Gly Leu Val
                805                 810                 815

Gln Leu Val Thr Gln Ser Ala Gln Gly Val Ile Phe Ala Ile Cys Ser
            820                 825                 830

Glu Ser Leu Ile Tyr Arg Ala Arg Ser Lys Ser Phe Arg Ala Met Leu
        835                 840                 845

Arg Gln Asp Ile Ala Phe Phe Asp Leu Pro Glu Asn Ser Thr Gly Ala
    850                 855                 860

Leu Thr Ser Phe Leu Ser Thr Glu Thr Lys His Leu Ser Gly Val Ser
865                 870                 875                 880

Gly Ala Thr Leu Gly Thr Ile Leu Met Val Ser Thr Thr Leu Ile Val
                885                 890                 895

Ala Leu Thr Val Ala Leu Ala Phe Gly Trp Lys Leu Ala Leu Val Cys
            900                 905                 910

Ile Ser Thr Val Pro Val Leu Leu Leu Cys Gly Phe Tyr Arg Phe Trp
        915                 920                 925

Ile Leu Ala Gln Phe Gln Thr Arg Ala Lys Lys Ala Tyr Glu Ser Ser
    930                 935                 940

Ala Ser Tyr Ala Cys Glu Ala Thr Ser Ser Ile Arg Thr Val Ala Ser
945                 950                 955                 960

Leu Thr Arg Glu Gln Gly Val Met Glu Ile Tyr Glu Gly Gln Leu Asn
                965                 970                 975

Asp Gln Ala Lys Lys Ser Leu Arg Ser Val Ala Lys Ser Ser Leu Leu
            980                 985                 990

Tyr Ala Ala Ser Gln Ser Phe Ser  Phe Phe Cys Leu Ala  Leu Gly Phe
        995                 1000                1005

Trp Tyr  Gly Gly Gly Leu Leu  Gly Lys Gly Glu Tyr  Asn Ala Phe
    1010                1015                1020

Gln Phe  Phe Leu Cys Ile Ser  Cys Val Ile Phe Gly  Ser Gln Ser
    1025                1030                1035

Ala Gly  Ile Val Phe Ser Phe  Ser Pro Asp Met Gly  Lys Ala Lys
    1040                1045                1050

Ser Ala  Ala Ala Asp Phe Lys  Arg Leu Phe Asp Arg  Val Pro Thr
    1055                1060                1065

Ile Asp  Ile Glu Ser Pro Asp  Gly Glu Lys Leu Glu  Thr Val Glu
    1070                1075                1080

Gly Thr  Ile Glu Phe Arg Asp  Val His Phe Arg Tyr  Pro Thr Arg
    1085                1090                1095

Pro Glu  Gln Pro Val Leu Arg  Gly Leu Asn Leu Thr  Val Lys Pro
    1100                1105                1110

Gly Gln  Tyr Ile Ala Leu Val  Gly Pro Ser Gly Cys  Gly Lys Ser
    1115                1120                1125
```

Thr Thr Ile Ala Leu Val Glu Arg Phe Tyr Asp Thr Leu Ser Gly
1130 1135 1140

Gly Val Tyr Ile Asp Gly Lys Asp Ile Ser Arg Leu Asn Val Asn
1145 1150 1155

Ser Tyr Arg Ser His Leu Ala Leu Val Ser Gln Glu Pro Thr Leu
1160 1165 1170

Tyr Gln Gly Thr Ile Arg Asp Asn Val Leu Leu Gly Val Asp Arg
1175 1180 1185

Asp Glu Leu Pro Asp Glu Gln Val Phe Ala Ala Cys Lys Ala Ala
1190 1195 1200

Asn Ile Tyr Asp Phe Ile Met Ser Leu Pro Asp Gly Phe Gly Thr
1205 1210 1215

Val Val Gly Ser Lys Gly Ser Met Leu Ser Gly Gly Gln Lys Gln
1220 1225 1230

Arg Ile Ala Ile Ala Arg Ala Leu Ile Arg Asp Pro Lys Val Leu
1235 1240 1245

Leu Leu Asp Glu Ala Thr Ser Ala Leu Asp Ser Glu Ser Glu Lys
1250 1255 1260

Val Val Gln Ala Ala Leu Asp Ala Ala Ala Lys Gly Arg Thr Thr
1265 1270 1275

Ile Ala Val Ala His Arg Leu Ser Thr Ile Gln Lys Ala Asp Ile
1280 1285 1290

Ile Tyr Val Phe Asp Gln Gly Arg Ile Val Glu Ser Gly Thr His
1295 1300 1305

His Glu Leu Leu Gln Asn Lys Gly Arg Tyr Tyr Glu Leu Val His
1310 1315 1320

Met Gln Ser Leu Glu Lys Thr Gln
1325 1330

<210> SEQ ID NO 53
<211> LENGTH: 5154
<212> TYPE: DNA
<213> ORGANISM: Artificial Sequence
<220> FEATURE:
<223> OTHER INFORMATION: Depicts the nucleic acid sequence of ABC Transporter

<400> SEQUENCE: 53
atgaccggtt ctatctctat cgacgcgtgg ctgtctggtg cgctggcgct ggttacctgc 60
ggttctgcgt tcgttctgtc tctgcagcgt acctacctgc acaaatctca gcagaaagac 120
cgtgcgccgc tggttttcga caaacagcgt gacacctctg ttccggttgc ggacgacgac 180
gcgcgtttcg ttcgtctgac cttcggtacc ctgaccctga ccctgctgtc tgcgctggac 240
ttctaccaca ccgttatcca gcagcagcag cagacctctg actggtggat caccgcgtct 300
gcgtgcaccc agttcgttgc gtggctgtac gcgtctgttc tggttctggt tgcgcgtcgt 360
taccgtttcc cgtctgaatg gggttggatc ctgaacgttc acctgtgcgt tttctactgc 420
atgatctggt gcatcgcggt ttacgacgtt tacgacgcgt acgttatcaa cccgtctgac 480
aactggatcc acatgctgcc gcgtctgctg gcgctgatcc tgggttctga cctggttttc 540
accaccgcga ccaccccgcg tggtgcgccg ttcctggacg aaaacggtcg taaagttgcg 600
gcgatcgacg ttgcgtctat ctactctttc ctgtacttct cttgggttac cccgctgatc 660
aacctggcgt acaaaaacaa aaaactgacc gacgaagacc tgccgaccct gccgccgctg 720
taccgtggtc acaacctgta ctacatcttc ggtgcgaccc gtaacaaatc tctgctgaaa 780

```
cgtatctaca ccaccaacaa acgtgcgatc accatccagg ttgttctggc gttcaccacc    840
tctctggttt actacgttcc ggcgtacttc gttaaccgtc tgctgaccct gatccaggac    900
atgcacggtg ttgaagacga cgtttctatc cgtaaaggtt tcgttctggt tgcgtctctg    960
ggtgcgacca tcctgatcct gggtatcctg gttggtcagc tgtggtacta cgcgtcttct   1020
tctctgcagg ttcgtgttaa agcgatgctg aacatcgaaa tctaccgtaa aaccctgcgt   1080
cgtcgtgacc tggcggttga atctccgaaa ctggacgacg acgaagacac cgacaaaaaa   1140
aaagacgacg acgaagcgtc tgacaaaaaa ggtgaatctg acgaaaaaga agacgtttct   1200
tcttctaccg gtaccatcgt taacctgatg tctaccgact ctaaccgtat ctctgaattc   1260
tctgtttggt ggttctctat cctggcggcg ccgaccgaac tggcggttgg tatctacttc   1320
ctgtaccagc tgctgggtaa atcttgcttc ctgggtctgc tggttatgat cgttgttctg   1380
ccgatcaacc actacaacgc gaaaaccttc gcgaaaaccc aggacaaact gatggaagcg   1440
cgtgacaaac gtgtttctct gatgaacgaa gttctgcagg gtatccgtca gatcaaattc   1500
ttcgcgtggg aaaaacgttg ggaaaaacgt gttatggaag cgcgtgaagt tgaactgcac   1560
cacctgggtg ttacctacat gaccgaagtt ctgttcaccc tgctgtggca gggttctccg   1620
atcctggtta ccctgctgtc tttctactct ttctgcaaac tggaaggtaa cgaactgacc   1680
gcgccgatcg cgttcacctc tatcaccgtt ttcaacgaac tgcgtttcgc gctgaacgtt   1740
ctgccggaag ttttcatcga atggctgcag gcgctgatct ctatccgtcg tatccagacc   1800
tacctggacg aagacgaaat cgaaccgccg tctaacgaag acgaaatcga cccgctgacc   1860
ggtcacatcc cggaacacat caccatcggt ttcaaagacg cgaccgttgg ttggtctaaa   1920
cacaactaca ccgaccaggt taccgacgaa tctgacaaca tcacctctga agcgtcttct   1980
acctctttca tcctgaaaga cctgaacatc gaattcccgc cgaacgaact gtctctgatc   2040
tctggtgcga ccggttctgg taaaaccctg atgatgctgg gtctgctggg tgaagcgatc   2100
gttctgaaag gtaccgcgca ctgcccgcgt caggcggttg ttgacaccgt ttctgacgac   2160
ttcgttacct ctaaagacat cgacccgaaa gactggctgc tgccgtacgc gctggcgtac   2220
gtttctcaga ccgcgtggct gcagaacgcg tctatccgtg acaacatcct gttcggtctg   2280
ccgtacgttg aatctcgtta ccgtgacacc ctgaccgcgt gcgcgctgga caaagacctg   2340
gaaatcctgg aagacggtga ccagaccgaa atcggtgaaa aaggtatcac cctgtctggt   2400
ggtcagaaag cgcgtgtttc tctggcgcgt gcggtttact ctcgtgcgca gaacgttctg   2460
atggacgacg ttctgtctgc ggttgacgcg cacaccgcga aacacctgta cgaaaaatgc   2520
ctgctgggtc cgctgatgaa agaacgtacc cgtgttctga tcacccacca cgttaaactg   2580
tgcgttaaag gttctggtta catcgttcac atcgacgcgg gtcgtgcgtc tctggttggt   2640
accccgaacg aactgcgtca gaacggtcag ctggcgtcta tcttcgaatc tgaagaagaa   2700
gaagttgcgc aggaagaaga cgcggaagaa gaaaaagcga tcgaagaagt tctgccggcg   2760
gttgcgaaca aagacctgaa aaaaccgcgt gcgctggttg aagaagaaac ccgtgcgacc   2820
ggtatggtta aagttcgtct gtacaaactg tacgtttcta tggttggttc tccgttcttc   2880
tggttcgtta tggttgcgct ggttctgggt tctcgtggtc tggacgttat cgaaaactgg   2940
tggatcaaac agtggtctca gtcttaccag accaaacaca acgacaacgc gaccaacaac   3000
gactacatgt tccagcagca gtctatcatc tctcagtcta aaccgatgtt cgcgtaccag   3060
ccggttgttg cgtctgaatc tgacaacgac ctggcgtcta tcatggacgc gaaagacgac   3120
```

```
cgtctgaact actacctggg tatctactgc ctgatcaccc tgaccaacat cgttgttggt   3180
accgcgcgtt tcgcggttct gtactggggt gttctgggtg cgaaccgtgc gctgtacgcg   3240
gaactgctgc accgtgtttt ccgtgcgccg ctgcgtttct tcgacaccac cccgatcggt   3300
cgtatcctga accgtttctc taaagacttc gaaaccatcg actctaacat cccgaacgac   3360
ctgctgaact tcgttatcca gtgggttatc atcgtttctt ctatgatcac cgtttcttct   3420
gttctgccga tcttcctggt tccgatgctg gcggttgcgc tggttaacgt ttacctgggt   3480
atgatgttcg tttctgcgtc tcgtgaactg aaacgtatgg actctgtttc tcgttctccg   3540
ctgttctcta acttcaccga aaccatcatc ggtgttgcga ccatccgtgc gttcggtgcg   3600
acccgtcagt tcctgcagga catgctgacc tacatcgaca ccaacacccg tccgttctac   3660
taccagtggc tggttaaccg ttgggtttct gttcgtttcg cgttctctgg tgcgctgatc   3720
aacatgttca cctctaccat catcctgctg tctgttgaca aaatggacgc gtctctggcg   3780
ggtttctgcc tgtctttcgt tctgctgttc accgaccaga tgttctgggg tatccgtcgt   3840
tacacctctc tggaaatgtc tttcaacgcg gttgaacgtg ttgttgaatt catggaaatg   3900
gaccaggaag cgccggcgat caccgaagtt cgtccgccgc acgaatggcc gacccgtggt   3960
cgtatcgacg ttaaagacct ggaaatcaaa tacgcggcgg acctggaccc ggttctgaaa   4020
ggtatctctt tctctgttaa accgcaggaa aaaatcggtg ttgttggtcg taccggttct   4080
ggtaaatcta ccctggcgct gtctttcttc cgtttcgttg aagcgtctca gggttctatc   4140
gttatcgaca acatcgacat caaagacctg ggtaccgaag acctgcgttc taacctgacc   4200
atcatcccgc aggacccgac cctgttctct ggttctctgc gttctaacat ggacccgttc   4260
gaccagttca ccgaccagga catcttcacc gcgctgcgtc gtgttcacct gctgccgatc   4320
gaagaaggtg acaactctgc ggaaaccgtt gtttctgact ctaccctgga cgaagttaac   4380
gcgaacgttt tcaaagacct gaccaccaac gttaccgaag gtggtaaaaa cttctctcag   4440
ggtcagcgtc agctgctgtg cctggcgcgt gcgctgctga aacgttctcg tatcgttctg   4500
atggacgaag cgaccgcgtc tgttgacttc gaaaccgaca aagcgatcca gaaaaccatc   4560
gcgaccgaat tcgcggactc taccatcctg tgcatcgcgc accgtctgca caccgttatc   4620
gaatacgacc gtatcctggt tctggaccag ggtcagatcc tggaattcga ctctccgctg   4680
accctgatca ccaacccgga atcttctttc tacaaaatgt gccgtaactc tgcgtctcag   4740
aacaaagcgc tggcggcgaa aaaagcggcg ctgaaaggtg ttcacggtaa agcggttcgt   4800
aaaatccgta cctctaccca cttccacatc ccgaaaaccc tggttctgaa ccgtgcgccg   4860
aaatacgcgc gtaaatctgt tgcgcacgcg ccgcgtatgg accagtaccg tgttatccgt   4920
cagccgctga acaccgaaac cgcgatgaaa aaaatcgaag aacacaacac cctgaccttc   4980
ctggttgacg ttaaagcgaa caaaaaccag atcaaagacg cggttaaacg tctgtacgac   5040
gttgaagcgg cgaaaatcaa caccctgatc cgtccggacg gttacaaaaa agcgttcgtt   5100
cgtctgaccg cggacgttga cgcgctggac gttgcgaaca aaatcggttt catc         5154
```

<210> SEQ ID NO 54
<211> LENGTH: 1718
<212> TYPE: PRT
<213> ORGANISM: Artificial Sequence
<220> FEATURE:
<223> OTHER INFORMATION: Depicts the amino acid sequence of ABC Transporter

<400> SEQUENCE: 54

-continued

```
Met Thr Gly Ser Ile Ser Ile Asp Ala Trp Leu Ser Gly Ala Leu Ala
1               5                   10                  15

Leu Val Thr Cys Gly Ser Ala Phe Val Leu Ser Leu Gln Arg Thr Tyr
            20                  25                  30

Leu His Lys Ser Gln Gln Lys Asp Arg Ala Pro Leu Val Phe Asp Lys
        35                  40                  45

Gln Arg Asp Thr Ser Val Pro Val Ala Asp Asp Asp Ala Arg Phe Val
    50                  55                  60

Arg Leu Thr Phe Gly Thr Leu Thr Leu Thr Leu Leu Ser Ala Leu Asp
65                  70                  75                  80

Phe Tyr His Thr Val Ile Gln Gln Gln Gln Gln Thr Ser Asp Trp Trp
                85                  90                  95

Ile Thr Ala Ser Ala Cys Thr Gln Phe Val Ala Trp Leu Tyr Ala Ser
            100                 105                 110

Val Leu Val Leu Val Ala Arg Arg Tyr Arg Phe Pro Ser Glu Trp Gly
        115                 120                 125

Trp Ile Leu Asn Val His Leu Cys Val Phe Tyr Cys Met Ile Trp Cys
    130                 135                 140

Ile Ala Val Tyr Asp Val Tyr Asp Ala Tyr Val Ile Asn Pro Ser Asp
145                 150                 155                 160

Asn Trp Ile His Met Leu Pro Arg Leu Leu Ala Leu Ile Leu Gly Ser
                165                 170                 175

Asp Leu Val Phe Thr Thr Ala Thr Thr Pro Arg Gly Ala Pro Phe Leu
            180                 185                 190

Asp Glu Asn Gly Arg Lys Val Ala Ala Ile Asp Val Ala Ser Ile Tyr
        195                 200                 205

Ser Phe Leu Tyr Phe Ser Trp Val Thr Pro Leu Ile Asn Leu Ala Tyr
    210                 215                 220

Lys Asn Lys Lys Leu Thr Asp Glu Asp Leu Pro Thr Leu Pro Pro Leu
225                 230                 235                 240

Tyr Arg Gly His Asn Leu Tyr Tyr Ile Phe Gly Ala Thr Arg Asn Lys
                245                 250                 255

Ser Leu Leu Lys Arg Ile Tyr Thr Thr Asn Lys Arg Ala Ile Thr Ile
            260                 265                 270

Gln Val Val Leu Ala Phe Thr Thr Ser Leu Val Tyr Tyr Val Pro Ala
        275                 280                 285

Tyr Phe Val Asn Arg Leu Leu Thr Leu Ile Gln Asp Met His Gly Val
    290                 295                 300

Glu Asp Asp Val Ser Ile Arg Lys Gly Phe Val Leu Val Ala Ser Leu
305                 310                 315                 320

Gly Ala Thr Ile Leu Ile Leu Gly Ile Leu Val Gly Gln Leu Trp Tyr
                325                 330                 335

Tyr Ala Ser Ser Ser Leu Gln Val Arg Val Lys Ala Met Leu Asn Ile
            340                 345                 350

Glu Ile Tyr Arg Lys Thr Leu Arg Arg Arg Asp Leu Ala Val Glu Ser
        355                 360                 365

Pro Lys Leu Asp Asp Asp Glu Asp Thr Asp Lys Lys Lys Asp Asp Asp
    370                 375                 380

Glu Ala Ser Asp Lys Lys Gly Glu Ser Asp Glu Lys Glu Asp Val Ser
385                 390                 395                 400

Ser Ser Thr Gly Thr Ile Val Asn Leu Met Ser Thr Asp Ser Asn Arg
                405                 410                 415

Ile Ser Glu Phe Ser Val Trp Trp Phe Ser Ile Leu Ala Ala Pro Thr
```

-continued

```
            420                 425                 430

Glu Leu Ala Val Gly Ile Tyr Phe Leu Tyr Gln Leu Leu Gly Lys Ser
        435                 440                 445

Cys Phe Leu Gly Leu Leu Val Met Ile Val Val Leu Pro Ile Asn His
    450                 455                 460

Tyr Asn Ala Lys Thr Phe Ala Lys Thr Gln Asp Lys Leu Met Glu Ala
465                 470                 475                 480

Arg Asp Lys Arg Val Ser Leu Met Asn Glu Val Leu Gln Gly Ile Arg
                485                 490                 495

Gln Ile Lys Phe Phe Ala Trp Glu Lys Arg Trp Glu Lys Arg Val Met
            500                 505                 510

Glu Ala Arg Glu Val Glu Leu His His Leu Gly Val Thr Tyr Met Thr
        515                 520                 525

Glu Val Leu Phe Thr Leu Leu Trp Gln Gly Ser Pro Ile Leu Val Thr
    530                 535                 540

Leu Leu Ser Phe Tyr Ser Phe Cys Lys Leu Glu Gly Asn Glu Leu Thr
545                 550                 555                 560

Ala Pro Ile Ala Phe Thr Ser Ile Thr Val Phe Asn Glu Leu Arg Phe
                565                 570                 575

Ala Leu Asn Val Leu Pro Glu Val Phe Ile Glu Trp Leu Gln Ala Leu
            580                 585                 590

Ile Ser Ile Arg Arg Ile Gln Thr Tyr Leu Asp Glu Asp Glu Ile Glu
        595                 600                 605

Pro Pro Ser Asn Glu Asp Glu Ile Asp Pro Leu Thr Gly His Ile Pro
    610                 615                 620

Glu His Ile Thr Ile Gly Phe Lys Asp Ala Thr Val Gly Trp Ser Lys
625                 630                 635                 640

His Asn Tyr Thr Asp Gln Val Thr Asp Glu Ser Asp Asn Ile Thr Ser
                645                 650                 655

Glu Ala Ser Ser Thr Ser Phe Ile Leu Lys Asp Leu Asn Ile Glu Phe
            660                 665                 670

Pro Pro Asn Glu Leu Ser Leu Ile Ser Gly Ala Thr Gly Ser Gly Lys
        675                 680                 685

Thr Leu Met Met Leu Gly Leu Leu Gly Glu Ala Ile Val Leu Lys Gly
    690                 695                 700

Thr Ala His Cys Pro Arg Gln Ala Val Val Asp Thr Val Ser Asp Asp
705                 710                 715                 720

Phe Val Thr Ser Lys Asp Ile Asp Pro Lys Asp Trp Leu Leu Pro Tyr
                725                 730                 735

Ala Leu Ala Tyr Val Ser Gln Thr Ala Trp Leu Gln Asn Ala Ser Ile
            740                 745                 750

Arg Asp Asn Ile Leu Phe Gly Leu Pro Tyr Val Glu Ser Arg Tyr Arg
        755                 760                 765

Asp Thr Leu Thr Ala Cys Ala Leu Asp Lys Asp Leu Glu Ile Leu Glu
    770                 775                 780

Asp Gly Asp Gln Thr Glu Ile Gly Glu Lys Gly Ile Thr Leu Ser Gly
785                 790                 795                 800

Gly Gln Lys Ala Arg Val Ser Leu Ala Arg Ala Val Tyr Ser Arg Ala
                805                 810                 815

Gln Asn Val Leu Met Asp Asp Val Leu Ser Ala Val Asp Ala His Thr
            820                 825                 830

Ala Lys His Leu Tyr Glu Lys Cys Leu Leu Gly Pro Leu Met Lys Glu
        835                 840                 845
```

```
Arg Thr Arg Val Leu Ile Thr His His Val Lys Leu Cys Val Lys Gly
    850                 855                 860

Ser Gly Tyr Ile Val His Ile Asp Ala Gly Arg Ala Ser Leu Val Gly
865                 870                 875                 880

Thr Pro Asn Glu Leu Arg Gln Asn Gly Gln Leu Ala Ser Ile Phe Glu
                885                 890                 895

Ser Glu Glu Glu Glu Val Ala Gln Glu Glu Asp Ala Glu Glu Glu Lys
            900                 905                 910

Ala Ile Glu Glu Val Leu Pro Ala Val Ala Asn Lys Asp Leu Lys Lys
        915                 920                 925

Pro Arg Ala Leu Val Glu Glu Glu Thr Arg Ala Thr Gly Met Val Lys
    930                 935                 940

Val Arg Leu Tyr Lys Leu Tyr Val Ser Met Val Gly Ser Pro Phe Phe
945                 950                 955                 960

Trp Phe Val Met Val Ala Leu Val Leu Gly Ser Arg Gly Leu Asp Val
                965                 970                 975

Ile Glu Asn Trp Trp Ile Lys Gln Trp Ser Gln Ser Tyr Gln Thr Lys
            980                 985                 990

His Asn Asp Asn Ala Thr Asn Asn  Asp Tyr Met Phe Gln  Gln Gln Ser
        995                 1000                1005

Ile Ile  Ser Gln Ser Lys Pro  Met Phe Ala Tyr Gln  Pro Val Val
    1010                1015                1020

Ala Ser  Glu Ser Asp Asn Asp  Leu Ala Ser Ile Met  Asp Ala Lys
    1025                1030                1035

Asp Asp  Arg Leu Asn Tyr Tyr  Leu Gly Ile Tyr Cys  Leu Ile Thr
    1040                1045                1050

Leu Thr  Asn Ile Val Val Gly  Thr Ala Arg Phe Ala  Val Leu Tyr
    1055                1060                1065

Trp Gly  Val Leu Gly Ala Asn  Arg Ala Leu Tyr Ala  Glu Leu Leu
    1070                1075                1080

His Arg  Val Phe Arg Ala Pro  Leu Arg Phe Phe Asp  Thr Thr Pro
    1085                1090                1095

Ile Gly  Arg Ile Leu Asn Arg  Phe Ser Lys Asp Phe  Glu Thr Ile
    1100                1105                1110

Asp Ser  Asn Ile Pro Asn Asp  Leu Leu Asn Phe Val  Ile Gln Trp
    1115                1120                1125

Val Ile  Ile Val Ser Ser Met  Ile Thr Val Ser Ser  Val Leu Pro
    1130                1135                1140

Ile Phe  Leu Val Pro Met Leu  Ala Val Ala Leu Val  Asn Val Tyr
    1145                1150                1155

Leu Gly  Met Met Phe Val Ser  Ala Ser Arg Glu Leu  Lys Arg Met
    1160                1165                1170

Asp Ser  Val Ser Arg Ser Pro  Leu Phe Ser Asn Phe  Thr Glu Thr
    1175                1180                1185

Ile Ile  Gly Val Ala Thr Ile  Arg Ala Phe Gly Ala  Thr Arg Gln
    1190                1195                1200

Phe Leu  Gln Asp Met Leu Thr  Tyr Ile Asp Thr Asn  Thr Arg Pro
    1205                1210                1215

Phe Tyr  Tyr Gln Trp Leu Val  Asn Arg Trp Val Ser  Val Arg Phe
    1220                1225                1230

Ala Phe  Ser Gly Ala Leu Ile  Asn Met Phe Thr Ser  Thr Ile Ile
    1235                1240                1245
```

-continued

```
Leu Leu  Ser Val Asp Lys Met  Asp Ala Ser Leu Ala  Gly Phe Cys
    1250                 1255                 1260

Leu Ser  Phe Val Leu Leu Phe  Thr Asp Gln Met Phe  Trp Gly Ile
    1265                 1270                 1275

Arg Arg  Tyr Thr Ser Leu Glu  Met Ser Phe Asn Ala  Val Glu Arg
    1280                 1285                 1290

Val Val  Glu Phe Met Glu Met  Asp Gln Glu Ala Pro  Ala Ile Thr
    1295                 1300                 1305

Glu Val  Arg Pro Pro His Glu  Trp Pro Thr Arg Gly  Arg Ile Asp
    1310                 1315                 1320

Val Lys  Asp Leu Glu Ile Lys  Tyr Ala Ala Asp Leu  Asp Pro Val
    1325                 1330                 1335

Leu Lys  Gly Ile Ser Phe Ser  Val Lys Pro Gln Glu  Lys Ile Gly
    1340                 1345                 1350

Val Val  Gly Arg Thr Gly Ser  Gly Lys Ser Thr Leu  Ala Leu Ser
    1355                 1360                 1365

Phe Phe  Arg Phe Val Glu Ala  Ser Gln Gly Ser Ile  Val Ile Asp
    1370                 1375                 1380

Asn Ile  Asp Ile Lys Asp Leu  Gly Thr Glu Asp Leu  Arg Ser Asn
    1385                 1390                 1395

Leu Thr  Ile Ile Pro Gln Asp  Pro Thr Leu Phe Ser  Gly Ser Leu
    1400                 1405                 1410

Arg Ser  Asn Met Asp Pro Phe  Asp Gln Phe Thr Asp  Gln Asp Ile
    1415                 1420                 1425

Phe Thr  Ala Leu Arg Arg Val  His Leu Leu Pro Ile  Glu Glu Gly
    1430                 1435                 1440

Asp Asn  Ser Ala Glu Thr Val  Val Ser Asp Ser Thr  Leu Asp Glu
    1445                 1450                 1455

Val Asn  Ala Asn Val Phe Lys  Asp Leu Thr Thr Asn  Val Thr Glu
    1460                 1465                 1470

Gly Gly  Lys Asn Phe Ser Gln  Gly Gln Arg Gln Leu  Leu Cys Leu
    1475                 1480                 1485

Ala Arg  Ala Leu Leu Lys Arg  Ser Arg Ile Val Leu  Met Asp Glu
    1490                 1495                 1500

Ala Thr  Ala Ser Val Asp Phe  Glu Thr Asp Lys Ala  Ile Gln Lys
    1505                 1510                 1515

Thr Ile  Ala Thr Glu Phe Ala  Asp Ser Thr Ile Leu  Cys Ile Ala
    1520                 1525                 1530

His Arg  Leu His Thr Val Ile  Glu Tyr Asp Arg Ile  Leu Val Leu
    1535                 1540                 1545

Asp Gln  Gly Gln Ile Leu Glu  Phe Asp Ser Pro Leu  Thr Leu Ile
    1550                 1555                 1560

Thr Asn  Pro Glu Ser Ser Phe  Tyr Lys Met Cys Arg  Asn Ser Ala
    1565                 1570                 1575

Ser Gln  Asn Lys Ala Leu Ala  Ala Lys Lys Ala Ala  Leu Lys Gly
    1580                 1585                 1590

Val His  Gly Lys Ala Val Arg  Lys Ile Arg Thr Ser  Thr His Phe
    1595                 1600                 1605

His Ile  Pro Lys Thr Leu Val  Leu Asn Arg Ala Pro  Lys Tyr Ala
    1610                 1615                 1620

Arg Lys  Ser Val Ala His Ala  Pro Arg Met Asp Gln  Tyr Arg Val
    1625                 1630                 1635

Ile Arg  Gln Pro Leu Asn Thr  Glu Thr Ala Met Lys  Lys Ile Glu
```

```
    1640                1645                1650

Glu His  Asn Thr Leu Thr Phe  Leu Val Asp Val Lys  Ala Asn Lys
    1655                1660                1665

Asn Gln  Ile Lys Asp Ala Val  Lys Arg Leu Tyr Asp  Val Glu Ala
    1670                1675                1680

Ala Lys  Ile Asn Thr Leu Ile  Arg Pro Asp Gly Tyr  Lys Lys Ala
    1685                1690                1695

Phe Val  Arg Leu Thr Ala Asp  Val Asp Ala Leu Asp  Val Ala Asn
    1700                1705                1710

Lys Ile  Gly Phe Ile
    1715


<210> SEQ ID NO 55
<211> LENGTH: 4395
<212> TYPE: DNA
<213> ORGANISM: Artificial Sequence
<220> FEATURE:
<223> OTHER INFORMATION: Depicts the nucleic acid sequence of ABC
      Transporter gene

<400> SEQUENCE: 55

atgtctgaac agcgtgacgg tatccgtcgt accgcgtctg gtcgtgaaac ctacgaaccg     60

gacggtctgc cggaccacgg tgttgaaccg cgtgaagacg ttgaagaaaa aaccttcgtt    120

gaagaagaag acgactctaa agaatacatg ccgatccgta ccggtgcgcg tcacgcggcg    180

tctgacacct ctatgaccga cgttgaaaac gaacgtttcg acctgtacaa atggctgcgt    240

ttcttcatgc gttctatgga cgaatctgac atcaaagttt ctcgtgcggg tgttctgttc    300

cgtaacctga acgtttctgg ttctggttct gcgctgaacc tgcagaaaaa cgttggttct    360

atcctgatga ccccgttccg tctgcaggaa tacctgggtc tgggtcagaa aaacgaaaaa    420

cgtatcctga aaaacttcga cggtctgctg aaatctggtg aactgctgat cgttctgggt    480

cgtccgggtt ctggttgctc taccctgctg aaaaccatct gcggtgaact gcacggtctg    540

gcgctggacg gtgactctac catcaactac aacggtatcc cgcagcgtca gatgctgaaa    600

gaattcaaag gtgaagttgt ttacaaccag gaagttgaca aacacttccc gcacctgacc    660

gttggtcaga ccctggaaat ggcggcggcg taccgtaccc cgtctaaccg tatcgaaggt    720

cagacccgtg aagacgcgat caaaatggcg gcgcgtgttg ttatggcggt tttcggtctg    780

tctcacacct acaacaccaa agttggtaac gacttcatcc gtggtgtttc tggtggtgaa    840

cgtaaacgtg tttctatcgc ggaaatggcg ctgtctgcgg cgccgatcgc ggcgtgggac    900

aactctaccc gtggtctgga cgcggcgacc gcgctggaat tcgttaaagc gctgcgtatc    960

atgtctgacc tggcgggtgc ggcgcaggcg gttgcgatct accaggcgtc tcaggcgatc   1020

tacgacgttt tcgacaaagc ggttgttctg tacgaaggtc gtcagatcta cttcggtccg   1080

accggtgcgg cgaaacagtt cttcgaagaa cagggttggt actgcccgcc gcgtcagacc   1140

accggtgact tcctgacctc tgttaccaac ccgggtgaac gtcagccgcg taaaggtatg   1200

gaaaacaaag ttccgcgtac cccggacgaa ttcgaagcgt actggcgtca gtctgcggcg   1260

tacaaagcgc tgcaggcgga aatcgacgaa cacgaacagg aattcccggt tggtggtgaa   1320

gttgtttctc agttccagga aaacaaacgt ctggcgcagt ctaaacactc tcgtccgacc   1380

tctccgtacc tgctgtctgt tccgatgcag gttaaactga acaccaaacg tgcgtaccag   1440

cgtatctgga acgacaaagc ggcgaccctg accatggttc tgtctcagat catccaggcg   1500

ctgatcatcg gttctctgtt ctacggtacc ccggcggcga cccagggttt cttctctcgt   1560
```

-continued

```
aacgcggcga tcttcttcgg tgttctgctg aacgcgctgg ttgcgatcgc ggaaatcaac   1620
gcgctgtacg accagcgtcc gatcgttgaa aaacacgcgt cttacgcgtt ctaccacccg   1680
ttcaccgaag cggttgcggg tgttgttgcg gacatcccgg ttaaattcgc gatggcgacc   1740
tgcttcaacc tgatctacta cttcatgacc ggtttccgtc gtgaaccgtc tcagttcttc   1800
atctacttcc tgatctcttt catcgcgatg ttcgttatgt ctgcggtttt ccgtaccatg   1860
gcggcgatca ccaaaaccgt ttctcaggcg atgatgttcg cgggtgttct ggttctggcg   1920
atcgttgttt acaccggttt cgcgatcccg gaatcttaca tggttgactg gttcggttgg   1980
atccgttgga tcaacccgat cttctacgcg ttcgaaatcc tgatcgcgaa cgaataccac   2040
ggtcgtgaat tcacctgctc tggtttcatc ccggcgtacc cgaacctgga aggtgactct   2100
ttcatctgca acatgcgtgg tgcggttgcg ggtgaacgta ccgtttctgg tgacgactac   2160
atctgggcga actacaaata ctcttactct cacgtttggc gtaacttcgg tatcctgctg   2220
gcgttcctgt tcttcttcat gttcatctac ttcctggcgg ttgaactgaa ctcttctacc   2280
acctctaccg cggaagttct ggttttccgt cgtggtcacg ttccggcgta catgaccgaa   2340
aacccgaaag gtaacgcgaa cgacgaagaa atcgcggcgc cggacgcggc gggtcgtgcg   2400
ggtgcggaag gtggtgacgt taacatgatc ccggcgcaga aagacatctt cacctggcgt   2460
gacgttgttt acgacatcga aatcaaaggt gaaccgcgtc gtctgctgga ccacgtttct   2520
ggttgggtta aaccgggtac cctgaccgcg ctgatgggtg tttctggtgc gggtaaaacc   2580
accctgctgg acgttctggc gcagcgtacc tctatgggtg ttatcaccgg tgacatgctg   2640
gttaacggtc gtccgctgga ctcttctttc cagcgtaaaa ccggttacgt tcagcagcag   2700
gacctgcacc tggcgaccgc gaccgttcgt gaatctctgc gtttctctgc gatgctgcgt   2760
cagccgaaaa acgtttctac cgaagaaaaa tacacctacg ttgaagacgt tatcaaaatg   2820
ctgaacatgg aagacttcgc ggaagcggtt gttggtgttc cgggtgaagg tctgaacgtt   2880
gaacagcgta aactgctgac catcggtgtt gaactggcgg cgaaaccgaa actgctgctg   2940
ttcctggacg aaccgacctc tggtctggac tctcagtctt cttgggcgat ctgcgcgttc   3000
ctgcgtaaac tggcgaactc tggtcaggcg atcctgtgca ccatccacca gccgtctgcg   3060
atcctgttcc aggaattcga ccgtctgctg ttcctggcga aaggtggtcg taccgtttac   3120
ttcggtgaca tcggtaccaa ctctcgtacc ctgctggact actacgaacg taacggttct   3180
cgtaaatgcg gtgacgacga aaacccggcg gaattcatgc tggaaatcgt tggtgcgggt   3240
gcgtctggta aagcgaccca ggactggcac gaagtttgga aaaactctaa cgaagcgcgt   3300
gcggttcagg acgaactgga ccgtatccac cgtgaaaaac agaacgaacc ggcggcgggt   3360
gacgacgaag ttggtggtac cgacgaattc gcgatgccgt tcacccagca gctgtaccac   3420
gttacctacc gtgttttcca gcagtactgg cgtatgccgg gttacatctg ggcgaaaatg   3480
ctgctgggtt tcgcgtctgc gttcttcatc ggtttctctt tctgggactc tgactcttct   3540
cagcagggta tgcagaacgt tatctactct gttttcatgg ttgcggcgat cttctctacc   3600
atcgttgaac agatcatgcc gctgttcctg acccagcgtt ctctgtacga agttcgtgaa   3660
cgtccgtcta aagcgtactc ttggaaagcg ttcctgatcg cgaacatctc tgttgaaatc   3720
ccgtaccaga tcctggttgg tatcatcgtt tacgcgtctt actactacgc ggttaacggt   3780
gttcagtctt ctgaccgtca gggtctggtt ctgctgtact gcgttcagtt cttcatctac   3840
gcgtctacct tcgcgcacat gtgcatcgcg gcggcgccgg acgcggaaac cgcggcgggt   3900
```

-continued

```
atcgttaccc tgctgttctc tatgatgatc gcgttcaacg gtgttatgca gccgccgcag   3960

gcgctgccgg gtttctggat cttcatgtac cgtgtttctc cgctgaccta ctggatctct   4020

ggtatcgttg cgaccgaact gcacgaccgt ccggttcagt gcaccgcggt tgaaacctct   4080

accttcaacc cgccgtctgg tcagacctgc cagcagtacc tgggtgaatt cctgcgtgcg   4140

gcgggtggta acctgcagaa cccggcggac accgcggact gccgttactg ctctatcacc   4200

gttgcggacg aatacatcgg tggttctaaa atcttctgga ccgaccgttg gcgtaacttc   4260

ggtctggttt gggcgtacgt tgttttcaac atcttcgcgg cgaccatgct gtactacctg   4320

ttccgtgttc gtaaatcttc tggtaaaggt ctgaaagaac gtgttgcggg tctgttcggt   4380

ggtaaaaaaa aacag                                                    4395


<210> SEQ ID NO 56
<211> LENGTH: 1465
<212> TYPE: PRT
<213> ORGANISM: Artificial Sequence
<220> FEATURE:
<223> OTHER INFORMATION: Depicts the amino acid sequence of ABC
      Transporter

<400> SEQUENCE: 56

Met Ser Glu Gln Arg Asp Gly Ile Arg Arg Thr Ala Ser Gly Arg Glu
1               5                   10                  15

Thr Tyr Glu Pro Asp Gly Leu Pro Asp His Gly Val Glu Pro Arg Glu
            20                  25                  30

Asp Val Glu Glu Lys Thr Phe Val Glu Glu Glu Asp Asp Ser Lys Glu
        35                  40                  45

Tyr Met Pro Ile Arg Thr Gly Ala Arg His Ala Ala Ser Asp Thr Ser
    50                  55                  60

Met Thr Asp Val Glu Asn Glu Arg Phe Asp Leu Tyr Lys Trp Leu Arg
65                  70                  75                  80

Phe Phe Met Arg Ser Met Asp Glu Ser Asp Ile Lys Val Ser Arg Ala
                85                  90                  95

Gly Val Leu Phe Arg Asn Leu Asn Val Ser Gly Ser Gly Ser Ala Leu
            100                 105                 110

Asn Leu Gln Lys Asn Val Gly Ser Ile Leu Met Thr Pro Phe Arg Leu
        115                 120                 125

Gln Glu Tyr Leu Gly Leu Gly Gln Lys Asn Glu Lys Arg Ile Leu Lys
    130                 135                 140

Asn Phe Asp Gly Leu Leu Lys Ser Gly Glu Leu Leu Ile Val Leu Gly
145                 150                 155                 160

Arg Pro Gly Ser Gly Cys Ser Thr Leu Leu Lys Thr Ile Cys Gly Glu
                165                 170                 175

Leu His Gly Leu Ala Leu Asp Gly Asp Ser Thr Ile Asn Tyr Asn Gly
            180                 185                 190

Ile Pro Gln Arg Gln Met Leu Lys Glu Phe Lys Gly Glu Val Val Tyr
        195                 200                 205

Asn Gln Glu Val Asp Lys His Phe Pro His Leu Thr Val Gly Gln Thr
    210                 215                 220

Leu Glu Met Ala Ala Ala Tyr Arg Thr Pro Ser Asn Arg Ile Glu Gly
225                 230                 235                 240

Gln Thr Arg Glu Asp Ala Ile Lys Met Ala Ala Arg Val Val Met Ala
                245                 250                 255

Val Phe Gly Leu Ser His Thr Tyr Asn Thr Lys Val Gly Asn Asp Phe
            260                 265                 270
```

-continued

Ile Arg Gly Val Ser Gly Gly Glu Arg Lys Arg Val Ser Ile Ala Glu
275 280 285

Met Ala Leu Ser Ala Ala Pro Ile Ala Ala Trp Asp Asn Ser Thr Arg
290 295 300

Gly Leu Asp Ala Ala Thr Ala Leu Glu Phe Val Lys Ala Leu Arg Ile
305 310 315 320

Met Ser Asp Leu Ala Gly Ala Ala Gln Ala Val Ala Ile Tyr Gln Ala
325 330 335

Ser Gln Ala Ile Tyr Asp Val Phe Asp Lys Ala Val Val Leu Tyr Glu
340 345 350

Gly Arg Gln Ile Tyr Phe Gly Pro Thr Gly Ala Ala Lys Gln Phe Phe
355 360 365

Glu Glu Gln Gly Trp Tyr Cys Pro Pro Arg Gln Thr Thr Gly Asp Phe
370 375 380

Leu Thr Ser Val Thr Asn Pro Gly Glu Arg Gln Pro Arg Lys Gly Met
385 390 395 400

Glu Asn Lys Val Pro Arg Thr Pro Asp Glu Phe Glu Ala Tyr Trp Arg
405 410 415

Gln Ser Ala Ala Tyr Lys Ala Leu Gln Ala Glu Ile Asp Glu His Glu
420 425 430

Gln Glu Phe Pro Val Gly Gly Glu Val Val Ser Gln Phe Gln Glu Asn
435 440 445

Lys Arg Leu Ala Gln Ser Lys His Ser Arg Pro Thr Ser Pro Tyr Leu
450 455 460

Leu Ser Val Pro Met Gln Val Lys Leu Asn Thr Lys Arg Ala Tyr Gln
465 470 475 480

Arg Ile Trp Asn Asp Lys Ala Ala Thr Leu Thr Met Val Leu Ser Gln
485 490 495

Ile Ile Gln Ala Leu Ile Ile Gly Ser Leu Phe Tyr Gly Thr Pro Ala
500 505 510

Ala Thr Gln Gly Phe Phe Ser Arg Asn Ala Ala Ile Phe Phe Gly Val
515 520 525

Leu Leu Asn Ala Leu Val Ala Ile Ala Glu Ile Asn Ala Leu Tyr Asp
530 535 540

Gln Arg Pro Ile Val Glu Lys His Ala Ser Tyr Ala Phe Tyr His Pro
545 550 555 560

Phe Thr Glu Ala Val Ala Gly Val Val Ala Asp Ile Pro Val Lys Phe
565 570 575

Ala Met Ala Thr Cys Phe Asn Leu Ile Tyr Tyr Phe Met Thr Gly Phe
580 585 590

Arg Arg Glu Pro Ser Gln Phe Phe Ile Tyr Phe Leu Ile Ser Phe Ile
595 600 605

Ala Met Phe Val Met Ser Ala Val Phe Arg Thr Met Ala Ala Ile Thr
610 615 620

Lys Thr Val Ser Gln Ala Met Met Phe Ala Gly Val Leu Val Leu Ala
625 630 635 640

Ile Val Val Tyr Thr Gly Phe Ala Ile Pro Glu Ser Tyr Met Val Asp
645 650 655

Trp Phe Gly Trp Ile Arg Trp Ile Asn Pro Ile Phe Tyr Ala Phe Glu
660 665 670

Ile Leu Ile Ala Asn Glu Tyr His Gly Arg Glu Phe Thr Cys Ser Gly
675 680 685

```
Phe Ile Pro Ala Tyr Pro Asn Leu Glu Gly Asp Ser Phe Ile Cys Asn
    690                 695                 700

Met Arg Gly Ala Val Ala Gly Glu Arg Thr Val Ser Gly Asp Asp Tyr
705                 710                 715                 720

Ile Trp Ala Asn Tyr Lys Tyr Ser Tyr Ser His Val Trp Arg Asn Phe
                725                 730                 735

Gly Ile Leu Leu Ala Phe Leu Phe Phe Phe Met Phe Ile Tyr Phe Leu
            740                 745                 750

Ala Val Glu Leu Asn Ser Ser Thr Thr Ser Thr Ala Glu Val Leu Val
        755                 760                 765

Phe Arg Arg Gly His Val Pro Ala Tyr Met Thr Glu Asn Pro Lys Gly
    770                 775                 780

Asn Ala Asn Asp Glu Glu Ile Ala Ala Pro Asp Ala Ala Gly Arg Ala
785                 790                 795                 800

Gly Ala Glu Gly Gly Asp Val Asn Met Ile Pro Ala Gln Lys Asp Ile
                805                 810                 815

Phe Thr Trp Arg Asp Val Val Tyr Asp Ile Glu Ile Lys Gly Glu Pro
            820                 825                 830

Arg Arg Leu Leu Asp His Val Ser Gly Trp Val Lys Pro Gly Thr Leu
        835                 840                 845

Thr Ala Leu Met Gly Val Ser Gly Ala Gly Lys Thr Thr Leu Leu Asp
    850                 855                 860

Val Leu Ala Gln Arg Thr Ser Met Gly Val Ile Thr Gly Asp Met Leu
865                 870                 875                 880

Val Asn Gly Arg Pro Leu Asp Ser Ser Phe Gln Arg Lys Thr Gly Tyr
                885                 890                 895

Val Gln Gln Gln Asp Leu His Leu Ala Thr Ala Thr Val Arg Glu Ser
            900                 905                 910

Leu Arg Phe Ser Ala Met Leu Arg Gln Pro Lys Asn Val Ser Thr Glu
        915                 920                 925

Glu Lys Tyr Thr Tyr Val Glu Asp Val Ile Lys Met Leu Asn Met Glu
    930                 935                 940

Asp Phe Ala Glu Ala Val Val Gly Val Pro Gly Glu Gly Leu Asn Val
945                 950                 955                 960

Glu Gln Arg Lys Leu Leu Thr Ile Gly Val Glu Leu Ala Ala Lys Pro
                965                 970                 975

Lys Leu Leu Leu Phe Leu Asp Glu Pro Thr Ser Gly Leu Asp Ser Gln
            980                 985                 990

Ser Ser Trp Ala Ile Cys Ala Phe  Leu Arg Lys Leu Ala  Asn Ser Gly
        995                 1000                 1005

Gln Ala  Ile Leu Cys Thr Ile  His Gln Pro Ser Ala  Ile Leu Phe
    1010                 1015                 1020

Gln Glu  Phe Asp Arg Leu Leu  Phe Leu Ala Lys Gly  Gly Arg Thr
    1025                 1030                 1035

Val Tyr  Phe Gly Asp Ile Gly  Thr Asn Ser Arg Thr  Leu Leu Asp
    1040                 1045                 1050

Tyr Tyr  Glu Arg Asn Gly Ser  Arg Lys Cys Gly Asp  Asp Glu Asn
    1055                 1060                 1065

Pro Ala  Glu Phe Met Leu Glu  Ile Val Gly Ala Gly  Ala Ser Gly
    1070                 1075                 1080

Lys Ala  Thr Gln Asp Trp His  Glu Val Trp Lys Asn  Ser Asn Glu
    1085                 1090                 1095

Ala Arg  Ala Val Gln Asp Glu  Leu Asp Arg Ile His  Arg Glu Lys
```

```
    1100                1105                1110

Gln Asn  Glu Pro Ala Ala Gly  Asp Asp Glu Val Gly  Gly Thr Asp
    1115                1120                1125

Glu Phe  Ala Met Pro Phe Thr  Gln Gln Leu Tyr His  Val Thr Tyr
    1130                1135                1140

Arg Val  Phe Gln Gln Tyr Trp  Arg Met Pro Gly Tyr  Ile Trp Ala
    1145                1150                1155

Lys Met  Leu Leu Gly Phe Ala  Ser Ala Phe Phe Ile  Gly Phe Ser
    1160                1165                1170

Phe Trp  Asp Ser Asp Ser Ser  Gln Gln Gly Met Gln  Asn Val Ile
    1175                1180                1185

Tyr Ser  Val Phe Met Val Ala  Ala Ile Phe Ser Thr  Ile Val Glu
    1190                1195                1200

Gln Ile  Met Pro Leu Phe Leu  Thr Gln Arg Ser Leu  Tyr Glu Val
    1205                1210                1215

Arg Glu  Arg Pro Ser Lys Ala  Tyr Ser Trp Lys Ala  Phe Leu Ile
    1220                1225                1230

Ala Asn  Ile Ser Val Glu Ile  Pro Tyr Gln Ile Leu  Val Gly Ile
    1235                1240                1245

Ile Val  Tyr Ala Ser Tyr Tyr  Tyr Ala Val Asn Gly  Val Gln Ser
    1250                1255                1260

Ser Asp  Arg Gln Gly Leu Val  Leu Leu Tyr Cys Val  Gln Phe Phe
    1265                1270                1275

Ile Tyr  Ala Ser Thr Phe Ala  His Met Cys Ile Ala  Ala Ala Pro
    1280                1285                1290

Asp Ala  Glu Thr Ala Ala Gly  Ile Val Thr Leu Leu  Phe Ser Met
    1295                1300                1305

Met Ile  Ala Phe Asn Gly Val  Met Gln Pro Pro Gln  Ala Leu Pro
    1310                1315                1320

Gly Phe  Trp Ile Phe Met Tyr  Arg Val Ser Pro Leu  Thr Tyr Trp
    1325                1330                1335

Ile Ser  Gly Ile Val Ala Thr  Glu Leu His Asp Arg  Pro Val Gln
    1340                1345                1350

Cys Thr  Ala Val Glu Thr Ser  Thr Phe Asn Pro Pro  Ser Gly Gln
    1355                1360                1365

Thr Cys  Gln Gln Tyr Leu Gly  Glu Phe Leu Arg Ala  Ala Gly Gly
    1370                1375                1380

Asn Leu  Gln Asn Pro Ala Asp  Thr Ala Asp Cys Arg  Tyr Cys Ser
    1385                1390                1395

Ile Thr  Val Ala Asp Glu Tyr  Ile Gly Gly Ser Lys  Ile Phe Trp
    1400                1405                1410

Thr Asp  Arg Trp Arg Asn Phe  Gly Leu Val Trp Ala  Tyr Val Val
    1415                1420                1425

Phe Asn  Ile Phe Ala Ala Thr  Met Leu Tyr Tyr Leu  Phe Arg Val
    1430                1435                1440

Arg Lys  Ser Ser Gly Lys Gly  Leu Lys Glu Arg Val  Ala Gly Leu
    1445                1450                1455

Phe Gly  Gly Lys Lys Lys Gln
    1460                1465
```

<210> SEQ ID NO 57
<211> LENGTH: 1725
<212> TYPE: DNA
<213> ORGANISM: Artificial Sequence
<220> FEATURE:
<223> OTHER INFORMATION: Depicts the nucleic acid sequence of ABC
transporter gene

<400> SEQUENCE: 57
atgcactggc tgaaaaacga acactgggtt cgtccggacc tgaaacgtta ccgtggtctg 60
ctgttctggt ctctgatcct gggtgttatg accttcgttt tcgcgggtgc gctgatgttc 120
acctctggtt tcctgatcga caaatctgcg accaaaccgc tgttcgcggc gatctacgtt 180
accgttgttc tgacccgtgc gttcggtatc ggtcgtccgg ttttccagta catcgaacgt 240
ctgacctctc acaactgggt tctgcgtatc acctctcaca tgcgtcgtaa actgtacaaa 300
gttctggaaa ccgacgcggc gttcgtttct gaacaccacc agaccggtga catcctgggt 360
ctgctggcgg acgacatcgg tcacatccag aacctgtacc tgcgtatgat cttcccgacc 420
gttgttggtg cgggtctgac cgttatcgcg accctgctgc tgggttggtt caactggggt 480
ttcgcgctgt ggatcatgct gctgctgctg ttccaggttc tgatcctgcc gtggtggggt 540
ctggttgttg aacgtttccg taaagcggaa cagaaacagc tgaaccacga cgcgtacgtt 600
tctctgaccg actctgttct gggtctgtct gactgggtta tcacccaccg tgaaaaagac 660
ttcatgtctc agtctctggc ggcgccgaaa aaactggcgg cgtctaccgt taaatctaaa 720
cgtttccagt ggcgtcgtga cttcgttggt cagctgctgt tcgttctgat cgttatctct 780
atgctgatct ggaccaacct ggaatggacc ggtaaccagg cgtctgcgaa ctgggttggt 840
gcgttcgttc tggttgtttt cccgctggac caggcgttct ctggtatcgc gcagggtgtt 900
ggtgaatggc cgacctaccg tgacgcgatc cgtcacctga acgacctgca gccggttacc 960
cgtcagctgc cgcagcagca ggcggttccg acccagttca aagaaatgac cctgcagcac 1020
ctgtctttcc agtacacccc gaaagacccg gaactgatca ccgacatcga cctgaccgtt 1080
cactctggtg aaaaaatcgc gatcctgggt ccgtctggta tgggtaaaac caccctgctg 1140
cagctggttc tgggtgacct gaccccgacc accggtaacg ttctggttga cggtcaggac 1200
gttctgacct accagcagca ccgtaccaac ctgttcgcgg ttctggacca gtctccgttc 1260
ctgttcaaca cctctatcgt taacaacgtt cgtctgggta acgaacaggc gtctgacgcg 1320
gacgttgcgg cggcgctgaa agcggttaaa ctggaccagc tggttgcgca gctgccgaac 1380
ggtatcaact cttctgttga agaagcgggt ttcggtttct ctggtggtga acgtcagcgt 1440
ctgtctctgg cgcgtatcct gctgcaggac gcgccgatcg ttctgctgga cgaaccgacc 1500
gttggtctgg acccgatcac cgaacaggcg ctgctggaaa ccatgttcac cgttctgcag 1560
ggtaaaacca tcctgtgggt tacccaccac ctgcagggtg ttaaccagac cgaccgtgtt 1620
atcttcctgg aagacggtcg tctgaccatg aacgacaccc cgtctcacct ggcgaaacac 1680
gacgaacgtt accagaacct gtacgcgctg gacgcgggtc tgcgt 1725

<210> SEQ ID NO 58
<211> LENGTH: 575
<212> TYPE: PRT
<213> ORGANISM: Artificial Sequence
<220> FEATURE:
<223> OTHER INFORMATION: Depicts the amino acid sequence of ABC
Transporter

<400> SEQUENCE: 58

Met His Trp Leu Lys Asn Glu His Trp Val Arg Pro Asp Leu Lys Arg
1 5 10 15

Tyr Arg Gly Leu Leu Phe Trp Ser Leu Ile Leu Gly Val Met Thr Phe

```
            20                  25                  30

Val Phe Ala Gly Ala Leu Met Phe Thr Ser Gly Phe Leu Ile Asp Lys
        35                  40                  45

Ser Ala Thr Lys Pro Leu Phe Ala Ala Ile Tyr Val Thr Val Val Leu
    50                  55                  60

Thr Arg Ala Phe Gly Ile Gly Arg Pro Val Phe Gln Tyr Ile Glu Arg
65                  70                  75                  80

Leu Thr Ser His Asn Trp Val Leu Arg Ile Thr Ser His Met Arg Arg
                85                  90                  95

Lys Leu Tyr Lys Val Leu Glu Thr Asp Ala Ala Phe Val Ser Glu His
            100                 105                 110

His Gln Thr Gly Asp Ile Leu Gly Leu Leu Ala Asp Asp Ile Gly His
        115                 120                 125

Ile Gln Asn Leu Tyr Leu Arg Met Ile Phe Pro Thr Val Val Gly Ala
    130                 135                 140

Gly Leu Thr Val Ile Ala Thr Leu Leu Leu Gly Trp Phe Asn Trp Gly
145                 150                 155                 160

Phe Ala Leu Trp Ile Met Leu Leu Leu Leu Phe Gln Val Leu Ile Leu
                165                 170                 175

Pro Trp Trp Gly Leu Val Val Glu Arg Phe Arg Lys Ala Glu Gln Lys
            180                 185                 190

Gln Leu Asn His Asp Ala Tyr Val Ser Leu Thr Asp Ser Val Leu Gly
        195                 200                 205

Leu Ser Asp Trp Val Ile Thr His Arg Glu Lys Asp Phe Met Ser Gln
    210                 215                 220

Ser Leu Ala Ala Pro Lys Lys Leu Ala Ala Ser Thr Val Lys Ser Lys
225                 230                 235                 240

Arg Phe Gln Trp Arg Arg Asp Phe Val Gly Gln Leu Leu Phe Val Leu
                245                 250                 255

Ile Val Ile Ser Met Leu Ile Trp Thr Asn Leu Glu Trp Thr Gly Asn
            260                 265                 270

Gln Ala Ser Ala Asn Trp Val Gly Ala Phe Val Leu Val Val Phe Pro
        275                 280                 285

Leu Asp Gln Ala Phe Ser Gly Ile Ala Gln Gly Val Gly Glu Trp Pro
    290                 295                 300

Thr Tyr Arg Asp Ala Ile Arg His Leu Asn Asp Leu Gln Pro Val Thr
305                 310                 315                 320

Arg Gln Leu Pro Gln Gln Gln Ala Val Pro Thr Gln Phe Lys Glu Met
                325                 330                 335

Thr Leu Gln His Leu Ser Phe Gln Tyr Thr Pro Lys Asp Pro Glu Leu
            340                 345                 350

Ile Thr Asp Ile Asp Leu Thr Val His Ser Gly Glu Lys Ile Ala Ile
        355                 360                 365

Leu Gly Pro Ser Gly Met Gly Lys Thr Thr Leu Leu Gln Leu Val Leu
    370                 375                 380

Gly Asp Leu Thr Pro Thr Thr Gly Asn Val Leu Val Asp Gly Gln Asp
385                 390                 395                 400

Val Leu Thr Tyr Gln Gln His Arg Thr Asn Leu Phe Ala Val Leu Asp
                405                 410                 415

Gln Ser Pro Phe Leu Phe Asn Thr Ser Ile Val Asn Asn Val Arg Leu
            420                 425                 430

Gly Asn Glu Gln Ala Ser Asp Ala Asp Val Ala Ala Ala Leu Lys Ala
        435                 440                 445
```

-continued

Val Lys Leu Asp Gln Leu Val Ala Gln Leu Pro Asn Gly Ile Asn Ser
    450                 455                 460

Ser Val Glu Glu Ala Gly Phe Gly Phe Ser Gly Gly Glu Arg Gln Arg
465                 470                 475                 480

Leu Ser Leu Ala Arg Ile Leu Leu Gln Asp Ala Pro Ile Val Leu Leu
                485                 490                 495

Asp Glu Pro Thr Val Gly Leu Asp Pro Ile Thr Glu Gln Ala Leu Leu
            500                 505                 510

Glu Thr Met Phe Thr Val Leu Gln Gly Lys Thr Ile Leu Trp Val Thr
        515                 520                 525

His His Leu Gln Gly Val Asn Gln Thr Asp Arg Val Ile Phe Leu Glu
    530                 535                 540

Asp Gly Arg Leu Thr Met Asn Asp Thr Pro Ser His Leu Ala Lys His
545                 550                 555                 560

Asp Glu Arg Tyr Gln Asn Leu Tyr Ala Leu Asp Ala Gly Leu Arg
                565                 570                 575

<210> SEQ ID NO 59
<211> LENGTH: 318
<212> TYPE: DNA
<213> ORGANISM: Artificial Sequence
<220> FEATURE:
<223> OTHER INFORMATION: Depicts the nucleic acid sequence of GapA
      promoter

<400> SEQUENCE: 59
ttgctcacat ctcactttaa tcgtgctcac attacgtgac tgattctaac aaaacattaa     60
caccaactgg caaaattttg tcctaaactt gatctcgacg aaatggctgc acctaaatcg    120
tgatgaaaat cacattttta tcgtaattgc cctttaaaat tcggggcgcc gaccccatgt    180
ggtctcaagc ccaaaggaag agtgaggcga gtcagtcgcg taatgcttag gcacaggatt    240
gatttgtcgc aatgattgac acgattccgc ttgacgctgc gtaaggtttt tgtaatttta    300
caggcaacct tttattca                                                  318

<210> SEQ ID NO 60
<211> LENGTH: 182
<212> TYPE: DNA
<213> ORGANISM: Artificial Sequence
<220> FEATURE:
<223> OTHER INFORMATION: Depicts the nucleic acid sequence of TufB
      promoter

<400> SEQUENCE: 60
taaaaagaat tatggtttag caggagcgca ttgttgagca caatgatgtt gaaaaagtgt     60
gctaatctgc cctccgttcg gctgtttctt catcgtgtcg cataaaatgt gaccaataaa    120
acaaattatg caatttttta gttgcatgaa ctcgcatgtc tccatagaat gcgcgctact    180
tg                                                                   182

<210> SEQ ID NO 61
<211> LENGTH: 27
<212> TYPE: DNA
<213> ORGANISM: Artificial Sequence
<220> FEATURE:
<223> OTHER INFORMATION: Depicts the nucleic acid sequence of ribosome
      binding sites (RBS)

<400> SEQUENCE: 61
tcttaatcat gcacaggaga ctttcta                                         27

```
<210> SEQ ID NO 62
<211> LENGTH: 28
<212> TYPE: DNA
<213> ORGANISM: Artificial Sequence
<220> FEATURE:
<223> OTHER INFORMATION: Depicts the nucleic acid sequence of ribosome
      binding sites (RBS)

<400> SEQUENCE: 62

aagttcactt aaaaaggaga gatcaaca                                          28


<210> SEQ ID NO 63
<211> LENGTH: 15
<212> TYPE: DNA
<213> ORGANISM: Artificial Sequence
<220> FEATURE:
<223> OTHER INFORMATION: Depicts the sequence of Linker

<400> SEQUENCE: 63

ggggsggggs ggggs                                                        15


<210> SEQ ID NO 64
<211> LENGTH: 5
<212> TYPE: DNA
<213> ORGANISM: Artificial Sequence
<220> FEATURE:
<223> OTHER INFORMATION: Depicts the sequence of Linker

<400> SEQUENCE: 64

ggggs                                                                    5
```

PROGRAMMED MICROORGANISMS TO ATTENUATE A DISEASE

CROSS REFERENCE TO RELATED APPLICATIONS

This application claims the benefit of U.S. Provisional Application No. 63/058,662, filed Jul. 30, 2020, the entirety of which is incorporated herein for any and all purposes

SEQUENCE LISTING

The instant application contains a Sequence Listing which has been submitted in ASCII format via EFS-Web and is hereby incorporated by reference in its entirety. Said ASCII copy, created on Oct. 15, 2023 is named Sequence.txt and is 224 KB in size.

FIELD OF INVENTION

The present disclosure broadly relates to the field of genetically engineered microorganisms, and in particular the present disclosure discloses genetically engineered microorganisms capable of producing podophyllotoxin, and/or derivatives, and/or precursors thereof.

BACKGROUND OF THE INVENTION

Disease or disorders are treated at present by either surgical or non-surgical methods. Non-surgical methods include administering a therapy that could be either or a combination of chemical, biological or physical methods, given to the patient via various possible delivery routes as applicable for the disease and as found suitable by a qualified physician.

Many of these methods have short-comings, especially while treating terminally ill patients. This is due to the difficulty in managing the right dosages given to the patient. Many drug compounds are known to exert adverse effects on the patient, ranging from mild to severe, amplified by dosages over a prolonged period of drug intake while treating the disease.

Targeted therapies using innovative drug delivery systems mitigate the adverse reaction by precise delivery of dosages to the target site and organ and by reducing the dosages in the circulatory system. One such method includes treating a disease using immunotherapy.

One of the major limitations of immunotherapies is the limited number of responders to such therapies. In some terminal diseases, there are only one in five patients who responds positively to the immunotherapy. This is postulated due to variations of several factors, some of which are difficult to enumerate and have a complex association with an ecosystem as a whole.

Other innovative therapies such as gene therapy and cell therapy continue to be promising, but their lacunae include scalability and reproducibility in results. In some cases, patients have also developed severe side effects.

Few other physical targeted therapies, such as the use of electromagnetic pulse waves are futuristic at this point, leaving a huge unmet need in treating patients by minimizing adverse effects.

Therefore, studies focussing on different techniques for targeted drug delivery for treating diseases are the need of the hour.

SUMMARY OF INVENTION

In an aspect of the present disclosure, there is provided a recombinant microbe producing podophyllotoxin, or its derivatives, comprising genes encoding phenyl alanine ammonia-lyase (PAL), cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), cytochrome P450 oxidoreductase CYP719, O-methyltransferase (OMT), cytochrome P450 oxidoreductase CYP71, and 2-oxoglutarate/Fe(II)-dependent dioxygenase (2-ODD).

In another aspect of the present disclosure, there is provided a method for producing podophyllotoxin or its derivatives, said method comprising: (a) obtaining the recombinant microbe as described herein; and (b) culturing the recombinant microbe in a medium under suitable conditions for producing podophyllotoxin or its derivatives.

In another aspect of the present disclosure, there is provided a recombinant microbe producing etoposide, or its derivatives, comprising genes encoding phenyl alanine ammonia-lyase (PAL), cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (HCTC3H), caffeoyl CoA O-methyltransferase (CCoAOMT), bifunctional pinoresinol-lariciresinol reductase (DIRPLR), secoisolariciresinol dehydrogenase (SDH), cytochrome P450 oxidoreductase CYP719, O-methyltransferase (OMT), cytochrome P450 oxidoreductase CYP71, 2-oxoglutarate/Fe(II)-dependent dioxygenase (2-ODD), cytochrome P450 oxidoreductase CYP82D, UDP glucosyl transferase, and 2-Deoxy-d-ribose-5-phosphate aldolase.

In another aspect of the present disclosure, there is provided a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives.

In another aspect of the present disclosure, there is provided a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of at least one regulatory circuit.

In another aspect of the present disclosure, there is provided a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a hypoxia-responsive regulatory circuit.

In another aspect of the present disclosure, there is provided a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a nitric oxide-responsive regulatory circuit.

In another aspect of the present disclosure, there is provided a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of an arabinose-responsive regulatory circuit.

In another aspect of the present disclosure, there is provided method for treating cancer in a subject, said method comprising: administering a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a hypoxia-responsive regulatory circuit, to a subject, wherein the expression of genes is induced by hypoxic conditions to enable the recombinant microbe to secrete etoposide, or its derivatives for treating cancer in the subject.

In another aspect of the present disclosure, there is provided a method for treating cancer in a subject, said method comprising: administering a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a nitric oxide-responsive regulatory circuit, to a subject, wherein the expression of genes is induced by the presence of nitric oxide to enable the recombinant microbe to secrete etoposide, or its derivatives for treating cancer in the subject.

In another aspect of the present disclosure, there is provided a method for treating cancer in a subject, said method comprising: administering a recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of an arabinose-responsive regulatory circuit, to a subject, wherein the expression of genes is induced by the presence of arabinose to enable the recombinant microbe to secrete etoposide, or its derivatives for treating cancer in the subject In another aspect of the present disclosure, there is provided a composition comprising: (a) the recombinant microbe as described herein; and (b) at least one pharmaceutically acceptable carrier.

In another aspect of the present disclosure, there is provided a method for treating cancer, said method comprising: administering the composition as described herein to a subject for treating cancer.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIG. 1 depicts production of etoposide under the control of AraC regulatory unit by recombinant *E. coli* Nissle, in accordance with an embodiment of the present disclosure.

FIG. 2 depicts production of etoposide under the control of NorR regulatory unit by recombinant *E. coli* Nissle, in accordance with an embodiment of the present disclosure.

DETAILED DESCRIPTION OF THE INVENTION

Figure 3:
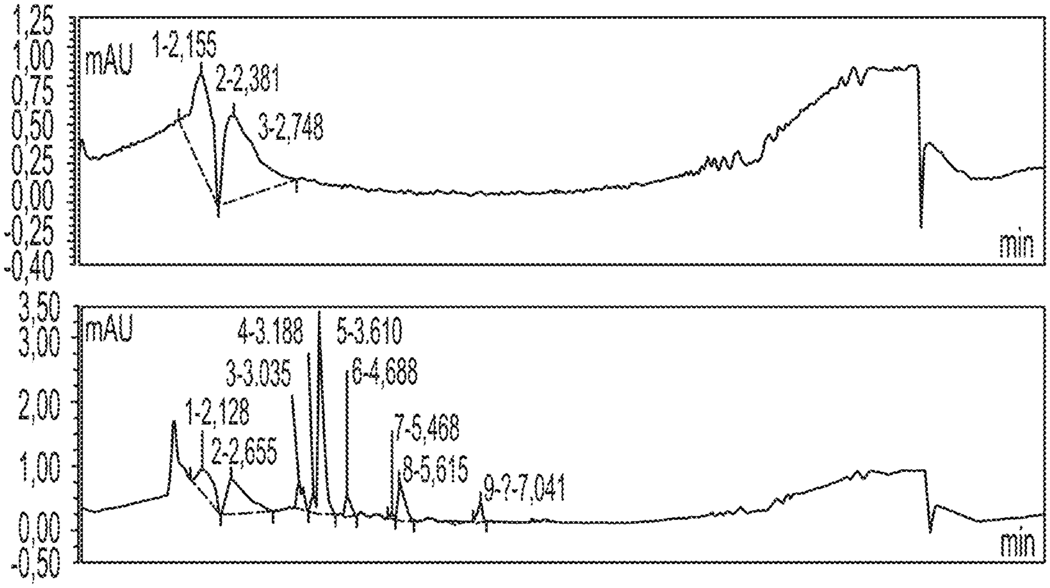
FIG. 3 depicts production of etoposide under the control of FNR regulatory unit by recombinant *E. coli* Nissle, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably. The term "recombinant" refers to the microbe which is constructed artificially, and such a microbe does not occur in nature. The term "programmed microbe" refers to the microbe which is recombinantly constructed or programmed to fulfil a specific purpose. The term "derivatives" refers to any derivative of the molecule disclosed in the present disclosure. The term "precursor" refers to any molecule that is produced earlier in the pathway as compared to the final product. The term "pharmaceutically acceptable carrier" refers to carrier or a diluent that does not cause significant irritation to an organism and does not abrogate the biological activity and properties of the administered bacterial or viral compound.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

As discussed in the background section, the main problems that are faced with the current treatment modalities for cancer are: (a) lack of targeted therapies; and (b) use of higher dosage of the drug leading to adverse effects. In order to solve the problems existing in the art, the present disclosure discloses recombinant microbe which is used for producing podophyllotoxin or its derivatives like etoposide, Further, the recombinant microbes as disclosed herein are used for treating cancer. As per one of the implementations, the recombinant microbe is administered to a subject such that the microbe lodges itself near the affected area. Post administration, the microorganism is designed to produce the drug compound at the intended site of action within the human lungs. This is expected to bring down the circulating dosage of the drug to considerably low level to mitigate adverse effects of the drug.

Recombinant Microbes and the Genes for Construction of the Same

In an implementation of the present disclosure, there is provided a recombinant microbe for producing podophyllotoxin, or its derivatives, comprising genes encoding phenyl alanine ammonia-lyase (PAL), cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), cytochrome P450 oxidoreductase CYP719, O-methyltransferase (OMT), cytochrome P450 oxidoreductase CYP71, and 2-oxoglutarate/Fe(II)-dependent dioxygenase (2-ODD), wherein the derivative produced is deoxypodophyllotoxin. It is further disclosed that the recombinant microbe further comprising gene encoding cytochrome P450 oxidoreductase CYP82D produces desmethylepipodophyllotoxin. In another implementation, the recombinant microbe further comprising gene encoding UDP glucosyl transferase produces desmethylepipodophyllotoxin glucopyranoside. In yet another implementation, the recombinant microbe further comprising gene encoding 2-Deoxy-d-ribose-5-phosphate aldolase produces etoposide.

In another implementation of the present disclosure, two or more genes are fused together to encode the respective fusion proteins. As per one implementation the genes encoding cinnamate-4-hydroxylate (C4H) and 4-coumaroyl CoA-ligase (4CL) are fused, and wherein the genes encoding hydroxycinnamoyl-CoA quinate hydroxycinnamoyltransferase (HCT) and p-coumaroyl quinate 3'-hydroxylase (C3H) are fused to encode the fusion proteins. It can be contemplated that genes as described herein if amenable to fusion can be fused to obtain the recombinant microbe of the present disclosure. As per an implementation, the genes are fused using a flexible linker—GGGGSGGGGSGGGGS. Other linkers can also be used in order to perform the fusion of the genes.

In another implementation of the present disclosure, the genes are separated by a ribosome binding sequence (RBS) in order to obtain enhanced translation efficiency.

The RBS can have a nucleic acid sequence as set forth in SEQ ID NO: 61 (TCTTAATCATGCACAGGA-GACTTTCTA) or the nucleic acid sequence as set forth in SEQ ID NO: 62 (AAGTTCACTTAAAAAGGAGAGAT-CAACA). Further, a person skilled in the art can use any other well-known RBS sequences in order to increase the translation efficiency.

As per an implementation, the genes encoding: PAL having an amino acid sequence as set forth in SEQ ID NO: 2, C4H4CL having an amino acid sequence as set forth in SEQ ID NO: 12, HCTC3H having an amino acid sequence as set forth in SEQ ID NO: 14, CCoAOMT having an amino acid sequence as set forth in SEQ ID NO: 18, DIRPLR having an amino acid sequence as set forth in SEQ ID NO: 20, SDH having an amino acid sequence as set forth in SEQ ID NO: 22, and CYP719 having an amino acid sequence as set forth in SEQ ID NO: 26 were assembled in pRSF vector. The next six genes of the pathway were selected as follows: the genes encoding OMT having an amino acid sequence as set forth in SEQ ID NO: 30, CYP71 having an amino acid sequence as set forth in SEQ ID NO: 32, 2-ODD having an amino acid sequence as set forth in SEQ ID NO: 36, CYP82D having an amino acid sequence as set forth in SEQ ID NO: 40, UGT having an amino acid sequence as set forth in SEQ ID NO: 46, DERA having an amino acid sequence as set forth in SEQ ID NO: 50 were assembled in p15A vector.

As per an implementation, there is provided a recombinant vector comprising at least one nucleic acid fragment encoding phenyl alanine ammonia-lyase (PAL), Cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, at least one gene encoding a protein transporter selected from the group consisting of ATP-Binding Cassette (ABC) transporter, Major Facilitator Superfamily (MFS) transporters, SMR (small multidrug resistant) family, RND (Resistance-Nodulation-Cell Division) family, and the MATE (multidrug and toxic compound extrusion) family, and at least one regulatory circuit selected from the group consisting of nitric oxide (NO) operon, arabinose (AraC) operon, fumarate and nitrate reductase (FNR) operon, thiosulphate-responsive regulatory circuit, and tetrathionate-responsive regulatory circuit. Also, there is provided a method for obtaining recombinant vector as described herein, said method comprises method comprising: (a) obtaining one or more recombinant vector, said recombinant vector encoding a repertoire of genes encoding phenyl alanine ammonia-lyase (PAL), Cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, UDP glucosyl transferase, at least one gene encoding a protein transporter selected from the group consisting of ATP-Binding Cassette (ABC) transporter, Major Facilitator Superfamily (MFS) transporters, SMR (small multidrug resistant) family, RND (Resistance-Nodulation-Cell Division) family, and the MATE (multidrug and toxic compound extrusion) family, and at least one regulatory circuit selected from the group consisting of nitric oxide (NO) operon, arabinose (AraC) operon, fumarate and nitrate reductase (FNR) operon, thiosulphate-responsive regulatory circuit, and tetrathionate-responsive regulatory circuit; and (b) transforming a host microbe with the recombinant vector obtained in step (a), to obtain the recombinant microbe.

Microbe as Per the Present Disclosure

In an implementation of the present disclosure, the recombinant microbe refers to any microbe as per the requirement. As per one implementation, the microbe is a bacterium including, but not limited to the genus *Escherichia, Bacillus, Bacteroides, Bifidobacterium, Brevibacteria, Clostridium, Enterococcus, Lactobacillus, Lactococcus, Saccharomyces, Staphylococcus, Klebsiella, Citrobacter, Pseudobutyrivibrio*, and *Ruminococcus*. The bacterium can be a species including, but not limited to *Escherichia coli, Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis, Firmicutes* (including species of *Eubacterium*), *Roseburia, Faecalibacterium, Enterobacter, Faecalibacterium prausnitzii, Clostridium difficile, Subdoligranulum, Clostridium sporogenes, Campylobacter jejuni, Clostridium saccharolyticum.*

As per another implementation, the recombinant microbe can be any one selected from commensal bacteria.

As per another implementation, the microbe is *E. coli* Nissle 1917 strain. The genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* a-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic. (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella,*

*Yersinia*, and *Shigella* in vitro (Altenhoefer et al., 2004). It is commonly accepted that *E. coli* Nissle's therapeutic efficacy and safety have convincingly been proven (Ukena et al., 2007).

*E. coli* Nissle 1917 was isolated in 1917 by the German physician Alfred Nissle from the stool of a German soldier who, unlike his comrades, survived an outbreak of enterocolitis. This strain is widely used as a probiotic, produced under the trade name of Mutoflor™, to treat intestinal disorders including diarrhoea, irritable bowel disease, ulcerative colitis and Crohn's disease (Altenhoefer et al., 2004; Lodinova-Zadnikova et al., 1997; Rembacken et al., 1999). *E. coli* Nissle 1917 is furthermore of interest due to its specific ability to grow in tumours. Bacteriolytic tumortherapy was first described in the 1950s (Parker et al., 1947; Malmgren and Flanigan, 1955), based on the fact that some types of anaerobic bacteria can selectively propagate in tumours but not in other organs. These bacterial strains include *Bifidobacterium* (Yi et al., 2005), Clostridia species (Agrawal et al., 2004), *Corynebacterium parvum* (Fisher et al., 1990), *Salmonella typhimurium* (Zhao et al., 2005, 2006), *Salmonella choleraesuis* (Lee et al., 2004, 2005a,b) and *Bordetella pertussis* (Pawelek, 2005). Most anticancer drugs are delivered into patients orally or somatically, which results in prolonged side-effects. Therefore, it will be greatly advantageous to specifically deliver anticancer drugs into tumours to increase the effect of the drugs on the tumour and to reduce side-effects on other organs. Many trials have been performed to express anticancer peptides and RNAi in the bacterial strains selectively growing in tumours (Jia et al. 2005; Dang et al. 2001; Loeffler et al. 2007). However, so far, no work has been performed using these strains to express anticancer drugs like podophyllotoxin derivatives such as etoposide. *E. coli* in general is extremely easy to culture and is highly amenable to experimentation and manipulation. *E. coli* Nissle 1917 is particularly useful due to its non-pathogenic nature and its ability to specifically grow in tumours. Therefore, *Escherichia coli* Nissle 1917 is a particularly suitable heterologous host for the expression of genes capable of etoposide biosynthesis, according to the present invention.

Etoposide pathway may be integrated into the bacterial chromosome at one or more integration sites. For example, one or more copies of the gene cassette may be integrated into the bacterial chromosome. Having multiple copies of the gene cassette integrated into the chromosome allows for greater production of the Etoposide and also permits fine-tuning of the level of expression. As per one implementation, exemplary integration sites within the *E. coli* 1917 Nissle chromosome are NupG, AslB, AraC, LacZ, dapA, Cea, YfeD, ThyA, malP, GalK, GTP. One skilled in the art can identify other safe harbour sites where the genes can be integrated without interfering with expression of essential genes.

Transporter Proteins to Enable Secretion of Podophyllotoxin or its Derivatives Outside the Recombinant Microbe In an implementation of the present disclosure, apart from the genes encoding the enzymes for podophyllotoxin pathway, the recombinant microbe further comprises at least one gene encoding a protein transporter. The protein transporter is selected from the group consisting of ATP-Binding Cassette (ABC) transporter, Major Facilitator Superfamily (MFS) transporters, SMR (small multidrug resistant) family, RND (Resistance-Nodulation-Cell Division) family, and the MATE (multidrug and toxic compound extrusion) family. The protein transporter as disclosed herein is capable of secreting the end product outside the cell. Typically, ABC family transporters are multicomponent primary active transporters, capable of transporting molecules in response to ATP hydrolysis. Non-limiting examples of endogenous ABC transporter genes include the genes at the loci PDRS, PDR10, PDR15, SNQ2, YOR1, YOL075c and PDR18 (or a functional homolog thereof). The Major Facilitator Superfamily (MFS) transporters are polypeptides that can transport small solutes in response to chemiosmotic ion gradients. Saier, Jr. et al., J. Mol. Microbiol. Biotechnol. 1:257-279 (1999). The MFS transporter family is sometimes referred to as the uniporter-symporter-antiporter family. MFS transporters function, inter alia, in sugar uptake and drug efflux systems. MFS transporters typically contain conserved MFS-specific motifs. Non-limiting examples of endogenous MFS transporter genes include the genes at the TPO1, TPO3, and FLR1 loci (or a functional homolog thereof).

Other transporter families include the SMR (small multidrug resistant) family, RND (Resistance-Nodulation-Cell Division) family, and the MATE (multidrug and toxic compound extrusion) family. The SMR family members are integral membrane proteins characterized by four alpha-helical transmembrane strands that confer resistance to a broad range of antiseptics, lipophilic quaternary ammonium compounds (QAC), and aminoglycoside resistance in bacteria. See, Bay and Turner, BMC Evol Biol., 9: 140 (2009).

As per an implementation, the ABC transporter genes encoding proteins having an amino acid sequence selected from the group consisting of SEQ ID NO: 52, SEQ ID NO: 54, SEQ ID NO: 56, and SEQ ID NO: 58 can be used for constructing the recombinant microbe as disclosed herein.

Regulatory Circuits for Controlling the Expression of Genes of Podophyllotoxin Pathway Transcriptional repressors and activators bind to operator sequences in DNA and respectively inhibit and enhance the transcription of genes by RNA polymerase, thus increasing or decreasing output signal flux. The transcription rate can be controlled by varying the concentration of regulator. For example, in addition to classical examples of inducible promoters controlled by regulators that bind to metabolites (e.g. LacI, AraC), signalling molecules (e.g. LuxR), and metal ions (e.g. ArsR), more recent CRISPR (clustered regularly interspaced short palindromic repeats)-based tools which require binding of guide RNA (gRNA) sequences have been developed (Qi et al, 2013, Kiani et al, 2014). Nuclease inactive Cas9 protein can function as a repressor that works by steric hindrance of RNAP at the promoter, or Cas9 can also be fused with other repressors or activators. Synthetic promoters and genes can be designed to contain multiple different regulator binding sites in order to increase the number of inputs that control the transcriptional output (Stanton et al, 2013). Recently, the interlinked relationship between the microbiome and pH of the niches they occupy have been under investigation in regard to conditions such as acne and bacterial vaginosis. In order to provide some growth or survival advantage in acidic conditions, the PcadC region of the cadBA operon in *E. coli* activates transcription under external acidic pH and in the presence of lysine. Using b-galactosidase assays, it was shown that PcadC could significantly increase expression when the pH was decreased from 7.6 to 5.4. A system like this could be used to design a biosensor circuit to only activate in predetermined locations or to detect dysbiotic pH at microbial niches. Propionate inducible system (pPro) was identified and characterised from the prpBCDE operons of *E. coli* and *Salmonella enterica*. It was shown that after intake into the cell, propionate is activated to propionyl-CoA by prpE-encoded propionyl-CoA synthetase. the prpR transcriptional activator gene, the PprpB promoter region can be used to create the pPro inducible expression system as sensing circuit (Lee and Keasling, 2005).

In an implementation of the present disclosure, the recombinant microbe as described herein further comprises at least one regulatory circuit selected from the group consisting of nitric oxide (NO) operon, arabinose (AraC) operon, fumarate and nitrate reductase (FNR) operon, thiosulphate-responsive regulatory circuit, and tetrathionate-responsive regulatory circuit. The presence of a regulatory circuit is important to control the expression of the genes responsible for the synthesis of podophyllotoxin or its derivatives.

Once the recombinant microbe is administered to a subject in need thereof, the expression of the genes can be controlled. As per one implementation, to create inducible systems for use in *E. coli* Nissle 1917, parts from a large repertoire of systems that govern carbohydrate utilization are used, which include cytoplasmic transcription factors, extracytoplasmic function sigma/anti-sigma pairs, and hybrid two-component systems (HTCS), among others. In *E. coli* nissle, arabinose and rhamnose metabolism is mediated by the AraC/Xy1S-family transcriptional activator, RhaR, which activates transcription at the Pbad promoter. The AraC operon can be cloned upstream of the genes responsible for synthesis of podophyllotoxin or its derivatives in such a manner that on providing arabinose or rhamnose, the genes could be induced and the absence of arabinose or rhamnose would ensure that the genes are not expressed.

Nitric oxide is a natural marker of inflammation in lung cancer, making it an ideal input signal for this engineered microorganism. Inflamed lung epithelial cells produce nitric oxide by up-regulating inducible nitric oxide synthase (iNOS), an enzyme that produces nitric oxide from L-arginine. Therefore, as per another implementation, nitric oxide sensing can be combined through NorR regulatory unit with podophyllotoxins pathway biosynthesis genes. The recombinant microbes harboring the genes controlled by NorR circuitry would ensure the secretion of podophyllotoxin or its derivatives in the presence of nitric oxide and would limit unnecessary production of the compound.

Since hypoxia is a prevalent condition in the tumour microenvironment, the recombinant microbe can also be engineered with an FNR regulatory operon. Under oxygen rich conditions binding of the transcription factor FNR to the hypoxia-inducible promoter will be impeded, leading to repressed expression of the downstream gene. In tumor microenvironment with relatively low levels of oxygen the FNR transcription factor can bind to the promoter, leading to the expression of the downstream gene.

Treatment Modalities with the Recombinant *E. coli* Nissle Capable of Producing Etoposide As per one implementation of the present disclosure, there is provided a recombinant microbe capable of treating cancer. The recombinant microbe is capable of producing podophyllotoxin, or its precursor, or its derivatives. In another aspect, the recombinant microbe is *E. coli* Nissle 1917 genetically engineered to produce etoposide which can be used for treating cancer in a subject. The recombinant microbe is capable of targeting cancer cells. The targeting can be done by low oxygen condition such as hypoxic environment prevalent among cancerous cells.

As per another implementation, the recombinant microbe is capable of producing one or more anti-cancer molecule, and said anti-cancer molecule can be any derivative, or precursor of podophyllotoxin or any molecule from the podophyllotoxin pathway. The recombinant microbe can be administered locally at the site of tumour (intratumoral administration). The recombinant microbe can be administered orally through aerosol formulation, such a route of administration will provide the opportunity for the recombinant bacteria to lodge in the lung and produce the anti-cancer molecules for treating lung cancer. In order to ensure targeted production of etoposide, or podophyllotoxin derivative (anti-cancer molecule), the recombinant microbe can be cloned under a regulatory circuit such that the production of the anti-cancer molecules can be restricted to the presence of the relevant inducer. The inducer can be hypoxic conditions, or the presence of nitric oxide which are the hallmarks of the conditions prevalent in cancerous cells such that the production of the anti-cancer molecule takes place only in the niche of cancerous cells.

In another implementation, the inducer can also be provided externally in form of arabinose for inducing production of the anti-cancer molecule, the genes for which are cloned under the control of AraC regulatory operon.

In one another implementation, the treatment regime can be decided based on the survival of the recombinant microbe inside the human subject. A fresh dose of the recombinant microbe can be provided at a pre-decided interval of a few days to few weeks to few months depending on the requirement of the anti-cancer molecule and the stage of the tumour. The formulation for oral administration can be prepared as per the technique well known in the art. The dosage of the recombinant microbe can be adjusted based on the requirement of the anti-cancer molecule and the type and stage of the tumour. The administration technique can be adjusted as per the requirement.

In some implementations, the treatment regimen can include one or more intratumoral administrations. In some implementations, a treatment regimen can include an initial dose, followed by at least one subsequent dose. One or more doses can be administered sequentially in two or more cycles. For instance, a first dose may be administered at day 1, and a second dose may be administered after 1, 2, 3, 4, 5, 6, days or 1, 2, 3, or 4 weeks or after a longer interval. Additional doses may be administered after 1, 2, 3, 4, 5, 6, days or after 1, 2, 3, or 4 weeks or longer intervals. In some implementations, the first and subsequent administrations have the same dosage. In other implementations, different doses are administered. In some implementations, more than one dose is administered per day, for example, two, three or more doses can be administered per day.

As per one implementation of the present disclosure, the recombinant microbe capable of producing at least one derivative, or at least one pre-cursor of podophyllotoxin is capable of killing cancerous cells. The recombinant microbe is capable of killing 10%, or 20%, or 30%, or 40%, or 50%, or 60%, or 70%, or 80%, or 90% cancerous cells over a particular site.

In an implementation of the present disclosure, there is provided a composition comprising the recombinant microbe as disclosed in the present disclosure, and a pharmaceutically acceptable carrier. The carrier can be any pharmaceutically acceptable substance well described in the art. The carriers can be selected from the group consisting of thickeners, diluents, buffers, buffering agents, surface active agents, neutral or cationic lipids, lipid complexes, liposomes, and penetration enhancers. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the present disclosure may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The present section highlights the examples of the present disclosure. The criticality of the disclosure is mentioned in this section and the method of using the recombinant microbe has been disclosed herein.

Example 1

Sequences Used in the Present Disclosure.

Several nucleic acid sequences encoding different enzymes of the podophyllotoxin were studied for their ability to encode the respective enzymes for showing the desirable enzyme activity. As is mentioned in the later part of the examples, that not all genes are able to encode the proteins (enzymes) having desirable enzyme activity. Therefore, Table 1 depicts the nucleic acid sequence of the genes which provided desirable results in terms of expressing a protein having the desirable enzyme activity. The nucleic acid sequences of different genes were codon optimised to achieve optimal expression in *E. coli* Nissle 1917 cell. Table 1 provides the sequence of the codon optimised genes. Table 2 depicts the amino acid sequence of the corresponding nucleic acid sequences listed in Table 1.

Genes from different microbes that encode ABC transporter proteins were studied, and interestingly it was found that not all ABC transporter proteins were able to provide the desirable secretion of etoposide outside the cell. Therefore, Table 3 lists the codon optimised nucleic acid sequences of the genes which provided the desirable results. Similarly, Table 4 lists the amino acid sequences encoded by the nucleic acid mentioned in the Table 3.

TABLE 1

List of nucleic acid sequences encoding enzymes of podophyllotoxin pathway

| Ref. No. | Genes | SEQ ID NO: | Organism | Sequence (codon optimized) |
|---|---|---|---|---|
| 1 | Phenylalanine ammonia-lyase (PAL) | 1 | *Rhodosporidium toruloides* | ATGGCGCCGTCTCTGGACTCTATCTCTCACTCTTTCGCGAACGGT<br>GTTGCGTCTGCGAAA<br>CAGGCGGTTAACGGTGCGTCTACCAACCTGGCGGTTGCGGGTTC<br>TCACCTGCCGACCACC<br>CAGGTTACCCAGGTTGACATCGTTGAAAAAATGCTGGCGGCGCC<br>GACCGACTCTACCCTG<br>GAACTGGACGGTTACTCTCTGAACCTGGGTGACGTTGTTTCTGCG<br>GCGCGTAAAGGTCGT<br>CCGGTTCGTGTTAAAGACTCTGACGAAATCCGTTCTAAAATCGAC<br>AAATCTGTTGAATTC<br>CTGCGTTCTCAGCTGTCTATGTCTGTTTACGGTGTTACCACCGGTT<br>TCGGTGGTTCTGCG<br>GACACCCGTACCGAAGACGCGATCTCTCTGCAGAAAGCGCTGCT<br>GGAACACCAGCTGTGC<br>GGTGTTCTGCCGTCTTCTTTCGACTCTTTCCGTCTGGGTCGTGGTC<br>TGGAAAACTCTCTG<br>CCGCTGGAAGTTGTTCGTGGTGCGATGACCATCCGTGTTAACTCT<br>CTGACCCGTGGTCAC<br>TCTGCGGTTCGTCTGGTTGTTCTGGAAGCGCTGACCAACTTCCTG<br>AACCACGGTATCACC<br>CCGATCGTTCCGCTGCGTGGTACCATCTCTGCGTCTGGTGACCTG<br>TCTCCGCTGTCTTAC<br>ATCGCGGCGGCGATCTCTGGTCACCCGGACTCTAAAGTTCACGTT<br>GTTCACGAAGGTAAA<br>GAAAAAATCCTGTACGCGCGTGAAGCGATGGCGCTGTTCAACCT<br>GGAACCGGTTGTTCTG<br>GGTCCGAAAGAAGGTCTGGGTCTGGTTAACGGTACCGCGGTTTC<br>TGCGTCTATGGCGACC<br>CTGGCGCTGCACGACGCGCACATGCTGTCTCTGCTGTCTCAGTCT |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CTGACCGCGATGACC<br>GTTGAAGCGATGGTTGGTCACGCGGGTTCTTTCCACCCGTTCCTG<br>CACGACGTTACCCGT<br>CCGCACCCGACCCAGATCGAAGTTGCGGGTAACATCCGTAAACT<br>GCTGGAAGGTTCTCGT<br>TTCGCGGTTCACCACGAAGAAGAAGTTAAAGTTAAAGACGACGA<br>AGGTATCCTGCGTCAG<br>GACCGTTACCCGCTGCGTACCTCTCCGCAGTGGCTGGGTCCGCTG<br>GTTTCTGACCTGATC<br>CACGCGCACGCGGTTCTGACCATCGAAGCGGGTCAGTCTACCAC<br>CGACAACCCGCTGATC<br>GACGTTGAAAACAAAACCTCTCACCACGGTGGTAACTTCCAGGC<br>GGCGGCGGTTGCGAAC<br>ACCATGGAAAAAACCCGTCTGGGTCTGGCGCAGATCGGTAAACT<br>GAACTTCACCCAGCTG<br>ACCGAAATGCTGAACGCGGGTATGAACCGTGGTCTGCCGTCTTG<br>CCTGGCGGCGGAAGAC<br>CCGTCTCTGTCTTACCACTGCAAAGGTCTGGACATCGCGGCGGCG<br>GCGTACACCTCTGAA<br>CTGGGTCACCTGGCGAACCCGGTTACCACCCACGTTCAGCCGGC<br>GGAAATGGCGAACCAG<br>GCGGTTAACTCTCTGGCGCTGATCTCTGCGCGTCGTACCACCGAA<br>TCTAACGACGTTCTG<br>TCTCTGCTGCTGGCGACCCACCTGTACTGCGTTCTGCAGGCGATC<br>GACCTGCGTGCGATC<br>GAATTCGAATTCAAAAAACAGTTCGGTCCGGCGATCGTTTCTCTG<br>ATCGACCAGCACTTC<br>GGTTCTGCGATGACCGGTTCTAACCTGCGTGACGAACTGGTTGA<br>AAAAGTTAACAAAACC<br>CTGGCGAAACGTCTGGAACAGACCAACTCTTACGACCTGGTTCC<br>GCGTTGGCACGACGCG<br>TTCTCTTTCGCGGCGGGTACCGTTGTTGAAGTTCTGTCTTCTACCT<br>CTCTGTCTCTGGCG<br>GCGGTTAACGCGTGGAAAGTTGCGGCGGCGGAATCTGCGATCTC<br>TCTGACCCGTCAGGTT<br>CGTGAAACCTTCTGGTCTGCGGCGTCTACCTCTTCTCCGGCGCTG<br>TCTTACCTGTCTCCG<br>CGTACCCAGATCCTGTACGCGTTCGTTCGTGAAGAACTGGGTGTT<br>AAAGCGCGTCGTGGT<br>GACGTTTTCCTGGGTAAACAGGAAGTTACCATCGGTTCTAACGTT<br>TCTAAAATCTACGAA<br>GCGATCAAATCTGGTCGTATCAACAACGTTCTGCTGAAAATGCT<br>GGCG |
| 3 | Phenylalanine ammonia-lyase (PAL) | 3 | *Populus kitakamiensis* | ATGGAATTCTGCCAGGACTCTCGTAACGGTAACGGTTCTCCGGGT<br>TTCAACACCAACGAC<br>CCGCTGAACTGGGGTATGGCGGCGGAATCTCTGAAAGGTTCTCA<br>CCTGGACGAAGTTAAA<br>CGTATGATCGAAGAATACCGTAACCCGGTTGTTAAACTGGGTGG<br>TGAAACCCTGACCATC<br>GGTCAGGTTACCGCGATCGCGTCTCGTGACGTTGGTGTTATGGTT<br>GAACTGTCTGAAGAA<br>GCGCGTGCGGGTGTTAAAGCGTCTTCTGACTGGGTTATGGACTCT<br>ATGTCTAAAGGTACC<br>GACTCTTACGGTGTTACCACCGGTTTCGGTGCGACCTCTCACCGT<br>CGTACCAAACAGGGT<br>GGTGAACTGCAGAAAGAACTGATCCGTTTCCTGAACGCGGGTAT<br>CTTCGGTAACGGTACC<br>GAATCTTCTCACACCCTGCCGCGTTCTGCGACCCGTGCGGCGATG<br>CTGGTTCGTACCAAC<br>ACCCTGCTGCAGGGTTACTCTGGTATCCGTTTCGAAATGCTGGAA<br>GCGATCACCAAAATG<br>ATCAACCACAACATCACCCCGTGCCTGCCGCTGCGTGGTACCATC<br>ACCGCGTCTGGTGAC<br>CTGGTTCCGCTGTCTTACATCGCGGGTCTGCTGACCGGTCGTCCG<br>AACTCTAAAGCGGTT<br>GGTCCGAACGGTGAACCGCTGACCCCGGCGGAAGCGTTCACCCA<br>GGCGGGTATCGACGGT<br>GGTTTCTTCGAACTGCAGCCGAAAGAAGGTCTGGCGCTGGTTAA<br>CGGTACCGCGGTTGGT<br>TCTGGTCTGGCGTCTATGGTTCTGTTCGAAGCGAACGTTCTGGCG<br>ATCCTGTCTGAAGTT<br>CTGTCTGCGATCTTCGCGGAAGTTATGCAGGGTAAACCGGAATT<br>CACCGACCACCTGACC |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CACAAACTGAAACACCACCCGGGTCAGATCGTTGCGGCGGCGAT CATGGAACACATCCTG GACGGTTCTGCGTACGTTAAAGAAGCGCAGAAACTGCACGAAAT CGACCCGCTGCAGAAA CCGAAACAGGACCGTCACGCGCTGCGTACCTCTCCGCAGTGGCT GGGTCCGCTGATCGAA GTTATCCGTACCTCTACCAAAATGATCGAACGTGAAATCAACTCT GTTAACGACAACCCG CTGATCGACGTTTCTCGTAACAAAGCGCTGCACGGTGGTAACTTC CAGGGTACCCCGATC GGTGTTTCTATGGACAACACCCGTCTGGCGATCGCGTCTATCGGT AAACTGATGTTCGCG CAGTTCTCTGAACTGGTTAACGACCTGTACAACAACGGTCTGCCG TCTAACCTGACCGGT GGTCGTAACCCGTCTCTGGACTACGGTTTCAAAGGTGCGGAAAT CGCGATGGCGTCTTAC TGCTCTGAACTGCAGTTCCTGGACCAGTCTTGCACCAACCACGTT CAGTCTGCGGAACAG CACAACCAGGACGTTAACTCTCTGGGTCTGATCTCTTCTCGTAAA ACCGCGGAAGCGATC GACATCCTGAAACTGATGTCTACCACCTTCCTGGTTGGTCTGTGC CACTCTGTTGACCTG CGTCACATCGAAGAAAACCTGAAAAACACCGTTAAAATCTCTGT TTCTCAGCTGCCGCGT GTTCTGACCATGGGTTTCAACGGTGAACTGCACCCGTCTCGTTTC TGCGAAAAAGACCTG CTGAAAGTTGTTGACCGTGAACACGTTTTCTCTTACATCGACGAC CCGTGCTCTGCGACC TACCCGCTGATGCAGAAACTGCGTCAGGTTCTGGTTGAACACGC GCTGGTTAACGGTGAA AAAGTTCGTAACTCTACCACCTCTATCTTCCAGAAAATCGGTTCT TTCGAAGAAGAACTG AAAACCCTGCTGCCGAAAGAAGTTGAATCTGCGCGTCTGGAAGT TGAAAACGGTAACCCG GCGATCCCGAACCGTATCAAAGAATGCCGTTCTTACCCGCTGTAC AAATTCGTTCGTGAA GAACTGGGTACCTCTCTGCTGACCGGTGAAAAAGTTAAATCTCC GGGTGAAGAATTCGAC AAAGTTTTCACCGCGATCTGCGCGGGTAAACTGATCGACCCGCT GCTGGAATGCCTGAAA GAATGGGACGGTGCGCCGCTGCCGATCTGC |
| 5 | Phenylalanine ammonia-lyase (PAL) | 5 | *Strobilurus tenacellus* | ATGCCGATCACCCACGAACAGCCGAACGGTTTCCACTCTAAACA GCTGAACGGTTCTGGT ATCGCGAAAGCGAAAGCGATGCCGTACCCGTCTGACCTGCTGTC TCACTTCGTTAAACAG CACCTGGAACTGGAATCTTACAAAAACGGTCAGGAAATCGAAAT CGACGGTTACTCTCTG TCTATCTCTGCGGTTTCTGCGGCGGCGCGTTACAACGCGCCGGTT ATCCTGCGTGACTCT TCTACCATCCGTGACCGTCTGGAAAAAGCGCGTTCTGTTATCGTT GAAAAAATCGAAGGT TCTAAATCTGTTTACGGTGTTTCTACCGGTTTCGGTGGTTCTGCG GACACCCGTACCTCT AACACCCTGGCGCTGGGTAACGCGCTGCTGCAGCACCAGCACTC TGGTGTTCTGCCGTCT ACCACCAACACCCTGTCTCTGTTCTGCCGCTGCTGGACCCGATCGCG TCTACCTCTATGCCG GAATCTTGGGTTCGTGGTGCGATCCTGATCCGTATCAACTCTCTG ATCCGTGGTCACTCT GGTGTTCGTTGGGAACTGATCGCGAAAATGGTTGAACTGCTGCA GGCGAACATCACCCCG CTGGTTCCGCTGCGTGGTTCTATCTCTGCGTCTGGTGACCTGTCTC CGCTGTCTTACGTT GCGGGTACCCTGATGGGTAACCCGTCTATCCGTGTTTTCGACGGT CCGGCGGCGTTCGGT GCGCGTCAGATCGTTTCTTCTGTTAAAGCGCTGGAAGAACACAA CATCACCCCGATCTCT CTGCTGGCGAAAGAACACCTGGGTATCCTGAACGGTACCGCGTT CTCTGCGTCTGTTGCG TCTCTGGTTCTGTCTGACGTTACCCACCTGGCGATGCTGGCGCAG GTTTGCACCGCGATG GGTACCGAAGTTCTGCTGGGTGAACGTATGAACTACGCGCCGTT CATCCACGCGGTTGCG |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CGTCCGCACCCGGGTCAGACCGAAGCGGCGCGTACCATCTGGGA<br>CCTGCTGTCTGGTTCT<br>AAACTGGCGCACGGTCACGAAGAAGAAGTTACCATCGACCAGG<br>ACCAGGGTGAACTGCGT<br>CAGGACCGTTACCCGCTGCGTACCGCGCCGCAGTTCCTGGGTCC<br>GCAGATCGAAGACATC<br>CTGTCTGCGCTGAACACCGTTACCCTGGAATGCAACTCTACCACC<br>GACAACCCGCTGATC<br>GACGGTGAAACCGGTGACATCCACCACGGTGGTAACTTCCAGGC<br>GATGTCTGTTTCTAAC<br>GCGATGGAAAAAACCCGTCTGTCTCTGCACCACATCGGTAAACT<br>GCTGTTCGCGCAGTGC<br>GCGGAACTGGTTCACCCGGACATGAACCGTGGTCTGCCGCCGTC<br>TCTGGCGGCGACCGAC<br>CCGTCTATCAACTACCACGGTAAAGGTATCGACATCGGTATCGC<br>GGCGTACGTTTCTGAA<br>CTGGGTTACCTGGCGAACCCGGTTTCTACCCACATCCAGTCTGCG<br>GAACTGCACAACCAG<br>GCGGTTAACTCTCTGGCGCTGATCTCTGCGCGTGCGACCATCAAC<br>TCTCTGGAAGTTCTG<br>TCTCTGCTGACCTCTTCTTACCTGTACATGCTGTGCCAGGCGTAC<br>GACCTGCGTGCGCTG<br>CAGGCGGACTTCCGTCAGGGTCTGGCGGAAATCGTTCAGGAAGA<br>ACTGCGTGCGCACTTC<br>TCTGCGCACATCGAATCTCTGGACGAATCTCCGCTGTTCGACAAA<br>GTTATCTCTTCTATG<br>TACAAAGAACTGAACCACACCACCACCATGGACGCGGTTCCGCG<br>TATGGTTAAAGTTGCG<br>GGTGCGTCTACCTCTCTGCTGGTTGACTTCTTCATGGCGAACCAG<br>ACCTCTGACGCGATG<br>TCTGTTGCGGCGCTGACCGCGCTGCCGAAATTCCGTGAAACCGTT<br>GCGCTGCGTGCGGCG<br>GCGAAACTGGTTGCGCTGCGTGAAGAATACCTGCTGGGTGCGCG<br>TGGTCCGGCGCCGGCG<br>TCTGCGTGGCTGGGTCGTACCCGTCCGATCTACGAATTCATCCGT<br>GTTACCCTGGGTATC<br>CGTATGCACGGTACCGAAAACCTGGGTGTTTTCCAGCAGGGTCT<br>GGGTGTTCAGGACGTT<br>ACCATCGGTCAGAACGTTTCTCTGATCCACGAAGCGATCCGTGA<br>CGGTAAAATGCGTGGT<br>GTTGTTGTTGGTCTGTTCGCG |
| 7 | Phenylalanine ammonia-lyase (PAL) | 7 | *Penicillium antarcticum* | ATGTCTCCGGCGTCTTACACCGCGACCCCGGTTTCTTCTCTGGTT<br>ACCCCGTCTCACCCG<br>ACCCCGCACAAAGACGAAACCCTGAAATCTTGGGCGAAAATCGG<br>TTCTCTGGTTCACCGT<br>GGTGTTGTTAACGTTGACGGTGAAACCCTGGACATCGCGTCTGTT<br>GTTGCGGTTGCGCGT<br>TTCGAAGGTTGCGGTGCGAAAGTTTCTAAAGACACCAAAGTTAC<br>CGAACGTGTTGAAGCG<br>GGTATCGAAACCTTCAACGACTACCTGTACAAAGGTTACTGCAT<br>CTACGGTGTTAACACC<br>GGTTTCGGTGGTTCTGCGGACACCCGTACCTCTGACGTTATCCGT<br>CTGCAGCAGTCTCTG<br>CTGCAGCTGACCCAGTCTGGTATCCTGTCTGGTTCTGACTTCTCT<br>CCGCGTATGGGTGAC<br>TACAACCTGTCTTCTCACGCGATGCCGGTTACCTGGGTTCGTGCG<br>ACCATGCTGGTTCGT<br>TGCAACCACCTGCTGCGTGGTCACTCTGGTGTTCGTCTGGAAATC<br>ATCGACACCGTTCTG<br>CGTCTGCTGCGTGCGGGTCTGACCCCGATCATCCCGCTGCGTGGT<br>TCTATCTCTGCGTCT<br>GGTGACCTGATGCCGCTGTCTTACCTGGTTGGTATCCTGGAAGGT<br>AACCCGGACATCAAA<br>GTTTACTGGGACCGTAAACCGGAAGCGGCGATCGTTTCTGCGAC<br>CAAAGCGCTGGAAATC<br>ATCGGTATCCCGCCGTTCATCCTGAAACCGAAAGAAGGTCTGTCT<br>CTGATCAACGGTTCT<br>GCGGCGTCTGCGGCGGTTGCGTCTCTGGCGGCGCACGAAGCGTC<br>TCAGCTGGTTCTGCTG<br>GCGCAGGGTCTGACCGCGCTGACCTGCGAAGCGATGATGGGTAA<br>CGCGGAAAACTACCAC<br>GAATTCCCGGCGAAAATCCGTCCGCACCCGGGTCAGATCGAAGT<br>TGCGGCGAACATCCGT |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | AAAGGTATCATCAACTCTAAACTGATCGAAACCTCTGGTACCAA<br>AGACCGTCTGCGTCAG<br>GGTCTGATCCAGGACCGTTACGCGCTGCGTGGTGCGTCTCAGTG<br>GCTGGGTCCGGTTGTT<br>GAAGACCTGCGTCTGGCGATCCAGCAGCTGACCACCGAACTGAA<br>CTCTACCCAGGACAAC<br>CCGGTTATCGACTCTGAATCTGGTGAAGTTTACTTCTGCTCTAAC<br>TTCCAGGCGGCGTCT<br>GTTTCTATGGCGATGGAAAAAACCCGTGGTGGTCTGCAGATGAT<br>CGGTAAACTGCTGTTC<br>TCTTACTCTTCTGAACTGATCAACCCGGACATGAACAAAGGTCTG<br>CCGGCGAACCTGGCG<br>GCGGACGACCCGTCTCTGTCTTTCACCATGAAAGGTGTTGACATC<br>AACATGGCGGCGTAC<br>ATGTCTGAACTGGGTTTCCTGGCGAACTCTGTTACCTCTCACGTT<br>CAGTCTGCGGAAATG<br>AACAACCAGCCGATCAACTCTCTGGCGCTGATCTCTGCGCGTTAC<br>ACCCTGCAGGCGGTT<br>GAACTGGTTTCTATGATGTCTGCGGCGCTGCTGTACGTTACCTGC<br>CAGGCGGTTGACCTG<br>CGTATCCTGCACGAAACCTTCCTGGAAAACCTGTACTCTGTTCTG<br>TACCTGGCGTTCGAC<br>TCTGTTCAGATGCGTCAGGACAAATCTTCTGCGATCCGTACCGAA<br>CTGCTGCAGGCGCTG<br>CGTAACTCTTGGGGTCACTCTGCGCGTGACGACCTGTCTGTTCGT<br>ATCCAGGCGCTGTCT<br>ACCGCGATGGCGCCGGTTCTGCTGGCGAACGCGAAAGAACTGTC<br>TACCGAAGACCCGTTC<br>GCGGTTATCGAACACCTGCAGAAAGAAATCCGTCAGGAAGCGAA<br>AACCCTGTTCCTGGGT<br>CTGCGTGTTAAATCTTTCTGCGGTGACCTGAACGCGGAATCTTCT<br>CTGGGTCCGGCGGCG<br>AAAGCGCTGTACCGTTTCGTTCGTCGTGAACTGGACGTTCCGTTC<br>CACTGCGGTATCGGT<br>GAACACCCGACCGGTGACACCGAAGCGGCGGCGGACATCCCGCC<br>GCGTCCGCGTAAAACC<br>GTTGGTTCTTGGATCTCTATCATCTACGACGCGATCCGTGACGGT<br>CGTATCCGTCAGCCG<br>CTGGGTGACGACTGGCGTTGCTGCAACGGTTTC |
| 8 | Phenylalanine ammonia-lyase (PAL) | 9 | *Ganoderma sinense* | ATGCCGGGTTACACCCTGACCAAAACCCAGTCTACCTCTACCTTC<br>GAACCGTCTCCGGTT<br>ACCCTGAAAAAAGCGGCGGTTTCTTCTCCGCTGCACGCGGAACC<br>GGAACTGCCGAAACAG<br>TCTTCTGCGCCGACCCTGCTGCACAAATTCGTTGAAGCGCACCGT<br>GCGCTGAACAACTAC<br>AAACAGGGTCAGCCGATCGTTGTTGACGGTCAGACCCTGTCTAT<br>CCCGGCGGTTGCGGCG<br>GTTGCGCGTTACAACGCGGACGTTGTTCTGGACGACTCTTCTGAC<br>ATCCAGACCCGTGTT<br>CTGAAATCTCGTCAGGTTATCGTTGACAAAGTTTCTTCTCAGAAA<br>TCTGTTTACGGTGTT<br>TCTACCGGTTTCGGTGGTTCTGCGGACACCCGTACCTCTGACCCG<br>CTGACCCTGGGTCTG<br>GCGCTGTTCCAGCACCAGCACTGCGGTGTTCTGCCGTCTGACACC<br>GACTCTGTTCCGGTT<br>GCGCTGCCGCTGCTGGACCCGCTGACCTCTACCTCTATGCCGGAA<br>TCTTGGGTTCGTGGT<br>GCGATCCTGATCCGTATGAACTCTCTGATCCGTGGTCACTCTGGT<br>GTTCGTTGGGAACTG<br>ATCGAACGTATGTCTGCGCTGCTGCGTGAAAACATCGTTCCGCTG<br>GTTCCGCTGCGTGGT<br>TCTATCTCTGCGTCTGGTGACCTGTCTCCGCTGTCTTACATCGCG<br>GGTCTGCTGATCGGT<br>AACCCGTCTATCCGTGTTTTCGACGGTCCGTCTACCTTCCGTGGT<br>CGTCGTATCGTTTCT<br>TCTCGTGAAGCGCTGTCTGCGCACCACATCGAACCGATCTCTCTG<br>GGTTCTAAAGAACAC<br>CTGGGTATCCTGAACGGTACCGCGTTCTCTGCGTCTGTTGGTGCG<br>CTGGCGGTTCACGAA<br>GCGGTTCACCTGTCTCTGCTGGGTCAGGTTTGCACCGCGATGTGC<br>ACCGAAGCGATGCTG<br>GGTGCGAAAGGTTCTTTCGCGCCGTTCATCCACTCTGTTGCGCGT<br>CCGCACCCGGGTCAG |

TABLE 1-continued

| List of nucleic acid sequences encoding enzymes of podophyllotoxin pathway | | | | |
|---|---|---|---|---|
| Ref. No. | Genes | SEQ ID NO: | Organism | Sequence (codon optimized) |
| | | | | GTTGAAGTTGCGGAAACCGTTACCGACCTGCTGGAAGGTTCTCA<br>CTTCGCGGTTACCGCG<br>GAAGAAGAAAAACACATCTCTGCGGACATCGGTGAACTGCGTCA<br>GGACCGTTACCCGCTG<br>CGTACCTCTGCGCAGTTCCTGGGTCCGCAGGTTGAAGACGTTCTG<br>TCTGCGTTCGCGGCG<br>ATCACCATCGAATGCAACTCTACCACCGACAACCCGCTGATCGA<br>CGGTGAAACCGGTGAA<br>GTTCACCACGGTGGTAACTTCCAGGCGATGTCTGTTACCAACGCG<br>ATGGAAAAAACCCGT<br>CTGGCGATGCACCACATCGGTAAACTGCTGTTCGCGCAGTGCAC<br>CGAACTGCTGAACCCG<br>TCTATGAACCGTGGTCTGCCGCCGAACCTGGCGGCGACCGACCC<br>GTCTCACAACTACTTC<br>GCGAAAGGTGTTGACATCCACGCGGCGGCGTACGTTGGTGAACT<br>GGGTTACCTGGCGAAC<br>CCGGTTTCTACCCACGTTCAGTCTGCGGAAATGCACAACCAGGC<br>GGTTAACTCTCTGGCG<br>CTGATCTCTGCGCGTGCGACCCTGAACTCTCTGGAAGTTCTGTCT<br>ATCCTGACCTCTTCT<br>TTCCTGTACGTTCTGTGCCAGGCGCTGGACCTGCGTGCGATGCAG<br>CACGAATTCGAACTG<br>GAAGTTGACGGTATCCTGCGTCAGCAGCTGGCGCTGTCTTTCGGT<br>CGTCACCTGTCTGCG<br>GCGGACCTGGACGCGCTGTTCTCTGTTCTGTCTCGTCACGTTCGT<br>CGTTCTCTGGAAACC<br>ACCTCTACCATGGACGCGGCGCTGCGTATGCGTACCGTTGCGGC<br>GGCGACCACCACCCCG<br>TTCGTTGACTTCTGCGCGAAACGTAACACCTCTCTGGACCTGGAC<br>GAAATCGTTGCGTTC<br>CGTGCGGGTCTGTCTGAAGGTATGGTTGGTTCTCTGGTTCGTCTG<br>CGTGAAGAATACCTG<br>CGTGGTTCTAAAGGTCCGGCGCCGGCGGCGAAATACCTGGGTCG<br>TTCTCGTGCGGTTTAC<br>GAATTCGTTCGTGTTACCCTGGGTATCCGTATGCACGGTTCTGAA<br>AACCTGCACGACTTC<br>AAAGAAGGTCCGGGTGTTGAAGACCCGACCATCGGTCAGGACAT<br>CGCGCTGATCCACGAA<br>GCGATCCGTGACGGTAAAATGCAGGACGTTGTTGTTGGTATCTTC<br>GCG |
| 12 | Cinnamte 4 hydroxylase 4 coumarate coenzyme ligase fusion (C4H4CL) | 11 | *Azospirillum* sp. | ATGGACCTGCTGCTGCTGGAAAAAACCCTGCTGGCGCTGTTCATC<br>GCGGCGACCATCGCG<br>ATCACCATCTCTAAACTGCGTGGTAAACGTTTCAAACTGCCGCCG<br>GGTCCGATCCCGGTT<br>CCGGTTTTCGGTAACTGGCTGCAGGTTGGTGACGACCTGAACCA<br>CCGTAACCTGACCGAC<br>CTGGCGAAACGTTTCGGTGACATCTTCCTGCTGCGTATGGGTCAG<br>CGTAACCTGGTTGTT<br>GTTTCTTCTCCGGAACTGGCGAAAGAAGTTCTGCACACCCAGGG<br>TGTTGAATTCGGTTCT<br>CGTACCCGTAACGTTGTTTTCGACATCTTCACCGGTAAAGGTCAG<br>GACATGGTTTTCACC<br>GTTTACGGTACCCTGGCGGAAATGCGTCGTATCATGACCGTTCCG<br>TTCTTCACCAACAAA<br>GTTGTTCAGCAGTACCGTTTCGGTTGGGAATTCGAAGCGCAGTCT<br>GTTGTTGACGACGTT<br>AAAAAAAACCCGGAAGCGTGCTCTTCTGGTATCGTTCTGCGTCGT<br>CGTCTGCAGCTGATG<br>ATGTACAACATCATGTACCGTATCATGTTCGACCGTCGTTTCGAA<br>TCTGAAGAAGACCCG<br>CTGTTCGTTAAACTGAAAGCGCTGAACGGTGAACGTTCTCGTCTG<br>GCGCAGTCTTTCGAA<br>TACAACTACGGTGACTTCATCCCGATCCTGCGTCCGTTCCTGAAA<br>GGTTACCTGAAACTG<br>TGCAAAGAAGTTAAAGACCGTCGTCTGCAGCTGTTCAAAGACTA<br>CTTCGTTGACGAACGT<br>AAAAAACTGGGTTCTACCAAATCTACCACCAACGAAGGTCTGAA<br>ATGCGCGATCGACCAC<br>ATCCTGGACGCGCAGCAGAAAGGTGAAATCAACGACGACAACG<br>TTCTGTACATCGTTGAA<br>AACATCAACGTTGCGGCGATCGAAACCACCCTGTGGTCTATCGA<br>ATGGGGTATCGCGGAA<br>CTGGTTAACCACCAGAAAATCCAGAACAAAGTTCGTGAAGAAAT |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CGACCGTGTTCTGGGT<br>CCGGGTCACCAGGTTACCGAACCGGACCTGCAGAAACTGCCGTA<br>CCTGCAGGCGGTTATC<br>AAAGAAACCCTGCGTCTGCGTATGGCGATCCCGCTGCTGGTTCC<br>GCACATGAACCTGCAC<br>GACGCGAAACTGTCTGGTTTCGACATCCCGGCGGAATCTAAAAT<br>CCTGGTTAACGCGTGG<br>TGGCTGGCGAACAACCCGGCGCAGTGGAAAAAACCGGAAGAAT<br>TCCGTCCGGAACGTTTC<br>CTGGAAGAAGAATCTCACGTTGAAGCGAACGGTAACGACTTCCG<br>TTACCTGCCGTTCGGT<br>GTTGGTCGTCGTTCTTGCCCGGGTATCATCCTGGCGCTGCCGATC<br>CTGGGTATCACCCTG<br>GGTCGTCTGGTTCAGAACTTCGAACTGCTGCCGCCGCCGGGTCA<br>GTCTAAAATCGACACC<br>GCGGAAAAAGGTGGTCAGTTCTCTCTGCACATCCTGAAACACTC<br>TACCATCGTTTGCAAA<br>CCGCGTTCTTTCAACGGTGGTGGTGGTTCTGGTGGTGGTGGTTCT<br>GGTGGTGGTGGTTCT<br>ATGACCATCCAGCGTTGGTGGCGTAACCGTGAATCTCTGAACCG<br>TGTTCTGTGCGACCTG<br>CTGGCGGGTGAATTCGCGCGTCTGCGTCCGGGTGGTTCTCCGCCG<br>GCGCACCCGCACCGT<br>TGGCCGGAAACCCTGCCGCTGGGTCCGGACGGTGTTGGTGCGGA<br>CTCTCTGGACCTGCTG<br>CAGCTGGCGGCGGCGCTGAACGAAGCGCTGCACCTGCACCGTTC<br>TGGTATCGAAGACTAC<br>CTGCTGATGCACCGTACCGTTGGTGACTGGCTGGACGTTTGCGAA<br>GCGGCGCTGGGTCGT<br>TTCGACGGTGCGCTGTCTTTCCGTACCTCTGGTTCTACCGGTGAA<br>GGTAAACGTTGCGAA<br>CACCCGCTGGCGGCGCTGGAAGAAGAAGCGGACGCGCTGGCGG<br>CGCTGCTGTCTGGTGGT<br>GCGGAAGCGCCGCGTCGTGTTGTTTCTGTTGTTCCGGCGCACCAC<br>ATCTACGGTTTCCTG<br>TTCACCGTTCTGCTGCCGGACCGTCTGGCGGTTCCGGTTGTTGAC<br>GGTCGTGGTACCTCT<br>CCGGGTGGTCTGGCGGCGCGTCTGGGTCCGGGTGACCTGGTTGTT<br>GCGCACCCGGACTGG<br>TGGGGTGCGCTGCTGCGTTCTGGTGCGGCGCTGCCGGACGGTGTT<br>ACCGGTACCTCTTCT<br>ACCGCGCCGTGCCCGCCGGACACCGCGCGTGGTGTTCGTGGTGT<br>TGGTCTGGCGCGTCTG<br>GTTGAAGTTTTCGGTTCTTCTGAAACCGCGGGTCTGGGTTGGCGT<br>GAATCTCCGGACGCG<br>CCGTTCCGTCCGTTCCCGTGGTGGCGTTTCGGTGACGACGGTCGT<br>GTTACCCGTCGTCTG<br>GCGGACGGTACCGTTCTGTCTGCGACCCTGCAGGACCGTCTGTCT<br>CACGACGAAGAAGGT<br>TTCCGTCCGTCTGGTCGTCTGGACACCGTTGTTCAGGTTGGTGGT<br>GTTAACGTTTCTCTG<br>GCGGGTGTTCAGGCGCACCTGGCGGGTCACCCGGACGTTGAAGC<br>GGCGGCGGTTCGTCTG<br>ATGCGTCCGGAAGAAGGTACCCGTCTGAAAGCGTTCATCGTTCC<br>GGCGCGTACCGCGCCG<br>CCGCGTGAAGAACTGTACCGTCGTCTGACCGACTGGATCGAAGC<br>GACCCTGCCGGCGCCG<br>CACCGTCCGCGTGCGCTGGCGTTCGGTCCGGCGCTGCCGGTTAAC<br>GGTATGGGTAAACCG<br>TGCGACTGGCCGCTGGCGACCTGCCGT |
| 17 | hydroxycinnamoyl-<br>CoA:<br>quinate<br>hydroxycinnamoyl-<br>transferase<br>p-<br>coumaroyl<br>quinate 3'-<br>hydroxylase<br>fusion<br>(HCTC3H) | 13 | *Coffea canephora* | ATGAAAATCGAAGTTAAAGAATCTACCATGGTTCGTCCGGCGCA<br>GGAAACCCCGGGTCGT<br>AACCTGTGGAACTCTAACGTTGACCTGGTTGTTCCGAACTTCCAC<br>ACCCCGTCTGTTTAC<br>TTCTACCGTCCGACCGGTTCTTCTAACTTCTTCGACGCGAAAGTT<br>CTGAAAGACGCGCTG<br>TCTCGTGCGCTGGTTCCGTTCTACCCGATGGCGGGTCGTCTGAAA<br>CGTGACGAAGACGGT<br>CGTATCGAAATCGAATGCAACGGTGAAGGTGTTCTGTTCGTTGA<br>AGCGGAATCTGACGGT<br>GTTGTTGACGACTTCGGTGACTTCGCGCCGACCCTGGAACTGCGT<br>CGTCTGATCCCGGCG<br>GTTGACTACTCTCAGGGTATCTCTTCTTACGCGCTGCTGGTTCTG |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CAGGTTACCTACTTC<br>AAATGCGGTGGTGTTTCTCTGGGTGTTGGTATGCGTCACCACGCG<br>GCGGACGGTTTCTCT<br>GGTCTGCACTTCATCAACTCTTGGTCTGACATGGCGCGTGGTCTG<br>GACGTTACCCTGCCG<br>CCGTTCATCGACCGTACCCTGCTGCGTGCGCGTGACCCGCCGCAG<br>CCGCAGTTCCAGCAC<br>ATCGAATACCAGCCGCCGCCGGCGCTGAAAGTTTCTCCGCAGAC<br>CGCGAAATCTGACTCT<br>GTTCCGGAAACCGCGGTTTCTATCTTCAAACTGACCCGTGAACAG<br>ATCTCTGCGCTGAAA<br>GCGAAATCTAAAGAAGACGGTAACACCATCTCTTACTCTTCTTAC<br>GAAATGCTGGCGGGT<br>CACGTTTGGCGTTGCGCGTGCAAAGCGCGTGGTCTGGAAGTTGA<br>CCAGGGTACCAAACTG<br>TACATCGCGACCGACGGTCGTGCGCGTCTGCGTCCGTCTCTGCCG<br>CCGGGTTACTTCGGT<br>AACGTTATCTTCACCGCGACCCCGATCGCGATCGCGGGTGACCT<br>GGAATTCAAACCGGTT<br>TGGTACGCGGCGTCTAAAATCCACGACGCGCTGGCGCGTATGGA<br>CAACGACTACCTGCGT<br>TCTGCGCTGGACTACCTGGAACTGCAGCCGGACCTGAAAGCGCT<br>GGTTCGTGGTGCGCAC<br>ACCTTCAAATGCCCGAACCTGGGTATCACCTCTTGGGTTCGTCTG<br>CCGATCCACGACGCG<br>GACTTCGGTTGGGGTCGTCCGATCTTCATGGGTCCGGGTGGTATC<br>GCGTACGAAGGTCTG<br>TCTTTCATCCTGCCGTCTCCGACCAACGACGGTTCTATGTCTGTT<br>GCGATCTCTCTGCAG<br>GGTGAACACATGAAACTGTTCCAGTCTTTCCTGTACGACATCGGT<br>GGTGGTGGTTCTGGT<br>GGTGGTGGTTCTGGTGGTGGTGGTTCTATGGCGCTGCTGCTGATC<br>CTGCTGCCGGTTGCG<br>TTCATCTTCCTGGCGTACTCTCTGTACGAACGTCTGCGTTTCAAA<br>CTGCCGCCGGGTCCG<br>CGTCCGAAACCGGTTGTTGGTAACATCTACGACATCAAACCGGT<br>TCGTTTCAAATGCTAC<br>GCGGAATGGTCTAAACTGTACGGTCCGATCTTCTCTGTTTACTTC<br>GGTTCTCAGCTGAAC<br>ACCGTTGTTAACACCGCGGAACTGGCGAAAGAAGTTCTGAAAGA<br>CAACGACCAGCAGCTG<br>GCGGACCGTTACCGTTCTCGTCCGTCTGCGCGTATGTCTCGTAAC<br>GGTCAGGACCTGATC<br>TGGGCGGACTACGGTCCGCACTACGTTAAAGTTCGTAAACTGTG<br>CAACCTGGAACTGTTC<br>ACCCCGAAACGTCTGGAAGGTCTGCGTCCGCTGCGTGAAGACGA<br>AGTTACCGCGATGGTT<br>GACTCTATCTTCAAAGACTGCACCAAACCGGAAAACAAAGGTAA<br>ATCTCTGCTGATGCGT<br>AACTACCTGGGTTCTGTTGCGTTCAACAACATCACCCGTCTGACC<br>TTCGGTAAACGTTTC<br>ATGAACTCTGAAGGTGTTGTTGACGAACAGGGTCAGGAATTCAA<br>AGGTATCGTTTCTAAC<br>GGTATCCGTATCGGTGCGAAACTGTCTGTTGCGGACCACATCCCG<br>TGGCTGCGTTGGATG<br>TTCGTTGGTGAAAACGAAGACCTGGACAAACACAACGCGCGTCG<br>TGACAAACTGACCCGT<br>ATGATCATGGAAGAACACACCCTGGCGCGTCAGAAATCTGGTAA<br>CACCAAACAGCACTTC<br>GTTGACGCGCTGCTGACCCTGCAGAAACAGTACGAACTGTCTGA<br>CGACACCGTTATCGGT<br>CTGCTGTGGGACATGATCACCGCGGGTATGGACACCACCACCAT<br>CTCTGTTGAATGGGCG<br>ATGGCGGAACTGGTTAAAAACCCGCGTGTTCAGCAGAAAGCGCA<br>GGAAGAACTGGACCGT<br>GTTATCGGTTCTGACCGTATCATGACCGAAGCGGACTTCGCGAA<br>ACTGCCGTACCTGCAG<br>TGCGTTGCGAAAGAAGCGCTGCGTCTGCACCCGCCGACCCCGCT<br>GATGCTGCCGCACCGT<br>GCGAACGCGAACGTTAAAATCGGTGGTTACGACATCCCGAAAGG<br>TTCTATCGTTCACGTT<br>AACGTTTGGGCGATCGCGCGTGACCCGGCGGCGTGGAAAAACCC<br>GCTGGAATTCCGTCCG<br>GAACGTTTCCTGGAAGAAGACGTTGACATCAAAGGTCACGACTA |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CCGTCTGCTGCCGTTC GGTGCGGGTCGTCGTATCTGCCCGGGTGCGCAGCTGGCGCTGAA CCTGGTTACCTCTATG CTGGGTCACCTGCTGCACCACTTCACCTGGTCTCCGCCGCCGGGT GTTCGTCCGGAAGAA ATCGACCTGGAAGAATCTCCGGGTACCGTTACCTACATGCGTAC CCCGCTGCAGGCGGTT GCGACCCCGCGTCTGCCGGCGCACCTGTACAACCGTGTTCCGGTT GAA |
| 20 | Caffeoyl CoA O-methyhransferase (CCoAO MT) | 15 | *Eleocharis dulcis* | ATGTCTACCACCACCACCACCCAGACCAAAACCGAAACCCAGTC TCAGACCGGTGCGCAG AACGGTGCGGAACAGCAGACCCGTCACTCTGAAGTTGGTCACAA ATCTCTGCTGCAGTCT GACGCGCTGTACCAGTACATCCTGGAAACCTCTGTTTACCCGCGT GAACCGGAATGCATG AAAGAACTGCGTGACATCACCGCGAAACACCCGTGGAACCTGAT GACCACCTCTGCGGAC GAAGGTCAGTTCCTGAACCTGCTGCTGAAACTGATCGGTGCGAA AAAAACCATGGAAATC GGTGTTTACACCGGTTACTCTCTGCTGGCGACCGCGCTGGCGATC CCGGAAGACGGTACC ATCCTGGCGATGGACATCAACCGTGAAAACTACGAACTGGGTCT GCCGGTTATCGAAAAA GCGGGTGTTGCGCACAAAATCGACTTCCGTGAAGGTCCGGCGCT GCCGGTTCTGGACCAG CTGATCGAAGACCCGGCGAACCTGGGTTCTTTCGACTTCATCTTC GTTGACGCGGACAAA GACAACTACCTGAACTACCACAAACGTCTGATCGAACTGGTTAA AGTTGGTGGTGTTATC GGTTACGACAACACCCTGTGGAACGGTTCTGTTGTTCTGCCGGCG GACGCGCCGATGCGT AAATACATCCGTTACTACCGTGACTTCGTTCTGGAACTGAACAAA GCGCTGGCGGCGGAC CCGCGTATCGAAATCTCTCAGCTGCCGGTTGGTGACGGTATCACC CTGTGCCGTCGTGTT AAA |
| 21 | Caffeoyl CoA O-methyhransferase (CCoAO MT) | 17 | *Chamaecyparis formosensis* | ATGGCGACCGTTGAAGCGACCAAAGACTCTACCCAGCAGGTTTC TCGTCACCAGGAAGTT GGTCACAAATCTCTGCTGCAGTCTGACGCGCTGTACCAGTACATC CTGGAAACCTCTGTT TACCCGCGTGAACCGGAACCGATGCGTGAACTGCGTGAAATCAC CGCGAAACACCCGTGG AACCTGATGACCACCTCTGCGGACGAAGGTCAGTTCCTGCACCT GCTGCTGAAACTGATC AACGCGAAAAACACCATGGAAATCGGTGTTTACACCGGTTACTC TCTGCTGTCTACCGCG CTGGCGCTGCCGGACGACGGTAAAATCCTGGCGATGGACATCAA CCGTGAAAACTACGAA CTGGGTCTGCCGGTTATCCAGAAAGCGGGTGTTGCGCACAAAAT CGACTTCCGTGAAGGT CCGGCGCTGCCGGTTCTGGACCAGATGCTGGAAAACAAAGAAAT GCACGGTTCTTTCGAC TTCATCTTCGTTGACGCGGACAAAGACAACTACCTGAACTACCA CAAACGTCTGATCGAC CTGGTTAAAATCGGTGGTGTTATCGGTTACGACAACACCCTGTGG AACGGTTCTGTTGTT GCGCCGCCGGACGCGCCGATGCGTAAATACGTTCGTTACTACCG TGACTTCGTTATCGAA CTGAACAAAGCGCTGGCGGCGGACCCGCGTATCGAAATCTCTCA GATCCCGGTTGGTGAC GGTATCACCCTGTGCCGTCGTATCATC |
| 24 | Bifunctional pinoresinol-lariciresinol reductase (DIRPLR) | 19 | *Linum usitatissimum* | ATGGGTCGTTGCCGTGTTCTGGTTGTTGGTGGTACCGGTTACATC GGTAAACGTATCGTT AAAGCGTCTATCGAACACGGTCACGACACCTACGTTCTGAAACG TCCGGAAACCGGTCTG GACATCGAAAAAATTCCAGCTGCTGCTGTCTTTCAAAAAACAGGG TGCGCACCTGGTTGAA GCGTCTTTCTCTGACCACGAATCTCTGGTTCGTGCGGTTAAACTG GTTGACGTTGTTATC TGCACCGTTTCTGGTGCGCACTCTCGTTCTCTGCTGCTGCAGCTG AAACTGGTTGAAGCG |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | ATCAAAGAAGCGGGTAACGTTAAACGTTTCATCCCGTCTGAATT<br>CGGTATGGACCCGGCG<br>CGTATGGGTGACGCGCTGGAACCGGGTCGTGAAACCTTCGACCT<br>GAAAATGGTTGTTCGT<br>AAAGCGATCGAAGACGCGAACATCCCGCACACCTACATCTCTGC<br>GAACTGCTTCGGTGGT<br>TACTTCGTTGGTAACCTGTCTCAGCTGGGTCCGCTGACCCCGCCG<br>TCTGACAAAGTTACC<br>ATCTACGGTGACGGTAACGTTAAAGTTGTTTACATGGACGAAGA<br>CGACGTTGCGACCTAC<br>ACCATCATGACCATCGAAGACGACCGTACCCTGAACAAAACCAT<br>GTACTTCCGTCCGCCG<br>GAAAACGTTATCACCCACCGTCAGCTGGTTGAAACCTGGGAAAA<br>ACTGTCTGGTAACCAG<br>CTGCAGAAAACCGAACTGTCTTCTCAGGACTTCCTGGCGCTGATG<br>GAAGGTAAAGACGTT<br>GCGGAACAGATCGTTATCGGTCACCTGTACCACATCTACTACGA<br>AGGTTGCCTGACCAAC<br>TTCGACATCGACGCGGACCAGGACCAGGTTGAAGCGTCTTCTCT<br>GTACCCGGAAGTTGAA<br>TACACCCGTATGAAAGACTACCTGATGATCTACCTG |
| 27 | Secoisolar iciresinol dehydrogenase (SDH) | 21 | *Juglans regia* | ATGAACGGTACCTCTTCTCTGCTGGCGCCGATCGCGAAACGTCTG<br>GCGGGTAAAGTTGCG<br>CTGATCACCGGTGGTGCGTCTGGTATCGGTGAATCTACCGCGCGT<br>CTGTTCGCGGAACAG<br>GGTGCGAAAGTTATCATCGCGGACGTTCAGGACGAACTGGGTTT<br>CTCTGTTTCTCAGGAC<br>AAATCTATCAACGGTGCGATCTCTTACATCCACTGCGACGTTACC<br>TCTGAATCTGACGTT<br>CAGAACGCGGTTAACACCGCGGTTTCTAAACACGGTAAACTGGA<br>CATCATGTTCAACACC<br>GCGGGTTGCACCGGTCAGAACAAAGCGTCTATCCTGGACCACGA<br>ACAGAAAGACTACAAA<br>ACCGTTTTCGACGTTAACGTTCTGGGTTCTTTCCTGGGTGCGAAA<br>CACGCGGCGAAAGTT<br>ATGATCCCGGTTAAACGTGGTACCATCCTGTTCACCGCGTCTTGC<br>GTTACCGAATCTCAC<br>GGTCTGGCGTCTCACTCTTACACCGCGTCTAAACACGCGGTTGTT<br>GGTCTGACCAAAAAC<br>CTGTGCGTTGAACTGGGTCAGTACGGTATCCGTGTTAACTGCATC<br>TCTCCGTACGGTGCG<br>GCGACCCCGCTGTTCCTGAAAGGTATGGGTATCGACAAAAAAGA<br>AAAAGCGGAAGAAATC<br>CTGTCTTCTGCGGCGAACCTGAAAGGTCCGGTTCTGGAAGCGGG<br>TGACCTGGCGGAAGCG<br>GCGCTGTTCCTGGCGTCTGAAGAATCTAAATACGTTTCTGTTCTG<br>AACCTGGTTGTTGAC<br>GGTGGTTACTCTGCGACCAACGTTGCGTTCACCGAAACCATCCA<br>GAAATTCTTCACC |
| 32 | CYP719 | 23 | *Papaver somniferum* | ATGATCATGTCTAACCTGTGGATCCTGACCCTGATCTCTACCATC<br>CTGGCGGTTTTCGCG<br>GCGGTTCTGATCATCTTCCGTCGTCGTATCTCTGCGTCTACCACC<br>GAATGGCCGGTTGGT<br>CCGAAAACCCTGCCGATCATCGGTAACCTGCACATCCTGGGTGG<br>TACCGCGCTGCACGTT<br>GTTCTGCACAAACTGGCGGAAGTTTACGGTTCTGTTATGACCATC<br>TGGATCGGTTCTTGG<br>AAACCGGTTATCATCGTTTCTGACTTCGACCGTGCGTGGGAAGTT<br>CTGGTTAACAAATCT<br>TCTGACTACTCTGCGCGTGAAATGCCGGAAATCACCAAAATCGG<br>TACCGCGAACTGGCGT<br>ACCATCTCTTCTTCTGACTCTGGTCCGTTCTGGGCGACCCTGCGT<br>AAAGGTCTGCAGTCT<br>GTTGCGCTGTCTCCGCAGCACCTGGCGTCTCAGACCGCGCACCA<br>GGAACGTGACATCATC<br>AAACTGATCAAAAACCTGAAAGACGAAGCGGCGTCTGGTATGGT<br>TAAACCGCTGGACCAC<br>CTGAAAAAAGCGACCGTTCGTCTGATCTCTCGTCTGATCTACGGT<br>CAGGACTTCGACGAC<br>GACAAATACGTTGAAGACATGCACGACGTTATCGAATTCCTGAT<br>CCGTATCTCTGGTTAC<br>GCGCAGCTGGCGGAAGTTTTCTACTACGCGAAATACCTGCCGGG |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | TCACAAACGTGCGGTT<br>ACCGGTGCGGAAGAAGCGAAACGTCGTGTTATCGCGCTGGTTCG<br>TCCGTTCCTGCAGTCT<br>AACCCGGCGACCAACACCTACCTGCACTTCCTGAAATCTCAGCT<br>GTACCCGGAAGAAGTT<br>ATCATCTTCGCGATCTTCGAAGCGTACCTGCTGGGTGTTGACTCT<br>ACCTCTTCTACCACC<br>GCGTGGGCGCTGGCGTTCCTGATCCGTGAACCGTCTGTTCAGGA<br>AAAACTGTACCAGGAA<br>CTGAAAAACTTCACCGCGAACAACAACCGTACCATGCTGAAAGT<br>TGAAGACGTTAACAAA<br>CTGCCGTACCTGCAGGCGGTTGTTAAAGAAACCATGCGTATGAA<br>ACCGATCGCGCCGCTG<br>GCGATCCCGCACAAAGCGTGCAAAGACACCTCTCTGATGGGTAA<br>AAAAGTTGACAAAGGT<br>ACCAAAGTTATGGTTAACATCCACGCGCTGCACCACACCGAAAA<br>AGTTTGGAAAGAACCG<br>TACAAATTCATCCCGGAACGTTTCCTGCAGAAACACGACAAAGC<br>GATGGAACAGTCTCTG<br>CTGCCGTTCTCTGCGGGTATGCGTATCTGCGCGGGTATGGAACTG<br>GGTAAACTGCAGTTC<br>TCTTTCTCTCTGGCGAACCTGGTTAACGCGTTCAAATGGTCTTGC<br>GTTTCTGACGGTGTT<br>CTGCCGGACATGTCTGACCTGCTGGGTTTCGTTCTGTTCATGAAA<br>ACCCCGCTGGAAGCG<br>CGTATCGTTCCGCGT |
| 33 | CYP719 | 25 | *Cinnamomum micranthum* | ATGGAAGCGATCTGGACCGCGGTTGCGATCGGTATCGCGGCGGC<br>GGTTCTGATGGCGTTC<br>CGTGGTCGTCAGCGTCAGCGTCTGTCTCGTAAACCGACCCAGTG<br>GCCGCCGGGTCCGACC<br>CGTCTGCCGCTGATCGGTAACATGCACCAGATCCTGCTGAAAGG<br>TGGTGACCCGTTCCAC<br>GTTGCGATCAACAAACTGGCGCAGGTTTACGGTCCGCTGATGAC<br>CGTTTGGTTCGGTACC<br>CGTCAGCCGACCATCATCGTTTCTGACCACAACCTGGTTTGGGAA<br>GTTCTGGTTTCTAAA<br>TCTGCGGACTACGCGGCGCGTGAAATCCCGATCACCCTGAAACC<br>GTCTCTGGCGGACTTC<br>CGTACCATCGTTTCTTCTAACGCGGGTCCGCTGTGGCACTCTCTG<br>CGTCGTGGTCTGCAG<br>AACGGTGCGATCGGTCCGCACTCTCTGTCTCTGCAGGCGCCGTTC<br>CAGGAATCTGACATG<br>GCGCAGATGATCAACAACATGATCAAAGAAGCGAACCTGAACG<br>GTGGTGTTGTTAAACCG<br>TTCCCGCACATCCGTCGTGCGATCATCAAACTGCTGGCGCGTATC<br>TGCTTCGGTTGCGAC<br>TTCTCTGACGAAGAATTCGACGCGACCATGGACTTCATGGTTGA<br>AGAAGCGCTGCGTTAC<br>TCTGACGACTCTCGTATCCTGGACACCTTCCCGCCGGCGCGTTTC<br>CTGCCGTCTGTTAAA<br>CGTGCGGTTATGCAGATGGAAAAAGTTAAACTGCGTCTGATGGA<br>ATGCATCGGTCGTCCG<br>CTGGACTCTCCGCTGCCGCCGACCTGCTACGCGCACTTCCTGCTG<br>TCTCAGTCTTTCCCG<br>CGTGAAGTTGCGATCTTCTCTATCTTCGAACTGTTCCTGCTGGGT<br>GTTGACTCTACCGGT<br>TCTACCACCATGTGGGGTCTGGGTCTGCTGATGCAGAACCAGGA<br>AGCGCAGCAGAAACTG<br>TACCAGGAAATCCGTGAACACGCGTCTTGCAACGAAAAAGGTGT<br>TGTTAAAGTTGAAGAA<br>CTGGGTAAACTGGAATACCTGCAGGCGGTTGCGAAAGAAACCAT<br>GCGTATGAAACCGATC<br>GCGCCGCTGGCGGTTCCGCACCAGGCGGCGCGTGACACCACCCT<br>GGACGGTCTGCACGTT<br>GCGGAAGGTACCACCGTTCTGGCGAACCTGTACGCGCTGCACTA<br>CGACCCGAAAGTTTGG<br>GACGAACCGGAACGTTTCAAACCGGAACGTTTCCTGGAATCTTC<br>TAAAGAATTCCTGGGT<br>AAACGTGGTCAGTACTCTTTCCTGCCGTTCGGTGCGGGTATGCGT<br>GCGTGCGCGGGTATG<br>GAAGTTGGTAAACTGCAGCTGCCGTTCGCGATCTGCAACCTGGTT<br>AACGCGTTCAACTGG<br>TCTAACGTTGTTGAAAAAGAAGCGCCGAAACTGATCGAAGGTTT |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CTCTTTCATCCTGTCT<br>ATGAAAACCCCGCTGGAAGCGCGTATCGTTCCGCGTGGTATC |
| 34 | O-methyhransferase 3 (OMT) | 27 | *Papaver somniferum* | ATGGAAGTTGTTTCTAAAATCGACCAGGAAAACCAGGCGAAAAT<br>CTGGAAACAGATCTTC<br>GGTTTCGCGGAATCTCTGGTTCTGAAATGCGCGGTTCAGCTGGAA<br>ATCGCGGAAACCCTG<br>CACAACAACGTTAAACCGATGTCTCTGTCTGAACTGGCGTCTAA<br>ACTGCCGGCGCAGCCG<br>GTTAACGAAGACCGTCTGTACCGTATCCTGCACTTCCTGGTTCAC<br>ATGAAACTGTTCAAC<br>AAAGACGCGACCACCCAGAAATACTCTCTGGCGCCGCCGGCGAA<br>ATACCTGCTGAAAGGT<br>TGGGAAAAAATCTATGGTTCCGTCTATCCTGTCTGTTACCGACAAA<br>GACTTCACCGCGCCG<br>TGGAACCACCTGGGTGACGGTCTGACCGGTAACTGCAACGCGTT<br>CGAAAAAGCGCTGGGT<br>AAAGGTATCCGTGTTTACATGCGTGAAAACCCGGAAAAAGACCA<br>GCTGTTCAACGAAGGT<br>ATGGCGTGCGACACCCGTCTGTTCGCGTCTGCGCTGGTTAACGAA<br>TGCAAATCTATCTTC<br>TCTGACGGTATCAACACCCTGGCGGGTGTTGGTCGTGGTACCGGT<br>ACCGCGGTTAAAGCG<br>ATCTCTAAAGCGTTCCCGGACATCAAATGCACCATCCACGACCT<br>GCCGGAAGTTACCTCT<br>AAAAACTCTAAAATCCCGCGTGACGTTTTCAAATCTGTTCCGTCT<br>GCGGACGCGATCTTC<br>ATGAAATCTATCCTGCACGAATGGAACGACGAAGAATGCATCCA<br>GATCCTGAAACGTTGC<br>AAAGAAGCGATCCCGAAAGGTGGTAAAGTTATCATCGCGGACGT<br>TGTTATCGACATGGAC<br>TCTACCCACCCGTACTCTAAATCTCGTCTGGCGATGGACCTGGCG<br>ATGATGCTGCACACC<br>GGTGGTAAAGAACGTACCGAAGAAGACTGGAAAAAACTGATCG<br>ACGCGGCGGGTTTCGCG<br>TCTTGCAAAATCACCAAACTGTCTGCGCTGCAGTCTGTTATCGAA<br>GCGTACCCGCAC |
| 37 | O-methyhransferase 3 (OMT) | 29 | *Sinopodophyllum hexandrum* | ATGGAAATGGCGCCGACCATGGACCTGGAAATCCGTAACGGTAA<br>CGGTTACGGTGACTCT<br>GGTGAAGAACTGCTGGCGGCGCAGGCGCACATCTACAACCACAT<br>CTTCAACTTCATCTCT<br>TCTATGGCGCTGAAATGCGCGGTTGAACTGAACATCCCGGAAAT<br>CCTGCACAACCACCAG<br>CCGAAAGCGGTTACCCTGTCTGAACTGGTTCAGGCGCTGCAGAT<br>CCCGCAGGCGAAATCT<br>GCGTGCCTGTACCGTCTGCTGCGTATCCTGGTTCACTCTGGTTTCT<br>TCGCGATCACCAAA<br>ATCCAGTCTGAAGGTGACGAAGAAGGTTACCTGCCGACCCTGTC<br>TTCTAAACTGCTGCTG<br>AAAAACCACCCGATGTCTATGTCTCCGTGCCTGCTGGGTCTGGTT<br>AACCCGACCATGGTT<br>GCGCCGATGCACTTCTTCTCTGACTGGTTCAAACGTTCTGACGAC<br>ATGACCCCGTTCGAA<br>GCGACCCACGGTGCGTCTCTGTGGAAATACTTCGGTGAAACCCC<br>GCACATGGCGGAAATC<br>TTCAACGAAGCGATGGGTTGCGAAACCCGTCTGGCGATGTCTGT<br>TGTTCTGAAAGAATGC<br>AAAGGTAAACTGGAAGGTATCTCTTCTCTGGTTGACGTTGGTGGT<br>GGTACCGGTAACGTT<br>GGTCGTGCGATCGCGGAAGCGTTCCCGAACGTTAAATGCACCGT<br>TCTGGACCTGCCGCAG<br>GTTGTTGGTAACCTGAAAGGTTCTAACAACCTGGAATTCGTTTCT<br>GGTGACATGTTCCAG<br>TTCATCCCGCCGGCGGACGTTGTTTTCCTGAAATGGATCCTGCAC<br>GACTGGAACGACGAA<br>GAATGCATCAAAATCCTGAAACGTTGCAAAGAAGCGATCCCGTC<br>TAAAGAAGAAGGTGGT<br>AAACTGATCATCATCGACATGGTTGTTAACGACCACAACAAAGG<br>TTCTTACGAATCTACC<br>GAAACCCAGCTGTTCTACGACCTGACCCTGATGGCGCTGCTGAC<br>CGGTACCGAACGTACC |

TABLE 1-continued

| Ref. No. | Genes | SEQ ID NO: | Organism | Sequence (codon optimized) |
|---|---|---|---|---|
| List of nucleic acid sequences encoding enzymes of podophyllotoxin pathway | | | | |
| | | | | GAAACCGAATGGAAAAAACTGTTCGTTGCGGCGGGTTTCACCTC<br>TTACATCATCTCTCCG<br>GTTCTGGGTCTGAAATCTATCATCGAAGTTTTCCCG |
| 39 | CYP71 | 31 | *Cinnamomum micranthum* | ATGGCGCTGCTGCTGTCTCTGCTGTTCTTCGCGTCTGCGCTGATCT<br>TCCTGCTGAAACTG<br>AACGGTCAGCGTGCGAACAAAACCGACGTTCCGCCGTCTCCGCC<br>GAAACTGCCGCTGATC<br>GGTAACCTGCACCAGCTGGGTACCCTGCCGCACCGTTCTCTGCGT<br>TCTCTGGCGGGTAAA<br>TACGGTCCGCTGATGCTGCTGTACCTGGGTCGTATCCCGACCCTG<br>ATCGTTTCTTCTGAA<br>GAAATGGCGGAACAGATCATGAAAACCCACGACCTGATCTTCGC<br>GTCTCGTCCGTCTATC<br>ACCGCGGCGAAAGAACTGCTGTACGGTTGCACCGACCTGGCGTT<br>CGCGTCTTACGGTGAA<br>TACTGGCGTCAGGTTCGTAAAATGTGCGTTCTGGAACTGCTGTCT<br>ATCAAACGTGTTAAC<br>TCTTTCCGTTCTATCATGGAAGAAGAAGTTGGTCTGATGATCGAA<br>CGTATCTCTCAGTCT<br>TCTTCTACCGGTGCGGCGGTTAACCTGGCGGAACTGTTCCTGTCT<br>CTGACCGGTGGTACC<br>ATCGCGCGTGCGGCGCTGGGTAAAAAATACGAAGGTGAAGCGG<br>AAGAAGGTCGTAACAAA<br>TACGCGGACCTGGTTAAAGAACTGCACGCGCTGCTGGGTGCGTT<br>CTCTGTTGGTGACTAC<br>TTCCCGTCTCTGGCGTGGGTTGACGTTGTTACCGGTCTGCACGGT<br>AAACTGAAACGTAAC<br>TCTCGTGAACTGGACCGTTTCCTGGACCAGGTTATCGAACACCAC<br>CTGATGCGTCCGCTG<br>GACGGTTGCGACGTTGGTGAACACACCGACCTGGTTGACGTTAT<br>GCTGCAGGTTCAGAAA<br>GACTCTAACCGTGACATCCACCTGACCCGTGACAACATCAAAGC<br>GATCATCCTGGACATG<br>TTCTCTGCGGGTACCGACACCACCGCGCTGACCCTGGAATGGGTT<br>ATGGCGGAACTGGCG<br>AAACACCCGAACGTTATGAAAAAAGCGCAGGGTGAAGTTCGTCG<br>TGTTGTTGACGTTAAA<br>GCGAACATCTCTGAAGAACACCTGTGCCAGCTGAACTACATGAA<br>ATCTATCATCAAAGAA<br>ACCCTGCGTCTGCACCCGCCGGCGCCGCTGCTGGTTCCGCGTGAA<br>TCTACCACCAACGTT<br>AAAATCCAGAACTTCCACATCCCGCCGAAAACCCGTGTTTTCATC<br>AACGCGTACGCGATC<br>GGTCGTGACCCGACCTCTTGGGAAAACCCGGAAGAATTCCTGCC<br>GGAACGTTTCGCGAAC<br>AACTCTGTTGACTTCAAAGGTCAGGACTTCCAGTTCATCCCGTTC<br>GGTGCGGGTCGTCGT<br>GGTTGCCCGGGTCTGTCTTTCGCGATCACCTCTCTGGAACTGGCG<br>CTGGCGAACCTGCTG<br>TACTGGTTCGACTGGGAACTGCCGCAGGGTGTTACCGAAGAAGA<br>CCTGGACATGTCTGAA<br>GCGCTGGGTATCACCGTTCACAAAAAACTGCCGCTGTACCTGGTT<br>CCGAAAAACCACTTC<br>TCT |
| 46 | 2-oxoglutarate/Fe(II)-dependent dioxygenase (2-ODD) | 33 | *Microcystis viridis* | ATGACCACCGACTTCATCGAAATCTACGAACGTGCGCTGCGTCG<br>TGAACTGTGCGAAGAA<br>ATCCGTCACCGTTTCGAAGCGTCTAACCGTAAATCTGACGGTCGT<br>ATCGGTCACGGTGTT<br>GACAAATCTAAAAAAAACTCTACCGACATCACCATCACCGGTCT<br>GTCTGAATGGTCTGAC<br>CTGCACTCTCAGATCCTGGACTCTACCCTGCGTCACCTGATGCTG<br>TACATCCGTAAATAC<br>CCGTACCTGATCACCTCTGCGTTCGCGCTGTCTCTGCAGGAACCG<br>GCGACCGGTCTGGTT<br>CGTCCGCTGACCGCGTCTGACGTTGGTGCGGCGTCTGACCTGGA<br>ACTGGGTGAATACCTG<br>TTCCGTGTTTTCCGTCCGGGTGCGATCAACGTTCAGAAATACTCT<br>AAATCTCTGGGTGGT<br>TACTACTACTGGCACTCTGAAATCTACCCGCGTGACCCGGCGGC<br>GGAAACCCTGCACCGT<br>GTTCTGCTGTTCATGTTCTACCTGAACGACGTTGAACGTGGTGGT<br>GAAACCGAATTCCTG |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | TACCAGGAACGTAAACTGAAACCGACCTCTGGTACCATGGTTAT<br>CGCGCCGGCGGGTTTC<br>ACCCACACCCACCGTGGTAACGTTCCGGAATCTCACGACAAATA<br>CATCCTGACCTCTTGG<br>ATCCTGTTCAACCGTGCGGAACAGCTGTACCCGCGTAAACCGAA<br>CCCGGCG |
| 48 | 2-oxoglutarate/ Fe(II)-dependent dioxygenase (2-ODD) | 35 | *Nitrospira moscoviensis* | ATGGTTTCTAACATGGCGATGGGTATCACCGAAGCGGTTGACCG<br>TGCGGTTGCGGCGCTG<br>GACGTTGACCGTCTGCACCGTGAATACTGGGAACAGAACGAATT<br>CCTGGTTATCCGTCAG<br>TTCCTGCCGCGTGCGTTCGTTGAAGAAGTTCTGGTTCCGCAGGCG<br>CAGGGTGTTAAAACC<br>GAACTGAACCGTAACTACATCCCGGGTCACAAAAAAGGTGGTTC<br>TGTTTCTTACTACACC<br>GTTCGTCGTCGTGCGCCGCTGTTCCTGGACCTGTACCGTTCTGAC<br>TCTTTCCGTGCGTTC<br>CTGGACCGTCTGGTTGACGCGAAACTGCTGCTGTGCCCGGAAAA<br>CGACCCGCACTCTTGC<br>GCGCTGTACTACTACACCGAACCGGGTGACCACATCGGTTTCCA<br>CTACGACACCTCTTAC<br>TACAAAGGTGCGCGTTACACCATCCTGATGGGTCTGGTTGACCGT<br>TCTACCCAGTGCAAA<br>CTGGTTTGCGAACTGTTCAAAGACCACCCGACCAAAGCGCCGCA<br>GCGTCTGGAACTGATC<br>ACCGAACCGGGTGACATGGTTATCTTCAACGGTGACAAACTGTG<br>GCACGCGGTTACCCCG<br>CTGGGTGAAGGTGAAGAACGTATCGCGCTGACCATGGAATACGT<br>TACCAACCCGGAAATG<br>GGTGCGTTCAAACGTCTGTACTCTAACCTGAAAGACTCTTTCGCG<br>TACTTCGGTCTGAAA<br>ACCGTTTTCAAACAGGCGCTGGCGAAAAAATCTTCT |
| 49 | 2-oxoglutarate/ Fe(II)-dependent dioxygenase (2-ODD) | 37 | *Nifrospira japonica* | ATGATGGGTGGTGCGATGACCACCCAGACCCTGGACACCATCGC<br>GGAAGCGGTTGACCAG<br>GCGGTTGCGCGTCTGGACTTCGACCGTCTGCACCGTGAATACTGG<br>GAACAGAACGAATTC<br>CTGGTTATCCCGCAGTTCCTGGACCGTGCGATGGTTGAAGAATG<br>GCTGGTTCCGCAGGCG<br>CAGGGTGTTAAAGGTGACCTGAACCGTAACTACATCCCGGGTCA<br>CAAAAAAGGTGGTTCT<br>GTTTCTTACTACACCGTTATGGAAAAAGCGCCGCGTTTCCTGGAC<br>CTGTACCGTTCTCAG<br>GTTTTCATCGAATTCCTGTCTCGTCTGTCTCACGCGAAACTGCGT<br>CTGTGCCCGGACAAC<br>GACCCGCACTCTTGCGCGCTGTACTACTACACCGAACCGGGTGA<br>CCACATCGGTTTCCAC<br>TACGACACCTCTTACTACAAAGGTTCTCGTTACACCATCCTGATG<br>GGTCTGGTTGACCAG<br>TCTACCCACTGCAAACTGGTTTGCGAACTGTTCAAAGACGACCC<br>GGTTCGTCCGTCTAAA<br>CGTCTGGAACTGATCACCCAGCCGGGTGACATGGTTATCTTCAAC<br>GGTGACAAACTGTGG<br>CACGCGGTTACCCCGCTGGGTCCGAACGAAGAACGTATCGCGCT<br>GACCATGGAATACGTT<br>ACCAACCCGGACATGGGTACCTTCAAACGTCTGTACTCTAACCTG<br>AAAGACTCTTTCGCG<br>TACTTCGGTCTGCGTGCGGTTTTCAAACGTGCGCTGTCTCTGCCG<br>CGTCGT |
| 52 | CYP82D | 39 | *Panax ginseng* | ATGGAAACCTTCCTGGCGCAGCTGTACTCTACCACCACCATCGCG<br>GCGCTGTTCGTTCTG<br>CTGGTTCTGTACTACTTCTCTCCGTGGACCCGTATCAACAAAAAA<br>AACGTTGCGCCGGAA<br>GCGGGTGGTGGTTGGCCGATCATCGGTCACCTGCACCTGCTGGG<br>TGGTTCTAAACTGCCG<br>CACCTGGTTTTCGGTTCTATGGCGGACAAATACGGTCCGATCTTC<br>ACCGTTCGTCTGGGT<br>GTTCAGCGTTCTCTGGTTGTTTCTTCTTGGGAAATGGTTAAAGAC<br>ATCTTCACCACCAAC<br>GACGTTATCGTTTCTGGTCGTCCGAAATTCCTGGCGGCGAAACAC<br>CTGTCTTACAACTAC<br>GCGATGTTCGGTTTCTCTCCGTACGGTTCTTTCTGGCTGGAACTG<br>CGTAAAATCACCTCT |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | CTGCAGCTGCTGTCTAACCGTCGTCTGGAACTGCTGAAACACGTT<br>CGTGTTTCTGAAATG<br>GAAATCTCTATGCGTCAGCTGTACAAACTGTGGTCTGAAAAAAA<br>AAACGGTTCTGGTCGT<br>GTTCTGATGGACATGAAAAAATGGTTCGGTGAACTGAACCTGAA<br>CGTTACCTTCCGTATG<br>GTTGCGGGTAAACGTTACTTCGGTGGTGGTGCGGCGTCTAACGA<br>CGAAGAAGCGCGTCGT<br>TGCCGTCGTGTTGTTCGTGAATTCTTCCGTCTGCTGGGTGTTGTTG<br>TTGTTGCGGACTCT<br>CTGCCGTTCCTGCGTTGGCTGGACCTGGGTGGTTACGAACGTGCG<br>ATGAAAGAAACCGCG<br>CGTGAAATGGACTCTATCGTTTCTGTTTGGCTGGAAGAACACCGT<br>ATCAAATCTGACTCT<br>TCTGGTGACGACGCGAACATGGAACAGGACTTCATGGACGTTAT<br>GCTGTCTGCGGTTAAA<br>AACGTTGACCTGTGCGGTTTCGACGCGCACACCGTTATCAAAGC<br>GACCTGCATGGTTATC<br>ATCTCTTCTGGTACCGACACCACCACCGTTGAACTGACCTGGGCG<br>CTGTGCCTGCTGCTG<br>AACAACCGTCACGTTCTGAAAAAAGCGCAGGAAGAACTGGACA<br>ACGTTGTTGGTAAACAG<br>CGTCGTGTTAAAGAATCTGACCTGAACAACCTGATCTACCTGCA<br>GGCGATCGTTAAAGAA<br>ACCCTGCGTCTGTACCCGGCGGGTCAGCTGGGTGGTCAGCGTGA<br>ATTCTCTGACGACTGC<br>ACCGTTGGTGGTTACCACGTTCCGAAACGTACCCGTCTGGTTGTT<br>AACCTGTGGAAACTG<br>CACCGTGACCCGCGTATCTGGTCTGACCCGACCGAATTCCGTCCG<br>GAACGTTTCCTGGAA<br>CGTCACAAAGAAATCGACGTTAAAGGTCAGCACTTCGAACTGAT<br>CCCGTTCGGTGCGGGT<br>CGTCGTGTTTGCCCGGGTATCACCTTCGGTCTGCAGATGTTCCAC<br>CTGGTTCTGGCGTCT<br>CTGCTGCACGGTTTCGACATCTCTACCCCGTCTGACGCGCCGGTT<br>GACATGGCGGAAGGT<br>GCGGGTCTGACCAACGCGAAAATCACCCCGCTGGAAATCCTGAT<br>CGCGCCGCGTCTGTCT<br>CCGTCTCTGTACGAA |
| 57 | Glycosyltransferase (UGT) | 41 | *Malus domestica* | ATGAAAAAAGTTGAACTGGTTTTCATCCCGTCTCCGGGTGCGGGT<br>CACCACCTGCCGACC<br>CTGCAGTTCGTTAAACGTCTGATCGACCGTAACGACCGTATCTCT<br>ATCACCATCCTGGCG<br>ATCCAGTCTTACTTCCCGACCACCCTGTCTTCTTACACCAAATCT<br>ATCGCGGCGTCTGAA<br>CCGCGTATCCGTTTCATCGACGTTCCGCAGCCGCAGGACCGTCCG<br>CCGCAGGAAATGTAC<br>AAATCTCGTGCGCAGATCTTCTCTCTGTACATCGAATCTCACGTT<br>CCGTCTGTTAAAAAA<br>ATCATCACCAACCTGGTTTCTTCTTCTGCGAACTCTTCTGACTCTA<br>TCCGTGTTGCGGCG<br>CTGGTTGTTGACCTGTTCTGCGTTTCTATGATCGACGTTGCGAAA<br>GAACTGAACATCCCG<br>TCTTACCTGTTCCTGACCTCTAACGCGGGTTACCTGGCGTTCATG<br>CTGCACCTGCCGATC<br>CTGCACGAAAAAAACCAGATCGCGGTTGAAGAATCTGACCCGGA<br>CTGGTCTATCCCGGGT<br>ATCGTTCACCCGGTTCCGCCGCGTGTTCTGCCGGCGGCGCTGACC<br>GACGGTCGTCTGTCT<br>GCGTACATCAAACTGGCGTCTCGTTTCCGTGAAACCCGTGGTATC<br>ATCGTTAACACCTTC<br>GTTGAACTGGAAACCCACGCGATCACCCTGTTCTCTAACGACGA<br>CCGTGTTCCGCCGGTT<br>TACCCGGTTGGTCCGGTTATCGACCTGGACGACGGTCAGGAACA<br>CTCTAACCTGGACCAG<br>GCGCAGCGTGACAAAATCATCAAATGGCTGGACGACCAGCCGCA<br>GAAATCTGTTGTTTTC<br>CTGTGCTTCGGTTCTATGGGTTCTTTCGGTGCGGAACAGGTTAAA<br>GAAATCGCGGTTGGT<br>CTGGAACAGTCTGGTCAGCGTTTCCTGTGGTCTCTGCGTATGCCG<br>TCTCCGAAAGGTATC<br>GTTCCGTCTGACTGCTCTAACCTGGAAGAAGTTCTGCCGGACGGT<br>TTCCTGGAACGTACC |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | AACGGTAAAAAAGGTCTGATCTGCGGTTGGGCGCCGCAGGTTGA<br>AATCCTGGCGCACTCT<br>GCGACCGGTGGTTTCCTGTCTCACTGCGGTTGGAACTCTATCCTG<br>GAATCTCTGTGGCAC<br>GGTGTTCCGATCGCGACCTGGCCGATGTACGCGGAACAGCAGCT<br>GAACGCGTTCCGTATG<br>GTTCGTGAACTGGGTATGGCGCTGGAAATGCGTCTGGACTACAA<br>AGCGGGTTCTGCGGAC<br>GTTGTTGGTGCGGACGAAATCGAAAAAGCGGTTGTTGGTGTTAT<br>GGAAAAAGACTCTGAA<br>GTTCGTAAAAAAGTTGAAGAAATGGGTAAAATGGCGCGTAAAGC<br>GGTTAAAGACGGTGGT<br>TCTTCTTTCGCGTCTGTTGGTCGTTTCATCGAAGACGTTATCGGTC<br>AGAAC |
| 58 | Glycosyltransferase (UGT) | 43 | *Lycium barbarum* | ATGGGTCACCTGGTTTCTACCGTTGAAATGGCGAAACAGCTGGTT<br>GACCGTGAAGACCAG<br>CTGTCTATCACCGTTCTGATCATGACCCTGCCGACCGAAACCAAA<br>ATCCCGTCTTACACC<br>AAATCTCTGTCTTCTAACTACACCTCTCGTATCCGTCTGCTGGAA<br>CTGACCCAGCCGGAA<br>ACCTCTGTTAACATGGGTTCTGCGACCCACCCGATGAAATTCATG<br>TCTGAATTCATCACC<br>TCTTACAAAGGTCGTGTTAAAGACGCGGTTGCGGACATGTTCTCT<br>TCTCTGTCTTCTGTT<br>AAACTGGCGGGTTTCGTTATCGACATGTTCTGCACCGCGATGATC<br>GACGTTGCGAACGAC<br>TTCGGTGTTCCGTCTTACCTGTTCTACACCTCTGGTGCGGCGATG<br>CTGGGTCTGCAGTTC<br>CACTTCCAGTCTCTGATCTCTCAGAACGTTCTGTCTTACCTGGAC<br>TCTGAATCTGAAGTT<br>CTGATCCCGACCTACATCAACCCGGTTCCGGTTAAATTCCTGCCG<br>GGTCTGATCCTGGAC<br>AACGACGAATACTCTATCATGTTCCTGGACCTGGCGGGTCGTTTC<br>AAAGAAACCAAAGGT<br>ATCATGGTTAACACCTTCGTTGAAGTTGAATCTCACGCGCTGAAA<br>GCGCTGTCTGACGAC<br>GAAAAAATCCCGCCGATCTACCCGGTTGGTCCGATCCTGAACCT<br>GGGTGGTGGTAACGAC<br>GGTCACGGTGAAGAATACGACTCTATCATGAAATGGCTGGACGG<br>TCAGCCGAACTCTTCT<br>GTTGTTTTCCTGTGCTTCGGTTCTATGGGTTCTTTCGAAGAAGAC<br>CAGGTTAAAGAAGTT<br>GCGAACGCGCTGGAATCTTCTGGTTACCAGTTCCTGTGGTCTCTG<br>CGTCAGCCGCCGCCG<br>AAAGACAAACTGCAGTTCCCGTCTGAATTCGAAAACCTGGAAGA<br>AGTTCTGCCGGAAGGT<br>TTCCTGCAGCGTACCAAAGGTCGTGGTAAAATGATCGGTTGGGC<br>GCCGCAGGTTGCGATC<br>CTGTCTCACCCGTCTGTTGGTGGTTTCGTTTCTCACTGCGGTTGGA<br>ACTCTACCCTGGAA<br>TCTGTTCGTTCTGGTGTTCCGATGGCGACCTGGCCGATGTACGCG<br>GAACAGCAGTCTAAC<br>GCGTTCCAGCTGGTTAAAGACCTGGAAATGGCGGTTGAAATCAA<br>AATGGACTACCGTAAA<br>GACTTCATGACCATCAACCAGCCGGTTCTGGTTAAAGCGGAAGA<br>AATCGGTAACGGTATC<br>CGTCAGCTGATGGACCTGGTTAACAAAATCCGTGCGAAAGTTCG<br>TAAAATGAAAGAAAAA<br>TCTGAAGCGGCGATCATGGAAGGTGGTTCTTCTTACGTTGCGCTG<br>GGTAACTTCGTTGAA<br>ACCGTTATGAAATCT |
| 61 | Glycosyltransferase (UGT) | 45 | *Cicer arietinum* | ATGAAAAAAATCGAAGTTGTTTTCATCCCGTCTCCGGGTGTTGGT<br>CACCTGATCTCTACC<br>CTGGAATTCGCGAACCTGCTGATCAACCGTAACAACCGTCTGAA<br>CATCACCGTTCTGGTT<br>ATCAACTTCCCGAAAACCGTTGAAAAACAGACCAACTACTCTCT<br>GACCGAATCTGAAAAC<br>CTGCACGTTATCAACCTGCCGCAGACCACCACCCACGTTCCGTCT<br>ACCTCTGACGTTGGT<br>AACTCTATCTCTGCGCTGGTTGAAACCCAGAAATCTAACGTTAAA<br>CAGGCGGTTTCTAAC<br>CTGACCGGTACCCTGGCGGCGTTCGTTGTTGACATGTTCTGCACC |

TABLE 1-continued

List of nucleic acid sequences encoding enzymes of podophyllotoxin pathway

| Ref. No. | Genes | SEQ ID NO: | Organism | Sequence (codon optimized) |
|---|---|---|---|---|
| | | | | ACCATGATCGACGTT<br>GCGAACGAACTGGGTGTTCCGTCTCTGGTTTTCTTCACCTCTGGT<br>GTTGCGTTCCTGGGT<br>CTGATGCTGCACCTGCACACCATCTGGGAACAGCAGGACACCGA<br>ACTGCTGCTGCAGCAG<br>GACGAACTGGACATCCCGTCTTTCGCGAACCCGGTTGCGACCAA<br>CACCCTGCCGACCCTG<br>GTTCTGCGTAAAGAATGGGAATCTTCTTTCATCAAATACGGTAAC<br>GGTCTGAAAAAAGCG<br>TCTGGTATCATCGTTAACTCTTTCCACGAACTGGAACCGCACGCG<br>GTTCGTTCTTTCCTG<br>GAAGACCCGACCCTGCGTGACCTGCCGATCTACCCGGTTGGTCC<br>GATCCTGAACCCGAAA<br>TCTAACGTTGACTCTGACGACGTTATCAAATGGCTGGACGACCA<br>GCCGCCGTCTTCTGTT<br>GTTTTCCTGTGCTTCGGTTCTATGGGTACCTTCGACGAAGAACAG<br>GTTCGTGAAATCGCG<br>CTGGCGATCGAACGTTCTGGTGTTCGTTTCCTGTGGTCTCTGCGT<br>AAACCGCAGCCGCAG<br>GGTACCATGGTTCCGCCGTCTGACTACACCCTGTCTCAGATGCTG<br>GAAGTTCTGCCGGAA<br>GGTTTCCTGGACCGTACCGCGAACATCGGTCGTGTTATCGGTTGG<br>GCGCCGCAGGTTCAG<br>GTTCTGGCGCACCAGGCGACCGGTGGTTTCGTTTCTCACTGCGGT<br>TGGAACTCTACCCTG<br>GAATCTATCTACTACGGTGTTCCGATCGCGACCTGGCCGCTGTTC<br>GCGGAACAGCAGACC<br>AACGCGTTCGAACTGGTTCGTGAACTGAAAATCGCGGTTGAAAT<br>CGCGCTGGACTACCGT<br>CTGGAATTCGACATCGGTCGTAACTACCTGCTGGACGCGGACAA<br>AATCGAACGTGGTATC<br>CGTGGTGTTCTGGACAAAGACGGTGAAGTTCGTAAAAAAGTTAA<br>AGAAATGTCTCAGAAA<br>TCTCGTAACGTTCTGCTGGAAGGTGGTTCTTCTTACACCTACCTG<br>GGTCAGCTGATCGAC<br>TACATCACCAACCAGGTT |
| 63 | Glycosyltransferase (UGT) | 47 | *Barbarea vulgaris* | ATGAAATCTGAACTGGTTTTCATCCCGTACCCGGGTATCGGTCAC<br>CTGCGTCCGACCGTT<br>GAAGTTGCGAAACTGCTGGTTGACCGTGAACCGCGTCTGTCTATC<br>TCTGTTTTCATCCTG<br>CCGTTCATCTCTGGTGACGAAGTTGGTGCGTCTGACTACATCTCT<br>GCGCTGTCTGCGGCG<br>TCTAACGACCGTCTGCGTTACAAAGTTATCTTCACCGGTGACCAG<br>GAAACCGCGGAACCG<br>ACCAAACTGACCCTGCACATCGAAAACCAGGTTCCGAAAGTTCG<br>TACCGCGGTTGCGAAA<br>CTGATCGACGAATACTCTAAACTGCTGGACTCTCCGAAAATCGTT<br>GGTTTCGTTCTGGAC<br>ATGTTCTGCACCTCTATGATCGACGTTGCGAACGAATTCGAACTG<br>CCGTCTTACATGTTC<br>TTCACCTCTTCTGCGGGTATCCTGGCGGTTTCTTTCCACGTTCAGG<br>TTCTGTACGACGAA<br>AAAAAATGCAACTTCTCTGAAACCATGTTCGAAGACTCTGAAGC<br>GGAACTGATCCTGCCG<br>TCTCTGACCCGTCCGTACCCGGTTAAATCTCTGCCGTACGCGCTG<br>TTCCGTACCGAAATG<br>CTGATCATGCACGTTAACCTGGCGCGTCGTTTCCGTGAACTGAAA<br>GGTATCCTGGTTAAC<br>ACCGTTGACGAACTGGAACCGCACGCGCTGAAATTCCTGCTGTC<br>TGGTATCACCCCGCCG<br>GCGTACCCGGTTGGTCCGCTGCTGCACCTGGAATCTAACCAGGA<br>CGACGAATCTGAAGAC<br>GAAAAACGTTCTGAAATCATCATGTGGCTGGACGAACAGCCGGC<br>GTCTTCTGTTGTTTTC<br>CTGTGCTTCGGTTCTATGGGTGGTTTCTCTGAAGAACAGACCCGT<br>GAAATCGCGATCGCG<br>CTGGAACGTTCTGGTCACCGTTTCCTGTGGTCTCTGCGTCGTGAA<br>TCTCCGAACATCGAC<br>AAAGAACTGCCGGGTGAATTCACCAACCTGGAAGAAGTTCTGCC<br>GGAAGGTTTCTTCGAC<br>CGTACCAAAGGTATCGGTAAAGTTATCGGTTGGGCGCCGCAGGT<br>TGCGGTTCTGGAAAAC<br>CCGGCGATCGGTGGTTTCGTTACCCACGGTGGTTGGAACTCTGTT |

TABLE 1-continued

| List of nucleic acid sequences encoding enzymes of podophyllotoxin pathway | | | | |
|---|---|---|---|---|
| Ref. No. | Genes | SEQ ID NO: | Organism | Sequence (codon optimized) |
| | | | | CTGGAATCTCTGTGG TTCGGTGTTCCGACCGCGATGTGGCCGCTGTACGCGGAACAGAA ATTCAACGCGTTCGTT ATGGTTGAAGAACTGGGTCTGGCGGTTGAAATCAAAAAATACTG GCGTGGTGACCTGCTG CTGGGTCGTTCTGCGATGGAAATCGTTACCGCGGACGAAATCGA ACGTGGTATCACCTGC CTGATGCAGCAGGACTCTGACGTTCGTAAACGTGTTAAAGAAAT GAAAGGTAAATGCCAC GTTGCGCTGATGGACGGTGGTTCTTCTACCCTGGCGCTGGACAAA TTCGTTGAAGACGTT ACCAAAAACATC |
| 66 | 2-Deoxy-d-ribose-5-phosphate aldolase (DERA) | 49 | *Desulfatibacillum aliphaticivorans* | ATGACCGGTCCGAAAATCTGCGTTGTTGGTGCGTGCAACATCGA CCTGATCTCTTACGTT GAACGTCTGCCGGTTCTGGGTGAAACCCTGCACGGTAAAAAATT CTCTATGGGTTTCGGT GGTAAAGGTGCGAACCAGGCGGTTATGGCGGCGAAACTGGGTG GTGAAGTTGCGATGGTT GGTAAACTGGGTCGTGACGTTTTCGGTGAAAACACCCTGGCGAA CTTCAAAAAACTGGGT GTTAACGTTTCTCACGTTCACTTCACCGAAGAAGCGTTCTCTGGT GTTGCGCCGATCGCG GTTGACGACAACGGTGCGAACTCTATCATCATCGTTACCGGTGC GTCTGACCTGCTGTCT GCGGAAGAAATCCGTGCGGCGGAAAACGCGATCGCGAAATCTA AAGTTCTGGTTTGCCAG CTGGAAATCCCGATGGAACAGAACCTGGAAGCGCTGCGTATCGC GCGTAAAAACAACGTT CCGACCATCTTCAACCCGGCGCCGGCGCGTCCGGGTCTGCCGGA CGAACTGTACCAGCTG TCTGACATCTTCTGCCCGAACGAATCTGAAACCGAAATCCTGACC GGTATGCCGGTTGAA ACCATGGAACAGGCGGAACAGGCGGCGAAAGCGCTGCTGGAAC GTGGTCCGAAAACCGTT ATCCTGACCCTGGGTGAACGTGGTTGCCTGCTGGTTGACGCGAA CGGTGCGCGTCACATC CCGACCCGTAAAGTTGAAGCGATCGACACCACCGGTGCGGGTGA CTGCTTCGTTGGTTCT CTGGCGTTCTTCCTGGCGGCGGGTAAATCTCTGGAAGACGCGAT CAACCGTGCGAACAAA ATCGCGGCGGTTTCTGTTTGCGGTCAGGGTACCCAGTCTTCTTTC CCGGGTGCGTCTGAA CTGGACCCGGAAATCCTGTCTGACATCCAGCCGGCGGAATCTCA GGCGCCGGCGATGTCT GCGAAAGACCTGGCGCAGTACATCGACCACACCCTGCTGAAACC GGAAGCGCCGCTGTCT GCGTTCGACAAAATCTGCGAAGAAGCGATCCTGCACCAGTTCCG TTCTGTTTGCGTTAAC TCTTGCAAAATCTCTTACATCGCGAAAAAACTGAAAGGTACCGG TGTTGACGCGTGCGCG GTTATCGGTTTCCCGCTGGGTGCGATGTCTACCGCGGCGAAAGC GTTCGAAGCGAAACAG GCGGTTATGGACGGTGCGGCGGAACTGGACATGGTTATCAACGT TGGTGCGCTGAAATCT GGTGACTTCGACGCGGTTTTCGACGACATCAAAGCGGTTCGTGA CGCGGCGCCGCTGCCG ATCATCCTGAAAGTTATCATCGAAACCTGCCTGCTGACCGACGA AGAAAAAGCGCGTGCG TGCCGTATCGCGAAAGCGGCGGACGCGGACTTCGTTAAAACCTC TACCGGTTTCTCTACC GGTGGTGCGACCCTGGAAGACATCGCGCTGATGCGTGACACCGT TGGTCCGTACATGGGT GTTAAAGCGTCTGGTGGTATCAAAGACGCGAAAACCGCGATCGC GATGATCGAAGCGGGT GCGACCCGTATCGGTGCGGGTGCGGGTGTTGAAATCGTTTCTGGT CTGCAGTCTGACGCG GACGGTTCTTAC |

Table 2 depicts the amino acid sequence of the enzymes which the recombinant microbe expresses in order to produce podophyllotoxin and its derivates. The table only depicts the sequences of those proteins which provided the desirable results.

TABLE 2

List of proteins (enzymes) of the podophyllotoxin pathway

| Ref. No. | Genes | SEQ ID NO: | Organism | Sequence |
|---|---|---|---|---|
| 1 | Phenylalanine ammonia-lyase (PAL) | 2 | *Rhodosporidium toruloides* | MAPSLDSISHSFANGVASAKQAVNGASTNLAVAGSHLPTTQVTQVD<br>IVEKMLAAPTDSTLELDGYSLNLGDVVSAARKGRPVRVKDSDEIRSKI<br>DKSVEFLRSQLSMSVYGVTTGFGGSADTRTEDAISLQKALLEHQLCG<br>VLPSSFDSFRLGRGLENSLPLEVVRGAMTIRVNSLTRGHSAVRLVVLE<br>ALTNFLNHGITPIVPLRGTISASGDLSPLSYIAAAISGHPDSKVHVVHEG<br>KEKILYAREAMALFNLEPVVLGPKEGLGLVNGTAVSASMATLALHD<br>AHMLSLLSQSLTAMTVEAMVGHAGSFHPFLHDVTRPHPTQIEVAGNI<br>RKLLEGSRFAVHHEEEVKVKDDEGILRQDRYPLRTSPQWLGPLVSDLI<br>HAHAVLTIEAGQSTTDNPLIDVENKTSHHGGNFQAAAVANTMEKTRL<br>GLAQIGKLNFTQLTEMLNAGMNRGLPSCLAAEDPSLSYHCKGLDIAA<br>AAYTSELGHLANPVTTHVQPAEMANQAVNSLALISARRTTESNDVLS<br>LLLATHLYCVLQAIDLRAIEFEFKKQFGPAIVSLEDQHFGSAMTGSNLR<br>DELVEKVNKTLAKRLEQTNSYDLVPRWHDAFSFAAGTVVEVLSSTSL<br>SLAAVNAWKVAAAESAISLTRQVRETFWSAASTSSPALSYLSPRTQIL<br>YAFVREELGVKARRGDVFLGKQEVTIGSNVSKIYEAIKSGRINNVLLK<br>MLA |
| 3 | Phenylalanine ammonia-lyase (PAL) | 4 | *Populus kitakamiensis* | MEFCQDSRNGNGSPGFNTNDPLNWGMAAESLKGSHLDEVKRMIEE<br>YRNPVVKLGGETLTI<br>GQVTAIASRDVGVMVELSEEARAGVKASSDWVMDSMSKGTDSYG<br>VTTGFGATSHRRTKQG<br>GELQKELIRFLNAGIFGNGTESSHTLPRSATRAAMLVRTNTLLQGYS<br>GIRFEMLEAITKM<br>INHNITPCLPLRGTITASGDLVPLSYIAGLLTGRPNSKAVGPNGEPLTP<br>AEAFTQAGIDG<br>GFFELQPKEGLALVNGTAVGSGLASMVLFEANVLAILSEVLSAIFAE<br>VMQGKPEFTDHLT<br>HKLKHHPGQIVAAAIMEHILDGSAYVKEAQKLHEIDPLQKPKQDRH<br>ALRTSPQWLGPLIE<br>VIRTSTKMIEREINSVNDNPLIDVSRNKALHGGNFQGTPIGVSMDNT<br>RLAIASIGKLMFA<br>QFSELVNDLYNNGLPSNLTGGRNPSLDYGFKGAEIAMASYCSELQF<br>LDQSCTNHVQSAEQ<br>HNQDVNSLGLISSRKTAEAIDILKLMSTTFLVGLCHSVDLRHIEENLK<br>NTVKISVSQLPR<br>VLTMGFNGELHPSRFCEKDLLKVVDREHVFSYIDDPCSATYPLMQK<br>LRQVLVEHALVNGE<br>KVRNSTTSIFQKIGSFEEELKTLLPKEVESARLEVENGNPAIPNREKEC<br>RSYPLYKFVRE<br>ELGTSLLTGEKVKSPGEEFDKVFTAICAGKLIDPLLECLKEWDGAPL<br>PIC |
| 5 | Phenylalanine ammonia-lyase (PAL) | 6 | *Strobilurus tenacellus* | MPITHEQPNGFHSKQLNGSGIAKAKAMPYPSDLLSHFVKQHLELES<br>YKNGQEIEIDGYSL<br>SISAVSAAARYNAPVILRDSSTIRDRLEKARSVIVEKIEGSKSVYGVS<br>TGFGGSADTRTS<br>NTLALGNALLQHQHSGVLPSTTNTLSVLPLLDPIASTSMPESWVRGA<br>ILIRINSLIRGHS<br>GVRWELIAKMVELLQANITPLVPLRGSISASGDLSPLSYVAGTLMGN<br>PSIRVFDGPAAFG<br>ARQIVSSVKALEEHNITPISLLAKEHLGILNGTAFSASVASLVLSDVT<br>HLAMLAQVCTAM<br>GTEVLLGERMNYAPFIHAVARPHPGQTEAARTIWDLLSGSKLAHGH<br>EEEVTIDQDQGELR<br>QDRYPLRTAPQFLGPQIEDILSALNTVTLECNSTTDNPLIDGETGDIH<br>HGGNFQAMSVSN<br>AMEKTRLSLHHIGKLLFAQCAELVHPDMNRGLPPSLAATDPSINYH<br>GKGEDIGIAAYVSE<br>LGYLANPVSTHIQSAELHNQAVNSLALISARATINSLEVLSLLTSSYL<br>YMLCQAYDLRAL<br>QADFRQGLAEIVQEELRAHFSAHIESLDESPLFDKVISSMYKELNHT<br>TTMDAVPRMVKVA<br>GASTSLLVDFFMANQTSDAMSVAALTALPKFRETVALRAAAKLVA<br>LREEYLLGARGPAPA<br>SAWLGRTRPIYEFIRVTLGIRMHGTENLGVFQQGLGVQDVTIGQNV<br>SLIHEAIRDGKMRG<br>VVVGLFA |

TABLE 2-continued

List of proteins (enzymes) of the podophyllotoxin pathway

| Ref. No. | Genes | SEQ ID NO: | Organism | Sequence |
|---|---|---|---|---|
| 7 | Phenylalanine ammonia-lyase (PAL) | 8 | Penicillium antarcticum | MSPASYTATPVSSLVTPSHPTPHKDETLKSWAKIGSLVHRGVVNVD<br>GETLDIASVVAVAR<br>FEGCGAKVSKDTKVTERVEAGIETFNDYLYKGYCIYGVNTGFGGSA<br>DTRTSDVIRLQQSL<br>LQLTQSGILSGSDFSPRMGDYNLSSHAMPVTWVRATMLVRCNHLL<br>RGHSGVRLEIIDTVL<br>RLLRAGLTPIIPLRGSISASGDLMPLSYLVGILEGNPDEKVYWDRKPE<br>AAIVSATKALEI<br>IGIPPFILKPKEGLSLINGSAASAAVASLAAHEASQLVLLAQGLTALT<br>CEAMMGNAENYH<br>EFPAKIRPHPGQIEVAANERKGIINSKLIETSGTKDRLRQGLIQDRYAL<br>RGASQWLGPVV<br>EDLRLAIQQLTTELNSTQDNPVIDSESGEVYFCSNFQAASVSMAMEK<br>TRGGLQMIGKLLF<br>SYSSELINPDMNKGLPANLAADDPSLSFTMKGVDINMAAYMSELGF<br>LANSVTSHVQSAEM<br>NNQPINSLALISARYTLQAVELVSMMSAALLYVTCQAVDLRILHETF<br>LENLYSVLYLAFD<br>SVQMRQDKSSAIRTELLQALRNSWGHSARDDLSVRIQALSTAMAPV<br>LLANAKELSTEDPF<br>AVIEHLQKEIRQEAKTLFLGLRVKSFCGDLNAESSLGPAAKALYRFV<br>RRELDVPFHCGIG<br>EHPTGDTEAAADIPPRPRKTVGSWISIIYDAIRDGRIRQPLGDDWRCC<br>NGF |
| 8 | Phenylalanine ammonia-lyase (PAL) | 10 | *Ganoderma sinense* | MPAPSDTRTTPRRSYSISGGHMMRDTTVLKPEKSTAPPSPTTYLATP<br>VLPSSQGRPTALV<br>EKFIQNFKDIESHKNGKAIVVDGQNLSIAAVTAAARYNAPVVLDESF<br>AVAVKLEKSRKVV<br>TDKMSNGTSVYGVSTGFGGSATTRTDEPILLGNALLQHQHSGVLPS<br>STKKLEALPLLDPI<br>ASTSMPESWVRGAILIRMNSLIRGHSGVRRELIEKMGDLLRENITPL<br>VPLRGSISASGDL<br>SPLSYIAGTLIGNPSIRVFDGPTAFGARQIVSSRKALEAHGIAPLPLAS<br>KEHLGILNGTA<br>FSASVASLVLNDAVHMGLLAQVCTAMGTEALNGTRLSFDSFINCTA<br>RPHPGQIETARNMVV<br>NLLEGSKFAVTEEEEVSIKEDGGVLRQDRYPLRTAPQFIGPQVEDLL<br>HAVETITIECNST<br>TDNPLVDGETGTVHHGGNFQAMAVSNAMEKTRLALHHLGKILFAQ<br>CAELMDPAMNRGLPP<br>SLAATDPSLDYHCKGIDIGTAAYVAELGYLANPVSTHIQSAEMEINQ<br>AVNSMALVSGRATI<br>NSLEVLSILISSYLYALCQALDLRALQSEFMDGLVNVVSEEFDAAFG<br>LSPSEAAPVKIAL<br>FKELKKTFEETSILDAGERMVKVAASATVIIVDHFTGPAAKEENVSS<br>LSSLPSFRSKVAS<br>RLTTLLDQLRRDYLLGARGPAPASRFLNKTRPVYEFVRLTLGIRMH<br>GSENYHRFANGLGV<br>EDITVGGNVSLIHEAIRDGKLQSVVANLFS |
| 12 | Cinnamte 4 hydroxylase 4 coumarate coenzyme ligase fusion (C4H4CL) | 12 | *Azospirillum* sp. | MDLLLLEKTLLALFIAATIAITISKLRGKRFKLPPGPIPVPVFGNWLQ<br>VGDDLNHRNLTD<br>LAKRFGDIFLLRMGQRNLVVVSSPELAKEVLHTQGVEFGSRTRNVV<br>FDIFTGKGQDMVFT<br>VYGTLAEMRRIMTVPFFTNKVVQQYRFGWEFEAQSVVDDVKKNPE<br>ACSSGIVLRRRLQLM<br>MYNIMYRIMFDRRFESEEDPLFVKLKALNGERSRLAQSFEYNYGDFI<br>PILRPFLKGYLKL<br>CKEVKDRRLQLFKDYFVDERKKLGSTKSTTNEGLKCAEDHILDAQQ<br>KGEINDDNVLYIVE<br>NINVAAIETTLWSIEWGIAELVNHQKIQNKVREEIDRVLGPGHQVTE<br>PDLQKLPYLQAVI<br>KETLRLRMAIPLLVPHMNLHDAKLSGFDIPAESKILVNAWWLANNP<br>AQWKKPEEFRPERF<br>LEEESHVEANGNDFRYLPFGVGRRSCPGIILALPILGITLGRLVQNFE<br>LLPPPGQSKEDT<br>AEKGGQFSLHILKHSTIVCKPRSFNGGGGSGGGGSGGGGSMTIQRW<br>WRNRESLNRVLCDLLAGEFARLRPGGSPPAHPHRWPETLPLGPDGVG<br>ADSLDLL<br>QLAAALNEALHLHRSGIEDYLLMHRTVGDWLDVCEAALGRFDGAL<br>SFRTSGSTGEGKRCE<br>HPLAALEEEADALAALLSGGAEAPRRVVSVVPAHHIYGFLFTVLLP |

TABLE 2-continued

List of proteins (enzymes) of the podophyllotoxin pathway

| Ref. No. | Genes | SEQ ID NO: | Organism | Sequence |
|---|---|---|---|---|
| | | | | DRLAVPVVDGRGTS<br>PGGLAARLGPGDLVVAHPDWWGALLRSGAALPDGVTGTSSTAPCP<br>PDTARGVRGVGLARL<br>VEVFGSSETAGLGWRESPDAPFRPFPWWRFGDDGRVTRRLADGTV<br>LSATLQDRLSHDEEG<br>FRPSGRLDTVVQVGGVNVSLAGVQAHLAGHPDVEAAAVRLMRPEE<br>GTRLKAFIVPARTAP<br>PREELYRRLTDWIEATLPAPHRPRALAFGPALPVNGMGKPCDWPLA<br>TCR |
| 17 | hydroxycinnamoyl-CoA: quinate hydroxycinnamoyl-transferase p-coumaroyl quinate 3'-hydroxylase fusion (HCTC3H) | 14 | *Coffea canephora* | MKIEVKESTMVRPAQETPGRNLWNSNVDLVVPNFHTPSVYFYRPTG<br>SSNFFDAKVLKDAL<br>SRALVPFYPMAGRLKRDEDGRIEIECNGEGVLFVEAESDGVVDDFG<br>DFAPTLELRRLIPA<br>VDYSQGISSYALLVLQVTYFKCGGVSLGVGMRHHAADGFSGLHFIN<br>SWSDMARGLDVTLP<br>PFIDRTLLRARDPPQPQFQHIEYQPPPALKVSPQTAKSDSVPETAVSIF<br>KLTREQISALK<br>AKSKEDGNTISYSSYEMLAGHVWRCACKARGLEVDQGTKLYIATD<br>GRARLRPSLPPGYFG<br>NVIFTATPIAIAGDLEFKPVWYAASKIHDALARMDNDYLRSALDYL<br>ELQPDLKALVRGAH<br>TFKCPNLGITSWVRLPIHDADFGWGRPIFMGPGGIAYEGLSFILPSPT<br>NDGSMSVAISLQ<br>GEHMKLFQSFLYDIGGGGSGGGGSGGGGSMALLLILLPVAFIFLAYS<br>LYERLRFKLPPGPRPKPVVGNIYDIKPVRFKCYAEWSKLYGP<br>IFSVYFGSQLNTVVNTAELAKEVLKDNDQQLADRYRSRPSARMSRN<br>GQDLIWADYGPHYV<br>KVRKLCNLELFTPKRLEGLRPLREDEVTAMVDSIFKDCTKPENKGK<br>SLLMRNYLGSVAFN<br>NITRLTEGKRFMNSEGVVDEQGQEFKGIVSNGIRIGAKLSVADHIPW<br>LRWMFVGENEDLD<br>KHNARRDKLTRMIMEEHTLARQKSGNTKQHFVDALLTLQKQYELS<br>DDTVIGLLWDMITAG<br>MDTTTISVEWAMAELVKNPRVQQKAQEELDRVIGSDRIMTEADFA<br>KLPYLQCVAKEALRL<br>HPPTPLMLPHRANANVKIGGYDIPKGSIVHVNVWAIARDPAAWKNP<br>LEFRPERFLEEDVD<br>EKGHDYRLLPFGAGRRICPGAQLALNLVTSMLGHLLHHFTWSPPPG<br>VRPEEIDLEESPGT<br>VTYMRTPLQAVATPRLPAHLYNRVPVE |
| 20 | Caffeoyl CoA O-methyltransferase (CCoAO MT) | 16 | *Eleocharis dulcis* | MSTTTTTQTKTETQSQTGAQNGAEQQTRHSEVGHKSLLQSDALYQ<br>YILETSVYPREPECM<br>KELRDITAKHPWNLMTTSADEGQFLNLLLKLIGAKKTMEIGVYTGY<br>SLLATALAIPEDGT<br>ILAMDINRENYELGLPVIEKAGVAHKIDFREGPALPVLDQLIEDPAN<br>LGSFDFIFVDADK<br>DNYLNYHKRLIELVKVGGVIGYDNTLWNGSVVLPADAP1VIRKYIRY<br>YRDFVLELNKALAAD<br>PRIEISQLPVGDGITLCRRVK |
| 21 | Caffeoyl CoA O-methyltransferase (CCoAO MT) | 18 | *Chamaecyparis formosensis* | MATVEATKDSTQQVSRHQEVGHKSLLQSDALYQYILETSVYPREPE<br>PMRELREITAKHPW<br>NLMTTSADEGQFLHLLLKLINAKNTMEIGVYTGYSLLSTALALPDD<br>GKILAMDINRENYE<br>LGLPVIQKAGVAHKIDFREGPALPVLDQMLENKEMHGSFDFIFVDA<br>DKDNYLNYHKRLID<br>LVKIGGVIGYDNTLWNGSVVAPPDAPMRKYVRYYRDFVIELNKAL<br>AADPRIEISQIPVGD<br>GITLCRRII |
| 24 | Bifunctional pinoresinol-lariciresinol reductase (DIRPLR) | 20 | *Linum usitatissimum* | MGRCRVLVVGGTGYIGKRIVKASIEHGHDTYVLKRPETGLDIEKFQ<br>LLLSFKKQGAHLVE<br>ASFSDHESLVRAVKLVDVVICTVSGAHSRSLLLQLKLVEAIKEAGN<br>VKRFIPSEFGMDPA<br>RMGDALEPGRETFDLKMVVRKAIEDANIPHTYISANCFGGYFVGNL<br>SQLGPLTPPSDKVT<br>IYGDGNVKVVYMDEDDVATYTIMTIEDDRTLNKTMYFRPPENVITH<br>RQLVETWEKLSGNQ<br>LQKTELSSQDFLALMEGKDVAEQIVIGHLYHIYYEGCLTNFDIDADQ<br>DQVEASSLYPEVE<br>YTRMKDYLMIYL |

TABLE 2-continued

List of proteins (enzymes) of the podophyllotoxin pathway

| Ref. No. | Genes | SEQ ID NO: | Organism | Sequence |
|---|---|---|---|---|
| 27 | Secoisolariciresinol dehydrogenase (SDH) | 22 | *Juglans regia* | MNGTSSLLAPIAKRLAGKVALITGGASGIGESTARLFAEQGAKVIIA DVQDELGFSVSQD KSINGAISYIHCDVTSESDVQNAVNTAVSKHGKLDIMFNTAGCTGQ NKASILDHEQKDYK TVFDVNVLGSFLGAKHAAKVMIPVKRGTILFTASCVTESHGLASHS YTASKHAVVGLTKN LCVELGQYGIRVNCISPYGAATPLFLKGMGIDKKEKAEEILSSAANL KGPVLEAGDLAEA ALFLASEESKYVSVLNLVVDGGYSATNVAFTETIQKFFT |
| 32 | CYP719 | 24 | *Papaver somniferum* | MIMSNLWILTLISTILAVFAAVLIIFRRRISASTTEWPVGPKTLPIIGNL HILGGTALHV VLHKLAEVYGSVMTIWIGSWKPVIIVSDFDRAWEVLVNKSSDYSAR EMPEITKIGTANWR TISSSDSGPFWATLRKGLQSVALSPQHLASQTAHQERDIIKLIKNLKD EAASGMVKPLDH LKKATVRLISRLIYGQDFDDDKYVEDMHDVIEFLIRISGYAQLAEVF YYAKYLPGHKRAV TGAEEAKRRVIALVRPFLQSNPATNTYLHFLKSQLYPEEVIIFAIFEA YLLGVDSTSSTT AWALAFLIREPSVQEKLYQELKNFTANNNRTMLKVEDVNKLPYLQ AVVKETMRMKPIAPL AIPHKACKDTSLMGKKVDKGTKVMVNIHALHHTEKVWKEPYKFIP ERFLQKHDKAMEQSL LPFSAGMRICAGMELGKLQFSFSLANLVNAFKWSCVSDGVLPDMS DLLGFVLFMKTPLEA RIVPRL |
| 33 | CYP719 | 26 | *Cinnamomum micranthum* | MEAIWTAVAIGIAAAVLMAFRGRQRQRLSRKPTQWPPGPTRLPLIG NMHQILLKGGDPFH VAINKLAQVYGPLMTVWFGTRQPTIIVSDHNLVWEVLVSKSADYA AREIPITLKPSLADF RTIVSSNAGPLWHSLRRGLQNGAIGPHSLSLQAPFQESDMAQMINN MEKEANLNGGVVKP FPHIRRAIIKLLARICFGCDFSDEEFDATMDFMVEEALRYSDDSRILD TFPPARFLPSVK RAVMQMEKVKLRLMECIGRPLDSPLPPTCYAHFLLSQSFPREVAIFSI FELFLLGVDSTG STTMWGLGLLMQNQEAQQKLYQEIREHASCNEKGVVKVEELGKLE YLQAVAKETMRMKPI APLAVPHQAARDTTLDGLHVAEGTTVLANLYALHYDPKVWDEPER FKPERFLESSKEFLG KRGQYSFLPFGAGMRACAGMEVGKLQLPFAICNLVNAFNWSNVVE KEAPKLIEGFSFILS MKTPLEARIVPRGI |
| 34 | O-methyltranserase 3 (OMT) | 28 | *Papaver somniferum* | MEVVSKIDQENQAKIWKQIFGFAESLVLKCAVQLEIAETLHNNVKP MSLSELASKLPAQP VNEDRLYRILHFLVHMKLFNKDATTQKYSLAPPAKYLLKGWEKSM VPSILSVTDKDFTAP WNHLGDGLTGNCNAFEKALGKGIRVYMRENPEKDQLFNEGMACD TRLFASALVNECKSIF SDGINTLAGVGRGTGTAVKAISKAFPDIKCTIHDLPEVTSKNSKIPRD VFKSVPSADAIF MKSILHEWNDEECIQILKRCKEAIPKGGKVIIADVVIDMDSTHPYSKS RLAMDLAMMLHT GGKERTEEDWKKLIDAAGFASCKITKLSALQSVIEAYPH |
| 37 | O-methyltranserase 3 (OMT) | 30 | Sinopodophyllum hexandrum | MEMAPTMDLEIRNGNGYGDSGEELLAAQAHIYNHIFNFISSMALKC AVELNIPEILHNHQ PKAVTLSELVQALQIPQAKSACLYRLLRILVHSGFFAITKIQSEGDEE GYLPTLSSKLLL KNHPMSMSPCLLGLVNPTMVAPMHFFSDWFKRSDDMTPFEATHGA SLWKYFGETPHMAEI FNEAMGCETRLAMSVVLKECKGKLEGISSLVDVGGGTGNVGRAIA EAFPNVKCTVLDLPQ VVGNLKGSNNLEFVSGDMFQFIPPADVVFLKWILHDWNDEECEKIL KRCKEAIPSKEEGG KLIIIDMVVNDHNKGSYESTETQLFYDLTLMALLTGTERTETEWKK LFVAAGFTSYIISP VLGLKSIIEVFP |
| 39 | CYP71 | 32 | *Cinnamomum micranthum* | MALLLSLLFFASALIFLLKLNGQRANKTDVPPSPPKLPLIGNLHQLGT LPHRSLRSLAGK |

TABLE 2-continued

List of proteins (enzymes) of the podophyllotoxin pathway

| Ref. No. | Genes | SEQ ID NO: | Organism | Sequence |
|---|---|---|---|---|
| | | | | YGPLMLLYLGRIPTLIVSSEEMAEQIMKTHDLIFASRPSITAAKELLY<br>GCTDLAFASYGE<br>YWRQVRKMCVLELLSIKRVNSFRSIMEEEVGLMIERISQSSSTGAAV<br>NLAELFLSLTGGT<br>IARAALGKKYEGEAEEGRNKYADLVKELHALLGAFSVGDYFPSLA<br>WVDVVTGLHGKLKRN<br>SRELDRFLDQVIEHHLMRPLDGCDVGEHTDLVDVMLQVQKDSNRD<br>IHLTRDNIKAIILDM<br>FSAGTDTTALTLEWVMAELAKHPNVMKKAQGEVRRVVDVKANIS<br>EEHLCQLNYMKSIIKE<br>TLRLHPPAPLLVPRESTTNVKIQNFHIPPKTRVFINAYAIGRDPTSWE<br>NPEEFLPERFAN<br>NSVDFKGQDFQFIPFGAGRRGCPGLSFAITSLELALANLLYWFDWEL<br>PQGVTEEDLDMSE<br>ALGITVHKKLPLYLVPKNHFS |
| 46 | 2-oxoglutarate/Fe(II)-dependent dioxygenase (2-ODD) | 34 | *Microcystis viridis* | MTTDFIEIYERALRRELCEEIRHRFEASNRKSDGRIGHGVDKSKKNS<br>TDITITGLSEWSD<br>LHSQILDSTLRHLMLYERKYPYLITSAFALSLQEPATGLVRPLTASDV<br>GAASDLELGEYL<br>FRVFRPGAINVQKYSKSLGGYYYWHSEIYPRDPAAETLHRVLLFMF<br>YLNDVERGGETEFL<br>YQERKLKPTSGTMVIAPAGFTHTHRGNVPESHDKYILTSWILFNRAE<br>QLYPRKPNPA |
| 48 | 2-oxoglutarate/Fe(II)-dependent dioxygenase (2-ODD) | 36 | *Nitrospira moscoviensis* | MVSNMAMGITEAVDRAVAALDVDRLHREYWEQNEFLVIRQFLPRA<br>FVEEVLVPQAQGVKT<br>ELNRNYIPGHKKGGSVSYYTVRRRAPLFLDLYRSDSFRAFLDRLVD<br>AKLLLCPENDPHSC<br>ALYYYTEPGDHIGFHYDTSYYKGARYTILMGLVDRSTQCKLVCELF<br>KDHPTKAPQRLELI<br>TEPGDMVIFNGDKLWHAVTPLGEGEERIALTMEYVTNPEMGAFKR<br>LYSNLKDSFAYFGLK<br>TVFKQALAKKSS |
| 49 | 2-oxoglutarate/Fe(II)-dependent dioxygenase (2-ODD) | 38 | *Nitrospira japonica* | MMGGAMTTQTLDTIAEAVDQAVARLDFDRLHREYWEQNEFLVIPQ<br>FLDRAMVEEWLVPQA<br>QGVKGDLNRNYIPGHKKGGSVSYYTVMEKAPRFLDLYRSQVFIEFL<br>SRLSHAKLRLCPDN<br>DPHSCALYYYTEPGDHIGFHYDTSYYKGSRYTILMGLVDQSTHCKL<br>VCELFKDDPVRPSK<br>RLELITQPGDMVIFNGDKLWHAVTPLGPNEERIALTMEYVTNPDMG<br>TFKRLYSNLKDSFA<br>YFGLRAVFKRALSLPRR |
| 52 | CYP82D | 40 | *Panax ginseng* | METFLAQLYSTTTIAALFVLLVLYYFSPWTRINKKNVAPEAGGGWPI<br>IGHLHLLGGSKLP<br>HLVFGSMADKYGPIFTVRLGVQRSLVVSSWEMVKDIFTTNDVIVSG<br>RPKFLAAKHLSYNY<br>AMFGFSPYGSFWLELRKITSLQLLSNRRLELLKHVRVSEMEISMRQL<br>YKLWSEKKNGSGR<br>VLMDMKKWFGELNLNVTFRMVAGKRYFGGGAASNDEEARRCRR<br>VVREFFRLLGVVVVADS<br>LPFLRWLDLGGYERAMKETAREMDSIVSVWLEEHREKSDSSGDDA<br>NMEQDFMDVMLSAVK<br>NVDLCGFDAHTVIKATCMVIISSGTDTTTVELTWALCLLLNNRHVL<br>KKAQEELDNVVGKQ<br>RRVKESDLNNLIYLQAIVKETLRLYPAGQLGGQREFSDDCTVGGYH<br>VPKRTRLVVNLWKL<br>HRDPRIWSDPTEFRPERFLERHKEIDVKGQHFELIPFGAGRRVCPGIT<br>FGLQMFHLVLAS<br>LLHGFDISTPSDAPVDMAEGAGLTNAKITPLEILIAPRLSPSLYE |
| 57 | Glycosyltransferase (UGT) | 42 | *Malus domestica* | MKKVELVFIPSPGAGHHLPTLQFVKRLIDRNDRISITILAIQSYFPTTL<br>SSYTKSIAASE<br>PRIRFIDVPQPQDRPPQEMYKSRAQIFSLYIESHVPSVKKIITNLVSSS<br>ANSSDSIRVAA<br>LVVDLFCVSMIDVAKELNIPSYLFLTSNAGYLAFMLHLPILHEKNQI<br>AVEESDPDWSIPG<br>IVHPVPPRVLPAALTDGRLSAYIKLASRFRETRGIIVNTFVELETHAIT<br>LFSNDDRVPPV<br>YPVGPVIDLDDGQEHSNLDQAQRDKIIKWLDDQPQKSVVFLCFGSM<br>GSFGAEQVKEIAVG<br>LEQSGQRFLWSLRMPSPKGIVPSDCSNLEEVLPDGFLERTNGKKGLI |

TABLE 2-continued

List of proteins (enzymes) of the podophyllotoxin pathway

| Ref. No. | Genes | SEQ ID NO: | Organism | Sequence |
|---|---|---|---|---|
| | | | | CGWAPQVEILAHS ATGGFLSHCGWNSILESLWHGVPIATWPMYAEQQLNAFRMVRELG MALEMRLDYKAGSAD VVGADEIEKAVVGVMEKDSEVRKKVEEMGKMARKAVKDGGSSFA SVGRFIEDVIGQN |
| 58 | Glycosyltransferase (UGT) | 44 | *Lycium barbarum* | MGHLVSTVEMAKQLVDREDQLSITVLIMTLPTETKIPSYTKSLSSNY TSRIRLLELTQPE TSVNMGSATHPMKFMSEFITSYKGRVKDAVADMFSSLSSVKLAGF VEDMFCTAMIDVAND FGVPSYLFYTSGAAMLGLQFHFQSLISQNVLSYLDSESEVLIPTYINP VPVKFLPGLILD NDEYSIMFLDLAGRFKETKGIMVNTFVEVESHALKALSDDEKIPPIY PVGPILNLGGGND GHGEEYDSIMKWLDGQPNSSVVFLCFGSMGSFEEDQVKEVANALE SSGYQFLWSLRQPPP KDKLQFPSEFENLEEVLPEGFLQRTKGRGKMIGWAPQVAILSHPSVG GFVSHCGWNSTLE SVRSGVPMATWPMYAEQQSNAFQLVKDLEMAVEIKMDYRKDFMT INQPVLVKAEEIGNGI RQLMDLVNKIRAKVRKMKEKSEAAIMEGGSSYVALGNFVETVMKS |
| 61 | Glycosyltransferase (UGT) | 46 | *Cicer arietinum* | MKKIEVVFIPSPGVGHLISTLEFANLLINRNNRLNITVLVINFPKTVEK QTNYSLTESEN LHVINLPQTTTHVPSTSDVGNSISALVETQKSNVKQAVSNLTGTLAA FVVDMFCTTMIDV ANELGVPSLVFFTSGVAFLGLMLHLHTIWEQQDTELLLQQDELDIPS FANPVATNTLPTL VLRKEWESSFIKYGNGLKKASGIIVNSFHELEPHAVRSFLEDPTLRDL PIYPVGPILNPK SNVDSDDVIKWLDDQPPSSVVFLCFGSMGTFDEEQVREIALAIERSG VRFLWSLRKPQPQ GTMVPPSDYTLSQMLEVLPEGFLDRTANIGRVIGWAPQVQVLAHQ ATGGFVSHCGWNSTL ESIYYGVPIATWPLFAEQQTNAFELVRELKIAVEIALDYRLEFDIGRN YLLDADKIERGI RGVLDKDGEVRKKVKEMSQKSRNVLLEGGSSYTYLGQLIDYITNQ V |
| 63 | Glycosyltransferase (UGT) | 48 | *Barbarea vulgaris* | MKSELVFIPYPGIGHLRPTVEVAKLLVDREPRLSISVFILPFISGDEVG ASDYISALSAA SNDRLRYKVIFTGDQETAEPTKLTLHIENQVPKVRTAVAKLEDEYSK LLDSPKIVGFVLD MFCTSMIDVANEEELPSYMFFTSSAGILAVSFHVQVLYDEKKCNFSE TMFEDSEAELILP SLTRPYPVKSLPYALFRTEMLIMHVNLARRFRELKGILVNTVDELEP HALKFLLSGITPP AYPVGPLLHLESNQDDESEDEKRSEIIMWLDEQPASSVVFLCFGSMG GFSEEQTREIAIA LERSGHRFLWSLRRESPNIDKELPGEFTNLEEVLPEGFFDRTKGIGKV IGWAPQVAVLEN PAIGGFVTHGGWNSVLESLWFGVPTAMWPLYAEQKFNAFVMVEEL GLAVEIKKYWRGDLL LGRSAMEIVTADEIERGITCLMQQDSDVRKRVKEMKGKCHVALMD GGSSTLALDKFVEDV TKNI |
| 66 | 2-Deoxy-d-ribose-5-phosphate aldolase (DERA) | 50 | *Desulfatibacillum aliphaticivorans* | MTGPKICVVGACNIDLISYVERLPVLGETLHGKKFSMGFGGKGANQ AVMAAKLGGEVAMV GKLGRDVFGENTLANFKKLGVNVSHVHFTEEAFSGVAPIAVDDNG ANSIIIVTGASDLLS AEEIRAAENAIAKSKVLVCQLEIPMEQNLEALRIARKNNVPTIFNPAP ARPGLPDELYQL SDIFCPNESETEILTGMPVETMEQAEQAAKALLERGPKTVILTLGER GCLLVDANGARHI PTRKVEAIDTTGAGDCFVGSLAFFLAAGKSLEDAINRANKIAAVSVC GQGTQSSFPGASE LDPEILSDIQPAESQAPAMSAKDLAQYIDHTLLKPEAPLSAFDKICEE AILHQFRSVCVN SCKISYIAKKLKGTGVDACAVIGFPLGAMSTAAKAFEAKQAVMDG AAELDMVINVGALKS GDFDAVFDDIKAVRDAAPLPIILKVIIETCLLTDEEKARACRIAKAAD ADFVKTSTGFST GGATLEDIALMRDTVGPYMGVKASGGIKDAKTAIAMIEAGATRIGA |

TABLE 2-continued

| List of proteins (enzymes) of the podophyllotoxin pathway | | | | |
|---|---|---|---|---|
| Ref. No. | Genes | SEQ ID NO: | Organism | Sequence |
| | | | | GAGVEIVSGLQSDA<br>DGSY |

Table 3 depicts the nucleic acid sequence of different types of ABC transporter genes that provided desirable results as per the present disclosure.

TABLE 3

| List of ABC transporter genes providing the desirable results | | |
|---|---|---|
| SEQ ID NO | Organism | Nucleic acid sequence |
| 51 | *Trichophyton equinum* | ATGGTTGAAGTTTCTGAAAAACCGAACACCCAGGACGACGGTGT<br>TTCTAAACAGGAAAAC<br>CGTAACCCGGCGTCTTCTTCTTCTTCTACCTCTGACAAAGAAAAA<br>GTTGCGAAAAAAGGT<br>AACTCTGACGCGACCAAATCTTCTACCCCGGAAGACCTGGACGC<br>GCAGCTGGCGCACCTG<br>CCGGAACACGAACGTGAAATCCTGAAACAGCAGCTGTTCATCCC<br>GGACGTTAAAGCGACC<br>TACGGTACCCTGTTCCGTTACGCGACCCGTAACGACATGATCTTC<br>CTGGCGATCGTTTCT<br>CTGGCGTCTATCGCGGCGGGTGCGGCGCTGCCGCTGTTCACCGTT<br>CTGTTCGGTTCTCTG<br>GCGGGTACCTTCCGTGACATCGCGCTGCACCGTATCACCTACGAC<br>GAATTCAACTCTATC<br>CTGACCCGTAACTCTCTGTACTTCGTTTACCTGGGTATCGCGCAGT<br>TCATCCTGCTGTAC<br>GTTTCTACCGTTGGTTTCATCTACGTTGGTGAACACATCACCCAG<br>AAAATCCGTGCGAAA<br>TACCTGCACGCGATCCTGCGTCAGAACATCGGTTTCTTCGACAAA<br>CTGGGTGCGGGTGAA<br>GTTACCACCCGTATCACCGCGGACACCAACCTGATCCAGGACGGT<br>ATCTCTGAAAAAGTT<br>GGTCTGACCCTGACCGCGCTGTCTACCTTCTTCTCTGCGTTCATCA<br>TCGGTTACGTTCGT<br>TACTGGAAACTGGCGCTGATCTGCTCTTCTACCATCGTTGCGATG<br>ATCCTGGTTATGGGT<br>GGTATCTCTCGTTTCGTTGTTAAATCTGGTCGTATGACCCTGGTTT<br>CTTACGGTGAAGGT<br>GGTACCGTTGCGGAAGAAGTTATCTCTTCTATCCGTAACGCGACC<br>GCGTTCGGTACCCAG<br>GAAAAACTGGCGCGTCAGTACGAAGTTCACCTGAAAGAAGCGCG<br>TAAATGGGGTCGTCGT<br>CTGCAGATGATGCTGGGTATCATGTTCGGTTCTATGATGGCGATC<br>ATGTACTCTAACTAC<br>GGTCTGGGTTTCTGGATGGGTTCTCGTTTCCTGGTTGGTGGTGAA<br>ACCGACCTGTCTGCG<br>ATCGTTAACATCCTGCTGGCGATCGTTATCGGTTCTTTCTCTATCG<br>GTAACGTTGCGCCG<br>AACACCCAGGCGTTCGCGTCTGCGATCTCTGCGGGTGCGAAAATC<br>TTCTCTACCATCGAC<br>CGTGTTTCTGCGATCGACCCGGGTTCTGACGAAGGTGACACCATC<br>GAAAACGTTGAAGGT<br>ACCATCGAATTCCGTGGTATCAAACACATCTACCCGTCTCGTCCG<br>GAAGTTGTTGTTATG<br>GAAGACATCAACCTGGTTGTTCCGAAAGGTAAAACCACCGCGCT<br>GGTTGGTCCGTCTGGT<br>TCTGGTAAATCTACCGTTGTTGGTCTGCTGGAACGTTTCTACAAC<br>CCGGTTTCTGGTTCT<br>GTTCTGCTGGACGGTCGTGACATCAAAACCCTGAACCTGCGTTGG<br>CTGCGTCAGCAGATC<br>TCTCTGGTTTCTCAGGAACCGACCCTGTTCGGTACCACCATCTTCG<br>AAAACATCCGTCTG<br>GGTCTGATCGGTTCTCCGATGGAAAACGAATCTGAAGAACAGAT<br>CAAAGAACGTATCGTT<br>TCTGCGGCGAAAGAAGCGAACGCGCACGACTTCATCATGGGTCT<br>GCCGGACGGTTACGCG<br>ACCGACGTTGGTCAGCGTGGTTTCCTGCTGTCTGGTGGTCAGAAA |

TABLE 3-continued

List of ABC transporter genes providing the desirable results

| SEQ ID NO | Organism | Nucleic acid sequence |
|---|---|---|
| | | CAGCGTATCGCGATC<br>GCGCGTGCGATCGTTTCTGACCCGAAAATCCTGCTGCTGGACGAA<br>GCGACCTCTGCGCTG<br>GACACCAAATCTGAAGGTGTTGTTCAGGCGGCGCTGGACGCGGC<br>GTCTCGTGGTCGTACC<br>ACCATCGTTATCGCGCACCGTCTGTCTACCATCAAATCTGCGGAC<br>AACATCGTTGTTATC<br>GTTGGTGGTCGTATCGCGGAACAGGGTACCCACGACGAACTGGT<br>TGACAAAAAAGGTACC<br>TACCTGCAGCTGGTTGAAGCGCAGAAAATCAACGAAGAACGTGG<br>TGAAGAATCTGAAGAC<br>GAAGCGGTTCTGGAAAAAGAAAAAGAAATCTCTCGTCAGATCTC<br>TGTTCCGGCGAAATCT<br>GTTAACTCTGGTAAATACCCGGACGAAGACGTTGAAGCGAACCT<br>GGGTCGTATCGACACC<br>AAAAAATCTCTGTCTTCTGTTATCCTGTCTCAGAAACGTTCTCAG<br>GAAAACGAAACCGAA<br>TACTCTCTGGGTACCCTGATCCGTTTCATCGCGGGTTTCAACAAA<br>CCGGAACGTCTGATC<br>ATGCTGTGCGGTTTCTTCTTCGCGGTTCTGTCTGGTGCGGGTCAGC<br>CGGTTCAGTCTGTT<br>TTCTTCGCGAAAGGTATCACCACCCTGTCTCTGCCGCCGTCTCTGT<br>ACGGTAAACTGCGT<br>GAAGACGCGAACTTCTGGTCTCTGATGTTCCTGATGCTGGGTCTG<br>GTTCAGCTGGTTACC<br>CAGTCTGCGCAGGGTGTTATCTTCGCGATCTGCTCTGAATCTCTG<br>ATCTACCGTGCGCGT<br>TCTAAATCTTTCCGTGCGATGCTGCGTCAGGACATCGCGTTCTTC<br>GACCTGCCGGAAAAC<br>TCTACCGGTGCGCTGACCTCTTTCCTGTCTACCGAAACCAAACAC<br>CTGTCTGGTGTTTCT<br>GGTGCGACCCTGGGTACCATCCTGATGGTTTCTACCACCCTGATC<br>GTTGCGCTGACCGTT<br>GCGCTGGCGTTCGGTTGGAAACTGGCGCTGGTTTGCATCTCTACC<br>GTTCCGGTTCTGCTG<br>CTGTGCGGTTTCTACCGTTTCTGGATCCTGGCGCAGTTCCAGACC<br>CGTGCGAAAAAAGCG<br>TACGAATCTTCTGCGTCTTACGCGTGCGAAGCGACCTCTTCTATC<br>CGTACCGTTGCGTCT<br>CTGACCCGTGAACAGGGTGTTATGGAAATCTACGAAGGTCAGCT<br>GAACGACCAGGCGAAA<br>AAATCTCTGCGTTCTGTTGCGAAATCTTCTCTGCTGTACGCGGCGT<br>CTCAGTCTTTCTCT<br>TTCTTCTGCCTGGCGCTGGGTTTCTGGTACGGTGGTGGTCTGCTGG<br>GTAAAGGTGAATAC<br>AACGCGTTCCAGTTCTTCCTGTGCATCTCTTGCGTTATCTTCGGTT<br>CTCAGTCTGCGGGT<br>ATCGTTTTCTCTTTCTCTCCGGACATGGGTAAAGCGAAATCTGCG<br>GCGGCGGACTTCAAA<br>CGTCTGTTCGACCGTGTTCCGACCATCGACATCGAATCTCCGGAC<br>GGTGAAAAACTGGAA<br>ACCGTTGAAGGTACCATCGAATTCCGTGACGTTCACTTCCGTTAC<br>CCGACCCGTCCGGAA<br>CAGCCGGTTCTGCGTGGTCTGAACCTGACCGTTAAACCGGGTCAG<br>TACATCGCGCTGGTT<br>GGTCCGTCTGGTTGCGGTAAATCTACCACCATCGCGCTGGTTGAA<br>CGTTTCTACGACACC<br>CTGTCTGGTGGTGTTTACATCGACGGTAAAGACATCTCTCGTCTG<br>AACGTTAACTCTTAC<br>CGTTCTCACCTGGCGCTGGTTTCTCAGGAACCGACCCTGTACCAG<br>GGTACCATCCGTGAC<br>AACGTTCTGCTGGGTGTTGACCGTGACGAACTGCCGGACGAACA<br>GGTTTTCGCGGCGTGC<br>AAAGCGGCGAACATCTACGACTTCATCATGTCTCTGCCGGACGGT<br>TTCGGTACCGTTGTT<br>GGTTCTAAAGGTTCTATGCTGTCTGGTGGTCAGAAACAGCGTATC<br>GCGATCGCGCGTGCG<br>CTGATCCGTGACCCGAAAGTTCTGCTGCTGGACGAAGCGACCTCT<br>GCGCTGGACTCTGAA<br>TCTGAAAAAGTTGTTCAGGCGGCGCTGGACGCGGCGGCGAAAGG<br>TCGTACCACCATCGCG<br>GTTGCGCACCGTCTGTCTACCATCCAGAAAGCGGACATCATCTAC<br>GTTTTCGACCAGGGT |

TABLE 3-continued

| List of ABC transporter genes providing the desirable results | | |
|---|---|---|
| SEQ ID NO | Organism | Nucleic acid sequence |
| | | CGTATCGTTGAATCTGGTACCCACCACGAACTGCTGCAGAACAAA GGTCGTTACTACGAA CTGGTTCACATGCAGTCTCTGGAAAAAACCCAG |
| 53 | *Mucor ambiguus* | ATGACCGGTTCTATCTCTATCGACGCGTGGCTGTCTGGTGCGCTG GCGCTGGTTACCTGC GGTTCTGCGTTCGTTCTGTCTCTGCAGCGTACCTACCTGCACAAAT CTCAGCAGAAAGAC CGTGCGCCGCTGGTTTTCGACAAACAGCGTGACACCTCTGTTCCG GTTGCGGACGACGAC GCGCGTTTCGTTCGTCTGACCTTCGGTACCCTGACCCTGACCCTGC TGTCTGCGCTGGAC TTCTACCACACCGTTATCCAGCAGCAGCAGCAGACCTCTGACTGG TGGATCACCGCGTCT GCGTGCACCCAGTTCGTTGCGTGGCTGTACGCGTCTGTTCTGGTT CTGGTTGCGCGTCGT TACCGTTTCCCGTCTGAATGGGGTTGGATCCTGAACGTTCACCTG TGCGTTTTCTACTGC ATGATCTGGTGCATCGCGGTTTACGACGTTTACGACGCGTACGTT ATCAACCCGTCTGAC AACTGGATCCACATGCTGCCGCGTCTGCTGGCGCTGATCCTGGGT TCTGACCTGGTTTTC ACCACCGCGACCACCCCGCGTGGTGCGCCGTTCCTGGACGAAAA CGGTCGTAAAGTTGCG GCGATCGACGTTGCGTCTATCTACTCTTTCCTGTACTTCTCTTGGG TTACCCCGCTGATC AACCTGGCGTACAAAAACAAAAAACTGACCGACGAAGACCTGCC GACCCTGCCGCCGCTG TACCGTGGTCACAACCTGTACTACATCTTCGGTGCGACCCGTAAC AAATCTCTGCTGAAA CGTATCTACACCACCAACAAACGTGCGATCACCATCCAGGTTGTT CTGGCGTTCACCACC TCTCTGGTTTACTACGTTCCGGCGTACTTCGTTAACCGTCTGCTGA CCCTGATCCAGGAC ATGCACGGTGTTGAAGACGACGTTTCTATCCGTAAAGGTTTCGTT CTGGTTGCGTCTCTG GGTGCGACCATCCTGATCCTGGGTATCCTGGTTGGTCAGCTGTGG TACTACGCGTCTTCT TCTCTGCAGGTTCGTGTTAAAGCGATGCTGAACATCGAAATCTAC CGTAAAACCCTGCGT CGTCGTGACCTGGCGGTTGAATCTCCGAAACTGGACGACGACGA AGACACCGACAAAAAA AAAGACGACGACGAAGCGTCTGACAAAAAAGGTGAATCTGACGA AAAAGAAGACGTTTCT TCTTCTACCGGTACCATCGTTAACCTGATGTCTACCGACTCTAACC GTATCTCTGAATTC TCTGTTTGGTGGTTCTCTATCCTGGCGGCGCCGACCGAACTGGCG GTTGGTATCTACTTC CTGTACCAGCTGCTGGGTAAATCTTGCTTCCTGGGTCTGCTGGTT ATGATCGTTGTTCTG CCGATCAACCACTACAACGCGAAAACCTTCGCGAAAACCCAGGA CAAACTGATGGAAGCG CGTGACAAACGTGTTTCTCTGATGAACGAAGTTCTGCAGGGTATC CGTCAGATCAAATTC TTCGCGTGGGAAAAACGTTGGGAAAAACGTGTTATGGAAGCGCG TGAAGTTGAACTGCAC CACCTGGGTGTTACCTACATGACCGAAGTTCTGTTCACCCTGCTG TGGCAGGGTTCTCCG ATCCTGGTTACCCTGCTGTCTTTCTACTCTTTCTGCAAACTGGAAG GTAACGAACTGACC GCGCCGATCGCGTTCACCTCTATCACCGTTTTCAACGAACTGCGT TTCGCGCTGAACGTT CTGCCGGAAGTTTTCATCGAATGGCTGCAGGCGCTGATCTCTATC CGTCGTATCCAGACC TACCTGGACGAAGACGAAATCGAACCGCCGTCTAACGAAGACGA AATCGACCCGCTGACC GGTCACATCCCGGAACACATCACCATCGGTTTCAAAGACGCGAC CGTTGGTTGGTCTAAA CACAACTACACCGACCAGGTTACCGACGAATCTGACAACATCAC CTCTGAAGCGTCTTCT ACCTCTTTCATCCTGAAAGACCTGAACATCGAATTCCCGCCGAAC GAACTGTCTCTGATC TCTGGTGCGACCGGTTCTGGTAAAACCCTGATGATGCTGGGTCTG CTGGGTGAAGCGATC GTTCTGAAAGGTACCGCGCACTGCCCGCGTCAGGCGGTTGTTGAC |

TABLE 3-continued

List of ABC transporter genes providing the desirable results

| SEQ ID NO | Organism | Nucleic acid sequence |
|---|---|---|
| | | ACCGTTTCTGACGAC<br>TTCGTTACCTCTAAAGACATCGACCCGAAAGACTGGCTGCTGCCG<br>TACGCGCTGGCGTAC<br>GTTTCTCAGACCGCGTGGCTGCAGAACGCGTCTATCCGTGACAAC<br>ATCCTGTTCGGTCTG<br>CCGTACGTTGAATCTCGTTACCGTGACACCCTGACCGCGTGCGCG<br>CTGGACAAAGACCTG<br>GAAATCCTGGAAGACGGTGACCAGACCGAAATCGGTGAAAAAGG<br>TATCACCCTGTCTGGT<br>GGTCAGAAAGCGCGTGTTTCTCTGGCGCGTGCGGTTTACTCTCGT<br>GCGCAGAACGTTCTG<br>ATGGACGACGTTCTGTCTGCGGTTGACGCGCACACCGCGAAACA<br>CCTGTACGAAAAATGC<br>CTGCTGGGTCCGCTGATGAAAGAACGTACCCGTGTTCTGATCACC<br>CACCACGTTAAACTG<br>TGCGTTAAAGGTTCTGGTTACATCGTTCACATCGACGCGGGTCGT<br>GCGTCTCTGGTTGGT<br>ACCCCGAACGAACTGCGTCAGAACGGTCAGCTGGCGTCTATCTTC<br>GAATCTGAAGAAGAA<br>GAAGTTGCGCAGGAAGAAGACGCGGAAGAAGAAAAAGCGATCG<br>AAGAAGTTCTGCCGGCG<br>GTTGCGAACAAAGACCTGAAAAAACCGCGTGCGCTGGTTGAAGA<br>AGAAACCCGTGCGACC<br>GGTATGGTTAAAGTTCGTCTGTACAAACTGTACGTTTCTATGGTT<br>GGTTCTCCGTTCTTC<br>TGGTTCGTTATGGTTGCGCTGGTTCTGGGTTCTCGTGGTCTGGACG<br>TTATCGAAAACTGG<br>TGGATCAAACAGTGGTCTCAGTCTTACCAGACCAAACACAACGA<br>CAACGCGACCAACAAC<br>GACTACATGTTCCAGCAGCAGTCTATCATCTCTCAGTCTAAACCG<br>ATGTTCGCGTACCAG<br>CCGGTTGTTGCGTCTGAATCTGACAACGACCTGGCGTCTATCATG<br>GACGCGAAAGACGAC<br>CGTCTGAACTACTACCTGGGTATCTACTGCCTGATCACCCTGACC<br>AACATCGTTGTTGGT<br>ACCGCGCGTTTCGCGGTTCTGTACTGGGGTGTTCTGGGTGCGAAC<br>CGTGCGCTGTACGCG<br>GAACTGCTGCACCGTGTTTTCCGTGCGCCGCTGCGTTTCTTCGAC<br>ACCACCCCGATCGGT<br>CGTATCCTGAACCGTTTCTCTAAAGACTTCGAAACCATCGACTCT<br>AACATCCCGAACGAC<br>CTGCTGAACTTCGTTATCCAGTGGGTTATCATCGTTTCTTCTATGA<br>TCACCGTTTCTTCT<br>GTTCTGCCGATCTTCCTGGTTCCGATGCTGGCGGTTGCGCTGGTTA<br>ACGTTTACCTGGGT<br>ATGATGTTCGTTTCTGCGTCTCGTGAACTGAAACGTATGGACTCT<br>GTTTCTCGTTCTCCG<br>CTGTTCTCTAACTTCACCGAAACCATCATCGGTGTTGCGACCATC<br>CGTGCGTTCGGTGCG<br>ACCCGTCAGTTCCTGCAGGACATGCTGACCTACATCGACACCAAC<br>ACCCGTCCGTTCTAC<br>TACCAGTGGCTGGTTAACCGTTGGGTTTCTGTTCGTTTCGCGTTCT<br>CTGGTGCGCTGATC<br>AACATGTTCACCTCTACCATCATCCTGCTGTCTGTTGACAAAATG<br>GACGCGTCTCTGGCG<br>GGTTTCTGCCTGTCTTTCGTTCTGCTGTTCACCGACCAGATGTTCT<br>GGGGTATCCGTCGT<br>TACACCTCTCTGGAAATGTCTTTCAACGCGGTTGAACGTGTTGTT<br>GAATTCATGGAAATG<br>GACCAGGAAGCGCCGGCGATCACCGAAGTTCGTCCGCCGCACGA<br>ATGGCCGACCCGTGGT<br>CGTATCGACGTTAAAGACCTGGAAATCAAATACGCGGCGGACCT<br>GGACCCGGTTCTGAAA<br>GGTATCTCTTTCTCTGTTAAACCGCAGGAAAAAATCGGTGTTGTT<br>GGTCGTACCGGTTCT<br>GGTAAATCTACCCTGGCGCTGTCTTTCTTCCGTTTCGTTGAAGCGT<br>CTCAGGGTTCTATC<br>GTTATCGACAACATCGACATCAAAGACCTGGGTACCGAAGACCT<br>GCGTTCTAACCTGACC<br>ATCATCCCGCAGGACCCGACCCTGTTCTCTGGTTCTCTGCGTTCTA<br>ACATGGACCCGTTC<br>GACCAGTTCACCGACCAGGACATCTTCACCGCGCTGCGTCGTGTT<br>CACCTGCTGCCGATC<br>GAAGAAGGTGACAACTCTGCGGAAACCGTTGTTTCTGACTCTACC<br>CTGGACGAAGTTAAC |

TABLE 3-continued

List of ABC transporter genes providing the desirable results

| SEQ ID NO | Organism | Nucleic acid sequence |
| --- | --- | --- |
| | | GCGAACGTTTTCAAAGACCTGACCACCAACGTTACCGAAGGTGG<br>TAAAAACTTCTCTCAG<br>GGTCAGCGTCAGCTGCTGTGCCTGGCGCGTGCGCTGCTGAAACGT<br>TCTCGTATCGTTCTG<br>ATGGACGAAGCGACCGCGTCTGTTGACTTCGAAACCGACAAAGC<br>GATCCAGAAAACCATC<br>GCGACCGAATTCGCGGACTCTACCATCCTGTGCATCGCGCACCGT<br>CTGCACACCGTTATC<br>GAATACGACCGTATCCTGGTTCTGGACCAGGGTCAGATCCTGGAA<br>TTCGACTCTCCGCTG<br>ACCCTGATCACCAACCCGGAATCTTCTTTCTACAAAATGTGCCGT<br>AACTCTGCGTCTCAG<br>AACAAAGCGCTGGCGGCGAAAAAAGCGGCGCTGAAAGGTGTTCA<br>CGGTAAAGCGGTTCGT<br>AAAATCCGTACCTCTACCCACTTCCACATCCCGAAAACCCTGGTT<br>CTGAACCGTGCGCCG<br>AAATACGCGCGTAAATCTGTTGCGCACGCGCCGCGTATGGACCA<br>GTACCGTGTTATCCGT<br>CAGCCGCTGAACACCGAAACCGCGATGAAAAAAATCGAAGAACA<br>CAACACCCTGACCTTC<br>CTGGTTGACGTTAAAGCGAACAAAAACCAGATCAAAGACGCGGT<br>TAAACGTCTGTACGAC<br>GTTGAAGCGGCGAAAATCAACACCCTGATCCGTCCGGACGGTTA<br>CAAAAAAGCGTTCGTT<br>CGTCTGACCGCGGACGTTGACGCGCTGGACGTTGCGAACAAAAT<br>CGGTTTCATC |
| 55 | *Cutibacterium granulosum* | ATGTCTGAACAGCGTGACGGTATCCGTCGTACCGCGTCTGGTCGT<br>GAAACCTACGAACCG<br>GACGGTCTGCCGGACCACGGTGTTGAACCGCGTGAAGACGTTGA<br>AGAAAAAACCTTCGTT<br>GAAGAAGAAGACGACTCTAAAGAATACATGCCGATCCGTACCGG<br>TGCGCGTCACGCGGCG<br>TCTGACACCTCTATGACCGACGTTGAAAACGAACGTTTCGACCTG<br>TACAAATGGCTGCGT<br>TTCTTCATGCGTTCTATGGACGAATCTGACATCAAAGTTTCTCGTG<br>CGGGTGTTCTGTTC<br>CGTAACCTGAACGTTTCTGGTTCTGGTTCTGCGCTGAACCTGCAG<br>AAAAACGTTGGTTCT<br>ATCCTGATGACCCCGTTCCGTCTGCAGGAATACCTGGGTCTGGGT<br>CAGAAAAACGAAAAA<br>CGTATCCTGAAAAACTTCGACGGTCTGCTGAAATCTGGTGAACTG<br>CTGATCGTTCTGGGT<br>CGTCCGGGTTCTGGTTGCTCTACCCTGCTGAAAACCATCTGCGGT<br>GAACTGCACGGTCTG<br>GCGCTGGACGGTGACTCTACCATCAACTACAACGGTATCCCGCAG<br>CGTCAGATGCTGAAA<br>GAATTCAAAGGTGAAGTTGTTTACAACCAGGAAGTTGACAAACA<br>CTTCCCGCACCTGACC<br>GTTGGTCAGACCCTGGAAATGGCGGCGGCGTACCGTACCCCGTCT<br>AACCGTATCGAAGGT<br>CAGACCCGTGAAGACGCGATCAAAATGGCGGCGCGTGTTGTTAT<br>GGCGGTTTTCGGTCTG<br>TCTCACACCTACAACACCAAAGTTGGTAACGACTTCATCCGTGGT<br>GTTTCTGGTGGTGAA<br>CGTAAACGTGTTTCTATCGCGGAAATGGCGCTGTCTGCGGCGCCG<br>ATCGCGGCGTGGGAC<br>AACTCTACCCGTGGTCTGGACGCGGCGACCGCGCTGGAATTCGTT<br>AAAGCGCTGCGTATC<br>ATGTCTGACCTGGCGGGTGCGGCGCAGGCGGTTGCGATCTACCA<br>GGCGTCTCAGGCGATC<br>TACGACGTTTTCGACAAAGCGGTTGTTCTGTACGAAGGTCGTCAG<br>ATCTACTTCGGTCCG<br>ACCGGTGCGGCGAAACAGTTCTTCGAAGAACAGGGTTGGTACTG<br>CCCGCCGCGTCAGACC<br>ACCGGTGACTTCCTGACCTCTGTTACCAACCCGGGTGAACGTCAG<br>CCGCGTAAAGGTATG<br>GAAAACAAAGTTCCGCGTACCCCGGACGAATTCGAAGCGTACTG<br>GCGTCAGTCTGCGGCG<br>TACAAAGCGCTGCAGGCGGAAATCGACGAACACGAACAGGAATT<br>CCCGGTTGGTGGTGAA<br>GTTGTTTCTCAGTTCCAGGAAAACAAACGTCTGGCGCAGTCTAAA<br>CACTCTCGTCCGACC<br>TCTCCGTACCTGCTGTCTGTTCCGATGCAGGTTAAACTGAACACC<br>AAACGTGCGTACCAG |

TABLE 3-continued

List of ABC transporter genes providing the desirable results

| SEQ ID NO | Organism | Nucleic acid sequence |
|---|---|---|
| | | CGTATCTGGAACGACAAAGCGGCGACCCTGACCATGGTTCTGTCT |
| | | CAGATCATCCAGGCG |
| | | CTGATCATCGGTTCTCTGTTCTACGGTACCCCGGCGGCGACCCAG |
| | | GGTTTCTTCTCTCGT |
| | | AACGCGGCGATCTTCTTCGGTGTTCTGCTGAACGCGCTGGTTGCG |
| | | ATCGCGGAAATCAAC |
| | | GCGCTGTACGACCAGCGTCCGATCGTTGAAAAACACGCGTCTTAC |
| | | GCGTTCTACCACCCG |
| | | TTCACCGAAGCGGTTGCGGGTGTTGTTGCGGACATCCCGGTTAAA |
| | | TTCGCGATGGCGACC |
| | | TGCTTCAACCTGATCTACTACTTCATGACCGGTTTCCGTCGTGAAC |
| | | CGTCTCAGTTCTTC |
| | | ATCTACTTCCTGATCTCTTTCATCGCGATGTTCGTTATGTCTGCGG |
| | | TTTTCCGTACCATG |
| | | GCGGCGATCACCAAAACCGTTTCTCAGGCGATGATGTTCGCGGGT |
| | | GTTCTGGTTCTGGCG |
| | | ATCGTTGTTTACACCGGTTTCGCGATCCCGGAATCTTACATGGTT |
| | | GACTGGTTCGGTTGG |
| | | ATCCGTTGGATCAACCCGATCTTCTACGCGTTCGAAATCCTGATC |
| | | GCGAACGAATACCAC |
| | | GGTCGTGAATTCACCTGCTCTGGTTTCATCCCGGCGTACCCGAAC |
| | | CTGGAAGGTGACTCT |
| | | TTCATCTGCAACATGCGTGGTGCGGTTGCGGGTGAACGTACCGTT |
| | | TCTGGTGACGACTAC |
| | | ATCTGGGCGAACTACAAATACTCTTACTCTCACGTTTGGCGTAAC |
| | | TTCGGTATCCTGCTG |
| | | GCGTTCCTGTTCTTCTTCATGTTCATCTACTTCCTGGCGGTTGAAC |
| | | TGAACTCTTCTACC |
| | | ACCTCTACCGCGGAAGTTCTGGTTTTCCGTCGTGGTCACGTTCCG |
| | | GCGTACATGACCGAA |
| | | AACCCGAAAGGTAACGCGAACGACGAAGAAATCGCGGCGCCGG |
| | | ACGCGGCGGGTCGTGCG |
| | | GGTGCGGAAGGTGGTGACGTTAACATGATCCCGGCGCAGAAAGA |
| | | CATCTTCACCTGGCGT |
| | | GACGTTGTTTACGACATCGAAATCAAAGGTGAACCGCGTCGTCTG |
| | | CTGGACCACGTTTCT |
| | | GGTTGGGTTAAACCGGGTACCCTGACCGCGCTGATGGGTGTTTCT |
| | | GGTGCGGGTAAAACC |
| | | ACCCTGCTGGACGTTCTGGCGCAGCGTACCTCTATGGGTGTTATC |
| | | ACCGGTGACATGCTG |
| | | GTTAACGGTCGTCCGCTGGACTCTTCTTTCCAGCGTAAAACCGGT |
| | | TACGTTCAGCAGCAG |
| | | GACCTGCACCTGGCGACCGCGACCGTTCGTGAATCTCTGCGTTTC |
| | | TCTGCGATGCTGCGT |
| | | CAGCCGAAAAACGTTTCTACCGAAGAAAAATACACCTACGTTGA |
| | | AGACGTTATCAAAATG |
| | | CTGAACATGGAAGACTTCGCGGAAGCGGTTGTTGGTGTTCCGGGT |
| | | GAAGGTCTGAACGTT |
| | | GAACAGCGTAAACTGCTGACCATCGGTGTTGAACTGGCGGCGAA |
| | | ACCGAAACTGCTGCTG |
| | | TTCCTGGACGAACCGACCTCTGGTCTGGACTCTCAGTCTTCTTGG |
| | | GCGATCTGCGCGTTC |
| | | CTGCGTAAACTGGCGAACTCTGGTCAGGCGATCCTGTGCACCATC |
| | | CACCAGCCGTCTGCG |
| | | ATCCTGTTCCAGGAATTCGACCGTCTGCTGTTCCTGGCGAAAGGT |
| | | GGTCGTACCGTTTAC |
| | | TTCGGTGACATCGGTACCAACTCTCGTACCCTGCTGGACTACTAC |
| | | GAACGTAACGGTTCT |
| | | CGTAAATGCGGTGACGACGAAAACCCGGCGGAATTCATGCTGGA |
| | | AATCGTTGGTGCGGGT |
| | | GCGTCTGGTAAAGCGACCCAGGACTGGCACGAAGTTTGGAAAAA |
| | | CTCTAACGAAGCGCGT |
| | | GCGGTTCAGGACGAACTGGACCGTATCCACCGTGAAAAACAGAA |
| | | CGAACCGGCGGCGGGT |
| | | GACGACGAAGTTGGTGGTACCGACGAATTCGCGATGCCGTTCAC |
| | | CCAGCAGCTGTACCAC |
| | | GTTACCTACCGTGTTTTCCAGCAGTACTGGCGTATGCCGGGTTAC |
| | | ATCTGGGCGAAAATG |
| | | CTGCTGGGTTTCGCGTCTGCGTTCTTCATCGGTTTCTCTTTCTGGG |
| | | ACTCTGACTCTTCT |
| | | CAGCAGGGTATGCAGAACGTTATCTACTCTGTTTTCATGGTTGCG |
| | | GCGATCTTCTCTACC |
| | | ATCGTTGAACAGATCATGCCGCTGTTCCTGACCCAGCGTTCTCTG |
| | | TACGAAGTTCGTGAA |
| | | CGTCCGTCTAAAGCGTACTCTTGGAAAGCGTTCCTGATCGCGAAC |

TABLE 3-continued

List of ABC transporter genes providing the desirable results

| SEQ ID NO | Organism | Nucleic acid sequence |
|---|---|---|
| | | ATCTCTGTTGAAATC<br>CCGTACCAGATCCTGGTTGGTATCATCGTTTACGCGTCTTACTACT<br>ACGCGGTTAACGGT<br>GTTCAGTCTTCTGACCGTCAGGGTCTGGTTCTGCTGTACTGCGTTC<br>AGTTCTTCATCTAC<br>GCGTCTACCTTCGCGCACATGTGCATCGCGGCGGCGCCGGACGCG<br>GAAACCGCGGCGGGT<br>ATCGTTACCCTGCTGTTCTCTATGATGATCGCGTTCAACGGTGTTA<br>TGCAGCCGCCGCAG<br>GCGCTGCCGGGTTTCTGGATCTTCATGTACCGTGTTTCTCCGCTGA<br>CCTACTGGATCTCT<br>GGTATCGTTGCGACCGAACTGCACGACCGTCCGGTTCAGTGCACC<br>GCGGTTGAAACCTCT<br>ACCTTCAACCCGCCGTCTGGTCAGACCTGCCAGCAGTACCTGGGT<br>GAATTCCTGCGTGCG<br>GCGGGTGGTAACCTGCAGAACCCGGCGGACACCGCGGACTGCCG<br>TTACTGCTCTATCACC<br>GTTGCGGACGAATACATCGGTGGTTCTAAAATCTTCTGGACCGAC<br>CGTTGGCGTAACTTC<br>GGTCTGGTTTGGGCGTACGTTGTTTTCAACATCTTCGCGGCGACC<br>ATGCTGTACTACCTG<br>TTCCGTGTTCGTAAATCTTCTGGTAAAGGTCTGAAAGAACGTGTT<br>GCGGGTCTGTTCGGT<br>GGTAAAAAAAAACAG |
| 57 | *Magnetospirillum magneticum* | ATGCACTGGCTGAAAAACGAACACTGGGTTCGTCCGGACCTGAA<br>ACGTTACCGTGGTCTG<br>CTGTTCTGGTCTCTGATCCTGGGTGTTATGACCTTCGTTTTCGCGG<br>GTGCGCTGATGTTC<br>ACCTCTGGTTTCCTGATCGACAAATCTGCGACCAAACCGCTGTTC<br>GCGGCGATCTACGTT<br>ACCGTTGTTCTGACCCGTGCGTTCGGTATCGGTCGTCCGGTTTTCC<br>AGTACATCGAACGT<br>CTGACCTCTCACAACTGGGTTCTGCGTATCACCTCTCACATGCGT<br>CGTAAACTGTACAAA<br>GTTCTGGAAACCGACGCGGCGTTCGTTTCTGAACACCACCAGACC<br>GGTGACATCCTGGGT<br>CTGCTGGCGGACGACATCGGTCACATCCAGAACCTGTACCTGCGT<br>ATGATCTTCCCGACC<br>GTTGTTGGTGCGGGTCTGACCGTTATCGCGACCCTGCTGCTGGGT<br>TGGTTCAACTGGGGT<br>TTCGCGCTGTGGATCATGCTGCTGCTGCTGTTCCAGGTTCTGATCC<br>TGCCGTGGTGGGGT<br>CTGGTTGTTGAACGTTTCCGTAAAGCGGAACAGAAACAGCTGAA<br>CCACGACGCGTACGTT<br>TCTCTGACCGACTCTGTTCTGGGTCTGTCTGACTGGGTTATCACCC<br>ACCGTGAAAAAGAC<br>TTCATGTCTCAGTCTCTGGCGGCGCCGAAAAAACTGGCGGCGTCT<br>ACCGTTAAATCTAAA<br>CGTTTCCAGTGGCGTCGTGACTTCGTTGGTCAGCTGCTGTTCGTTC<br>TGATCGTTATCTCT<br>ATGCTGATCTGGACCAACCTGGAATGGACCGGTAACCAGGCGTC<br>TGCGAACTGGGTTGGT<br>GCGTTCGTTCTGGTTGTTTTCCCGCTGGACCAGGCGTTCTCTGGTA<br>TCGCGCAGGGTGTT<br>GGTGAATGGCCGACCTACCGTGACGCGATCCGTCACCTGAACGA<br>CCTGCAGCCGGTTACC<br>CGTCAGCTGCCGCAGCAGCAGGCGGTTCCGACCCAGTTCAAAGA<br>AATGACCCTGCAGCAC<br>CTGTCTTTCCAGTACACCCCGAAAGACCCGGAACTGATCACCGAC<br>ATCGACCTGACCGTT<br>CACTCTGGTGAAAAAATCGCGATCCTGGGTCCGTCTGGTATGGGT<br>AAAACCACCCTGCTG<br>CAGCTGGTTCTGGGTGACCTGACCCCGACCACCGGTAACGTTCTG<br>GTTGACGGTCAGGAC<br>GTTCTGACCTACCAGCAGCACCGTACCAACCTGTTCGCGGTTCTG<br>GACCAGTCTCCGTTC<br>CTGTTCAACACCTCTATCGTTAACAACGTTCGTCTGGGTAACGAA<br>CAGGCGTCTGACGCG<br>GACGTTGCGGCGGCGCTGAAAGCGGTTAAACTGGACCAGCTGGT<br>TGCGCAGCTGCCGAAC<br>GGTATCAACTCTTCTGTTGAAGAAGCGGGTTTCGGTTTCTCTGGT<br>GGTGAACGTCAGCGT<br>CTGTCTCTGGCGCGTATCCTGCTGCAGGACGCGCCGATCGTTCTG<br>CTGGACGAACCGACC |

TABLE 3-continued

| List of ABC transporter genes providing the desirable results | | |
|---|---|---|
| SEQ ID NO | Organism | Nucleic acid sequence |
| | | GTTGGTCTGGACCCGATCACCGAACAGGCGCTGCTGGAAACCAT GTTCACCGTTCTGCAG GGTAAAACCATCCTGTGGGTTACCCACCACCTGCAGGGTGTTAAC CAGACCGACCGTGTT ATCTTCCTGGAAGACGGTCGTCTGACCATGAACGACACCCCGTCT CACCTGGCGAAACAC GACGAACGTTACCAGAACCTGTACGCGCTGGACGCGGGTCTGCG T |

TABLE 4

| Depicts the amino acid sequence of ABC transporter providing the desirable results as per the present disclosure. | | |
|---|---|---|
| SEQ ID NO | Organism | Amino acid sequence |
| 52 | *Trichophyton equinum* | MVEVSEKPNTQDDGVSKQENRNPASSSSSTSDKEKVAKKGNSDATKSSTPED LDAQLAHL PEHEREILKQQLFIPDVKATYGTLFRYATRNDMIFLAIVSLASIAAGAALPLFT VLFGSL AGTFRDIALHRITYDEFNSILTRNSLYFVYLGIAQFILLYVSTVGFIYVGEHITQ KIRAK YLHAILRQNIGFFDKLGAGEVTTRITADTNLIQDGISEKVGLTLTALSTFFSAFI IGYVR YWKLALICSSTIVAMILVMGGISRFVVKSGRMTLVSYGEGGTVAEEVISSIRN ATAFGTQ EKLARQYEVHLKEARKWGRRLQMMLGIMFGSMMAIMYSNYGLGFWMGSR FLVGGETDLSA IVNILLAIVIGSFSIGNVAPNTQAFASAISAGAKIFSTIDRVSAIDPGSDEGDTIE NVEG TIEFRGIKHIYPSRPEVVVMEDINLVVPKGKTTALVGPSGSGKSTVVGLLERF YNPVSGS VLLDGRDIKTLNLRWLRQQISLVSQEPTLFGTTIFENIRLGLIGSPMENESEEQI KERIV SAAKEANAHDFIMGLPDGYATDVGQRGFLLSGGQKQRIAIARAIVSDPKILLL DEATSAL DTKSEGVVQAALDAASRGRTTIVIAHRLSTIKSADNIVVIVGGRIAEQGTHDE LVDKKGT YLQLVEAQKINEERGEESEDEAVLEKEKEISRQISVPAKSVNSGKYPDEDVEA NLGRIDT KKSLSSVILSQKRSQENETEYSLGTLIRFIAGFNKPERLIMLCGFFFAVLSGAG QPVQSV FFAKGITTLSLPPSLYGKLREDANFWSLMFLMLGLVQLVTQSAQGVIFAICSE SLIYRAR SKSFRAMLRQDIAFFDLPENSTGALTSFLSTETKHLSGVSGATLGTILMVSTTL IVALTV ALAFGWKLALVCISTVPVLLLCGFYRFWILAQFQTRAKKAYESSASYACEAT SSIRTVAS LTREQGVMEIYEGQLNDQAKKSLRSVAKSSLLYAASQSFSFFCLALGFWYGG GLLGKGEY NAFQFFLCISCVIFGSQSAGIVFSFSPDMGKAKSAAADFKRLFDRVPTIDIESPD GEKLE TVEGTIEFRDVHFRYPTRPEQPVLRGLNLTVKPGQYIALVGPSGCGKSTTIAL VERFYDT LSGGVYIDGKDISRLNVNSYRSHLALVSQEPTLYQGTIRDNVLLGVDRDELP DEQVFAAC KAANIYDFIMSLPDGFGTVVGSKGSMLSGGQKQRIAIARALIRDPKVLLLDEA TSALDSE SEKVVQAALDAAAKGRTTIAVAHRLSTIQKADIIYVFDQGRIVESGTHHELLQ NKGRYYE LVHMQSLEKTQ |
| 54 | *Mucor ambiguus* | MTGSISIDAWLSGALALVTCGSAFVLSLQRTYLHKSQQKDRAPLVFDKQRDT SVPVADDD ARFVRLTFGTLTLTLLSALDFYHTVIQQQQQTSDWWITASACTQFVAWLYAS VLVLVARR YRFPSEWGWILNVHLCVFYCMIWCIAVYDVYDAYVINPSDNWIHMLPRLLA LILGSDLVF TTATTPRGAPFLDENGRKVAAIDVASIYSFLYFSWVTPLINLAYKNKKLTDED LPTLPPL |

TABLE 4-continued

Depicts the amino acid sequence of ABC transporter providing the desirable results as per the present disclosure.

| SEQ ID NO | Organism | Amino acid sequence |
|---|---|---|
| | | YRGHNLYYIFGATRNKSLLKRIYTTNKRAITIQVVLAFTTSLVYYVPAYFVNR LLTLIQD MHGVEDDVSIRKGFVLVASLGATILILGILVGQLWYYASSSLQVRVKAMLNI EIYRKTLR RRDLAVESPKLDDDEDTDKKKDDDEASDKKGESDEKEDVSSSTGTIVNLMS TDSNRISEF SVWWFSILAAPTELAVGIYFLYQLLGKSCFLGLLVMIVVLPINHYNAKTFAKT QDKLMEA RDKRVSLMNEVLQGIRQIKFFAWEKRWEKRVMEAREVELHHLGVTYMTEV LFTLLWQGSP ILVTLLSFYSFCKLEGNELTAPIAFTSITVFNELRFALNVLPEVFIEWLQALISIR RIQT YLDEDEIEPPSNEDEIDPLTGHIPEHITIGFKDATVGWSKHNYTDQVTDESDNI TSEASS TSFILKDLNIEFPPNELSLISGATGSGKTLMMLGLLGEAIVLKGTAHCPRQAV VDTVSDD FVTSKDIDPKDWLLPYALAYVSQTAWLQNASIRDNILFGLPYVESRYRDTLT ACALDKDL EILEDGDQTEIGEKGITLSGGQKARVSLARAVYSRAQNVLMDDVLSAVDAH TAKHLYEKC LLGPLMKERTRVLITHHVKLCVKGSGYIVHIDAGRASLVGTPNELRQNGQLA SIFESEEE EVAQEEDAEEEKAIEEVLPAVANKDLKKPRALVEEETRATGMVKVRLYKLY VSMVGSPFF WFVMVALVLGSRGLDVIENWWIKQWSQSYQTKHNDNATNNDYMFQQQSII SQSKPMFAYQ PVVASESDNDLASIMDAKDDRLNYYLGIYCLITLTNIVVGTARFAVLYWGVL GANRALYA ELLHRVFRAPLRFFDTTPIGRILNRFSKDFETIDSNIPNDLLNFVIQWVIIVSSMI TVSS VLPIFLVPMLAVALVNVYLGMMFVSASRELKRMDSVSRSPLFSNFTETIIGVA TIRAFGA TRQFLQDMLTYIDTNTRPFYYQWLVNRWVSVRFAFSGALINMFTSTIILLSVD KMDASLA GFCLSFVLLFTDQMFWGIRRYTSLEMSFNAVERVVEFMEMDQEAPAITEVRP PHEWPTRG RIDVKDLEIKYAADLDPVLKGISFSVKPQEKIGVVGRTGSGKSTLALSFFRFVE ASQGSI VIDNIDIKDLGTEDLRSNLTIIPQDPTLFSGSLRSNMDPFDQFTDQDIFTALRRV HLLPI EEGDNSAETVVSDSTLDEVNANVFKDLTTNVTEGGKNFSQGQRQLLCLARA LLKRSRIVL MDEATASVDFETDKAIQKTIAIEFADSTILCIAHRLHTVIEYDRILVLDQGQIL EFDSPL TLITNPESSFYKMCRNSASQNKALAAKKAALKGVHGKAVRKIRTSTHFHIPK TLVLNRAP KYARKSVAHAPRMDQYRVIRQPLNTETAMKKIEEHNTLTFLVDVKANKNQI KDAVKRLYD VEAAKINTLIRPDGYKKAFVRLTADVDALDVANKIGFI |
| 56 | *Cutibacterium granulosum* | MSEQRDGIRRTASGRETYEPDGLPDHGVEPREDVEEKTFVEEEDDSKEYMPI RTGARHAA SDTSMTDVENERFDLYKWLRFFMRSMDESDIKVSRAGVLFRNLNVSGSGSA LNLQKNVGS ILMTPFRLQEYLGLGQKNEKRILKNFDGLLKSGELLIVLGRPGSGCSTLLKTIC GELHGL ALDGDSTINYNGIPQRQMLKEFKGEVVYNQEVDKHFPHLTVGQTLEMAAAY RTPSNRIEG QTREDAIKMAARVVMAVFGLSHTYNTKVGNDFIRGVSGGERKRVSIAEMAL SAAPIAAWD NSTRGLDAATALEFVKALRIMSDLAGAAQAVAIYQASQAIYDVFDKAVVLY EGRQIYFGP TGAAKQFFEEQGWYCPPRQTTGDFLTSVTNPGERQPRKGMENKVPRTPDEF EAYWRQSAA YKALQAEIDEHEQEFPVGGEVVSQFQENKRLAQSKHSRPTSPYLLSVPMQVK LNTKRAYQ RIWNDKAATLTMVLSQIIQALIIGSLFYGTPAATQGFFSRNAAIFFGVLLNALV AIAEIN ALYDQRPIVEKHASYAFYHPFTEAVAGVVADIPVKFAMATCFNLIYYFMTGF RREPSQFF IYFLISFIAMFVMSAVFRTMAAITKTVSQAMMFAGVLVLAIVVYTGFAIPESY MVDWFGW |

TABLE 4-continued

Depicts the amino acid sequence of ABC transporter providing the desirable results as per the present disclosure.

| SEQ ID NO | Organism | Amino acid sequence |
|---|---|---|
| | | IRWINPIFYAFEILIANEYHGREFTCSGFIPAYPNLEGDSFICNMRGAVAGERT VSGDDY IWANYKYSYSHVWRNFGILLAFLFFFMFIYFLAVELNSSTTSTAEVLVFRRGH VPAYMTE NPKGNANDEEIAAPDAAGRAGAEGGDVNMIPAQKDIFTWRDVVYDIEIKGE PRRLLDHVS GWVKPGTLTALMGVSGAGKTTLLDVLAQRTSMGVITGDMLVNGRPLDSSF QRKTGYVQQQ DLHLATATVRESLRFSAMLRQPKNVSTEEKYTYVEDVIKMLNMEDFAEAVV GVPGEGLNV EQRKLLTIGVELAAKPKLLLFLDEPTSGLDSQSSWAICAFLRKLANSGQAILC TIHQPSA ILFQEFDRLLFLAKGGRTVYFGDIGTNSRTLLDYYERNGSRKCGDDENPAEF MLEIVGAG ASGKATQDWHEVWKNSNEARAVQDELDRIHREKQNEPAAGDDEVGGTDEF AMPFTQQLYH VTYRVFQQYWRMPGYIWAKMLLGFASAFFIGFSFWDSDSSQQGMQNVIYSV FMVAAIFST IVEQIMPLFLTQRSLYEVRERPSKAYSWKAFLIANISVEIPYQILVGIIVYASYY YAVNG VQSSDRQGLVLLYCVQFFIYASTFAHMCIAAAPDAETAAGIVTLLFSMMIAF NGVMQPPQ ALPGFWIFMYRVSPLTYWISGIVATELHDRPVQCTAVETSTFNPPSGQTCQQY LGEFLRA AGGNLQNPADTADCRYCSITVADEYIGGSKIFWTDRWRNFGLVWAYVVFNI FAATMLYYL FRVRKSSGKGLKERVAGLFGGKKKQ |
| 58 | *Magnetospirillum magneticum* | MHWLKNEHWVRPDLKRYRGLLFWSLILGVMTFVFAGALMFTSGFLIDKSAT KPLFAAIYV TVVLTRAFGIGRPVFQYIERLTSHNWVLRITSHMRRKLYKVLETDAAFVSEH HQTGDILG LLADDIGHIQNLYLRMIFPTVVGAGLTVIATLLLGWFNWGFALWIMLLLLFQ VLILPWWG LVVERFRKAEQKQLNHDAYVSLTDSVLGLSDWVITHREKDFMSQSLAAPKK LAASTVKSK RFQWRRDFVGQLLFVLIVISMLIWTNLEWTGNQASANWVGAFVLVVFPLDQ AFSGIAQGV GEWPTYRDAIRHLNDLQPVTRQLPQQQAVPTQFKEMTLQHLSFQYTPKDPEL ITDIDLTV HSGEKIAILGPSGMGKTTLLQLVLGDLTPTTGNVLVDGQDVLTYQQHRTNLF AVLDQSPF LFNTSIVNNVRLGNEQASDADVAAALKAVKLDQLVAQLPNGINSSVEEAGF GFSGGERQR LSLARILLQDAPIVLLDEPTVGLDPIIEQALLETMFTVLQGKTILWVTHHLQG VNQTDRV IFLEDGRLTMNDTPSHLAKHDERYQNLYALDAGLR |

Example 2

Enzyme Identification for Obtaining Recombinant Microbe as Per the Present Disclosure In order to identify highly active, stereo specific enzymes for the pathway steps, functional homologs from various species were shortlisted for each of the pathway step. Shortlisted pathway genes were codon optimized for *E. coli* and gene synthesized (Table 1 and Table 2).

Functional homologs of the polypeptides described above are also suitable for use in producing etoposide in a recombinant host. A functional homolog is a polypeptide that has sequence similarity to a reference polypeptide, and that carries out one or more of the biochemical or physiological function(s) of the reference polypeptide. A functional homolog and the reference polypeptide may be naturally occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide. Functional homologs can be identified by analysis of nucleotide and polypeptide sequence alignments. For example, performing a query on a database of nucleotide or polypeptide sequences can identify homologs of etoposide biosynthesis polypeptides. Sequence analysis can involve BLAST, Reciprocal BLAST, or PSI-BLAST analysis of nonredundant databases using a known podophyllotoxin biosynthesis gene sequence as the reference sequence. Amino acid sequence is, in some instances, deduced from the nucleotide sequence.

TABLE 5

Enzymes screened for constructing recombinant *E. coli*

| Recombinant *E. coli* BL21 clones expressing pathway enzymes | Organism | Substrate tested | Enzyme activity in terms of product formation (in %) |
|---|---|---|---|
| Phenylalanine ammonia-lyase (PAL) (SEQ ID NO: 2) | *Rhodosporidium toruloides* | Phenyl alanine | 61% |
| Phenylalanine ammonia-lyase (PAL) | *Phoma* sp. | Phenyl alanine | 14% |
| Phenylalanine ammonia-lyase (PAL) (SEQ ID NO: 4) | *Populus kitakamiensis* | Phenyl alanine | 52% |
| Phenylalanine ammonia-lyase (PAL) | *Trifolium subterraneum* | Phenyl alanine | 10% |
| Phenylalanine ammonia-lyase (PAL) (SEQ ID NO: 6) | *Strobilurus tenacellus* | Phenyl alanine | 73% |
| Phenylalanine ammonia-lyase (PAL) | *Cicer arietinum* | Phenyl alanine | 23% |
| Phenylalanine ammonia-lyase (PAL) (SEQ ID NO: 8) | *Penicillium antarcticum* | Phenyl alanine | 52% |
| Phenylalanine ammonia-lyase (PAL) (SEQ ID NO: 10) | *Ganoderma sinense* | Phenyl alanine | 98% |
| Phenylalanine ammonia-lyase (PAL) | *Psathyrella aberdarensis* | Phenyl alanine | 34% |
| Cinnamte 4 hydroxylase 4 coumarate coenzyme ligase fusion (C4H4CL) | *Vanilla planifolia* | Cinnamate | 31% |
| Cinnamte 4 hydroxylase 4 coumarate coenzyme ligase fusion (C4H4CL) | *Capsicum annuum* | Cinnamate | 5% |
| Cinnamte 4 hydroxylase 4 coumarate coenzyme ligase fusion (C4H4CL) (SEQ ID NO: 12) | *Azospirillum* sp. | Cinnamate | 97% |
| Cinnamte 4 hydroxylase 4 coumarate coenzyme ligase fusion (C4H4CL) | *Rhodobacter johrii* | Cinnamate | 21% |
| hydroxycinnamoyl-CoA: quinate hydroxycinnamoyltransferase p-coumaroyl quinate 3'-hydroxylase fusion (HCTC3H) | *Arabidopsis thaliana* | Coumaroyl coA | 2% |
| hydroxycinnamoyl-CoA: quinate hydroxycinnamoyltransferase p-coumaroyl quinate 3'-hydroxylase fusion (HCTC3H) | *Selaginella moellendorffii* | Coumaroyl coA | 12% |
| hydroxycinnamoyl-CoA: quinate hydroxycinnamoyltransferase p-coumaroyl quinate 3'-hydroxylase fusion (HCTC3H) | *Lonicera japonica* | Coumaroyl coA | 0% |
| hydroxycinnamoyl-CoA: quinate hydroxycinnamoyltransferase p-coumaroyl quinate 3'-hydroxylase fusion (HCTC3H) (SEQ ID NO: 14) | *Coffea canephora* | Coumaroyl coA | 89% |
| Caffeoyl CoA O-methyltransferase (CCoAOMT) | *Dictyostelium discoideum* | Caffeoyl coA | 0% |
| Caffeoyl CoA O-methyltransferase (CCoAOMT) | *Plagiochasma appendiculatum* | Caffeoyl coA | 8% |
| Caffeoyl CoA O-methyltransferase (CCoAOMT) (SEQ ID NO: 16) | *Eleocharis dulcis* | Caffeoyl coA | 61% |
| Caffeoyl CoA O-methyltransferase (CCoAOMT) (SEQ ID NO: 18) | *Chamaecyparis formosensis* | Caffeoyl coA | 95% |
| Caffeoyl CoA O-methyltransferase (CCoAOMT) | *Bambusa emeiensis* | Caffeoyl coA | 24% |
| Caffeoyl CoA O-methyltransferase (CCoAOMT) | *Taiwania cryptomerioides* | Caffeoyl coA | 0% |
| Bifunctional pinoresinol-lariciresinol reductase (DIRPLR) (SEQ ID NO: 20) | *Linum usitatissimum* | Coniferyl alcohol | 98% |
| Secoisolariciresinol dehydrogenase (SDH) | *Dysosma pleiantha* | Secoisolariciresinol | 0% |

TABLE 5-continued

Enzymes screened for constructing recombinant *E. coli*

| Recombinant *E. coli* BL21 clones expressing pathway enzymes | Organism | Substrate tested | Enzyme activity in terms of product formation (in %) |
|---|---|---|---|
| Secoisolariciresinol dehydrogenase (SDH) | *Dysosma versipellis* | Secoisolariciresinol | 0% |
| Secoisolariciresinol dehydrogenase (SDH) (SEQ ID NO: 22) | *Juglans regia* | Secoisolariciresinol | 99% |
| Secoisolariciresinol dehydrogenase (SDH) | *Cladophialophora carrionii* | Secoisolariciresinol | 17% |
| CYP719 | *Argemone mexicana* | Matairesinol | 0% |
| CYP719 | *Eschscholzia californica* | Matairesinol | 18% |
| CYP719 | *Coptis japonica* | Matairesinol | 0% |
| CYP719 (SEQ ID NO: 24) | *Papaver somniferum* | Matairesinol | 76% |
| CYP719 (SEQ ID NO: 26) | *Cinnamomum micranthum* | Matairesinol | 97% |
| O-methyltransferase 3 (OMT) (SEQ ID NO: 28) | *Papaver somniferum* | Pluviatolide | 88% |
| O-methyltransferase 3 (OMT) | *Plumulus lupulus* | Pluviatolide | 15% |
| O-methyltransferase 3 (OMT) | *Dictyostelium discoideum* | Pluviatolide | 0% |
| O-methyltransferase 3 (OMT) (SEQ ID NO: 30) | *Sinopodophyllum hexandrum* | Pluviatolide | 99% |
| O-methyltransferase 3 (OMT) | *Vanilla planifolia* | Pluviatolide | 0% |
| CYP71 (SEQ ID NO: 32) | *Cinnamomum micranthum* | Bursehernin | 94% |
| CYP71 | *Persea americana* | Bursehernin | 0% |
| CYP71 | *Populus trichocarpa* | Bursehernin | 0% |
| CYP71 | *Juglans regia* | Bursehernin | 10% |
| CYP71 | *Actinidia chinensis* | Bursehernin | 35% |
| CYP71 | *Acer yangbiense* | Bursehernin | 0% |
| 2-oxoglutarate/Fe(II)-dependent dioxygenase (2-ODD) | *Stigmatella aurantiaca* | Yatein | 0% |
| 2-oxoglutarate/Fe(II)-dependent dioxygenase (2-ODD) (SEQ ID NO: 34) | *Microcystis viridis* | Yatein | 45% |
| 2-oxoglutarate/Fe(II)-dependent dioxygenase (2-ODD) | *Candidates Nitrospira* | Yatein | 0% |
| 2-oxoglutarate/Fe(II)-dependent dioxygenase (2-ODD) (SEQ ID NO: 36) | *Nitrospira moscoviensis* | Yatein | 96% |
| 2-oxoglutarate/Fe(II)-dependent dioxygenase (2-ODD) (SEQ ID NO: 38) | *Nitrospira japonica* | Yatein | 88% |
| CYP82D | *Scutellaria baicalensis* | Deoxypodophyllotoxin | 0% |
| CYP82D | *Cucumis melo* | Deoxypodophyllotoxin | 0% |
| CYP82D (SEQ ID NO: 40) | *Panax ginseng* | Deoxypodophyllotoxin | 93% |
| CYP82D | *Fallopia sachalinensis* | Deoxypodophyllotoxin | 0% |
| CYP82D | *Juglans regia* | Deoxypodophyllotoxin | 0% |
| CYP82D | *Eschscholzia californica* | Deoxypodophyllotoxin | 0% |
| Glycosyltransferase (UGT) | *Arabidopsis thaliana* | Desmethylepipodophyllotoxin | 23% |
| Glycosyltransferase (UGT) (SEQ ID NO: 42) | *Mates domestica* | Desmethylepipodophyllotoxin | 54% |
| Glycosyltransferase (UGT) (SEQ ID NO: 44) | *Lycium barbarum* | Desmethylepipodophyllotoxin | 67% |
| Glycosyltransferase (UGT) | *Centella asiatica* | Desmethylepipodophyllotoxin | 0% |
| Glycosyltransferase (UGT) | *Centella asiatica* | Desmethylepipodophyllotoxin | 12% |
| Glycosyltransferase (UGT) (SEQ ID NO: 46) | *Cicer arietinum* | Desmethylepipodophyllotoxin | 97% |
| Glycosyltransferase (UGT) | *Lycium barbarum* | Desmethylepipodophyllotoxin | 15% |
| Glycosyltransferase (UGT) (SEQ ID NO: 48) | *Barbarea vulgaris* | Desmethylepipodophyllotoxin | 43% |
| Glycosyltransferase (UGT) | *Isatis tinctoria* | Desmethylepipodophyllotoxin | 0% |
| 2-Deoxy-d-ribose-5-phosphate aldolase (DERA) | *Rhodococcus erythropolis* | Desmethylepipodophyllotoxin glucopyranoside | 0% |
| 2-Deoxy-d-ribose-5-phosphate | *Desulfatibacillum* | Desmethylepipodophyllotoxin | 83% |

TABLE 5-continued

Enzymes screened for constructing recombinant *E. coli*

| Recombinant *E. coli* BL21 clones expressing pathway enzymes | Organism | Substrate tested | Enzyme activity in terms of product formation (in %) |
|---|---|---|---|
| aldolase (DERA) (SEQ ID NO: 50) | *aliphaticivorans* | glucopyranoside | |
| 2-Deoxy-d-ribose-5-phosphate aldolase (DERA) | *Ruminococcaceae bacterium* | Desmethylepipodophyllotoxin glucopyranoside | 0% |
| 2-Deoxy-d-ribose-5-phosphate aldolase (DERA) | *Thermo sulfurimonas dismutans* | Desmethylepipodophyllotoxin glucopyranoside | 0% |
| 2-Deoxy-d-ribose-5-phosphate aldolase (DERA) | *Aquifex aeolicus* | Desmethylepipodophyllotoxin glucopyranoside | 0% |
| 2-Deoxy-d-ribose-5-phosphate aldolase (DERA) | *Kocuria rhizophila* | Desmethylepipodophyllotoxin glucopyranoside | 0% |
| 2-Deoxy-d-ribose-5-phosphate aldolase (DERA) | *Alkaliphilus oremlandii* | Desmethylepipodophyllotoxin glucopyranoside | 0% |
| 2-Deoxy-d-ribose-5-phosphate aldolase (DERA) | *Gloeothece citriformis* | Desmethylepipodophyllotoxin glucopyranoside | 0% |
| 2-Deoxy-d-ribose-5-phosphate aldolase (DERA) | *Rhizobium meliloti* | Desmethylepipodophyllotoxin glucopyranoside | 0% |
| 2-Deoxy-d-ribose-5-phosphate aldolase (DERA) | *Photobacterium profundum* | Desmethylepipodophyllotoxin glucopyranoside | 0% |
| 2-Deoxy-d-ribose-5-phosphate aldolase (DERA) | *Synechocystis* sp. | Desmethylepipodophyllotoxin glucopyranoside | 0% |
| 2-Deoxy-d-ribose-5-phosphate aldolase (DERA) | *Proteus mirabilis* | Desmethylepipodophyllotoxin glucopyranoside | 0% |
| 2-Deoxy-d-ribose-5-phosphate aldolase (DERA) | *Pyrobaculum islandicum* | Desmethylepipodophyllotoxin glucopyranoside | 0% |
| 2-Deoxy-d-ribose-5-phosphate aldolase (DERA) | *Lactobacillus sakei* | Desmethylepipodophyllotoxin glucopyranoside | 0% |
| 2-Deoxy-d-ribose-5-phosphate aldolase (DERA) | *Desulfotalea psychrophila* | Desmediylepipodophyllotoxin glucopyranoside | 0% |
| 2-Deoxy-d-ribose-5-phosphate aldolase (DERA) | *Exiguobacterium sibiricum* | Desmethylepipodophyllotoxin glucopyranoside | 0% |
| 2-Deoxy-d-ribose-5-phosphate aldolase (DERA) | *Crocosphaera subtropica* | Desmethylepipodophyllotoxin glucopyranoside | 0% |
| 2-Deoxy-d-ribose-5-phosphate aldolase (DERA) | *Pasteurella multocida* | Desmethylepipodophyllotoxin glucopyranoside | 0% |
| 2-Deoxy-d-ribose-5-phosphate aldolase (DERA) | *Nocardia farcinica* | Desmethylepipodophyllotoxin glucopyranoside | 0% |
| 2-Deoxy-d-ribose-5-phosphate aldolase (DERA) | *Pelobacter carbinolicus* | Desmethylepipodophyllotoxin glucopyranoside | 0% |
| 2-Deoxy-d-ribose-5-phosphate aldolase (DERA) | *Trichormus variabilis* | Desmethylepipodophyllotoxin glucopyranoside | 0% |

It can be observed from Table 5, that not all homologs of a particular enzyme provide the desirable efficacy while being expressed in *E. coli* host cell.

PAL—In the case of Phenylalanine ammonia-lyase, the protein sequence of *Ganoderma sinense* provides the maximum enzyme activity in terms of 98%, whereas the protein sequence from *Phoma* sp., *Trifohum subterraneum, Cicer arietinum*, and *Psathyrella aberdarensis* did not provide satisfactory enzyme activity. Therefore, the sequence from *Ganoderma sinense* was considered for constructing the recombinant microbe.

C4CHL fusion—It can be observed from Table 5 that the fusion protein of *Azospirillum* sp. provides the maximum enzyme activity (97%), whereas the fusion protein from other organisms mentioned in Table 5 did not provide desirable results.

HCTC3H fusion—The maximum enzyme activity observed was from the fusion protein of *Coffea canephora* (89%), whereas, very little or no enzyme activity was observed from other microbes.

Caffeoyl CoA O-methyltransferase (CCoAOMT)—The maximum activity observed was from the protein of *Chamaecyparis formosensis* (95%). Further, the protein of *Eleocharis dulcis* also provided reasonable enzyme activity of 61%, whereas, the protein from other organisms did not yield desirable results.

Bifunctional pinoresinol-lariciresinol reductase (DIRPLR)—The desirable enzyme activity was observed for the protein from the microorganism *Linum usitatissimum.*

Secoisolariciresinol dehydrogenase (SDH)—Of the results described in Table 5, the protein from the microbe *Juglans regia* provided the desirable results of 99% enzyme activity.

CYP719—The highest enzyme activity was observed for the protein from the microbe *Cinnamomum micranthum*. Further, the enzyme activity of the protein from the microbe *Papaver somniferum* also provided satisfactory results.

O-methyltransferase 3 (OMT)—The results obtained with protein from *Papaver somniferum* and *Sinopodophyllum hexandrum* provided desirable enzyme activity of 88%, and 99%, respectively.

CYP71—The enzyme activity of the protein from *Cinnamomum micranthum* provided the desirable result of 94%.

2-oxoglutarate/Fe(II)-dependent dioxygenase (2-ODD)—The results obtained with protein from *Nitrospira moscoviensis* and *Nitrospira japonica* provided desirable enzyme activity of 96%, and 88%, respectively.

CYP82D—The enzyme activity of the protein from *Panax ginseng* was desirable around 93%, whereas the protein from other microbes failed to show any enzyme activity.

Glycosyltransferase (UGT)—Of the many proteins tested, the enzyme activity of the protein from *Cicer arietinum* was the highest (97%).

2-Deoxy-d-ribose-5-phosphate aldolase (DERA)—It can be observed from Table 5 that proteins of many microbes were tested for the enzyme activity, amongst them, the protein from *Desulfatibacillum ahphaticivorans* showed the highest enzyme activity of 83%.

Example 3

Construction of Fusion Enzymes

As per one of the possible implementations of the present disclosure, two proteins—cinnamate-4-hydroxylate (C4H) and 4-coumaroyl CoA-ligase (4CL) were expressed as one fusion protein. Also, other two proteins which were expressed as one fusion protein were hydroxycinnamoyl-CoA quinate hydroxycinnamoyltransferase (HCT) and p-coumaroyl quinate 3'-hydroxylase (HCTC3H). The fusion gene and the corresponding fusion protein was prepared using the following method. A flexible (GGGGS)3 (SEQ ID NO: 64) linker was inserted between the C-terminal of the upstream protein and the 15 N-terminal of the downstream protein i.e., (upstream protein C-terminal)-GGGGSGGGGSGGGGS (SEQ ID NO: 63)-(downstream protein N-terminal). The enzyme fusion constructs were made for the selected genes (Table 5). Pathway genes and the fusion constructs were individually cloned in *E. coli* expression vector pET28+ under T7 promoter and transformed in *E. coli* BL21 cells. Recombinant bacterial cells were induced with IPTG and enzyme functionality was tested with pathway specific substrates (Table 5) using lysed *E. coli* cell extracts. HPLC analysis was carried out to quantify the product formation and in turn shortlisting of efficient enzymes for functional pathway assembly towards Etoposide in *E. coli.*

The *E. coli* transformants were grown overnight at 37° C. in 1 ml of M9 minimal media containing ampicillin (100 mg/1), in 96-well format. The next day, 150 μl of each culture was inoculated into 3 ml M9 minimal media containing ampicillin (100 mg/1), IPTG 0.1 mM in 24-well format, and incubated at 30° C. and 200 rpm for ~20 hours. The following day, cells were spun down and pellets were resuspended in 100 μl of lysis buffer containing 10 mM Tris-HCl pH 8, 5 mM $MgCl_2$, 1 mM $CaCl_2$) and complete mini protease inhibitor EDTA-free (3 tablets/100 ml) (Hoffmann-La Roche, Basel, Switzerland) and frozen at −80° C. for at least 15 minutes to promote cell lysis. Pellets were thawed at room temperature and 50 μl of DNase mix (1 μl of 1.4 mg/ml DNase in $H_2O$ (~80000 u/ml), 1.2 μl of $MgCl_2$ 500 mM and 47.8 μl of 4×PBS buffer solution) was added to each well. Plates were shaken at 500 rpm for 5 min at room temperature to allow degradation of genomic DNA. Plates were spun down at 4000 rpm for 30 min at 4° C. and six μl of the lysates were used in in vitro using appropriate substrates for enzymes as per Table 6. In each case, the resulting compounds were measured by HPLC. Results were analysed in comparison with the lysates expressing the corresponding controls (the empty plasmid).

For extraction, 1 mL of the culture was centrifuged at maximum speed (>13,000 RPM) to pellet cells. Media was decanted to a fresh 1.5 mL microfuge tube and the pH was adjusted by addition of 50 μl hydrochloric acid (1N), followed by overnight freezing at −20° C. Tubes were thawed at room temperature and extracted twice with an equal volume (1 ml) of ethyl acetate. Ethyl acetate was dried under nitrogen gas, and the dried residue was resuspended in 100 μL methanol. All samples were stored at −20° C. prior to HPLC.

Example 4

Etoposide Pathway Assembly in *E. coli* Nissle 1917

Co-expression of multiple target genes in *E. coli* is advantageous for studying multi enzymatic pathways. Co-expression often achieves optimal yield, solubility, and activity and may protect individual subunits from degradation. The vectors used in the present disclosure carry compatible replicons and antibiotic resistance markers and may be used together in appropriate host strains to co-express multiple proteins either as monocistronic or polycistronic expression. The capability of vectors to be co-transformed, propagated, and induced for robust target protein co-expression makes them ideal for the analysis of multi enzymatic biosynthesis pathways. The vectors are designed with compatible replicons and drug resistance genes for effective propagation and maintenance of four plasmids in a single cell.

To facilitate constitutive production of Etoposide in *Escherichia coli* Nissle 1917, the first seven genes of the pathway (PAL, C4H4CL, HCTC3H, CCoAOMT, DIRPLR, SDH, and CYP719) are assembled in pRSF vector and next six genes of the pathway (OMT, CYP71, 2-ODD, CYP82D, UGT, DERA) are assembled in p15A vector.

As can be observed from Table 5, it can be appreciated that certain enzymes of the pathway when produced from recombinant *E. coli* Nissle 1917 performed better in terms of enzyme activity as compared to the others. In similar lines, the enzyme homolog providing the highest enzyme activity was selected per enzyme type for the construction of the recombinant *E. coli* Nissle 1917 in order to perform further experiments.

The genes encoding: PAL having an amino acid sequence as set forth in SEQ ID NO: 2, C4H4CL having an amino acid sequence as set forth in SEQ ID NO: 12, HCTC3H having an amino acid sequence as set forth in SEQ ID NO: 14, CCoAOMT having an amino acid sequence as set forth in SEQ ID NO: 18, DIRPLR having an amino acid sequence as set forth in SEQ ID NO: 20, SDH having an amino acid sequence as set forth in SEQ ID NO: 22, and CYP719 having an amino acid sequence as set forth in SEQ ID NO: 26 were assembled in pRSF vector.

The next six genes of the pathway were selected as follows. The genes encoding OMT having an amino acid sequence as set forth in SEQ ID NO: 30, CYP71 having an amino acid sequence as set forth in SEQ ID NO: 32, 2-ODD having an amino acid sequence as set forth in SEQ ID NO: 36, CYP82D having an amino acid sequence as set forth in SEQ ID NO: 40, UGT having an amino acid sequence as set forth in SEQ ID NO: 46, DERA having an amino acid sequence as set forth in SEQ ID NO: 50 were assembled in p15A vector. The corresponding nucleic acid sequences have been given in Table 1 as presented previously.

Although the recombinant microbe was constructed as per details mentioned above, however, it can be contemplated that other functional homologs of the enzymes showing desirable activity can be used to arrive at different recombinant microbes.

Transcriptional and translational elements, are synthesized (Gen9, Cambridge, MA) and cloned into vector pBR322 and p15A. The pathway cassette was placed under the control of either of the promoter sequences as follows.

GapA promoter having a nucleic acid sequence as set forth in SEQ ID NO: 59 (TTGCTCACATCTCACTT-TAATCGTGCTCACATTACGTGACTGATTCTAACA AAACATTAACACCAACTGGCAAAAT-TTTGTCCTAAACTTGATCTCGACGA AATGGCTGCACCTAAATCGTGATGAAAATCACAT-TTTTATCGTAATTGCCC TTTAAAAT-TCGGGGCGCCGACCCCATGTGGTCTCAAGCC-CAAAGGAAGAG TGAGGCGAGTCAGTCGCGTAATGCTTAGGCACAG-GATTGATTTGTCGCAA TGATTGACACGAT-TCCGCTTGACGCTGCGTAAGGTTTTTGTAATTTTA-CAG GCAACCTTTTATTCA)

TufB promoter having a nucleic acid sequence as set forth in SEQ ID NO: 60 (TAAAAAGAATTATGGTTTAGCAG-GAGCGCATTGTTGAGCACAATGATGTT GAAAAAGTGTGCTAATCTGCCCTCCGTTCGGCTGT TTCTTCATCGTGTCGC ATAAAATGTGAC-CAATAAAACAAATTATGCAATTTTTTAGTTGCAT-GAACT CGCATGTCTCCATAGAATGCGCGCTACTTG).

It can be contemplated that any well-known and suitable promoter sequences apart from the ones disclosed herein can also be used for constructing the recombinant microbe.

For efficient translation of genes, each synthetic gene in the operon was separated by ribosome binding sites (RBS). The RBS can have a nucleic acid sequence as set forth in SEQ ID NO: 61 (TCTTAATCATGCACAGGA-GACTTTCTA) or the nucleic acid sequence as set forth in SEQ ID NO: 62 (AAGTTCACTTAAAAAGGAGAGAT-CAACA). Further, a person skilled in the art can use any other well-known RBS sequence in order to increase the translation efficiency.

Plasmids p15A and pRSF assembled with entire etoposide pathway genes were co-transformed in *E. coli* Nissle and recombinant clones were selected on dual antibiotic LB agar plates containing kanamycin (25 µg/ml) and chloramphenicol (15 µg/ml). Recombinant clones were screened for biosynthesis of etoposide and the presence of etoposide was confirmed through mass analysis. *E. coli* Nissle recombinant clone (JNM2450) which produced highest etoposide levels was selected for further analysis like screening of ABC transporter genes for etoposide secretion and the like.

Example 5

ABC Transporter for Etoposide Secretion

A transporter (also referred to as a membrane transport protein) is a membrane protein involved in the movement of molecules and ions across a biological membrane. Transporters span the membrane in which they are localized and across which they transport substances. Transporters can operate to move substances by facilitated diffusion or by active transport. Transport proteins have been classified according to various criteria at the Transporter Classification Database. See, Saier Jr. et al., Nucl. Acids Res., 37:D274-278 (2009). Two families of plasma membrane transporters are thought to be ubiquitous among living organisms: the ATP-Binding Cassette (ABC) transporters and the Major Facilitator Superfamily (MFS) transporters. ATP-binding cassette transporters (ABC transporters) are transmembrane proteins that utilize the energy of adenosine triphosphate (ATP) hydrolysis to carry out translocation of various substrates across membranes. They can transport a wide variety of substrates across extra- and intracellular membranes, including metabolic products, lipids and sterols, and drugs. Proteins are classified as ABC transporters based on the sequence and organization of their ATP-binding cassette domain. Typically, ABC family transporters are multicomponent primary active transporters, capable of transporting molecules in response to ATP hydrolysis. Non-limiting examples of endogenous ABC transporter genes include the genes at the loci PDRS, PDR10, PDR15, SNQ2, YOR1, YOL075c and PDR18 (or a functional homolog thereof).

A total of 20 ABC transporter genes from various organisms (Table 6) were selected and codon optimized for expression in *E. coli* system. To determine the effect of various transporters on etoposide secretion in *E. coli* Nissle clone (JNM2450), a library of *E. coli* Nissle strains was constructed by cloning the transporter genes under a constitutive promoter GapA.

*E. coli* Nissle clone (JNM2450) producing etoposide was co-transformed with ColE1 plasmid harbouring various transporter genes. The recombinant clones were grown in M9 minimal media at 37° C. for overnight and the supernatant was subjected for HPLC analysis. Table 6 below depicts the percentage of etoposide secretion achieved by using the different ABC transporters.

TABLE 6

Comparison of different ABC transporters in secreting etoposide

| Clone name | Organism | Etoposide secretion (>90%) in growth media |
|---|---|---|
| JNM133 | *Candida albicans* | 0% |
| JNM134 | *Trichophyton rubrum* | 0% |
| JNM135 | *Neosartorya fumigata* | 0% |
| JNM136 | *Emericella nidulans* | 0% |
| JNM137 | *Aspergillus oryzae* | 0% |
| JNM138 | *Trichophyton rubrum* | 0% |
| JNM139 | *Trichophyton equinum* (SEQ ID NO: 52) | 10% |
| JNM140 | *Purpureocillium lilacinum* | 0% |
| JNM141 | *Wickerhamomyces ciferrii* | 0% |
| JNM142 | *Mucor ambiguous* (SEQ ID NO: 54) | 45% |
| JNM143 | *Sporisorium scitamineum* | 0% |
| JNM144 | *Cutibacterium granulosum* (SEQ ID NO: 56) | 98% |
| JNM145 | *Botryosphaeria parva* | 0% |
| JNM146 | *Colletotrichum fructicola* | 0% |
| JNM147 | *Clohesyomyces aquations* | 0% |
| JNM148 | *Cadophora* sp. | 0% |
| JNM149 | *Magnetospirillum magneticum* (SEQ ID NO: 58) | 64% |
| JNM150 | *Lactobacillus paracasei* | 0% |
| JNM151 | *Rothia kristinae* | 0% |
| JNM152 | *Acinetobacter baumannii* | 0% |

As can be observed from Table 6, that the clone (JNM144) harbouring ABC transporter gene (SEQ ID NO: 55), and encoding ABC transporter protein as per SEQ ID NO: 56 from *Cutibacterium granulosum* showed highest etoposide secretion in the supernatant compared to the control strain.

Therefore, along with the etoposide pathway assembly as discussed in Example 4, the gene encoding ABC transporter having an amino acid sequence as set forth in SEQ ID NO: 56 was also cloned to obtain the recombinant *E. coli* Nissle 1917. The recombinant *E. coli* Nissle 1917 obtained along with the ABC transporter as described herein was used for further studies as described in forthcoming examples. It can be contemplated that other transporters well-known in the art can also be used for obtaining the recombinant microbe.

Example 6

Controlling the Expression of the Genes Cloned in the Recombinant *E. coli* Nissle 1917

It is imperative to control the expression of genes comprised in the recombinant *E. coli* Nissle 1917 obtained as per the previous Examples 1-4. In order to effectuate the same, different kinds of regulatory circuit can be used for eventually controlling the secretion of etoposide by the recombinant bacterium.

Engineering *E. coli* Nissle 1917 with AraC Transcriptional Regulator that can Detect Arabinose and Rhamnose To create inducible systems for use in *E. coli* Nissle, parts from a large repertoire of systems that govern carbohydrate utilization were used, which included cytoplasmic transcription factors, extracytoplasmic function sigma/anti-sigma pairs, and hybrid two-component systems (HTCS), among others. In *E. coli* Nissle, arabinose and rhamnose metabolism is mediated by the AraC/Xy1S-family transcriptional activator, RhaR, which activates transcription at the Pbad promoter. To assay the functionality of Pbad as an inducible system, 250 bp of the promoter-RBS region was cloned upstream of the etoposide pathway (as described in Example 3) into the expression vectors. Gene expression was conditional on the concentration of arabinose and rhamnose and demonstrated a response curve with an output dynamic range of 104-fold. Fitting the response curve to a Hill function revealed a threshold K of 0.3 mM and a Hill coefficient n=1.4. FIG. 1 depicts the production of etoposide by *E. coli* Nissle in which the genes encoding enzymes of the etoposide pathway are under the control of AraC regulator. The production of etoposide can be observed in the presence of arabinose (induce), and the absence of the expression can be observed without arabinose.

Engineering *E. coli* Nissle 1917 with Lung Airway Epithelial Cell Specific Nitric Oxide (NO) Regulatory Operon Nitric oxide is a natural marker of inflammation in lung cancer, making it an ideal input signal for this engineered microorganism. Inflamed lung epithelial cells produce nitric oxide by up-regulating inducible nitric oxide synthase (iNOS), an enzyme that produces nitric oxide from L-arginine. Nitric oxide sensing was combined through NorR regulatory unit with podophyllotoxin (etoposide) pathway biosynthesis genes. The following design strategy is incorporated to successfully couple nitric oxide sensing to switch activation.

The sequence used for promoter PnorV extended into the coding sequence of NoR. Additionally, rather than using the sequence for the native ribosomal binding site (RBS) for norV, a stronger synthetic RBS was used and spacer to drive multiple genes. To characterize the switching properties of the nitric oxide responsive engineered *E. coli* Nissle strains, the nitric oxide donors DETA/NO (diethylenetriamine/nitric oxide adduct) and SNP (sodium nitro prusside) were used as sources of nitric oxide. FIG. 2 depicts the production of etoposide under the control of nitric oxide. *E. coli* Nissle was cloned with the genes encoding the enzymes of etoposide pathway under the control of Nor R regulatory circuit. After exposure to SNP, *E. coli* Nissle strain JNM1013 was detected with biosynthesis of podophyllotoxin.

Engineering *E. coli* Nissle 1917 with the FNR Regulatory Operon that can Detect Hypoxic Conditions

*E. coli* Nissle strain JNM1024 was genetically engineered to express genes for biosynthesis of podophyllotoxin under the control of an FNR transcriptional regulator. Under oxygen-rich conditions, binding of the transcription factor FNR to the hypoxia-inducible promoter will be impeded, leading to repressed expression of the downstream gene. In tumor microenvironment with relatively low levels of oxygen, the FNR transcription factor can bind to the promoter, leading to the expression of the downstream gene. Sodium sulphite is used to make an hypoxia environment in laboratory conditions. Comparing with a control, under oxygen-limiting conditions FNR controlled pathway genes showed expression leading to biosynthesis of podophyllotoxin (FIG. 3).

Therefore, it can be clearly observed that the production of etoposide by the recombinant *E. coli* Nissle takes place only in the presence of the respective inducers. Whereas, in the absence of any inducer, etoposide production is not observed. Hence, the production of etoposide can be controlled and limited to only the location where it is required to be produced.

Example 7

Laboratory Bioassay for Treating Lung Cancer Cell Lines with *E. coli* Nissle 1917 Producing Podophyllotoxins The lung cancer cell lines such as NCI-H69, NCI-H128, NCIH209, SHP-77, PC-9 were used to study the *E. coli* Nissle bacterial clones producing podophyllotoxin.

Lung cancer cells were added to each well of a 6-well plate containing 1.5 ml DMEM supplemented with 10% FBS. Cells were cultured in the wells overnight at 37° C., 95% air, and 5% $CO_2$ to allow them to form a ~90% confluent monolayer. The culture medium in each well was then replaced with 1 ml fresh medium supplemented before adding 50 μl of engineered bacterial suspension with $OD_{600}$~1.0. Wild type bacteria were also added to control wells containing fresh media. Inducers such as arabinose or rhamnose, sodium nitro prusside (SNP) and cobalt chloride were used for activating the AraC operon, NO generation and creating hypoxic conditions in tumour cell lines respectively. After incubating the plates for overnight under the same conditions as described above, the effects of native and engineered bacteria releasing podophyllotoxins on tumour cell viability were assessed using CellTiter 96® AQueous One Solution Cell Proliferation Assay (MTS) (Promega, Madison, WI). These experiments were repeated 5 times for each combination of tumor cell type. Statistical significance of sample difference was evaluated with the Mann-Whitney U test.

Figure 4:
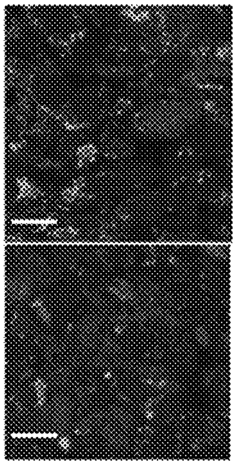
FIG. 4 depicts the calcein AM stained tumour cells for showing the effect of culturing recombinant *E. coli* Nissle capable of producing etoposide along with tumour cells, in accordance with an embodiment of the present disclosure.

To visualize *E. coli* interactions with tumour cells, 1.5 ml of DMEM supplemented with 10% FBS plus 0.5 ml of B16.F10 or EMT6 cell suspension (approximately $3\times10^6$ cells/ml) were added to each well of a 6-well plate. Cells were incubated in plates overnight at 37° C., 95% air, and 5% $CO_2$ to obtain confluent monolayers. For co-visualization of tumour cells and bacteria, tumour cells were stained prior to bacterial infection by incubating with 1 μM calcein-AM in serum-free DMEM at 37° C. for 15 min. The medium in each well was then replaced with fresh, serum-supplemented medium. Monolayers were inoculated with 40 μl of an overnight culture of *E. coli* (0D600 ~1.0) and incubated at 37° C., 95% air, and 5% $CO_2$ for overnight. Medium was then removed from each well and monolayers were gently washed three times with PBS before visualizing with confocal microscopy (Zeiss LSM 510). FIG. 4 depicts the interaction of tumour cells incubated overnight along with the recombinant *E. coli* Nissle capable of producing etoposide as per the present disclosure. It can be observed that in the absence of etoposide production majority of live tumour cells (green indicates live tumour cells) are visible (FIG. 4 A). Whereas, in the presence of etoposide production, tumour cell death (red indicates induced tumour cell death) can be observed (FIG. 4 B).

Advantages of the Present Disclosure:

The present disclosure discloses recombinant (programmed) microbe capable of producing podophyllotoxin, or its derivatives, or its precursors. As per one of the example, the recombinant microbe produces etoposide which is an anti-cancer molecule and can solve the problem of the targeted therapy and regulating the dosage of the molecule for the treatment. The recombinant microbe as disclosed herein is capable of producing etoposide in the presence of inducers like hypoxic conditions, or the presence of nitric oxide which are the hallmarks of the cancerous cells. Therefore, the production of etoposide by the recombinant bacteria present in the tumour microenvironment leads to targeted therapy and that too with a much lesser amount of etoposide. Such a treatment would lead to a reduction in the dosage of the anti-cancer molecule required for the cancer treatment, therefore, circumventing the problem of side effects of the chemotherapy, and increasing the chances of survival of the subject.

The present disclosure discloses the recombinant microbe which can be used to produce podophyllotoxin pathway precursors, or derivatives. The methods disclosed in the present disclosure provides three distinct advantages, first amongst them, such tools permit cloning of large fragments of nucleic acids into the bacterial genome (both episomally and integrated into its genome); second of them, they enable rapid scalability in cloning the metabolic pathway for the drug compound; third, is their versatile nature to adapt cloning variety of control circuitry inside the microorganism. Therefore, the recombinant microbe leads to a stable production of the end-product which further can have numerous applications.

We claim:

1. A recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71 Cytochrome P450 oxidoreductase CYP82D, and UDP glucosyl transferase, and a protein transporter, wherein the recombinant microbe secretes etoposide, or its derivatives.

2. A recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of at least one regulatory circuit.

3. The recombinant microbe as claimed in claim 2, wherein the regulatory circuit is selected from the group consisting of nitric oxide (NO) operon, arabinose (AraC) operon, fumarate and nitrate reductase (FNR) operon, thiosulphate-responsive regulatory circuit, and tetrathionate-responsive regulatory circuit.

4. The recombinant microbe as claimed in claim 1, wherein the gene encode phenyl alanine ammonia-lyase (PAL) having an amino acid sequence as set forth in SEQ ID NO: 10, cinnamate-4-hydroxylate 4-coumaroyl CoA-ligase fusion (C4H4CL) having an amino acid sequence as set forth in SEQ ID NO: 12, hydroxycinnamoyl-CoA quinate hydroxycinnamoyltransferase, p-coumaroyl quinate 3'-hydroxylase fusion (HCTC3H) having an amino acid sequence as set forth in SEQ ID NO: 14, caffeoyl CoA O-methyltransferase (CCoAOMT) having an amino acid sequence as set forth in SEQ ID NO: 18 bifunctional pinoresinol-lariciresinol reductase (DIRPLR) having an amino acid sequence as set forth in SEQ ID NO: 20, secoisolariciresinol dehydrogenase (SDH) having an amino acid sequence as set forth in SEQ ID NO: 22, cytochrome P450 oxidoreductase CYP719 having an amino acid sequence as set forth in SEQ ID NO: 26, O-methyltransferase (OMT) having an amino acid sequence as set forth in SEQ ID NO: 30, cytochrome P450 oxidoreductase CYP71 having an amino acid sequence as set forth in SEQ ID NO: 32, 2-oxoglutarate/Fe(II)-dependent dioxygenase (2-ODD) having an amino acid sequence as set forth in SEQ ID NO: 36, cytochrome P450 oxidoreductase CYP82D having an amino acid sequence as set forth in SEQ ID NO: 40, UDP glucosyl transferase having an amino acid sequence as set forth in SEQ ID NO: 46, and 2-Deoxy-d-ribose-5-phosphate aldolase having an amino acid sequence as set forth in SEQ ID NO: 50.

5. The recombinant microbe as claimed in claim 1, wherein the microbe is a bacterium selected from the group consisting of commensal bacteria.

6. The recombinant microbe as claimed in claim 1, wherein the recombinant microbe is *Escherichia coli.*

7. The recombinant microbe as claimed in claim 1, wherein the recombinant microbe is *E. coli* Nissle 1917.

8. The recombinant microbe as claimed in claim 1, wherein the genes are separated by a ribosome binding site.

9. The recombinant microbe as claimed in claim 1, wherein said genes have nucleic acid sequences as set forth in SEQ ID NO. 9, SEQ ID NO. 11, SEQ ID NO. 13, SEQ ID NO. 17, SEQ ID NO. 19, SEQ ID NO. 21, SEQ ID NO. 25, SEQ ID NO. 29, SEQ ID NO. 31, SEQ ID NO. 35, SEQ ID NO. 39, SEQ ID NO. 45, and SEQ ID NO. 49.

10. A recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a hypoxia-responsive regulatory circuit.

11. A recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of a nitric oxide-responsive regulatory circuit.

12. A recombinant microbe comprising genes encoding phenyl alanine ammonia-lyase (PAL), cinnamate-4-hydroxylate 4-coumaroyl CoA-ligase fusion (C4H4CL), hydroxycinnamoyl-CoA quinate hydroxycinnamoyltransferase p-coumaroyl quinate 3'-hydroxylase fusion (HCTC3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, and UDP glucosyl transferase, and a protein transporter, wherein the recombinant microbe secretes etoposide, or its derivatives, and wherein the expression of the genes is under the control of an arabinose-responsive regulatory circuit.

13. A composition comprising: (a) the recombinant microbe as claimed in any one of the claims 1, 2, 10, 11, or 12; and (b) at least one pharmaceutically acceptable carrier.

14. A method for treating cancer, said method comprising: administering the composition as claimed in claim 13 to a subject for treating cancer.

15. The method as claimed in claim 14, wherein administering is done by at least one method selected from the group consisting of oral, nasal, and intravenous.

16. A method for constructing the recombinant microbe as claimed in claim 1, said method comprising: (a) obtaining one or more recombinant vector, said recombinant vector encoding a repertoire of genes encoding phenyl alanine ammonia-lyase (PAL), Cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, UDP glucosyl transferase, and at least one gene encoding a protein transporter selected from the group consisting of ATP-Binding Cassette (ABC) transporter, Major Facilitator Superfamily (MFS) transporters, SMR (small multidrug resistant) family, RND (Resistance-Nodulation-Cell Division) family, and the MATE (multidrug and toxic compound extrusion) family; and (b) transforming a host microbe with the recombinant vector obtained in step (a), to obtain the recombinant microbe as claimed in claim 1.

17. A method for constructing the recombinant microbe as claimed in claim 2, said method comprising: (a) obtaining one or more recombinant vector, said recombinant vector encoding a repertoire of genes encoding phenyl alanine ammonia-lyase (PAL), Cinnamate-4-hydroxylate (C4H), 4-coumaroyl CoA-ligase (4CL), hydroxycinnamoyl-CoA quinate hydroxycinnamoyltransferase (HCT), p-coumaroyl quinate 3'-hydroxylase (C3H), caffeoyl CoA O-methyltransferase (CCoAOMT), bifunctional pinoresinol-lariciresinol reductase (DIRPLR), secoisolariciresinol dehydrogenase (SDH), O-methyltransferase (OMT), 2-oxoglutarate/Fe(II)-dependent dioxygenase (2-ODD), 2-Deoxy-d-ribose-5-phosphate aldolase, Cytochrome P450 oxidoreductase CYP719, Cytochrome P450 oxidoreductase CYP71, Cytochrome P450 oxidoreductase CYP82D, UDP glucosyl transferase, at least one gene encoding a protein transporter selected from the group consisting of ATP-Binding Cassette (ABC) transporter, Major Facilitator Superfamily (MFS) transporters, SMR (small multidrug resistant) family, RND (Resistance-Nodulation-Cell Division) family, and the MATE (multidrug and toxic compound extrusion) family, and at least one regulatory circuit selected from the group consisting of nitric oxide (NO) operon, arabinose (AraC) operon, fumarate and nitrate reductase (FNR) operon, thiosulphate-responsive regulatory circuit, and tetrathionate-responsive regulatory circuit; and (b) transforming a host microbe with the recombinant vector obtained in step (a), to obtain the recombinant microbe as claimed in claim 2.

* * * * *